US008604180B2

(12) United States Patent
Yukawa et al.

(10) Patent No.: US 8,604,180 B2
(45) Date of Patent: Dec. 10, 2013

(54) DNA FRAGMENT HAVING PROMOTER FUNCTION

(75) Inventors: Hideaki Yukawa, Soraku-gun (JP); Masayuki Inui, Soraku-gun (JP)

(73) Assignee: Research Institute of Innovative Technology for the Earth, Kyoto (JP)

( * ) Notice: Subject to any disclaimer, the term of this patent is extended or adjusted under 35 U.S.C. 154(b) by 987 days.

(21) Appl. No.: 11/662,358

(22) PCT Filed: Sep. 5, 2005

(86) PCT No.: PCT/JP2005/016269
§ 371 (c)(1),
(2), (4) Date: Mar. 8, 2007

(87) PCT Pub. No.: WO2006/028063
PCT Pub. Date: Mar. 16, 2006

(65) Prior Publication Data
US 2008/0171371 A1 Jul. 17, 2008

(30) Foreign Application Priority Data
Sep. 9, 2004 (JP) ................................. 2004-263077

(51) Int. Cl.
*C07H 21/04* (2006.01)
*C12N 1/21* (2006.01)
(52) U.S. Cl.
USPC ...................................... 536/24.1; 435/252.3
(58) Field of Classification Search
None
See application file for complete search history.

(56) References Cited

U.S. PATENT DOCUMENTS 4,963,482 A 10/1990 Birkmann et al.
7,368,268 B2 * 5/2008 Murakami et al. ............ 435/145

FOREIGN PATENT DOCUMENTS

| EP | 0285152 | 10/1988 |
| EP | 0629699 | 12/1994 |
| JP | 63-254985 | 10/1988 |
| JP | 7-95891 | 4/1995 |
| WO | 0100842 | 1/2001 |
| WO | 2004/074495 | 9/2004 |

OTHER PUBLICATIONS

AX 127148 (May 11, 2001).*
M. Inui et al., "Development of Novel Bioprocesses Based on the Anaerobic Metabolism of Corynebacteria", Abstr. Gen. Meet. Am. Soc. Microbiol., p. O-071, 2003.
European Search Report issued in EP 05776785.7 on Nov. 12, 2008.
Inui, M. et al., "Metabolic Engineering of *Corynebacterium glutamicum* for Fuel Ethanol Production under Oxygen-Deprivation Conditions", *J. Mol. Microbiol. Biotechnol.*, 2004, 8(4):243-254.
Kalinowski, J., "Corynebacterium glutamicum ATCC 13032, IS fingerprint type4-5, complete genome", Database EMBL, Accession No. BX927151, Jan. 22, 2004.
European Office Action dated Mar. 4, 2010 issued in corresponding EP Application No. 05776785.7.
Japanese Office Action issued Nov. 30, 2010 in Japanese Patent Application No. 2006-535746.
J. Kalinowski et al., "The complete *Corynebacterium glutamicum* ATCC 13032 genome sequence and its impact on the production of L-aspartate-derived amino acids and vitamins," Journal of Biotechnology (2003), vol. 104, pp. 5-25.
European Search Report issued Feb. 10, 2012 in corresponding European Application No. 11 19 5654.
Han, S.O., et al., "*Corynebacterium glutamicum* glyceraldehyde 3-phosphate dehydrogenase A (gapA), phosphoglycerate kinase (pgk), triosephosphate isomerase (tpi), and phosphoenolpyruvate carboxylase (ppc) genes, complete cds", Online Database EMBL, Nov. 14, 2005, XP002668254.

* cited by examiner

Primary Examiner — Celine Qian
(74) Attorney, Agent, or Firm — Wenderoth, Lind & Ponack, L.L.P.

(57) ABSTRACT

The present invention relates to a method of inducing expression of a promoter function of various genes in a *Coryneform* bacterium related to function exertion, in order to exert the function of a *Coryneform* bacterium highly and effectively under an anaerobic condition, for producing an organic compound useful under an anaerobic condition, more particularly, provides a method of enhancing and/or suppressing the promoter function related to various genes, for the purpose of highly and effectively expressing various protein genes necessary for production of an objective substance, and suppressing expression of an unnecessary protein gene.
The DNA fragment of the present invention is useful as a primer which is introduced into a transformed *Coryneform* bacterium producing a useful substance such as lactic acid and succinic acid highly and at a high efficiency.

3 Claims, 1 Drawing Sheet

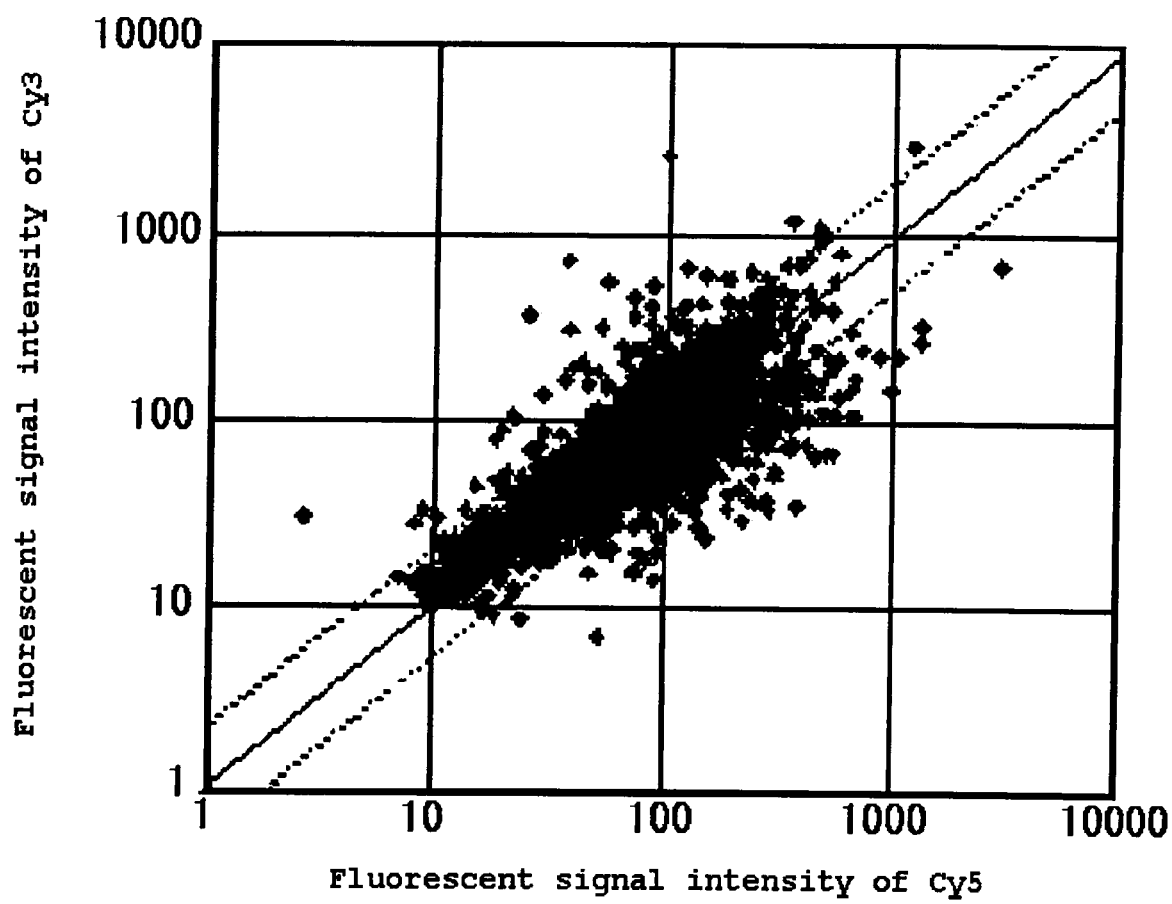

SEQUENCE LISTING

```
<160> NUMBER OF SEQ ID NOS: 595

<210> SEQ ID NO 1
<211> LENGTH: 575
<212> TYPE: DNA
<213> ORGANISM: Corynebacterium glutamiucm R

<400> SEQUENCE: 1
gtctcctagc gtgacatgtt tcttaagtac tttcaatttc ttttcgacgt gatttgaagt      60 cacttttct aaactgtgac ccaccaccca accatcaacg ggtgtaacca cacgtcacca     120
cgttgcattt tgcaaaaccc caggtaaaaa caggttcccc aaaatatgcg ggggtaaaat     180
gcgatctccc ctcttccgtc aacttgacta tgaggttgca caccttacg ccacttcccc      240 acccgacgca gacaacagga acccaaaacg acaccatgaa tttaattccc cggaacttct     300
tgacagaccg agcagtctag ggtttggttg aaaacgcaat cggttcactt ttaatcctct     360
ccctggagcc ccggatgatg aggaacgcca aagctttctg aatggaaatt ttaagcgtta     420
agtgggacga cctcgattac aaaaaggcga ggaaacccc ggggcagctt tctgccaccc      480
ggtgatttcg cgaaccttga aacatcgtca gaagattgcc gtgcgtccta gccgggatcc     540
gcacgttcgg ctcaagcaga aagtctttaa ctcac                                575

<210> SEQ ID NO 2
<211> LENGTH: 378
<212> TYPE: DNA
<213> ORGANISM: Corynebacterium glutamiucm R

<400> SEQUENCE: 2
ggccggcccc tgtccttctt aagcttgtct ctggtttcca agcataggca taagcgcagt      60
tcagtagggg aaatgaccaa gaaacaagtt ttattcacac actgggggtg attccagtca     120
ctaagtttag ctaaggtgtc ctgagttgct ttttgggtag cttaagtagc cttgacctgc     180
tgttatgttt tttgcggtct ggtataaatt gtgccgattt aaggattttg tggggtgga      240
```

```
ttgaaattag ttggcccgat cccactactt ttcgcctgga gtgcttgtag gttgatagaa      300
agtaaactaa agtaaacatc aggttaacag ccgggggttc aagtattaac tccctcggaa      360
acagaaagga acacgaca                                                    378

<210> SEQ ID NO 3
<211> LENGTH: 151
<212> TYPE: DNA
<213> ORGANISM: Corynebacterium glutamiucm R

<400> SEQUENCE: 3
aatcaccaac cctagtagcc ggtgcgccga tttgataaaa aactaagcgt ggcctgcggg       60
aatcggtact tttaggatag ggcaacctaa aataaataag cttaggctaa gagtcggtga      120
caatttatca agcagtgcta taatagggggt c                                    151

<210> SEQ ID NO 4
<211> LENGTH: 119
<212> TYPE: DNA
<213> ORGANISM: Corynebacterium glutamiucm R

<400> SEQUENCE: 4
gggaaagccc tcctcttggg aatcattttc aatagagtca acgcaagtgt acacttctta       60
atagaaatcg ttatcaataa ggtcaagttt ttttgacctt cgcttttttag gagcacccc      119

<210> SEQ ID NO 5
<211> LENGTH: 283
<212> TYPE: DNA
<213> ORGANISM: Corynebacterium glutamiucm R

<400> SEQUENCE: 5
gttttaacct ccgcttctaa caaacggcta accctttgg gttagccgtt tgttgaggtt       60
aaggggtttt aaaagagggc ttttcgacga gtgctgatgg gcattcttat ttcccacaat      120
ggcaaggggc ttcgtcgaaa agcgcgcttc gtgcccctga aaatagtttt tcccgcgcgg      180
gaggcgcctg atcaaaccgc gcggttattt ctacctaatc ctgttcagtg ccatattccc      240
gctcaacata cttgaaagcc tctaaagcct gtttaaatcc ttc                        283

<210> SEQ ID NO 6
<211> LENGTH: 913
<212> TYPE: DNA
<213> ORGANISM: Corynebacterium glutamiucm R

<400> SEQUENCE: 6
tttctttttc ttcataatca aattggccgc tttccactca tgtttttgag cgggaggcgg       60 cttttttgatg tccagggttg tttctgggggt tttatttgag gttttgggtt cgaaacgggc      120
tgtgggagtg catttcgatg cctcgaaagg gggatgcgag ggcgggggttc ttgcgcaacc      180 aaaccacagt gccacggaa ctcgaaaatg tgtttcgtgg gcactgtggt ttgttttatc      240
gccctccata ccggccacag atgcccaagt tttggatttg aggggttcgt gggcacgcct      300
gtctggtgcc catcgaagcg gggtaagttt cgagctcgcg cctaaaaact ttgccctctc      360
agaatcgctt ctaagcgccg ttcatggctg tgtccttaca agcgcacatt cagaaaattg      420
aggcccttaa aacgccatac agcacctctc tcgaaatgcg caaccacggc aaaacaagca      480
atcgacaata aaaagtaaa acttatttag aatcccacta aaattcccaa aaccccgcaa      540
caaccagcaa atttacataa accgcatgac tgattaaata ggtgttaaat attaaaaact      600
agcgagccct gaattaatct gttaaggtcc tacatggact tcagttagtt gaggctgaag      660
```

```
ttttttgacat gtatgtctcg tccgagttcg ctgccatcca ggcggtgcac cgaggtggat    720
tcatggtgaa tccttaatcg agtgaggccc cagaccaggg aagcctgccg cattaagtga    780
gttcctgatg gcttcgggtg gaggatgtag aacttttttgt acatggtctg tggcacgcat    840
tgtttcgttt gccctgccat gttggtgttt taagtgaagg ccgccttttg cggaatgggt    900
ataggaggca ttc                                                       913

<210> SEQ ID NO 7
<211> LENGTH: 158
<212> TYPE: DNA
<213> ORGANISM: Corynebacterium glutamiucm R

<400> SEQUENCE: 7
aacagttcat ttttctaaag gcagtgactc cgatgtgggt cgctgccttt agtcatttta     60
agtcactcag cccaggcaat cctatctttg aaaagactta ccgacataga ctgacctgca    120
aagttgttct agaatagcca tatcgttgac atagagat                            158

<210> SEQ ID NO 8
<211> LENGTH: 91
<212> TYPE: DNA
<213> ORGANISM: Corynebacterium glutamiucm R

<400> SEQUENCE: 8
gtccgcttca gttgtggtgg ctccgaatct gatgaacaat gatcattcct agttcattta     60
catctttatc aaagagagcc accacctact a                                    91

<210> SEQ ID NO 9
<211> LENGTH: 678
<212> TYPE: DNA
<213> ORGANISM: Corynebacterium glutamiucm R

<400> SEQUENCE: 9 tgattttttgg aaaaagtatc gcattagcga tgtctaaatc ttgactgaaa ccatcatatt     60
cgctgtggat aagctgtgta atcagctgat attgcgctgt gttcctgtga attagctgat    120
ttagtacttt tcgggggtgc tcattcttac caaagtgtca agttgtgggt agggtcactt    180
gaataataat tgcaccgcac aggtgataca tgcttacctc ctcaagtagc ccgaggttaa    240
gtctatttta ggtgaacaaa tttcagtttc aggtagaaaa ctttcgacct gcttcagagt    300
ttctattagg aaatctgaca ccacttgatt aaataaccta ccccgaatt gggggagggg    360 ttattttttt ctgtgaacgt agtttttggtg catatgacct cgttataa agaaatgtaa    420 acgtgatcag atcgatataa aagaaacagt ttgtactcag gtttgaagca ttttctccga    480
ttcgcctggc aagaatctca attgtcgctt acagtttttc tcaacgacag gctgctaagc    540
tgctagttcg gtggcctagt gagtggcgtt tacttgaatg aaaagtaatc ccatgtcgtg    600
atcagccaat ttgggttgtt tccatagcaa tccaaaggtt tcgtctttcg atacctattc    660
aaggagaccc tcgcctct                                                  678

<210> SEQ ID NO 10
<211> LENGTH: 75
<212> TYPE: DNA
<213> ORGANISM: Corynebacterium glutamiucm R

<400> SEQUENCE: 10
atccgacacg gccctttttt agacaacaca acaaagggc caccgggaaa ctttttagaa     60
aggtgtgttt caccc                                                      75
```

<210> SEQ ID NO 11
<211> LENGTH: 295
<212> TYPE: DNA
<213> ORGANISM: Corynebacterium glutamiucm R

<400> SEQUENCE: 11
gagcacgcca cacaaaagat cccggcatct gaattgacgt cagataccgg gattttt cat      60 gcctgctaca tgcccactac aaagcccag aaagcccag aaagccccca ccccacatac       120
ccccactctc aagtagacgt cgagatttt catttcaccg caaacatagt tctagatcag       180
accatttaaa aaatcacacc ctcacctgga attttgcaga aataggacaa gaatcaaaat      240
agtgggagat ccccatgttt cgcgaagtcc cattgttggg gttaggctta taccc          295

<210> SEQ ID NO 12
<211> LENGTH: 242
<212> TYPE: DNA
<213> ORGANISM: Corynebacterium glutamiucm R

<400> SEQUENCE: 12
ggttacgcgg aaaggctttc cgtcaagccc gccctatggc tgtgataagt actaagataa      60
cagctctgac ctgcgcccgc atgttttca acggggtttt ccgtatttaa ttaggcaaca      120
tatttgtgtc gtaattcact ttatgcaggt aaacgaattt gtgcttatat caacattcgt      180
aattcggcaa aattaattaa actgaaaaag gggattaatt gcccccactt gaggagaaat      240
tg                                                                     242

<210> SEQ ID NO 13
<211> LENGTH: 278
<212> TYPE: DNA
<213> ORGANISM: Corynebacterium glutamiucm R

<400> SEQUENCE: 13
gatctacagt gtacgtaagc gtgtattttt gcactttgga ggaaataatg aaccccatt       60 gatgcaggtc aatgggggtt aattgtgccc tggagaggaa tcgaacctcc gacacccgct      120
ttaggagagc ggtgctctat ccactgagct accaaggcgt accgaactag attacaacac      180
gcggggctgg aagaaaaag aggggttgt ttttgcttcg ataagctgtt tccacaggta       240
aggtgggagt taatacttcc cgaccttaag gagtggaa                              278

<210> SEQ ID NO 14
<211> LENGTH: 899
<212> TYPE: DNA
<213> ORGANISM: Corynebacterium glutamiucm R

<400> SEQUENCE: 14
cagcgccgta gtacgtgata attctgacgc gtcagacggt gaaacaatgg aagaagaact      60
tggggcgcct cgccgagaa aaacgcgagc tgaaatgagc aaacgggatt ctcaagactg       120
cttcggcttt tttcgcagcg gaactcattc gcgcccgaga tccgtggacg tcggtcggag      180
aagtcgaact ggccaccttg cggtgggtgc attggtggaa caccaagcgg cttcatgaag      240
cattggacta cgccatccta caagtggtag aaaccaagtg ctatctcacc cagcccatca      300 acacagggc gtaaaagaag cggaactaaa cccaggacac ttcaggttca ggccgctgac      360
ttggtagctt atggtgcgta gcaatggcat ttgcaggcgt atcctgagaa atggtcacaa      420
agaaattcgc cagtaaagga tgcgattcgc gcatccttag gactaaaacc acatggatac      480
ctgagtccga caatggcgtt atttgggtgg attaacgcaa aagcccctga ccattggcca      540

```
ggggcttgtg agatgcgaga ccccgtggac gactaagaaa ccgtataggg cctcgcagta    600
cttacggtaa caataaaggg tgttgttgca aagttggggc agtaggaaga gcgacgtgaa    660
ataatcacag ccaggggtat cttctccggt cgtcattttc cccatgacat cattctgtgg    720
gcagtgcggt ggtactgccc caactttgca acagcacccc cggtttcaac ctcgaagaag    780
tccgagttga tgcagcatct gtgctcgatg atggggagag ctgtgggaa aaatatcaac    840 gcacacctaa ttcagcgacg tttgtatctt ttagtggcga gccgcaaggt caccttcat    899

<210> SEQ ID NO 15
<211> LENGTH: 253
<212> TYPE: DNA
<213> ORGANISM: Corynebacterium glutamiucm R

<400> SEQUENCE: 15
gtgcgaagaa ctcctttgtt gaataaattc ttgagatagt ttgtccccac aggctagtcg     60
tcgcttcttg tgattgcgag gagtctggcg atttcgttag ggtttcgtct tgtgtgctgc    120
ctcacacccc caattggggc cgggtattta gcgcgctcgc cgagggtttc ggccttttaa    180
ctagcatggc gtatagatcc atgcggtcga ccttgcgcct gaccgtccac ttttttaggga    240 ctaggagtac agc                                                      253

<210> SEQ ID NO 16
<211> LENGTH: 176
<212> TYPE: DNA
<213> ORGANISM: Corynebacterium glutamiucm R

<400> SEQUENCE: 16
tttgcttgaa tttaggattt cccttgcgaa gttgagttgg taatttcaac ttcgcaaggg     60
aattttgaac ttcaaatgaa atagagcaag tgctgtaatt gttgatatag ttggttggag    120
accagatagt ttcttgagcc atatcaatgt gtctgaacat tctttaagga ggaatc       176

<210> SEQ ID NO 17
<211> LENGTH: 251
<212> TYPE: DNA
<213> ORGANISM: Corynebacterium glutamiucm R

<400> SEQUENCE: 17
cttttcgatt tccaccaaac ccgcacgtag atcgagttcc cgtttcatga aattggtgga     60
cgaaaaccag gtttggagtt tagacttggc gaaattcacg aaaactattt attgccgggc    120
tacctggatg aacatcggtg taattttagg gattattttc gagggtcccc acgttgtact    180
gagcagttgc caatacggtt gccagttcga aatttaaaaa atggtggctt agagctataa    240
aaggaggaaa a                                                        251

<210> SEQ ID NO 18
<211> LENGTH: 100
<212> TYPE: DNA
<213> ORGANISM: Corynebacterium glutamiucm R

<400> SEQUENCE: 18
caagcactgc tgcgggagcc actatcactt tgttaagtgc tgcgatattt tttgccacct     60
tattgacaaa gagtgccatt agtgggttaa acttcaccgc                         100

<210> SEQ ID NO 19
<211> LENGTH: 221
<212> TYPE: DNA
<213> ORGANISM: Corynebacterium glutamiucm R
```

-continued

<400> SEQUENCE: 19

```
ctaaaacgat ttatagcgaa atttaggcga ttttaaacg atacgaaaat cgcctacttt      60
ggcattttat tttcatgaac acgcaggtca agggttagtt gcagaaattt tccgaataac    120
aggctattgt gtctatcagg aatacagtta atacatcttg aaaagcccat gggccatccg    180
aattcccagg atcggcccgc tcactccaag ggggtcaggc a                        221
```

<210> SEQ ID NO 20
<211> LENGTH: 312
<212> TYPE: DNA
<213> ORGANISM: Corynebacterium glutamiucm R

<400> SEQUENCE: 20

```
aatcgatcaa ttcctttcgg gtaacgagaa aacgtgaact agaaacggag tcaaagtaaa     60
tatcaaaggt aacaccatcg gtaaatccaa actgacaact ataaatggtg cccgatatca    120
ggaaaaattg cttgcacacc gcgccgattc cccatgatgc cctaacatct tgcaggtaag    180
gggtacatat tggggcaatt cggggtgat tttgcagtat cgtcaagatc acccaaaact    240
ggtggctgtt ctcttttaag cgggatagca tgggttctta gggaccccc tacaaggatt    300 gaggattgtt ta                                                        312
```

<210> SEQ ID NO 21
<211> LENGTH: 417
<212> TYPE: DNA
<213> ORGANISM: Corynebacterium glutamiucm R

<400> SEQUENCE: 21

```
ctaacaggcc acagatctta gctttgacca gctgatttgt ggctaatcgc ccggtctgtg     60
tagagtattc atctgtgcgc aggacagtgt gacaaacact gaatagtgca tggctttaag    120
gccctgtggc gcagttggtt agcgcgccgc cctgtcacgg cggaggtcgc gggttcaagt    180
cccgtcaggg tcgctggagt tggtctatac tgtagagcag cccctggcca gatagctcag    240
tcggtagagc gttcgcctga aaagtgaaag gtcgccggtt cgatcccggc tctggccacc    300
atctacaccc tgttttattt cctaggaaat aaaacagggt gtctttgtgt ttaaaaggta    360
taaaggaaga gtagttccgg ttaattccac cggggtgaga taccgaggag aacgcac       417
```

<210> SEQ ID NO 22
<211> LENGTH: 100
<212> TYPE: DNA
<213> ORGANISM: Corynebacterium glutamiucm R

<400> SEQUENCE: 22

```
tgaatctgtg gcggcaccgg cgcgtgttgc cctggagagg atgctgtctg ttgtcccagc     60
ggctcctgtt actcctagct cctcgaagga tgcgtaattt                         100
```

<210> SEQ ID NO 23
<211> LENGTH: 81
<212> TYPE: DNA
<213> ORGANISM: Corynebacterium glutamiucm R

<400> SEQUENCE: 23

```
caggtcaagt gcgtaattga gggctagact ggttagtacc ggatattctt ttttctttag     60
tttgtaggag tggagataac t                                              81
```

<210> SEQ ID NO 24
<211> LENGTH: 276
<212> TYPE: DNA

<213> ORGANISM: Corynebacterium glutamiucm R

<400> SEQUENCE: 24

```
acttttgccg tacttacggt gcttaattat agctagtgtt acagatgtta cttttgtgac        60
gtgggaaaat gtccgaaatg ttatgaagtt taaaccttaa ctttagcttt agtaaatggg       120
ggataaagct taagttgagg gttgccgggg tccacttact caaccacaat cgcctgtgta       180
gtcattcaag gaattttgaa gcgagctcga ggccgttggg gaagacgaac ctcgtcttac       240
ttcctttagt aactgcacat atctacttgt atatgt                                 276
```

<210> SEQ ID NO 25
<211> LENGTH: 138
<212> TYPE: DNA
<213> ORGANISM: Corynebacterium glutamiucm R

<400> SEQUENCE: 25

```
caccgcgaat tatagactga actggtactt gggaagcttt ttatagtcat atgcgttgag        60
atacgtggac gacaaagcac cagttggttg ccttcccagt ccagcccaca tccgatttct       120
aaattaggag catatctt                                                     138
```

<210> SEQ ID NO 26
<211> LENGTH: 215
<212> TYPE: DNA
<213> ORGANISM: Corynebacterium glutamiucm R

<400> SEQUENCE: 26

```
accagcactc attggagaaa taagaacgcc ggaaatgagc actgccaggg ctttagttaa        60
ggagcttcgc attgttagag catacctacc accatgttgg aggcgctagg caacaagaga       120
gttttatgct tatcgacgcc accctccacc caccttctg cccacgcagg tgctaccgtg       180
aggctgaagt ggaaaatcta ctaggagggt attgc                                  215
```

<210> SEQ ID NO 27
<211> LENGTH: 84
<212> TYPE: DNA
<213> ORGANISM: Corynebacterium glutamiucm R

<400> SEQUENCE: 27

```
aaccgccaaa cttttgatag cgtagcaatg gcccttcgg tggatggggc catgtttgca        60
caatgcttga agaagggtag ggca                                              84
```

<210> SEQ ID NO 28
<211> LENGTH: 76
<212> TYPE: DNA
<213> ORGANISM: Corynebacterium glutamiucm R

<400> SEQUENCE: 28

```
aaatgctctg ctgctggctt tagctgcggg gctgttggga attctccaaa accttctaaa        60
ccgttcaggt aggaaa                                                        76
```

<210> SEQ ID NO 29
<211> LENGTH: 216
<212> TYPE: DNA
<213> ORGANISM: Corynebacterium glutamiucm R

<400> SEQUENCE: 29

```
ttagttcaca tcgctaacgt gggcgatcga tgctcacggt gatgtgtcat cccaatagcc        60
cggggtgtgc ctcggcgcac cccgggctat tttgtgtctt taatcaatac aattgaatac       120
```

```
cggtgccagc gccacacaat gtgtggcaat ctgggacagt gcatcacatt gcaccagaag    180
aattttttaa acaatcaaat ctccaaggag tacggc                              216

<210> SEQ ID NO 30
<211> LENGTH: 382
<212> TYPE: DNA
<213> ORGANISM: Corynebacterium glutamiucm R

<400> SEQUENCE: 30
gtgtttgaag ttgcctttcg tgagcccttt tatggaaaca agggtgtgaa atcaagtag     60 ttaaaggtgt ttcaagtcca ggttgtttaa ctctcctaga ccgcttggtc tgtaaacgta    120
gcagcgaaat gcgacaatgc gaagactttt gcttaattaa attcaaactc catcaaaaaa    180
ctagacagat cagtctatta tattcacggt gaacctaacc taatatcccc aggttaattc    240
atttaaacgg gcgtaaggtg actccattgc tttcagtctc atgaatgtaa tggttggtct    300
agacagagcg gtacgtctaa gtttgcggat agatcaaacc gagtgacatg tacttcacta    360
gctctttaag gattaactcc cc                                             382

<210> SEQ ID NO 31
<211> LENGTH: 156
<212> TYPE: DNA
<213> ORGANISM: Corynebacterium glutamiucm R

<400> SEQUENCE: 31
agcacagcct taaagcacaa gcactgtaaa agtgcggttt tgatgcgccc tgcaggccat    60
cgaaattaat cgcccagcca aacacaggtt ttgttgggcg tttttttatc tcatgcacgc    120
caacaccctc aatgtgaaag agtgtttaaa gtagtt                              156

<210> SEQ ID NO 32
<211> LENGTH: 488
<212> TYPE: DNA
<213> ORGANISM: Corynebacterium glutamiucm R

<400> SEQUENCE: 32
tcgctcgtct cataaaaacg accgagccta ttgggattac cattgaagcc agtgtgagtt    60
gcatcacact ggcttcaaat ctgagacttt actttgtgga ttcacggggg tgtagtgcaa    120
ttcataatta gccccattcg ggggagcaga tcgcggcgcg aacgatttca ggttcgttcc    180
ctgcaaaaac tatttagcgc aagtgttgga aatgcccccg tctggggtca atgtctattt    240
ttgaatgtgt ttgtatgatt ttgaatccgc tgcaaaatct ttgtttcccc gctaaagttg    300
gggacaggtt gacacggagt tgactcgacg aattatccaa tgtgagtagg tttggtgcgt    360
gagttggaaa atttcgccat actcgccctt gggttctgtc agctcaagaa ttcttgagtg    420
accgatgctc tgattgacct aactgcttga cacattgcat ttcctacaat ctttagagga    480
gacacaac                                                             488

<210> SEQ ID NO 33
<211> LENGTH: 197
<212> TYPE: DNA
<213> ORGANISM: Corynebacterium glutamiucm R

<400> SEQUENCE: 33
aagtcgcttg aaccggcatg aaaatctcgt gctggttttg ggctcacaag gccatatagg    60
aactttgtaa ttagttgcag gttccaattt tgggtcaatg tagcgtaata ttgttcaagg    120
cccatgtgcg ggctgtggag gacgtgcatt cacgttctgg tcaaatgaaa aacggtgaaa    180
```

```
gggattgaac gcagcag                                                    197

<210> SEQ ID NO 34
<211> LENGTH: 100
<212> TYPE: DNA
<213> ORGANISM: Corynebacterium glutamiucm R

<400> SEQUENCE: 34
gcttgcggga acaccgcacc gcccacccaa actgttcaga ttccaaagat aaattctgac     60
gctcattcca gcccaccgtt tagaagaaaa gaccccaatc                          100

<210> SEQ ID NO 35
<211> LENGTH: 138
<212> TYPE: DNA
<213> ORGANISM: Corynebacterium glutamiucm R

<400> SEQUENCE: 35
tcgaagttcg gtggtttgtg ggggcgtttc tgcatttaaa ggtgatagat ttgggcaaaa     60
atggacagct tggtctatca ttgcggaaaa gacctgttta caggtgtc ggaaatgagt     120 atcaggagct gatctacc                                                  138

<210> SEQ ID NO 36
<211> LENGTH: 82
<212> TYPE: DNA
<213> ORGANISM: Corynebacterium glutamiucm R

<400> SEQUENCE: 36
gcccgcgtac cggctacccc gaggcacgta atgagtaggg cagttctagc cataatcagc     60
agaaaaggtg gagtgattcg cc                                              82

<210> SEQ ID NO 37
<211> LENGTH: 65
<212> TYPE: DNA
<213> ORGANISM: Corynebacterium glutamiucm R

<400> SEQUENCE: 37
aatatgacct tgctggttg gctacttttg ggtcaaagtt ttgtgaaacg aagtaagctt      60
aagtt                                                                 65

<210> SEQ ID NO 38
<211> LENGTH: 76
<212> TYPE: DNA
<213> ORGANISM: Corynebacterium glutamiucm R

<400> SEQUENCE: 38
tacataccga tacccaagaa tgcctcaaag ttccgtattg tgggaggttg aagcagatat     60
ttaaggagag gttcaa                                                     76

<210> SEQ ID NO 39
<211> LENGTH: 100
<212> TYPE: DNA
<213> ORGANISM: Corynebacterium glutamiucm R

<400> SEQUENCE: 39
tccagcaatt gcaggatgaa gcccgccgag gcaccacagt actagcggtt tcgcatgatc     60
cgttgctgcg tgcggctgcc gatgaagtgg tggaggtcaa                          100

<210> SEQ ID NO 40
<211> LENGTH: 100
<212> TYPE: DNA
```

<210> SEQ ID NO 40
<211> LENGTH: 100
<212> TYPE: DNA
<213> ORGANISM: Corynebacterium glutamiucm R

<400> SEQUENCE: 40

```
tcataacgcc catcataact acatcgagcg aaatgccaac cacatgtccc atgctttttac    60
taatgtgggg tcttagaaga aagcgaccaa ttaaggagag                          100
```

<210> SEQ ID NO 41
<211> LENGTH: 100
<212> TYPE: DNA
<213> ORGANISM: Corynebacterium glutamiucm R

<400> SEQUENCE: 41

```
tgctggccta ttgtggcgac tgagggcctt tgaaggttcg acaaactgta taaggcctta    60
aatcttgaga atctattttg aggaagcaag aggaagtgtc                          100
```

<210> SEQ ID NO 42
<211> LENGTH: 100
<212> TYPE: DNA
<213> ORGANISM: Corynebacterium glutamiucm R

<400> SEQUENCE: 42

```
agatcgccac ctccacccct accgaacgtg gcgcaacccg cgccgatgac cgcctcagcg    60
aatccgcaat ggaagaccgc aagaaggaag gctacttctg                          100
```

<210> SEQ ID NO 43
<211> LENGTH: 328
<212> TYPE: DNA
<213> ORGANISM: Corynebacterium glutamiucm R

<400> SEQUENCE: 43

```
ctcacggtcg cagtcgtagc cggagcttat agaatctcgg ttcggatgct gaatagatcg    60
tttgaaggtg aagaatacgg agtgggggga attaatccgc cacctccgat tggaagcagt   120
gcacgaagac ctccgggatc ctcgcctcca gaacctgacc attttggcta ctggcatgca   180
ccacggcatg gcttccgggc tttgtcatag ggtccaaact agtgctaatg taataggtag   240
cactctagat ggcgcacagt gactcaattc actgtttctc acactacgga tcgttcggca   300
cgtacctgcc gatggaggag attctgca                                      328
```

<210> SEQ ID NO 44
<211> LENGTH: 242
<212> TYPE: DNA
<213> ORGANISM: Corynebacterium glutamiucm R

<400> SEQUENCE: 44

```
gtcggatgct ctcctccacg tcgaatgaaa aaataaccgt ccctttagg acatacccaa     60
ccaatcctag cccaactaac gatgttgctt ccgctgaccc cgtcattttg cggtcttcgc   120
gatgtaaact agttctaata actatttttt catttccctc ataaaaggtt tatatagaag   180
gtaaaatagc aagcgtgcta gatccattcc agacctagcc taaggacgga aggacttccc   240
cc                                                                  242
```

<210> SEQ ID NO 45
<211> LENGTH: 292
<212> TYPE: DNA
<213> ORGANISM: Corynebacterium glutamiucm R

<400> SEQUENCE: 45

```
tgacaccccca ccggatgtgg ctgcaaatga ccggttgccg ggcacttgcg taaagaggtg    60
```

-continued

| | |
|---|---|
| ggaacactac cctcacggcg aagaaaccc acgaagtcca cataaccagg cactgcgaca | 120 |
| gtggtgaacc tcggcatctg tgccaacggc ttctgacatg tgtgtcaacg cctcctgaca | 180 |
| ctgacagaga cacttctgat cccactattt ctactgtctc actaagtcct aatctactt | 240 |
| ttgatacact tgtctcaaga agttattaat cctattgaga cagcgggacg ac | 292 |

<210> SEQ ID NO 46
<211> LENGTH: 100
<212> TYPE: DNA
<213> ORGANISM: Corynebacterium glutamiucm R

<400> SEQUENCE: 46

| | |
|---|---|
| caattggatg cgaaacctgc acccttcccg ttgctgaagg acaagaccct agggccggcc | 60 |
| gttgggctgg aaacgccaag acagaatgcg gacttcactc | 100 |

<210> SEQ ID NO 47
<211> LENGTH: 125
<212> TYPE: DNA
<213> ORGANISM: Corynebacterium glutamiucm R

<400> SEQUENCE: 47

| | |
|---|---|
| tcacttcctg ttgtggctgc ctgttgcagc caaatacggc caacggctcc ttggaaattt | 60 |
| aaggggtcgt tggccttatt attttaggga agcccatcc ttgccttgcc aagggaagcc | 120 |
| tgtac | 125 |

<210> SEQ ID NO 48
<211> LENGTH: 59
<212> TYPE: DNA
<213> ORGANISM: Corynebacterium glutamiucm R

<400> SEQUENCE: 48

| | |
|---|---|
| gatacaacgt tcccggcgcg cacaactttg tcgcgccggg ctttggagag gagtttgtg | 59 |

<210> SEQ ID NO 49
<211> LENGTH: 126
<212> TYPE: DNA
<213> ORGANISM: Corynebacterium glutamiucm R

<400> SEQUENCE: 49

| | |
|---|---|
| ccagtcaagc ctaagagctt gaaacgcccc aatgtggggg tgttaagaac tccacaaaag | 60 |
| cgcttgggaa ctttttgtgg aagcagtccg ttgaacctct tgaaccgcga atttaggagg | 120 |
| ccagtt | 126 |

<210> SEQ ID NO 50
<211> LENGTH: 100
<212> TYPE: DNA
<213> ORGANISM: Corynebacterium glutamiucm R

<400> SEQUENCE: 50

| | |
|---|---|
| gtcggttcgg aaacaatgga aattatccga aactctcctg taccgaccat catttatccc | 60 |
| ggtctttagg ctctccaaca gcagaggact agactgaagt | 100 |

<210> SEQ ID NO 51
<211> LENGTH: 339
<212> TYPE: DNA
<213> ORGANISM: Corynebacterium glutamiucm R

<400> SEQUENCE: 51

| | |
|---|---|
| ttcaaaactc ccgcctcaat tgtttgccca catcttaact tttagccacg acacgttcga | 60 |

```
acaccaatac cgttcacatg ttcgactaag tttctatgtt cgatttatag cacccccgttc    120 gaacgttgtc tagagaagat ttagaaatct cgaacactcg taccatttcc gcaggaaaac    180
ctgtatggtt ggaaaataga aatactgaca gaggttcgaa tagctcagca ttcagcttca    240
gaagttcaca ctggatgaac cctcatcaag agtgaacatg gaagcgaaca gagtttttag    300
tgctttaacg ggcacacaat gagaggaagg gaacggaag                           339
```

<210> SEQ ID NO 52
<211> LENGTH: 131
<212> TYPE: DNA
<213> ORGANISM: Corynebacterium glutamiucm R

<400> SEQUENCE: 52

```
gatcaacctt tcgtatgaat tttctgtata aacccatgt tagatgtttt attcagggat     60
tttagttgat atgtccagta tctcgctgaa aacgctggtt gtcttgtaga aaaggcgta   120 acgtcatata c                                                        131
```

<210> SEQ ID NO 53
<211> LENGTH: 956
<212> TYPE: DNA
<213> ORGANISM: Corynebacterium glutamiucm R

<400> SEQUENCE: 53

```
gagctttcat ctctcgtgat gtgatgggca actaatctcc gggctaacgg tgttggctaa    60
ttttggctag agggtatttc ctgcaatttt ctaacccggc aacctgcaga tttggccgta   120
ttgcatggtt gtggttatag tattcctcgt tgaacagcgc gccatgcgag ttgcttggag   180
cgtaagtttt aaacattggc ctatggtgta attggcaaca caacggtttc tggtaccgtc   240
attctaggtt cgagtcctgg taggccagct gcgatcagct ggataaacaa ttgatcgtgt   300
cctaatgccc cgttcgtcta gcggcctagg acgccggcct ctcacgccgg taacacgggt   360
tcaaatcccg tacggggtac tccgcatcat gtatttgcgg taagttttta aatgttttac   420
aaggtttaca atcttgaaaa acgattggcc tatggtgtaa ttggcaacac aacggtttct   480
ggtaccgtca ttctaggttc gagtcctggt aggccagctg cgatcagctg gataaacaat   540
tgatcgtgtc ctaatgcccc gttcgtctag cggcctagga cgccggcctc tcacgccggt   600
aacacgggtt caaatcccgt acggggtact cttaaaagca tccaccttc atcaattgag    660 ggttggatgc ttttgtgttt gctaacacat ctgacatcac ccctcccag acaaatgta     720 cgggctcatg tagcagggga ttttaaagac gcggggtga aagatctcca gcggttgcgg   780
agttaaatcg caaaagcctt taccgagatt cggtctcggg ttaaagtcag gttcatacag   840
agaagttcat agccgatcac caacaagttg ttgctctaac cagcacaaat gcaactttgg   900
aggcttcgga aagggcgctc tggagtcaat ggaaccgacc agtaaaagga gagtgt       956
```

<210> SEQ ID NO 54
<211> LENGTH: 275
<212> TYPE: DNA
<213> ORGANISM: Corynebacterium glutamiucm R

<400> SEQUENCE: 54

```
agtgatttct cctcatggat gaaggtggac actcggccgc gaaaataaaa aatgcccgcg    60
accgactcga atgtcttggt cgagtcttcg caggcagcgc acaaaagtgc actttagaag   120
tctagatcgc gtcgataacg gttgagcact aaaagtactt gaccctcgcc gagacctaaa   180
tatgctagca cgatggccaa acctaatcca aaaaccggca gtatactggt tggggtcaca   240
```

```
ttagccaaaa ggcgctttga ggaagtggaa ctccc                              275
```

```
<210> SEQ ID NO 55
<211> LENGTH: 382
<212> TYPE: DNA
<213> ORGANISM: Corynebacterium glutamiucm R

<400> SEQUENCE: 55
ggggagttaa tccttaaaga gctagtgaag tacatgtcac tcggtttgat ctatccgcaa    60
acttagacgt accgctctgt ctagaccaac cattacattc atgagactga aagcaatgga   120
gtcaccttac gcccgtttaa atgaattaac ctggggatat taggttaggt tcaccgtgaa   180
tataatagac tgatctgtct agttttttga tggagtttga atttaattaa gcaaaagtct   240
tcgcattgtc gcatttcgct gctacgttta cagaccaagc ggtctaggag agttaaacaa   300
cctggacttg aaacaccttt aactacttga ttttcacacc cttgtttcca taaaagggct   360
cacgaaaggc aacttcaaac ac                                            382
```

```
<210> SEQ ID NO 56
<211> LENGTH: 297
<212> TYPE: DNA
<213> ORGANISM: Corynebacterium glutamiucm R

<400> SEQUENCE: 56
ctgtgtccat ttcgccgtcc atgccgcctc cactctcatg gtgtgctcgg aagcgggcgt    60
gaggttaacc ctaatagggc ccgcgggtgt tcttgtaaat tgcccaggga ccggtatctt   120
cccccggttc gcccctgca gggagcaccg acctgggaag aacaacaccc ggtgaaggcg   180
ccgtggccgg gaactttcct cccgcctgtt ccgactagtg tcttggcacc tcccgcaggc   240
aggtgtctta gtcgctcaca tccggttgaa gaaccggccc agtccaggag gactttc      297
```

```
<210> SEQ ID NO 57
<211> LENGTH: 1000
<212> TYPE: DNA
<213> ORGANISM: Corynebacterium glutamiucm R

<400> SEQUENCE: 57
accacgtttc tgaatctgga gcgatgagca ttggtcaaat attcgaggtt ttctttgctg    60
tcctgcgaaa taacatccgt gtgatttgga aagtgggttt tcactagggg ttttacctgt   120
gcttttgtgg cattgacttg gggatttgtg ttcgagggag cgttcggtct aaagttattc   180
cagcaccgca cagaacggaa caagcaggaa caagttctaa gtagtgcatg cggatgtagc   240
gcagttggta gcgcatcacc ttgccaaggt gagggtcgcg agttcgagtc tcgtcatccg   300
ctctcatttc accgggccaa tcgatgaaat gtcccgcgcg tttagctcag cgggagagcg   360
cttccctgac acggaagagg tcactggttc aatcccagta tcgcgcacca agaggacgaa   420
caacctcttt aatcaatgtt catgcggatg tagcgcagtt ggtagcgcat caccttgcca   480
aggtgagggt cgcgagttcg agtctcgtca tccgctcaat ttaaaacacc tatgggttaa   540
cgctcatagg tgttttttgcg tgcttcccaa aaagcgtttt aagggtcga agtgctcaag   600
atgggtcgat atatggattg aggtcattca ggcggctgag cgcgatttta ggggccctca   660
cttttgggc cggtggggca gttgtgaatc ctgaaagctt ccagggcaag gatccaccac   720
aaaccaggct ggactctaga aatcggtcct aaagttgcac acgcaggcag ataaagcgga   780
aatatccacc acagccagca ggaaatccgc ttttcgtggt gaatattcgc acattttttc   840
tattcatgta tgggtgcata tggtaatgcc ttcccgcccct tgagttctac cccggaatct   900
```

```
gctcaaggca cccccagaat gggaacgtag tctagatcac acgacttcga aaagtggctc    960
caagctggat agactctatt tacctactgg taacctccgc                         1000

<210> SEQ ID NO 58
<211> LENGTH: 100
<212> TYPE: DNA
<213> ORGANISM: Corynebacterium glutamiucm R

<400> SEQUENCE: 58
atcgattgtg ttgccgtaac ctggggctac ggcagcaaaa ctgaatggga cgctgcccgc     60
tacaccgtga gcaccgcaga agaattagaa aggatcatcc                          100

<210> SEQ ID NO 59
<211> LENGTH: 100
<212> TYPE: DNA
<213> ORGANISM: Corynebacterium glutamiucm R

<400> SEQUENCE: 59
gcatatgctg aagcagaaac taattcaggt tttgatcccc gcgctaactg ggcgggccag     60
aaccgctaga cgttctcttt gagaaggag gtgacgaaac                           100

<210> SEQ ID NO 60
<211> LENGTH: 246
<212> TYPE: DNA
<213> ORGANISM: Corynebacterium glutamiucm R

<400> SEQUENCE: 60
aacaggaatg ttcctttcaa aaattgagga agccttatga cctacaaccc tactcagctg     60
ccgattattc cgggtttgtg accagctacc cgataaatag gtcggctgaa aaatttcgtt    120
gcaatatcaa caaaaaggcc tatcattggg aagtgtcgca ccaagtactt ttgcgaagcg    180
ccatctgacg gattttcaaa agatgtatat gctcggtgcg gaaacctacg aaaggatttt    240
ttaccc                                                              246

<210> SEQ ID NO 61
<211> LENGTH: 145
<212> TYPE: DNA
<213> ORGANISM: Corynebacterium glutamiucm R

<400> SEQUENCE: 61
actaccccct tttgatgtaa cacataactc aatcttgcga tattagataa tgagtcagaa     60
aatgaaggta gcactacttg ctggattaat tttcaaggct ttctttcaga aattaatcca    120
tagccgatat ttaaggtgag aacac                                          145

<210> SEQ ID NO 62
<211> LENGTH: 167
<212> TYPE: DNA
<213> ORGANISM: Corynebacterium glutamiucm R

<400> SEQUENCE: 62
aactctcagt tagaccatta caagccaccg gagccacaag ttggaccggt ggctttgtcg     60
tctattcggg gagtggctgt ttatggagct ctttgacgca ggtcaaggaa gttcagtgag    120
cgcaaccata acgttaaaag taaggaaaag agagaaagga agaaatc                  167

<210> SEQ ID NO 63
<211> LENGTH: 87
<212> TYPE: DNA
<213> ORGANISM: Corynebacterium glutamiucm R
```

```
<400> SEQUENCE: 63
actgcgtgag gttgtggcct gtcacacata atcagcctag ggtgggactt taaggaaaca    60
gtgcacaaat aaatctcaag gagcccc                                        87

<210> SEQ ID NO 64
<211> LENGTH: 100
<212> TYPE: DNA
<213> ORGANISM: Corynebacterium glutamiucm R

<400> SEQUENCE: 64
gctactgccc tcaccattcc acgggcattc cgtgcggggt agaagcttaa aagattttg     60 cttttcgacg cctccctcca cctcggatta cgcttggggc                          100

<210> SEQ ID NO 65
<211> LENGTH: 100
<212> TYPE: DNA
<213> ORGANISM: Corynebacterium glutamiucm R

<400> SEQUENCE: 65
acaccgtggg aaagattgca tcaaccggtg tcgatgtcat ttccgttgga gcgcttaccc    60
attctgtgca tgcacttgac ctaggactcg atattttcta                          100

<210> SEQ ID NO 66
<211> LENGTH: 119
<212> TYPE: DNA
<213> ORGANISM: Corynebacterium glutamiucm R

<400> SEQUENCE: 66
ggggtgctcc taaaaagcga aggtcaaaaa aacttgacct tattgataac gatttctatt    60
aagaagtgta cacttgcgtt gactctattg aaaatgattc caagaggag ggctttccc      119

<210> SEQ ID NO 67
<211> LENGTH: 1000
<212> TYPE: DNA
<213> ORGANISM: Corynebacterium glutamiucm R

<400> SEQUENCE: 67
cgctggttcg gctgcgccaa ccaaaccaac tatttgaaag gagtcaatta tgtctaagcc    60
aaatgaattt gttccaccgg acgcttcatt aatggagctc acggtagtca actggacgtt    120
gagcaaaatg aaagaaaaaa tcctgactgg agttccgtca ggtcaggtta ttgaccaagc    180
actcaaagag gtattggata gttcattaag gaagtagctc aaatagatgt tgtccaagtt    240
ctccaagttg tgaggctgcc cagttcgctg gtgcagtagt cattgtgctt gtcgtgaatg    300
gccatacaaa cttgtctttt ataaaggtag cccaacgatt ttttctgtg gcatttgggg     360 cagacgaagc catgaaaagt actgtcattc tgaattgcat cgcagcttca tgaagttcaa    420
attcacctaa cttgtcaaag ttttcaatgc accactcgag atgattacgg actcgagcta    480
aataagcttt aagttcaaag gggtagtctt gagcaggctt atttaagata tctgagtcaa    540
gcatgtctct gagggaatct aggccaccct cgttaagttt gggacgtac aagtctaaga    600 aagcggacag cgaaagcaga ctattgagtg cgtgttcgtc gacaccccca ttagctcccg    660
agcttcctga ccaaggcaca tctaagccaa ataccgctct gttccaactt tctatgtacg    720
aagtccaagc agttatctgt tgtccgttgg cctccatttt gttgagaaga tcaatgcagt    780
tctgcaaatt cgttacagca aaacgcatat ccgaccatcc cacctcgcta gggaggttac    840
gtgtggtttt aagcgaaccg gtcttccgcc attcgctgag ctgagtatgg agtaattctg    900
```

```
ctgggtttgc catagttctt atcaaaccac atacatgtaa gttgcccgcc acctggatca    960
gaggtggcgg gcttttctga tttcaagaaa ggaaatcatt                         1000
```

<210> SEQ ID NO 68
<211> LENGTH: 241
<212> TYPE: DNA
<213> ORGANISM: Corynebacterium glutamiucm R

<400> SEQUENCE: 68

```
gtcttcggag gaaacccaat cccaaccgca accaccctct gtactgccca tactgcgcgg    60
gagaagttct tttccccgat gagcaaacag aattcgcgtg gttgtgtgcg gattgcacca   120 gagttttga agtgaaatat cacggccagg acgatccagt gcacaggcca gcaccagcaa    180
agtccacatc gcaagcatta aagaatctc tcgaaagaca caaaagaggt gagtcgcaac    240
a                                                                   241
```

<210> SEQ ID NO 69
<211> LENGTH: 89
<212> TYPE: DNA
<213> ORGANISM: Corynebacterium glutamiucm R

<400> SEQUENCE: 69

```
tctgggaaga aaccgctaat ctgggaagaa accgctaatc gacgctgcag gtggcggtca    60
gatccacggg agaaggagag gacacgcgg                                      89
```

<210> SEQ ID NO 70
<211> LENGTH: 100
<212> TYPE: DNA
<213> ORGANISM: Corynebacterium glutamiucm R

<400> SEQUENCE: 70

```
attgattggg taatcaaaga cgcaggcatt gaggatctgg caaccggtga gatcaccgtg    60
ttgatcaacc ccttcaggtt ccttcattct gggtggcccc                         100
```

<210> SEQ ID NO 71
<211> LENGTH: 232
<212> TYPE: DNA
<213> ORGANISM: Corynebacterium glutamiucm R

<400> SEQUENCE: 71

```
gaaagttttc cacactaaaa tagtgtgatt ctgtccgaat ctgttgtttt agttttgaaa    60
ctgcgggatc atggaaagta gtgaaaagtg aattttagtt ctgtgctttc tctgcccttt   120
aagtgaacct tttgttggat cttgcattaa aaaaatgaaa acctcgtcgg gaatgcaact   180
tgggatcacg tctcgggcaa gaaacgtcct taaaaaaggg gagtgattgt ga           232
```

<210> SEQ ID NO 72
<211> LENGTH: 75
<212> TYPE: DNA
<213> ORGANISM: Corynebacterium glutamiucm R

<400> SEQUENCE: 72

```
gcatggagaa tttacttgca ggcgcgttat attgcaagtg gtgttattat gaaagtgagt    60
tttaggaggt caacc                                                    75
```

<210> SEQ ID NO 73
<211> LENGTH: 67
<212> TYPE: DNA
<213> ORGANISM: Corynebacterium glutamiucm R -continued

<400> SEQUENCE: 73

| cataataagc ctaaagcttt cccatattta ttagcctctt agagttctca ggagaaaacg | 60 |
| aaatccc | 67 |

<210> SEQ ID NO 74
<211> LENGTH: 110
<212> TYPE: DNA
<213> ORGANISM: Corynebacterium glutamiucm R

<400> SEQUENCE: 74

| tgttaactct tccttttttc ctatgcatta ttttgggcat gcacttgtca tatcttcaca | 60 |
| gacgtatggt tttgtaacaa cctcccccaa aatccctaaa gtttccccccg | 110 |

<210> SEQ ID NO 75
<211> LENGTH: 376
<212> TYPE: DNA
<213> ORGANISM: Corynebacterium glutamiucm R

<400> SEQUENCE: 75

| aatcactgct tctgcgggaa tacttgtgcc agagacattg ttgcgttgtt cgtaggctcg | 60 |
| ttgcctacaa gcttggctgc agtatttcct tggacgtccc ctgcctgttg aggcgacgtc | 120 |
| tttaccgcac caggagcact ttgtagtctg ctggtttggt cttaatttct gcaccttttaa | 180 |
| caccttagtc gattgcctcc catacaacga ttcggggggtt ttggctatac ttataggtct | 240 |
| gatcacattt caagggcagc tgttgtgact ggcagcgtgt cgtttttattt gcacactagc | 300 |
| aggtaaactg tgtgagacga attcttttgc ggcaacttgg aggccgcatt ctagtgggca | 360 |
| aaggactgat acctag | 376 |

<210> SEQ ID NO 76
<211> LENGTH: 92
<212> TYPE: DNA
<213> ORGANISM: Corynebacterium glutamiucm R

<400> SEQUENCE: 76

| cacaattgca cattcgtctc atcgattccg atgagattgc cacccccaaa atggggcgcc | 60 |
| tattttttg acggccaccc gcggtagcgc tt | 92 |

<210> SEQ ID NO 77
<211> LENGTH: 103
<212> TYPE: DNA
<213> ORGANISM: Corynebacterium glutamiucm R

<400> SEQUENCE: 77

| ttgtttggat tcctttccga ttatgtcttg atcgcccatt ctgtcacatc cggttgtct | 60 |
| aaacacccgc gaagatttcc tgtgatgtgc cacactggtt ctc | 103 |

<210> SEQ ID NO 78
<211> LENGTH: 146
<212> TYPE: DNA
<213> ORGANISM: Corynebacterium glutamiucm R

<400> SEQUENCE: 78

| tcacatcaca ctgggattac cccgtgtagg ggtgaaaacc cgaatgatga ataaaattcc | 60 |
| gggtgcagtg accgtaggtg aggtaaacgc ggttagagtc gaatgagagt ttgatacttt | 120 |
| ctttcgactt ttagattgga ttttca | 146 |

<210> SEQ ID NO 79

```
<211> LENGTH: 143
<212> TYPE: DNA
<213> ORGANISM: Corynebacterium glutamiucm R

<400> SEQUENCE: 79
tcttggatat aaaaggggcc cctattggca atgtggttat gaccagaagt agtataagaa        60
gtgaagttga tcgcgtcatc gtagtacgag taattccact cacacatcaa tgcggtgacc       120
acaattggga ggagaagtag cac                                                143

<210> SEQ ID NO 80
<211> LENGTH: 82
<212> TYPE: DNA
<213> ORGANISM: Corynebacterium glutamiucm R

<400> SEQUENCE: 80
accagttgct gtgaaggcaa ggtgtcggct tagatgccgg cgcctagcct acatccagct        60
aagaccccct ttaggacacc tc                                                  82

<210> SEQ ID NO 81
<211> LENGTH: 212
<212> TYPE: DNA
<213> ORGANISM: Corynebacterium glutamiucm R

<400> SEQUENCE: 81
accagaagtg gtgacgtgag ttgggtgttc cgcagaaatc tatgcaggaa tcggccgaac        60
tgaagtagtt tacaccccaa aatcgattat tcaaatatgt gttcgaataa tggattttga       120
tgtccacccc tgtccatata gtgagggcta acaaaagaaa cgaaggtttc taagtcttca       180
aagctagagc ggattgaaag gagaggaaga ca                                     212

<210> SEQ ID NO 82
<211> LENGTH: 169
<212> TYPE: DNA
<213> ORGANISM: Corynebacterium glutamiucm R

<400> SEQUENCE: 82
attttgatcc ctatcatcga tatttcacaa aatgagcaag atagcgatat ttttatggcc        60
tttatttatc taggtactct cctagttctc attgggtgca tggctttgtg cgaccaccgt       120
tggaagctag cgttcttccg ccgtcccttc cgagcaattg tttcggtag                   169

<210> SEQ ID NO 83
<211> LENGTH: 84
<212> TYPE: DNA
<213> ORGANISM: Corynebacterium glutamiucm R

<400> SEQUENCE: 83
gtaggctggc gggcaggtgc ttgaaatact ctgattagtt ccaagcaaat tagcacaact        60
tcacacttta tttaggagca tgtt                                                84

<210> SEQ ID NO 84
<211> LENGTH: 341
<212> TYPE: DNA
<213> ORGANISM: Corynebacterium glutamiucm R

<400> SEQUENCE: 84
ggaggaccag accaaaccag cgtgcccacg gttggccatt tcaggatccg tgggcacgct        60
ggtttggttt atcaacctcg aaaccggcca cagctgccca cgaaactcga tttcgcgatc       120
cgtgggcact ctcgtttggt ttcctcggaa agctaccctc ggacggtcag aaaatgccct      180
```

```
ctcagaatcg cgtttaagag cctctcaccc aataatccgc acaaataccc gttccgcgat    240
cccaaccgct taaacgggcg tatattgact tccctgcaat acagcccaaa tcgaccaaac    300
tagttgaccg aaaactagcc agccgaaaga ttctcggcca c                        341
```

<210> SEQ ID NO 85
<211> LENGTH: 844
<212> TYPE: DNA
<213> ORGANISM: Corynebacterium glutamiucm R

<400> SEQUENCE: 85

```
ctccgtgcgg gtgccatgga cagatttcgc tctagggcgt ccgcagtgcg ctcatgatta     60
ggtaccctcg tggaactctg ctcaacatgt ggcggactga tcgcaagagg atgccatgag    120
cggataccaa gacggagtct cggggagtat accgcccgat gccgtgaact ttctggagtt    180
cgttgctttt ccggaggaac gtcggattcc caaggaatgg ttggaagaac aagaagagct    240
gctggcaaca gatccatcat caatcacgca acgcgcgttg actgtcatgc ccaggtgaga    300
tgctcatatt caacttggtg gagagcaaag aagactaccc gctagggttt gcgagatggg    360
gttccctgag gatgccttcg acgtcgggct gataatcgcg gaataccttg agctggcaaa    420
agagcttgcg ccgctggaag cccagatttt aagggctatc cattcgattc gatcgtcatg    480
gcggtcgagc gaacttggct gaagcaaagc aggacggcac ggcctcatct aggggctgta    540
aaacgtgatg ctgtgggaga atgagtcatg gactcgtaga acatccacga gcacccagga    600
cttgagctag ccgaaccggt agatggtgta gcgctggccg tcgccgatgc tttacgctcc    660
accccgctag caccggcgct cgtggagttt ttgaaactca gtgatggtgc acgcttaggt    720
gaggttgagg tcttttcctc agagcacatc gtggaggaaa ctaatttggc taagcactct    780
tggcagctgc ctgtctcatt ggttattggc agctccggac cggagcgagc gcttgtcatg    840
ctgg                                                                844
```

<210> SEQ ID NO 86
<211> LENGTH: 69
<212> TYPE: DNA
<213> ORGANISM: Corynebacterium glutamiucm R

<400> SEQUENCE: 86

```
ccagcagtgg ggagcgcaca ccaacaatca cgctcaccgc acaccaccac tcaagaaaga     60
agatcaaaa                                                            69
```

<210> SEQ ID NO 87
<211> LENGTH: 100
<212> TYPE: DNA
<213> ORGANISM: Corynebacterium glutamiucm R

<400> SEQUENCE: 87

```
cgacagcgcg tgatgatgcc accacagcgc tcaatacgat gctgggaatc ggagtggatc     60
atacccgcgc accagagcac cgcgtagagg agtagctgtc                          100
```

<210> SEQ ID NO 88
<211> LENGTH: 59
<212> TYPE: DNA
<213> ORGANISM: Corynebacterium glutamiucm R

<400> SEQUENCE: 88

```
atctttttag attaaaatca tgcgccccgc cagaacttgg cggggcgtaa atctattttt     59
```

<210> SEQ ID NO 89

<211> LENGTH: 176
<212> TYPE: DNA
<213> ORGANISM: Corynebacterium glutamiucm R

<400> SEQUENCE: 89

| ggagcagaag actcccgcta catcctgagc gccggtgtgc catgccgcgg gtcaatctcc | 60 |
| ctccaggctg acgcggtttc aggaccccac ctcccacctg acgttcgtcg acatccagg | 120 |
| ggcgaccacc ctagggacaa ttgcagacta atcagtcccc actgtatagt cagtgc | 176 |

<210> SEQ ID NO 90
<211> LENGTH: 246
<212> TYPE: DNA
<213> ORGANISM: Corynebacterium glutamiucm R

<400> SEQUENCE: 90

| gggtaaaaaa tcctttcgta ggtttccgca ccgagcatat acatcttttg aaaatccgtc | 60 |
| agatggcgct tcgcaaaagt acttggtgcg acacttccca atgataggcc ttttttgttga | 120 |
| tattgcaacg aaatttttca gccgacctat ttatcgggta gctggtcaca aacccggaat | 180 |
| aatcggcagc tgagtagggt tgtaggtcat aaggcttcct caattttga aaggaacatt | 240 |
| cctgtt | 246 |

<210> SEQ ID NO 91
<211> LENGTH: 100
<212> TYPE: DNA
<213> ORGANISM: Corynebacterium glutamiucm R

<400> SEQUENCE: 91

| atggaacatt cgacgcggaa ggttatgagt tccgcgatgt ccccgccact gccccagcaa | 60 |
| cccttttaagg ctttaccccct aatacttaag gagatagaac | 100 |

<210> SEQ ID NO 92
<211> LENGTH: 116
<212> TYPE: DNA
<213> ORGANISM: Corynebacterium glutamiucm R

<400> SEQUENCE: 92

| gatcgcgact gattcaaagt ggccggtgaa ctactcgcgg tagagcaacg tgagacgatt | 60 |
| tccggctaga gcgtgtttga taattgaggg tagcgcggca tgggatcaga gatccc | 116 |

<210> SEQ ID NO 93
<211> LENGTH: 100
<212> TYPE: DNA
<213> ORGANISM: Corynebacterium glutamiucm R

<400> SEQUENCE: 93

| accatcgtgg tttctccaga cggcaatgta gtggacacct tcccgcagcc tttcgaaacc | 60 |
| atcgatgacc tcgaaaccgc tgtggcaggg gcgctgcaga | 100 |

<210> SEQ ID NO 94
<211> LENGTH: 131
<212> TYPE: DNA
<213> ORGANISM: Corynebacterium glutamiucm R

<400> SEQUENCE: 94

| gtatatgacg ttacgccttt ttctacaaga caaccagcgt tttcagcgag atactggaca | 60 |
| tatcaactaa atccctgaa taaaacatct aacatgggtt ttatacagaa aattcatacg | 120 |
| aaaggttgat c | 131 |

<210> SEQ ID NO 95
<211> LENGTH: 100
<212> TYPE: DNA
<213> ORGANISM: Corynebacterium glutamiucm R

<400> SEQUENCE: 95
aacccctaac tactgacctc gcaccacttg ttgcagcccg ttaccacgct gcattgagcg     60
cactgctggc acaaatttaa aaccgctaag gaattcagct                          100

<210> SEQ ID NO 96
<211> LENGTH: 412
<212> TYPE: DNA
<213> ORGANISM: Corynebacterium glutamiucm R

<400> SEQUENCE: 96
agctgattat attaacaagg aaagtgactc tgatcaggga atactgaaac tgttgagcct     60 ataccctgg atgctctcac aggttcgaat cccgttagct ccgcatcgtt tgtggaattt    120
cactaccctg gtgaacgcac acatttatt ggttgcagga tgcttccgga tttccggggt    180
gtttccgatt gaactgatgt ggaccgcatt gtggcacagc ccgacgggct aattgggttc    240
gagtcccata ctcctttctg acatagagtc gccgtctact ggattcttct ggtagaagcc    300
tgcggttcgg cccaatcctg ttctgcttac aagttcaggg gacgcaccga aaccccgctg    360
ctgctagacc cagtggcggc gactcgctag agacgttttc gtaggtgatt gc             412

<210> SEQ ID NO 97
<211> LENGTH: 690
<212> TYPE: DNA
<213> ORGANISM: Corynebacterium glutamiucm R

<400> SEQUENCE: 97
ggctctgctg ggcttagttg ggcgctcaac ttagttaaaa ccagacacac gtgcccgcgg     60
ttcgggtttt ccgagttggt gggcactctg gtttggttta tcgctttcga aaccggtccc    120
agttgcccaa gtgtttcgat ttgaggattc gtgggcacgc ctgtctggtt ggccagaaaa    180
actggcctta gacccaaaaa accagactcg ctgtatggct gttagacgca cttccgtgac    240
ccactttagg ggaacgttcc ttcgaaaaac tcgacccttt aaacaggctt ctagagtgtt    300
gatgctttaa ggggccgtaa atgtaggggtt ctttggatag gagctaaggc cagggctcac    360
ttttgctttg atcgggaggc tccaagccag caaaccagac acacgtgccc gcggttcggg    420
ttttctgagt tggtgggcac tctggtttgg tttatcgctt tcgaaaccgg tcccagttgc    480
ccaagtgttt cgatttgagg attcgtgggc acgcctgtct ggttggccag aaaaactggc    540
cttagaccca aaaaccaga ctcgctgtat ggctgttaga cgcgctcccg tgacccactt    600
taggagaacg ttccttcgaa aaactcgacc ctttaaacgg gcttctagag ccttggaacc    660
atttggactt cttcggagtc taaccagagt                                    690

<210> SEQ ID NO 98
<211> LENGTH: 100
<212> TYPE: DNA
<213> ORGANISM: Corynebacterium glutamiucm R

<400> SEQUENCE: 98
ccgtgatgat cgtcgtgacg atcgccgcga tgaccgcgga gacgacctgg atgtacccag     60
cttcctccag taattaagaa ggagaataga cttatccact                         100

<210> SEQ ID NO 99

-continued

```
<211> LENGTH: 62
<212> TYPE: DNA
<213> ORGANISM: Corynebacterium glutamiucm R

<400> SEQUENCE: 99
tccctaggta aacgcactgg gtagtatttg tttaaccatc cacctcaagg agtaaaacgc      60
ac                                                                    62

<210> SEQ ID NO 100
<211> LENGTH: 179
<212> TYPE: DNA
<213> ORGANISM: Corynebacterium glutamiucm R

<400> SEQUENCE: 100
ctggtagggg ggggatatcg gccgcaccac tctttgcatc tagcgtgatt gtttctgaa       60 gtcctgcgcc caaggcgccc gtttgcgatg cgtgacgttc ggagctgatg cacatatttc    120
ctggcccatc ctccgggggc gggcaaggat tgttcagtgt ctgctgtata gttaagtgc     179

<210> SEQ ID NO 101
<211> LENGTH: 82
<212> TYPE: DNA
<213> ORGANISM: Corynebacterium glutamiucm R

<400> SEQUENCE: 101
ttcacaccca aggctagccc tgcgccccctt ctatatctag ctgaccagta ttaataccaa     60
taatagaaca tattatcgaa ca                                              82

<210> SEQ ID NO 102
<211> LENGTH: 87
<212> TYPE: DNA
<213> ORGANISM: Corynebacterium glutamiucm R

<400> SEQUENCE: 102
aaacttctcg ctaaaggctt ctcctagaag cttctccatg ggttaacaca acccatatcc     60
ctcccactac atatataagg actgaaa                                         87

<210> SEQ ID NO 103
<211> LENGTH: 1000
<212> TYPE: DNA
<213> ORGANISM: Corynebacterium glutamiucm R

<400> SEQUENCE: 103
gcgcctgacc agtgattttg agtttcttca agttcacgct aatctactta agacttcaac     60
ggagcacagc ctggctgttt ttgaagaagt agatgccccc ttagctcagt cggtagagcg    120
tttccatggt aaggaaaagg tcaacagttc gattctgtta gggggctctt tttgcatttc    180
tggaccattt tggaatcatt tctggatctc ttcaggccac aaatgcacac ctggcagacg    240
cactcaaggc gtgagttttt agtttcaggc cacatgcatc gcagtggggg tgcaatttaa    300
tccaagaaaa cctttagctt cctgcagatt tgtgttgcgg tagcggttcg ggttaaagtt    360
cttaaggctt caacggagcg cagcggtagt tatacggact gcatttcaaa gagcttgacg    420
cccccttagc tcagtcggta gagcgtttcc atggtaagga aaaggtcaac agttcgattc    480
tgttaggggg ctctgttgct tttattctcg taagagatgt tgagcaatgt ggcggtgtag    540
ctcagtggta gagcaagcga ctcataatcg ctgtgtcgcg agttcaattc tcgccatcgc    600
taccgcggat gaaaccgctt ctaactgcaa attttttgag gttagaagcg gtgttttcgc    660
aaattgacag gctgatggta acattgcctg tgctccatag gggcgtagct caattggcag    720
```

```
agcaacggtc tccaaaaccg taggttgcag gttcgattcc tgtcgcccct gcaagatgaa        780 caccettgat ctggttaaac aataaaacca gatcaagggt gttttttgtt tcatcaaggg        840
atctttcacc tgtagcaggt atgtcctaat aaatattgcg agggttcgcg ggattaatgt        900
actctcgaag gttaacaca gggctgcgat tgtgctggat caaatgtctg cacgaaaaat         960
tgttatcgcc cctggatgag tagtgattta gaggagtgct                              1000

<210> SEQ ID NO 104
<211> LENGTH: 100
<212> TYPE: DNA
<213> ORGANISM: Corynebacterium glutamiucm R

<400> SEQUENCE: 104
acctcgccag aaaaccactg tgcaggcgct ggattaccta acggaaattc aatactcatc         60
gtgcattcct tttctcatat cccatgcggg gcttataacc                              100

<210> SEQ ID NO 105
<211> LENGTH: 107
<212> TYPE: DNA
<213> ORGANISM: Corynebacterium glutamiucm R

<400> SEQUENCE: 105
gcgaccgaga ctagtggcgc tttgcctgtg ttgcttaggc ggcgttgaaa atgaattgcg         60
aatgaaaagt tcgggaattg tctaatccgt actaagctgt ctacaca                     107

<210> SEQ ID NO 106
<211> LENGTH: 112
<212> TYPE: DNA
<213> ORGANISM: Corynebacterium glutamiucm R

<400> SEQUENCE: 106
gactaggggc taattctact tgtctttgcc gaaagtccaa gtgaaagcag cccacgcggt         60
gccaggtagt ctggaggtga actaatcact atagggaggg cgacgaaaaa ca               112

<210> SEQ ID NO 107
<211> LENGTH: 478
<212> TYPE: DNA
<213> ORGANISM: Corynebacterium glutamiucm R

<400> SEQUENCE: 107
gtctcacgag cttagtgttt tctggttttg gggttgggtt ctagttgggt tctagtgctg         60
gataggctcc tctggcaggc ttgctgccat agaggactaa taggggaaag gatgtccgaa        120
aatccaccac aaattcctgg cgagttacag tttgtggtgg atccttgcgt cccagggtcg        180
gtttaatgca aaaatcagtt cgattaactg gttggacctc acggatgtgg tgagaatttg        240
atcagcaacc tttcaggttt cactcctgcc ccactagtcg caaaatggac accctccaga        300
tttgccccta agcactcaaa tcaacccgc ccacacttga aacattccg gaaatctaac         360 ccttttaaatc gcctcccacc ctcccgaaat tagaaatccc cttttaatgt gatatcactt       420
tctgttaaac tgatatcaca ttctttttca gcaccccaga cttaaaagga gcaccacc         478

<210> SEQ ID NO 108
<211> LENGTH: 374
<212> TYPE: DNA
<213> ORGANISM: Corynebacterium glutamiucm R

<400> SEQUENCE: 108
acaccaagaa ttgggcagaa ggtcattaac tttctgccca gttttttgct tttcgacgcc         60
```
tacctccagc gcaccttgca ggttgctgcg gatcgctgaa cggctgcccg cgaagcgacg    120
ggcaatctca atactgttta agaatcgaga atcggttga gaagagtgct acgtttcgaa     180
atgaactggg gtttgtttct gtggatcttt ttcattcagc ttgttgtgat gggattattc    240
tcggtcagaa aacgcactaa gaataagaga ttgcgcggat agggcggttg cggtgaggtg    300
ataaacgagg gcaggcacga gacctggtac atacggattc gaccaagaaa acgtaaaata    360
tctcaggagc actc                                                      374

<210> SEQ ID NO 109
<211> LENGTH: 100
<212> TYPE: DNA
<213> ORGANISM: Corynebacterium glutamiucm R

<400> SEQUENCE: 109
agaacaaagt actgcccata ctcatgaact ttgccgaacc cccaaccccg ctggccgtcg    60
atggcctaga aaaatcatc gactttgtgg aaacccaccc                           100

<210> SEQ ID NO 110
<211> LENGTH: 100
<212> TYPE: DNA
<213> ORGANISM: Corynebacterium glutamiucm R

<400> SEQUENCE: 110
tggatgagcc tgagtacctg aaaaagatcc atgccaagaa tgcgacagcg gaaaagcctg    60
cacctggcac cgatacgaac caagaggagg agaagtagcc                          100

<210> SEQ ID NO 111
<211> LENGTH: 341
<212> TYPE: DNA
<213> ORGANISM: Corynebacterium glutamiucm R

<400> SEQUENCE: 111
gtgttctcca gttcccccttt gcgcgttgtg gattactctg gagccacacc aaacaacaac    60
gccaacgtgc gtgccacccc cagttagcaa cacacatcga ttttttagta attaagaaac    120
caagtctgtc aactgagaaa cacttttaaa gctcagtcgg cgtcgcacag ggcgcgacca    180
atacaggggc agtctacctg tgtcttgact gagatcccaa cggaaatccg aattgcactg    240
tatatattgg gggctattgc gcacgcttgc caagtgttgc tgcagctcaa caggttgtag    300
caggtaggtg aaagatttat ggaaaatagt aaattccccg g                         341

<210> SEQ ID NO 112
<211> LENGTH: 200
<212> TYPE: DNA
<213> ORGANISM: Corynebacterium glutamiucm R

<400> SEQUENCE: 112
tcttgccatt ctatttgctc tagctgcgca acggcgtac tgtttattag gcgtgtcgtt       60
gcgtcatgta tcggtgtgtt catgtaggaa agcacattga gcctgaacgt gagatcaaaa    120
ccccgtctat acagggcatt tgaaagatac tgcatcctgt ccattatcta atttcctatc    180
catttcggag caatttacat                                                 200

<210> SEQ ID NO 113
<211> LENGTH: 100
<212> TYPE: DNA
<213> ORGANISM: Corynebacterium glutamiucm R

<400> SEQUENCE: 113

-continued

```
ctaatcagcg tttccgcatg gtcatcgctg atgcggtggc acagttgaag catccgcaag    60
gttataagcc ccgcatggga tatgagaaaa ggaatgcacg                         100

<210> SEQ ID NO 114
<211> LENGTH: 414
<212> TYPE: DNA
<213> ORGANISM: Corynebacterium glutamiucm R

<400> SEQUENCE: 114
tcgctagatg ggcgtgaaaa acttcccagt acctttcagt agaaggtgct ggggagtttt    60
ttatttaagt aagcccaatc ggttgtgatc tagttcggtg ttctatgctg ctgcgatctc   120
ctggcagatc tgaggatcgc gataaaactc atattttttc atcatggcaa aggcgcatta   180
atccgacgac gagccaatgc gttgttttgc ggcacctgat ctaagtccaa ttcttttca    240 ctttgggtta gttgccgctt cacggccgtt gccggttcag gtggaagtca ttgaatcagg   300
cttctccaaa tgggcagtag acaactactt ggcgggtctt aaatcagctg tgaaggattc   360
tgcataagct gggaaccaca cgagaatcag aacgcgaaac gaaggtaaaa gccc          414

<210> SEQ ID NO 115
<211> LENGTH: 100
<212> TYPE: DNA
<213> ORGANISM: Corynebacterium glutamiucm R

<400> SEQUENCE: 115
cactcgttgg tctcctccgg atctgagtcg ttcaaataag atgccacgcc atcgcggatc    60
atcgcgaagt tagagtcatc cgagggcttg ccaccaagtt                         100

<210> SEQ ID NO 116
<211> LENGTH: 100
<212> TYPE: DNA
<213> ORGANISM: Corynebacterium glutamiucm R

<400> SEQUENCE: 116
tagatatgaa ataagcccc caccaccata aggttgtgg ggaaattaat tttgtgccag      60
gacgaatatt aaagtaccag aactgacata aggtagcgtc                         100

<210> SEQ ID NO 117
<211> LENGTH: 100
<212> TYPE: DNA
<213> ORGANISM: Corynebacterium glutamiucm R

<400> SEQUENCE: 117
cactgatgac ctggatcagg ccgtcaaatt catcgtcgat gcacacgctg gattggacgt    60
agcgcgtcgc acaattaag cagtggctac attaggtgtt                         100

<210> SEQ ID NO 118
<211> LENGTH: 464
<212> TYPE: DNA
<213> ORGANISM: Corynebacterium glutamiucm R

<400> SEQUENCE: 118
cgagtacaaa caccgccagt atctgaacct caacagggaa cccggccata cctttaaggt    60
gcggccgtgt tccttgtttc tgtggcgggt aggaaacggg gcaccttaaa ccgaacgggc   120
atgtggtcgt ggagacaact tctgacggtg caaaagcggt gcggaaacgg caatgatgac   180
gagcggactg tgcaggcatt acaggagtac gtcggtccga aaaagagacg cgaccagagc   240
agccggaaaa atgcttcttt agggtatacc catgtgaaac gctcgatcgg ggcttatttt   300
```

```
cctgttcca catggtcaat ctgggttttt tggactacct gttgctcagg gtctaagaat      360
gccaagacag gtttagcagt gcttcgttag aatacatac gtcctgctca cccctcattg       420
tgcagttatg ggcggagaaa acagcaaacg tgcagaatgg gcat                      464
```

<210> SEQ ID NO 119
<211> LENGTH: 1000
<212> TYPE: DNA
<213> ORGANISM: Corynebacterium glutamiucm R

<400> SEQUENCE: 119

```
gagatctcgg tgcggtcgta caaggaaaga cagtcacaac tgaatatgga tactttgctc      60
ctggatcaag cacaaaccca ttcagtgtgg aacatactcc tggaggctcc tccagcggtt     120
ccgcagcggc ggttggggcc ggcacgattc aatgtgcgct aggtactcaa actgcgggtt     180
cactcactcg accagcatcg ttttctggag ccgcaggctt ggtcatgaca caaggtagta     240
cttctctgaa gggagtacac ggtatgagtg gctccttaga ttccttggga atcatgactc     300
gaaacgttga agatctagat tatgtgtacc gacacttctc tggaagagct ggagaacaat     360
cagttgatcc tgaaaatcta agtatcttta tttgggatgg ttccggggttg ctcaaccttg     420 atccagcaat gtcagatctc cttcgagccg tgaaaaaaat atttactgac agagaaatcc     480
gaacacatcg attcatctgg gacgatcata ttgcgtcttt agtagatgac cacaagacca     540
tcatgagcta cgaagctgct cgttcacttg gcgcgatgtt aaaggacaag agaaaacaac     600
tcagtcctca gttacagcga ctacttactg aaggcgatgc agcaactgat cagatgtact     660
cagaagcagt attccgtaga gacgcttcct accaagtgtt tttgaaaatt atgagtaggg     720
attcagtaat tatcgggcct gccgcacacg ggcaagcact aaggttagaa gagggactg      780 ggtcccccga attaagtcga ccatggcagt tactgggact tccagttgtg actgttccag     840
gagcctcaac ctcaactgga atgccattgg gaatacaact tatcggcaac aaacataatg     900
aattgacctt gttgcgtcta ggaaaagtac tggaaccgct gctgcgcgag ctcccgtcat     960
tttcaaacac ccagacacca tcaacactta aggaaatgaa                          1000
```

<210> SEQ ID NO 120
<211> LENGTH: 343
<212> TYPE: DNA
<213> ORGANISM: Corynebacterium glutamiucm R

<400> SEQUENCE: 120

```
agcgtaccgg aagtctattc tgtagcaggg ttcgtgagac agttcgttgg aatagcttgt      60
ggaacagttt tctcttggga ctatgcattt tcaattggtt tcattaaggg tgtcccactt     120
cctaggaagt gggacacctt gatcggtacg tgggtcgccg ctggcctggg ccggaagctg     180
ccggcgatag ccctcacctt taaatcacgt cgggaacacc gccaactagg cagctgcttc     240
cttcttgcgc agtgaaggcc tcagcctgaa agtgcagacg acctctggca acgacgccac     300
cccatgttga agttagttca gcaacagctg tatagttcag cac                       343
```

<210> SEQ ID NO 121
<211> LENGTH: 322
<212> TYPE: DNA
<213> ORGANISM: Corynebacterium glutamiucm R

<400> SEQUENCE: 121

```
acttagaagc aggcattaac actgccacct ttgcaaaatt aaccacccc tgatggggtg       60 gttttttcat gagttgaaaa aagtgtcttg attcactttg tgatgacggt taccatagcc     120
```

```
atcgtgacta aaaacattga ccttaagcga gtagccaagg ctacgtaccc tactgcggga    180
tagatggact ggctccccgc actagggaag tagtcgttaa tcaacaccaa gaagcttaag    240
agtcggtcct ccacctaaca ggatccttca caccctctt ttcaatatct agaaaagacc    300
gatcctcccc cacatctttt ta                                            322
```

<210> SEQ ID NO 122
<211> LENGTH: 100
<212> TYPE: DNA
<213> ORGANISM: Corynebacterium glutamiucm R

<400> SEQUENCE: 122

```
tgccggatga cctgcgcgcc ctaacccaca gcaatgttga agcagggccg gcggaggaac     60
gcgtcggcaa gctattcgcc ctttaaaaga aagcactgtc                           100
```

<210> SEQ ID NO 123
<211> LENGTH: 218
<212> TYPE: DNA
<213> ORGANISM: Corynebacterium glutamiucm R

<400> SEQUENCE: 123

```
tgaccccgcg agaaatattc attgaataga catcgtttta cctgcagata ctctcggtct     60 ataataatg aacagaactg tctattttta gaattgcttt ttgtgtaaac tcaagtcaca     120
gaggctgctt caagtaaatg tttcgtaatt gtttacagcg tttactcgag cggacaacca    180
acaaaaacag cacttcaacg attggagcac accccaca                            218
```

<210> SEQ ID NO 124
<211> LENGTH: 69
<212> TYPE: DNA
<213> ORGANISM: Corynebacterium glutamiucm R

<400> SEQUENCE: 124

```
attagtcaat tagttaaatg aggcggaagt gtagaacttc cgcctcattc cagacattaa     60
ggagttcaa                                                             69
```

<210> SEQ ID NO 125
<211> LENGTH: 100
<212> TYPE: DNA
<213> ORGANISM: Corynebacterium glutamiucm R

<400> SEQUENCE: 125

```
ttttcctccg cactgcaccc cgccaacgcg gacgcaccag caatcaagcc ggcaccccct     60
aggaaacccc tacgggaaac catgtcgctc cttatatata                           100
```

<210> SEQ ID NO 126
<211> LENGTH: 78
<212> TYPE: DNA
<213> ORGANISM: Corynebacterium glutamiucm R

<400> SEQUENCE: 126

```
tagctggtct ttacatttga cagaaacctc cgacaaaacc ccaatagttg acacggaaac     60
caattcattc tagctttta                                                  78
```

<210> SEQ ID NO 127
<211> LENGTH: 100
<212> TYPE: DNA
<213> ORGANISM: Corynebacterium glutamiucm R

<400> SEQUENCE: 127

```
tcccggcgcg caccattgct gctggtgatg aggattatgg cgattcggga gctgaaggcc      60
acgagggcca ctaaaccggc cactatatat aaggagcgac                           100

<210> SEQ ID NO 128
<211> LENGTH: 57
<212> TYPE: DNA
<213> ORGANISM: Corynebacterium glutamiucm R

<400> SEQUENCE: 128
ggcactataa tagacctagt atctatagat tgatagaaaa taatttagga agtttcc         57

<210> SEQ ID NO 129
<211> LENGTH: 719
<212> TYPE: DNA
<213> ORGANISM: Corynebacterium glutamiucm R

<400> SEQUENCE: 129
gcgaaaaata ctacgcgcgt gttacccgat ttttagtaaa tccctagcca ctgacactgg      60
attgttatag cccggaggtg tagagcaagg cagattagct ccctgggtgg gcggctccgg     120
aggggagtct gccggcttc gcccgctgtg gtgcaaacag gcgggtttc agctcgggat      180 ggtcgcttcg acgcgcgagc ttgccttgtt gtgcgcgcgg cgggtcaatc aaggcaggct     240
tcggcctggg atagccctc ccgtcgagga accgccctg ttttgcccgg gcgggaatcc      300
acgcgcgcga aaccgggcag attagcctcc cgaatggctg cattgccga caagttcgcc     360 ttgttttgca cggagcgggg acagcccctct cgaattcagg cgggttagct tcacagacgg     420
ccggtttcgc cgatgagtcc gccccgttgt gcgcgcggcg ggtcaatcaa ggcaggcttt     480
ggcccgggac agcccctcct gctgaggaac tcgccctgtt ttacacacgc ggcgaacgaa     540
acacggcgaa ctagcccgcc aaatggcacc cccggctggg aaattcgcct tgttttgcac     600
caacagggaa cctggagcgc agtttcgggg tctaagtagg tatgggagaa aaacggcgga     660
tgtggacggc gaaggaactg atcgggatgg ggtattcgcg gcggaggatc aacagtttg      719

<210> SEQ ID NO 130
<211> LENGTH: 100
<212> TYPE: DNA
<213> ORGANISM: Corynebacterium glutamiucm R

<400> SEQUENCE: 130
gatacaactc cttgatggag tgaataaatt cccgcgcctg ctcctgatct tgcacacgcg      60
tgatataggt caaaaatcgc gagcgcttga tctctagttc                           100

<210> SEQ ID NO 131
<211> LENGTH: 492
<212> TYPE: DNA
<213> ORGANISM: Corynebacterium glutamiucm R

<400> SEQUENCE: 131
gcggaaccgg ggatgtttcc cagccaggac tgaatcgttg gatgtttatg cgtgccgtag      60
ttgtcacaga tgcatggac atcgaggtgc tgttgcaaac aggaatttct gcttactcgc      120
tatcggttag cgtgcaccgc aactggtgcc ggatccgggg ttttcgtcaa aaacgcgagt     180
ttgcaacagc accaaagaaa gtattgacgc gccgtcaag gaagctcaac aggaccctgc      240
ggccgcgagg cggctctttc gtttcctgac tcattatcag cgcgacgacg aaaaatatgt     300
gcaagaggtc cgtgataact tcgaggaact tggtatcccc ctagaacact tgtcacataa     360 gttatttca cgccctctgc gatacgtagt taaaataacg tgttaagtga caaactttc      420
```

```
cgagacgacc tcggacatca aatttcaga agcgtgtcac gtaaacgatc gtataagtga      480
tggggaaaca cg                                                         492
```

<210> SEQ ID NO 132
<211> LENGTH: 100
<212> TYPE: DNA
<213> ORGANISM: Corynebacterium glutamiucm R

<400> SEQUENCE: 132

```
gatcagcgcg aatgaacgtc aagaacctat ccgactccgc aaagaaaacg ctgaactcaa      60
actcgataac gagttgcttt aagaaaagca gcagccttgc                           100
```

<210> SEQ ID NO 133
<211> LENGTH: 100
<212> TYPE: DNA
<213> ORGANISM: Corynebacterium glutamiucm R

<400> SEQUENCE: 133

```
tctcggcgct aatctggttt gttggtgata tccgagccaa gggaactccg agctcaccca      60
ttaccactga tccacaacac gaccatcttg agaggacagc                           100
```

<210> SEQ ID NO 134
<211> LENGTH: 187
<212> TYPE: DNA
<213> ORGANISM: Corynebacterium glutamiucm R

<400> SEQUENCE: 134

```
cggttggtga acaggacttc tgacacttgt cgtcttgtgc acgcgggtag tgaccagata      60
gtggtcagaa ggcgcgtgca cagccctgct caccacatcg tgtttgtgca atcgccttct    120
gaccctgaca acgatatttt ttcgatgcgt gtcacgtaaa tgatcgtata agtgatggga    180
gaacact                                                              187
```

<210> SEQ ID NO 135
<211> LENGTH: 81
<212> TYPE: DNA
<213> ORGANISM: Corynebacterium glutamiucm R

<400> SEQUENCE: 135

```
gcaccgcaac gctgcggcac aacaacaccg caacgctgcg gtactaccgc aaaactgccc      60
atttttactc aaaggagaac c                                               81
```

<210> SEQ ID NO 136
<211> LENGTH: 100
<212> TYPE: DNA
<213> ORGANISM: Corynebacterium glutamiucm R

<400> SEQUENCE: 136

```
gaccgcatgc aacaccgcag cagattatat gagctcctgc gatacgaaga ctacaacgtc      60
tttgaccagc acattttcac ctacagaaaa ggagaaaaca                           100
```

<210> SEQ ID NO 137
<211> LENGTH: 100
<212> TYPE: DNA
<213> ORGANISM: Corynebacterium glutamiucm R

<400> SEQUENCE: 137

```
gtttcggtca tgacagatga tccaacgcca caaagtggac tagcggtaga tccactttca      60
gccacttgca ttagaccact tttttgagga cgatgaagcc                           100
```

<210> SEQ ID NO 138
<211> LENGTH: 59
<212> TYPE: DNA
<213> ORGANISM: Corynebacterium glutamiucm R

<400> SEQUENCE: 138 ataggaagt tagccgcgtt gaatcgcgga ttttatcgtt gtgaggagat ggaatcaat                    59

<210> SEQ ID NO 139
<211> LENGTH: 100
<212> TYPE: DNA
<213> ORGANISM: Corynebacterium glutamiucm R

<400> SEQUENCE: 139
ccactcgtcc tcgacatact tctcctggca ctaaacgcag gggttgacac atctgggtag                    60
actatcgaag tacattttgt gtcattgagg aggatcaacg                                         100

<210> SEQ ID NO 140
<211> LENGTH: 100
<212> TYPE: DNA
<213> ORGANISM: Corynebacterium glutamiucm R

<400> SEQUENCE: 140
ggataagttt gtttctgagc gtattggtct tgatgatgtt gaagaggctt tcaacaccat                    60
gaaggctggc gacgtgctgc gttctgtggt ggagatctaa                                         100

<210> SEQ ID NO 141
<211> LENGTH: 278
<212> TYPE: DNA
<213> ORGANISM: Corynebacterium glutamiucm R

<400> SEQUENCE: 141
ttccactcct taaggtcggg aagtattaac tcccaccdtta cctgtggaaa cagcttatcg                    60
aagcaaaaac aaccccctct ttttcttccc agcccgcgt gttgtaatct agttcggtac                    120
gccttggtag ctcagtggat agagcaccgc tctcctaaag cgggtgtcgg aggttcgatt                    180
cctctccagg gcacaattaa cccccattga cctgcatcaa tggggttca ttatttcctc                    240 caaagtgcaa aaatacacgc ttacgtacac tgtagatc                                           278

<210> SEQ ID NO 142
<211> LENGTH: 103
<212> TYPE: DNA
<213> ORGANISM: Corynebacterium glutamiucm R

<400> SEQUENCE: 142 tttttttacag cagtagggga ctatgctggg acgtccaagg aaaccgtccc ttttttgcca                    60
agaagtggct ggttcgatca tcccaaactt tcaaagagga ttt                                      103

<210> SEQ ID NO 143
<211> LENGTH: 75
<212> TYPE: DNA
<213> ORGANISM: Corynebacterium glutamiucm R

<400> SEQUENCE: 143
atgggttact cagcggttgt gtattcgagg cctgggtgta tgaagtgcag ggctacggag                    60
aaggcgttgg tgaag                                                                     75

<210> SEQ ID NO 144
<211> LENGTH: 460
<212> TYPE: DNA

-continued

<213> ORGANISM: Corynebacterium glutamiucm R

<400> SEQUENCE: 144

```
ggatcgtaac tgtaacgaat ggtcggtaca gttacaactc ttttgttggt gttttaggcc      60
acggcgctgt gtggcgattt aaggcgtcgg aaatcgtagg ggactgtcag tgtgggtcgg     120
gtcctttgag gcgcttagag gctattctgt gaggtcactt tttatggggt cggggtctaa     180
atttggccag ttttcgaggc gaccagacag gcgtgcccac gatgtttaaa taggcgttcc     240
gtgggcatct gtgtttggtt tcgacgggct gaaaccaaac cagactgccc agcaacgacg     300
gaaatcccaa aagtgggcat ccctgtttgg taccgagtac ccacccgggc ctgaaactcc     360
ctggcaggcg ggcgaagcgt ggcaacaact cgaattgaag agcacaattg aagtcgcacc     420
aagttaggca acacaatagc cataacgttg aggagttcag                           460
```

<210> SEQ ID NO 145
<211> LENGTH: 57
<212> TYPE: DNA
<213> ORGANISM: Corynebacterium glutamiucm R

<400> SEQUENCE: 145

```
ctcaagtttc caggtaaaact gggaacaaat tttagggaaa gggagttgaa cctaacg        57
```

<210> SEQ ID NO 146
<211> LENGTH: 100
<212> TYPE: DNA
<213> ORGANISM: Corynebacterium glutamiucm R

<400> SEQUENCE: 146

```
cttggattcc aaccctgaag tacaactatg tccgtattgt tccgaatgaa atcactggcc      60
gtgagttcac cctcggcgag gagcctgagc gctactagct                           100
```

<210> SEQ ID NO 147
<211> LENGTH: 100
<212> TYPE: DNA
<213> ORGANISM: Corynebacterium glutamiucm R

<400> SEQUENCE: 147

```
ggaactgctg gcaggcaacg tccgcgatgg cgatgctgtg cttgtcgacg tcgccgacgg      60
cggtcagaag ctcgacgttt ccaaggcggt ctaacggctt                           100
```

<210> SEQ ID NO 148
<211> LENGTH: 100
<212> TYPE: DNA
<213> ORGANISM: Corynebacterium glutamiucm R

<400> SEQUENCE: 148

```
ttggcgacct attcacgaaa gccaagacat gatagcgttt gttattgact tgttattttc      60
cagttttcag acaactactg cacttcggag gtgaaccacg                           100
```

<210> SEQ ID NO 149
<211> LENGTH: 100
<212> TYPE: DNA
<213> ORGANISM: Corynebacterium glutamiucm R

<400> SEQUENCE: 149

```
tgaaggcggc actatcaaag ccgtgctccg agttgataaa accaaccagt aacccacaac      60
cactgaaccg actacgcatc aacgaaagca gctaagaaca                           100
```

<210> SEQ ID NO 150

<211> LENGTH: 61
<212> TYPE: DNA
<213> ORGANISM: Corynebacterium glutamiucm R

<400> SEQUENCE: 150
gtggcgcact cctatcacgt tccggtatca gtcttgcatc atttgtgtcg tttaaaagta    60
t    61

<210> SEQ ID NO 151
<211> LENGTH: 171
<212> TYPE: DNA
<213> ORGANISM: Corynebacterium glutamiucm R

<400> SEQUENCE: 151
gtctacatat cctagtcaat gatgcttcaa cgttctgcaa tgagatgaat gctcacttga    60
tttctaggga agtacatata gaatcgttaa cgcccaagca acgaaaaact tggcgcaacc   120
acttccattt cgaaggggag tagttccaca caaaggcgat ctgactcgtt t   171

<210> SEQ ID NO 152
<211> LENGTH: 82
<212> TYPE: DNA
<213> ORGANISM: Corynebacterium glutamiucm R

<400> SEQUENCE: 152
aaaacgccag ggaattttcc gcgcccgctt ccttgtttga ataaacgagg atgcgggctt    60
atttacaatt gcagttttac aa    82

<210> SEQ ID NO 153
<211> LENGTH: 67
<212> TYPE: DNA
<213> ORGANISM: Corynebacterium glutamiucm R

<400> SEQUENCE: 153
tagaaaactc caagaaagtt aaaactgaaa tggtcgtgct agtggtgggc acagaattaa    60
atcgctg    67

<210> SEQ ID NO 154
<211> LENGTH: 73
<212> TYPE: DNA
<213> ORGANISM: Corynebacterium glutamiucm R

<400> SEQUENCE: 154
aagcgcacag gttttttgcat ggctagactt tgaatgagta agcacgaaca catttcaaag    60
gaagggtttc acc    73

<210> SEQ ID NO 155
<211> LENGTH: 472
<212> TYPE: DNA
<213> ORGANISM: Corynebacterium glutamiucm R

<400> SEQUENCE: 155
attcccccta atcatttaca acacttatgg gctatgggtg gaagtggcat tatgcaactc    60
tcttttggcc cagaagcttc taaacgagtg tttgataacc aatcagctac gtcacggttg   120
ctggggtctg acactatccc cgccaggtat aaacactccg attcaacttc atccaaagat   180
tttcaaatta attccatctt gcatagataa tgaacagtcg gtggcattgt gtgtaaagag   240
ttttcatcca acccaaccta atttcggttc cgcgcgaggt aaatgtaatg cgggtggtat   300
ctaaataaag ttgcattggg gctgggtgga ttgtggttga gggggcgtcg ataagcaaaa   360

```
aagcttgcac cgggcatgta gcttgacggg gcgcctgcgc gctagatgcc tggaaaatag    420
catctcttat acacctgaaa gagggcagcg ctaacaggaa atagtaataa tt            472
```

<210> SEQ ID NO 156
<211> LENGTH: 100
<212> TYPE: DNA
<213> ORGANISM: Corynebacterium glutamiucm R

<400> SEQUENCE: 156

```
tttggtttgg aggggccgtc agatccattt gaggcgcaaa aactcattaa aagtgatgat    60
agggagcacc tgctgaaaat ggcaggaatg taaaaaacaa                          100
```

<210> SEQ ID NO 157
<211> LENGTH: 100
<212> TYPE: DNA
<213> ORGANISM: Corynebacterium glutamiucm R

<400> SEQUENCE: 157

```
aatcggattc atgctgtgtg gtgtgatcag tttgctggct gcggtcgcat ggatcttcgg    60
ccgggagacg ctgccaacgg cgaaagtcga gcaggtataa                          100
```

<210> SEQ ID NO 158
<211> LENGTH: 100
<212> TYPE: DNA
<213> ORGANISM: Corynebacterium glutamiucm R

<400> SEQUENCE: 158

```
ctgccacagc caactgtctg atcaggatcc cggcgcggac tacggtggag gaaaacgaca    60
tcgttaagat ctacccattc aactaacagg agttaattta                          100
```

<210> SEQ ID NO 159
<211> LENGTH: 216
<212> TYPE: DNA
<213> ORGANISM: Corynebacterium glutamiucm R

<400> SEQUENCE: 159

```
aaagaaagtg tgttaaggtt ccaaactatg ttcgcagcac gatttttattt tatgtccggc    60 tccggggcct ccccgcgtca gctggccatt ttttgtgcca cctaaaacgc gaacagaacc   120
ggagtcgagc agcacctccc cgcaagggta gaggggctgc ttttttgttt cctaaattca   180
ccccacccca tgcacagccc tgaaaggcaa gaaaaa                              216
```

<210> SEQ ID NO 160
<211> LENGTH: 100
<212> TYPE: DNA
<213> ORGANISM: Corynebacterium glutamiucm R

<400> SEQUENCE: 160

```
gccgaccacc agggtctggt ggactggtcg gtcagcatcg actcgacgat cagccgcgcc    60
catcagcacg ctacgaatat cacccgccac acaggggggct                         100
```

<210> SEQ ID NO 161
<211> LENGTH: 100
<212> TYPE: DNA
<213> ORGANISM: Corynebacterium glutamiucm R

<400> SEQUENCE: 161

```
gactgcgtcc cagaggatct ctgagccgcg gcgagcaaga gtgtgctcct cgatgacgga    60
accctgcaga tcagctacct ggtctgcggt gtagtcgcgg                          100
```

<210> SEQ ID NO 162
<211> LENGTH: 272
<212> TYPE: DNA
<213> ORGANISM: Corynebacterium glutamiucm R

<400> SEQUENCE: 162

```
tttactaatt attggggtaa ctctgggag gcgcgccgtt tattttatgt tgtcctttg      60
atgcaacttc actcctgcta attatccaat tcaggggac ttaacgaggg gtgtttaccc    120
aaaactttgc aatcaaactt atgatggata actgggtgcg cgttttgttg aacatgttg    180
ttggaacatg ccggcagagc cgacactacg attcattcgc taaagggtct ggccactgac   240
actggcaaag atccacgaaa ggaagttacc ct                                 272
```

<210> SEQ ID NO 163
<211> LENGTH: 382
<212> TYPE: DNA
<213> ORGANISM: Corynebacterium glutamiucm R

<400> SEQUENCE: 163

```
aaccctagtt ttaaagcagc agtcgaggca cccctcgac tgctttcgca tgcccaattc     60
tagccttaaa aaccatcaac taccagcata aatactaaaa attggccacg ttttttaccta 120
agggaattcc ctatatagca ccaccccaca gatgcataac atgacatatc acacacccta   180
ataaattta aggtgccgat caaggagag tgccatgcta agaagccct tgatgggtct      240
ccctgcttta ctcacttttt cattgttatt aactgggtgc gctgcatcca caaacgacaa   300
cactgacagc gctgaaagca acgtgacaat tcggtcgct agtggattcg ctcggaacca    360
ttcaaataat gatggattct gg                                            382
```

<210> SEQ ID NO 164
<211> LENGTH: 100
<212> TYPE: DNA
<213> ORGANISM: Corynebacterium glutamiucm R

<400> SEQUENCE: 164

```
cgaaactcga aacacccaac ggctgctcgt cgaaaagcga atcttcgagc tagaagcaca    60
agcacgttgg ctcgaccgaa ttgaagcatt ggacaaataa                         100
```

<210> SEQ ID NO 165
<211> LENGTH: 100
<212> TYPE: DNA
<213> ORGANISM: Corynebacterium glutamiucm R

<400> SEQUENCE: 165

```
acgccatcgc agcctgccct cccggccgca tcgaagtcct cgccaactac accgcattcc    60
gagacctcaa gaaggctctg gagaaaggga ccgaacaata                         100
```

<210> SEQ ID NO 166
<211> LENGTH: 261
<212> TYPE: DNA
<213> ORGANISM: Corynebacterium glutamiucm R

<400> SEQUENCE: 166

```
ggggttttcg cctttccatg cttcatgggt taatttctac ggatttaatc taattaaata    60
aatcccagga tccaagcaat ttggccttaa tatgatggca atcactaatt ggaaaaatgt   120
ttaaacgggc attaaaaacg gattcaaccg ggtttaatgc cgttttatcg cgatttaata   180
caggtctacc cccactaccc ccattcagtt cagggaatcc ccggatttaa aacaactaaa   240
```
aaccctctag aatgagacat t    261

<210> SEQ ID NO 167
<211> LENGTH: 398
<212> TYPE: DNA
<213> ORGANISM: Corynebacterium glutamiucm R

<400> SEQUENCE: 167
gttcatcttt ctcaacaatc tataaatatt cgcaacaact taggggcagt cggtgggaac    60
ttacgcaaag tactttcaag cggtaccgac tcgaatccaa ttcttaaagc ttgcttaagg   120
gaattgtaat ctaactctta ttatttggcg tcgctgtcca aaagcttaga aaaaggtgtt   180
ttcattaaat tagattttct atccgtttag aatagcctgt cacaagcgct gaaccaatta   240
agaggacagc gtgttggctg ccttaattaa atacacgtag aagtaccgat gtgattgaat   300
tcgctaatct ttaagtggcc aaattcgccc cccatacagg gtttctttga aattgaagtt   360
tatggggcaa atgaaaatat cctgggtagc atgggctt                           398

<210> SEQ ID NO 168
<211> LENGTH: 52
<212> TYPE: DNA
<213> ORGANISM: Corynebacterium glutamiucm R

<400> SEQUENCE: 168
tcgaaataga agtctccccc ttttcaaatc ccctcctcgg aaagcaggaa cc            52

<210> SEQ ID NO 169
<211> LENGTH: 246
<212> TYPE: DNA
<213> ORGANISM: Corynebacterium glutamiucm R

<400> SEQUENCE: 169
ttctcgagcc tatcaaggaa atcttatggg ggagatattt tccgaaagaa aatttaattg    60
gtaagaaccc atgattgggg acttgcattt gtttcgccgt tcacttaagg ttaactctcg   120
gttaacaaaa agagttctca aggtgaactc aagtgatcgg tggaacatcc actaacgggg   180
ttgccaaaag ccttcgcgga ctctcccgaa ggaacacttc ttgcgagaag gaaggaaga   240
agcact                                                              246

<210> SEQ ID NO 170
<211> LENGTH: 100
<212> TYPE: DNA
<213> ORGANISM: Corynebacterium glutamiucm R

<400> SEQUENCE: 170
ttcggtccgc tctggcaaaa atggctggct gccacctcgg cgcagcagct aaagggctgg    60
gcttaaattg cttgtcgacg cctagtgcca caatggagac                         100

<210> SEQ ID NO 171
<211> LENGTH: 100
<212> TYPE: DNA
<213> ORGANISM: Corynebacterium glutamiucm R

<400> SEQUENCE: 171
atatgtctcc tgtgttggat gatgcggtgg ataatccgag gtatgcggag ttttatcagg    60
cgatgcgcac ggaacggttt tgatcattta aggttcattc                         100

<210> SEQ ID NO 172
<211> LENGTH: 149
<212> TYPE: DNA

<213> ORGANISM: Corynebacterium glutamiucm R

<400> SEQUENCE: 172

| gatggcagag aaatacgcac gtcattgata ctggccagtc aactgcggaa aggtgctgtt | 60 |
| gcaaactcgc gtttctgatg aaaacgaccc agtcggccac ctgtgttgcg ctgcacgcta | 120 |
| tcaaatagtt agtaaacaga aaatcctct | 149 |

<210> SEQ ID NO 173
<211> LENGTH: 51
<212> TYPE: DNA
<213> ORGANISM: Corynebacterium glutamiucm R

<400> SEQUENCE: 173

| gccggaggtt ggcgtcgaaa agcaaaatgc ttttcgacgc ttccctatac t | 51 |

<210> SEQ ID NO 174
<211> LENGTH: 100
<212> TYPE: DNA
<213> ORGANISM: Corynebacterium glutamiucm R

<400> SEQUENCE: 174

| tggggccttc tgcgccagtc tttacagcgt tttctgaagc ggctttgtcg ttgaaatcca | 60 |
| tgatcccaaa ctacctcaaa gcgcttgtag gctaagactt | 100 |

<210> SEQ ID NO 175
<211> LENGTH: 91
<212> TYPE: DNA
<213> ORGANISM: Corynebacterium glutamiucm R

<400> SEQUENCE: 175

| ctccatatcg agaacttaat cgagcaacac ccctgaatag tgaatcaaat cggaatttat | 60 |
| ttattctgag ctggtcatca catctatact c | 91 |

<210> SEQ ID NO 176
<211> LENGTH: 100
<212> TYPE: DNA
<213> ORGANISM: Corynebacterium glutamiucm R

<400> SEQUENCE: 176

| gagcatatgg tgcgcgcggc cgatatgctg atcaattcca accccgatcc gcacgcttaa | 60 |
| cttctgccaa aaagtcgctt tggccataag ctaagcgatt | 100 |

<210> SEQ ID NO 177
<211> LENGTH: 100
<212> TYPE: DNA
<213> ORGANISM: Corynebacterium glutamiucm R

<400> SEQUENCE: 177

| tggaggtgga cggcagccaa cggcagaaga cgttgctcaa gagatctgtc tggcagtagc | 60 |
| tacctccatt aagaactttg tcgaccaggg taggccgttc | 100 |

<210> SEQ ID NO 178
<211> LENGTH: 100
<212> TYPE: DNA
<213> ORGANISM: Corynebacterium glutamiucm R

<400> SEQUENCE: 178

| ggcagaaccg tgtactgctc aatcacattg tgaccaagct cggtgatgat ccacaggcga | 60 |
| tcgtcgatgc cgctgtcaag gctgatcgtg aggggaaata | 100 |

<210> SEQ ID NO 179
<211> LENGTH: 100
<212> TYPE: DNA
<213> ORGANISM: Corynebacterium glutamiucm R

<400> SEQUENCE: 179
ccttcgatcc ttaaagccga ggaaacaaga gcaggtagaa tctgaaacgg ttgtcgagca    60
cacgtatcaa acatcggcag cgaattaaga aggtgaacag                         100

<210> SEQ ID NO 180
<211> LENGTH: 100
<212> TYPE: DNA
<213> ORGANISM: Corynebacterium glutamiucm R

<400> SEQUENCE: 180
gccaactcgc cggaggtggt gtcgcggaca tcatctaaaa tttcgtgcag gtactcgggt    60
atcggcatcg tcaacataga atcaagacta gtgatttctt                         100

<210> SEQ ID NO 181
<211> LENGTH: 96
<212> TYPE: DNA
<213> ORGANISM: Corynebacterium glutamiucm R

<400> SEQUENCE: 181
gcaatgactc cgaaaccttc aagaacgtgt ggcactaaca attgcggact atccttggga    60
actgttttag attttattca gggtagggag attgtt                              96

<210> SEQ ID NO 182
<211> LENGTH: 100
<212> TYPE: DNA
<213> ORGANISM: Corynebacterium glutamiucm R

<400> SEQUENCE: 182
tgcgcaccta cggcgccgaa ttcccgctgg tcctgcttaa agatggacag gcactgctta    60
tcgacgacca cggcgtccac ctaatttagg atggttcccc                         100

<210> SEQ ID NO 183
<211> LENGTH: 88
<212> TYPE: DNA
<213> ORGANISM: Corynebacterium glutamiucm R

<400> SEQUENCE: 183
atagtggaaa atcagcggtg ctacgattgg aattagcttt tgaatgtcag catattggac    60
gcacggtgga aaacttcgag gagtaatc                                       88

<210> SEQ ID NO 184
<211> LENGTH: 144
<212> TYPE: DNA
<213> ORGANISM: Corynebacterium glutamiucm R

<400> SEQUENCE: 184
tgttctcctt taaatcgaaa ttattgcatc atgcaatttt gttatgaaca caaactacca    60
tgtttattgc atgatgcaac acccctgcta ggatataaat tactctatga gtccaaacgt   120
ttttaaaggg agcgaattac cata                                          144

<210> SEQ ID NO 185
<211> LENGTH: 122
<212> TYPE: DNA
<213> ORGANISM: Corynebacterium glutamiucm R

<400> SEQUENCE: 185

```
accttaaatt catctcctac aacctttgt aggtaagaat ttaacaagag ccagttatct      60
tctcttaaaa tgaggaggta actggcttct ttatgcttaa gaggtgttag cataagtgaa    120
ac                                                                   122
```

<210> SEQ ID NO 186
<211> LENGTH: 131
<212> TYPE: DNA
<213> ORGANISM: Corynebacterium glutamiucm R

<400> SEQUENCE: 186

```
cagaccttat ccccgagggg tgggcaggca ccctcatcct cgtcatggtc accctaattt    60
taggcccatg ggcgatcttc tcaaaacaaa acgcagaaaa atggtgggca ctcggacact   120
tcaccaaatg g                                                        131
```

<210> SEQ ID NO 187
<211> LENGTH: 100
<212> TYPE: DNA
<213> ORGANISM: Corynebacterium glutamiucm R

<400> SEQUENCE: 187

```
agaaggtggt gcccaccagt ccgttagcgc agtggtgggc aatgaggtgg gagtggttta    60
aacgcaccgg cctgcaggtg accggggcgg tgttggaggg                         100
```

<210> SEQ ID NO 188
<211> LENGTH: 321
<212> TYPE: DNA
<213> ORGANISM: Corynebacterium glutamiucm R

<400> SEQUENCE: 188

```
ttttcgaagc tcgggataaa tctgcgaatc ggaaccactc cacacaaagc ccaccgaagc     60
cccaaatcgc tgggaggcgt catacccagt caatggtccg gaacttagta gcgcaagtaa   120
tgcagatcgt agagtcacgt actcattgtc ccatatctac ccccgccccg gagcatgaat   180
acccgcagct cagaggccct aggtgacatt atctcacatt taccccttga cagtgatttg   240
aaacacaagc aaaatatgac ccacgccata aactaactaa gagtttaggt atttgattac   300
atagttcttt aggagttcac c                                             321
```

<210> SEQ ID NO 189
<211> LENGTH: 100
<212> TYPE: DNA
<213> ORGANISM: Corynebacterium glutamiucm R

<400> SEQUENCE: 189

```
ctccgatgaa ctccctggta aaagagctag gagaaccgta gtgattgtga ggcatgtgag     60
gtaattttgc cccgctgtct tctgaccaga atgatgttag                         100
```

<210> SEQ ID NO 190
<211> LENGTH: 58
<212> TYPE: DNA
<213> ORGANISM: Corynebacterium glutamiucm R

<400> SEQUENCE: 190

```
gggtatacga tgggagggga aaccccgcct gatccccga tcccacagga gcgatccg       58
```

<210> SEQ ID NO 191
<211> LENGTH: 100
<212> TYPE: DNA

<213> ORGANISM: Corynebacterium glutamiucm R

<400> SEQUENCE: 191

```
cttcggtggt cagtgcttgg tgcaccttgc cgacgggctg attgatcgta atggtgtttt    60
ctgtacgcgt tgccatgagg ataagactac cgttagtgag                         100
```

<210> SEQ ID NO 192
<211> LENGTH: 170
<212> TYPE: DNA
<213> ORGANISM: Corynebacterium glutamiucm R

<400> SEQUENCE: 192

```
gtgctcacac tagcgccgta ggccggcttg cgctcggcaa gtgttttgct tatcgatgtc    60
tccccacata acaattccaa ctcgaagcac caacgattca agccttatca gtttcgtaca   120
ggaaaatagt gcaaaaatgg ggtttaagct tcgtggagag gattgtcatc              170
```

<210> SEQ ID NO 193
<211> LENGTH: 228
<212> TYPE: DNA
<213> ORGANISM: Corynebacterium glutamiucm R

<400> SEQUENCE: 193

```
tttacttacg acgctgcgta gttaaaaagc gtgactcccc acattctagg gagtcacgct    60
tttttgattc tgcccgcatt cttggacgtg tgatgtacgg caggtgaatt ccgctttgct   120
aggctgaaca ctaggcacgg ggtgccaacc ggatggaaaa attccggggg ctgagaaaac   180
acccgttgaa cctgctctag ctcgtactag cgaagggatg gccttaac                228
```

<210> SEQ ID NO 194
<211> LENGTH: 100
<212> TYPE: DNA
<213> ORGANISM: Corynebacterium glutamiucm R

<400> SEQUENCE: 194

```
tcattgtcta cgccacccctc ggtctgctgt ctgaagcgct gatcagagct tgggaacgtc    60
acaccttccg ctaccgaaac gcataagaaa gttgctcgcc                         100
```

<210> SEQ ID NO 195
<211> LENGTH: 149
<212> TYPE: DNA
<213> ORGANISM: Corynebacterium glutamiucm R

<400> SEQUENCE: 195

```
agggcactct aaaaccggaa gagccattaa aaccctgtg tccactttcc ggggtcaggc     60
ccaaaagaat actttaaaag gataagattt atatgacagc ctgattcaca ttgtaaaagc   120
cctattctcc gtgaaggatg acgattgct                                     149
```

<210> SEQ ID NO 196
<211> LENGTH: 105
<212> TYPE: DNA
<213> ORGANISM: Corynebacterium glutamiucm R

<400> SEQUENCE: 196

```
ggcggcagat tacctttccc agcatcatgc tggtttcagg gtgtccacca aacagggggtc    60
aggtccctgg atcaagtttc aattgattct ggggttgtaa gtgca                   105
```

<210> SEQ ID NO 197
<211> LENGTH: 216
<212> TYPE: DNA

<213> ORGANISM: Corynebacterium glutamiucm R

<400> SEQUENCE: 197

```
gtgaacctcc aagagagtga aaagaagttg gtattgccac cgcgatgtcg ttttcgtttt      60
tgctttgaag cggtgtgtga catttgcgag caattccgca gtgtcggtgg cgtatgacca     120
acagtgcccg atcaatgaag tgaatcacat taggggaatt cctagggttt gctcggggt     180
aggtgttcgc atgatgtaaa ttgacaggct gtttgt                               216
```

<210> SEQ ID NO 198
<211> LENGTH: 84
<212> TYPE: DNA
<213> ORGANISM: Corynebacterium glutamiucm R

<400> SEQUENCE: 198

```
gcccacattc tagatcgccg aagaaagcag cgggacgtct ctatatacta aagggcacta      60
aagcaacgca gttgaaggga cacc                                             84
```

<210> SEQ ID NO 199
<211> LENGTH: 130
<212> TYPE: DNA
<213> ORGANISM: Corynebacterium glutamiucm R

<400> SEQUENCE: 199

```
gggtttgcgt cgaaaagcaa gcacgcctgg tgcctgattt gagcggtttt acctatggcg      60
ctttggcgcc gtcaaactgt cccagcgatt tcattattat tttcgtgcat tcaccgttat     120
agttataggc                                                             130
```

<210> SEQ ID NO 200
<211> LENGTH: 100
<212> TYPE: DNA
<213> ORGANISM: Corynebacterium glutamiucm R

<400> SEQUENCE: 200

```
gcggtgtggc ccggtgctgc gatcgctttg acggtccttg gttttaatct tttcggtgat      60
ggtttacgcg atgccatcga tccaaagcgg gaggtcggcc                           100
```

<210> SEQ ID NO 201
<211> LENGTH: 533
<212> TYPE: DNA
<213> ORGANISM: Corynebacterium glutamiucm R

<400> SEQUENCE: 201

```
ggttgcccat gataatcggt tctgttgtac ctttcagtgc tccaactgct tgatttacca      60
tcaactattt aacctccact ctaaatttat cgcccgaggt tacttgatta tatttgtaga     120
aactacttag gcttcctcct tggctgttgt tttctactcg ggggacccac tggcctctat     180
tacttgagcc accttcctca gaagaagcaa acgggattca tcgcatgaag gcttggcat     240
tccaccacgt cgccaacttt catatgcaag acgtgttgca gctttttata tcaatttagt     300
ggttgatgaa gtctctaagt ggcctttttac ttttaatatc caggttgcaa aatcaataat     360
tgcccatcag gttttgatgc ttcaacccag cttaagacct gtggctgcca ggaatggctc     420
ctaaaaccaa tgcctgagcc tttccctgag ctgtaatgaa aggacattgg tatgggttg     480
cctctgacat cgttttgagct ctccatccct ttcatttcgc tattctggta tcc           533
```

<210> SEQ ID NO 202
<211> LENGTH: 100
<212> TYPE: DNA

<210> SEQ ID NO 203
<211> LENGTH: 228
<212> TYPE: DNA
<213> ORGANISM: Corynebacterium glutamiucm R

<400> SEQUENCE: 202
tggtccgcca ccaactggtt ggacacattg tggatgcata cgaagactat gaagaacgcg    60
aggcccgcga attgaaacgc aaacgccagg agacacggcc                          100

<210> SEQ ID NO 203
<211> LENGTH: 228
<212> TYPE: DNA
<213> ORGANISM: Corynebacterium glutamiucm R

<400> SEQUENCE: 203
caggtcagct aacctttcac aagacgaatc ccgcgcgtaa gacctcactc gcgggacagg    60
tacgcccaca agcatagacc gccgataccc atatataaaa gtatgggttc acttccatcg   120
tttcgcgcgc atgagtttac tcacgtgccc acgtcttttt gccacccatt gaagtgaaaa   180 ataaccccg atcacactaa tggagtagct aaggtgcaca atggattc                 228

<210> SEQ ID NO 204
<211> LENGTH: 100
<212> TYPE: DNA
<213> ORGANISM: Corynebacterium glutamiucm R

<400> SEQUENCE: 204
atggatcgat atttaagacg ccagcgcggg tggcgtcgat gccgaattga atcgcagaat    60
ccgggcggat cagaacttgg gcagagttgg ctaaagcgat                          100

<210> SEQ ID NO 205
<211> LENGTH: 153
<212> TYPE: DNA
<213> ORGANISM: Corynebacterium glutamiucm R

<400> SEQUENCE: 205
acatacagtc cccgtgatgt gaccatacac accacgggga ctgtggcgta ggtcttacaa    60
aattctccaa aaggagttat gatagtacca atacgttttt gtggcagcct cctgcattcg   120
gcagtcgaga cgccaccaaa gaaagggtaa gac                                153

<210> SEQ ID NO 206
<211> LENGTH: 100
<212> TYPE: DNA
<213> ORGANISM: Corynebacterium glutamiucm R

<400> SEQUENCE: 206
gttgcgggag tgtccaccaa aaatattgcc tgcataggg tctgaaaaac tcatagctca     60
ccaccctagt caaagcactg cactacactt ccctaacact                          100

<210> SEQ ID NO 207
<211> LENGTH: 100
<212> TYPE: DNA
<213> ORGANISM: Corynebacterium glutamiucm R

<400> SEQUENCE: 207
caggttggaa ccctgactgg ttcatgttct tcctcggcgg caccctactt ctggctgttt    60
tgctcaatca ccgattcgag cgtttcaaca aggagcgatc                          100

<210> SEQ ID NO 208
<211> LENGTH: 100
<212> TYPE: DNA
<213> ORGANISM: Corynebacterium glutamiucm R

```
<400> SEQUENCE: 208
caccaccgac tccgacgact tcgacgccga ctcctttacc accgaagtca tccggattac      60
cggctactcc cgccacgaag tcaacaacgg ccttaacgcc                           100

<210> SEQ ID NO 209
<211> LENGTH: 280
<212> TYPE: DNA
<213> ORGANISM: Corynebacterium glutamiucm R

<400> SEQUENCE: 209
ccaccgcaac caagcgtcga aaagcaaaat cttttcggcg cttttggtg actcgtcaac       60 aaggggagc aaaatcagcc attgccagga aaaggttgac ctctatcggg gttagccttt     120
ctaaagttaa gctgtgagcg ggaacttgag aatcaacttc aacgacaacc tttaagaagc    180
tcttattggt tcttcgtttt gtatcgataa atgcaatcga tttcctggct taataaggct    240
gttcctgtaa acctgcaatg aagaggaag gggacctagc                            280

<210> SEQ ID NO 210
<211> LENGTH: 100
<212> TYPE: DNA
<213> ORGANISM: Corynebacterium glutamiucm R

<400> SEQUENCE: 210
ggtcgcagaa gcactacatg gcatggtgcc gggcctcaaa aacacaggta gctcggtcaa      60
cgacgattct cgtcggaacg tggaaggaca gtagaaaaca                           100

<210> SEQ ID NO 211
<211> LENGTH: 269
<212> TYPE: DNA
<213> ORGANISM: Corynebacterium glutamiucm R

<400> SEQUENCE: 211
tgtccgacaa gatctggaaa gtcggcatta tcggttgcgg tgcaatcagc cgaaaccaca      60
tcgaagcagt tcaagcaatc cccggcgcgg aagtcagcgc agtctgtgat gtggatggtg    120
tgaaagcatc ggaaaccgca gcgaaatatg gaatttcttc cagcttcacg tctgtcgatg    180
agatcctcgc ctccggggtg gacatcgtcg cagtatgcac cccacatcca acccacgaaa    240
cagtggtcct cgccgctgct ccgccgga                                        269

<210> SEQ ID NO 212
<211> LENGTH: 92
<212> TYPE: DNA
<213> ORGANISM: Corynebacterium glutamiucm R

<400> SEQUENCE: 212
ctaagtatga acgcgaatcc gactttggtc gtactgcaag aatcgaccag agcccgatta      60
aaaaatgccc ccgcgcaacg aaactaataa tc                                    92

<210> SEQ ID NO 213
<211> LENGTH: 165
<212> TYPE: DNA
<213> ORGANISM: Corynebacterium glutamiucm R

<400> SEQUENCE: 213
ctaatttcac caaactcgtg agcgaggtac cgttccaaag ccatcatgag atcatttct        60 cctagcctga tccccatgac ttttcttct ccatcgaatt tgtggtatgg gcgagacagt     120
gccatatgag aagaccaagg ggatgaagaa gataacccccc caatc                    165
```

-continued

```
<210> SEQ ID NO 214
<211> LENGTH: 100
<212> TYPE: DNA
<213> ORGANISM: Corynebacterium glutamiucm R

<400> SEQUENCE: 214
tcgcggacat catctaaaat ttcgtgcagg tactcgggta tcggcatcgt caacatagaa      60
tcaagactag tgatttcttt tgcgctatat actcttgtgc                          100

<210> SEQ ID NO 215
<211> LENGTH: 100
<212> TYPE: DNA
<213> ORGANISM: Corynebacterium glutamiucm R

<400> SEQUENCE: 215
acatggagct catccgcagc ggtccaccag cagaaatggt gggcatcggc acgcctctac      60
cgttccccac ctcacaaccg gacattcact aggacacact                          100

<210> SEQ ID NO 216
<211> LENGTH: 91
<212> TYPE: DNA
<213> ORGANISM: Corynebacterium glutamiucm R

<400> SEQUENCE: 216
ggaacatcct tggcggagtt atgcaaacgt tttcataaag gggttattcc attctacgtc      60
gatctttgta gaaggtggtt attatggctt c                                    91

<210> SEQ ID NO 217
<211> LENGTH: 100
<212> TYPE: DNA
<213> ORGANISM: Corynebacterium glutamiucm R

<400> SEQUENCE: 217
acgcgttgct ggacgtcacg ctcgcggtgg atgagcacgc tccctgtctc gactcgggct      60
gtgacgtgcc cggttgtgtc accgggcagg agggcatgtg                          100

<210> SEQ ID NO 218
<211> LENGTH: 100
<212> TYPE: DNA
<213> ORGANISM: Corynebacterium glutamiucm R

<400> SEQUENCE: 218
gccggtgcag gcacgtgggc tggggcgaaa gacgccggcg cgctgctgaa aattttcgca      60
accatctcca cattccacta ctaaaggttt aaataggatc                          100

<210> SEQ ID NO 219
<211> LENGTH: 137
<212> TYPE: DNA
<213> ORGANISM: Corynebacterium glutamiucm R

<400> SEQUENCE: 219
ttagagattt acttgcttga accgccttcc catctttgaa ttcattcaag gtggtaaggc      60 ggttttgct ctttaaatac agttttaaag gtagatttgg gagagaagat ttcccttaag     120
aaaggttttt atcaacc                                                   137

<210> SEQ ID NO 220
<211> LENGTH: 100
<212> TYPE: DNA
<213> ORGANISM: Corynebacterium glutamiucm R
```

<400> SEQUENCE: 220

```
ccgagaagct ggagaaggcc aacaagcgtg gcctctacac ctccgcgtcc ttccacagcc      60
ccggcgccat cactggcgac cactaaaaga ggagacttcg                           100
```

<210> SEQ ID NO 221
<211> LENGTH: 464
<212> TYPE: DNA
<213> ORGANISM: Corynebacterium glutamiucm R

<400> SEQUENCE: 221

```
taggtgcgct cttcccttct acaaattttt ttgcttttcg acgccacaat gcagcgcgat      60
ttcagatcgc cagcttaccc caaccgaagc ccttcagaag acccgcccca gcctatcaat     120
tttggtcaag tcgcctagct ttagacctag ctttagagcg caatccccca ccccaaaacg     180
tgatcttagt cacttatttt ccattacgcc ccacagggtt cagtgtcgga ctaacgccac     240
aagaccacct ccatcagccc tcaaattcaa ccatttattg ccctaaatta tcgccactag     300
cacgtcattt agagaaaacc tttaatgtga acaggtctc aaactgggcc attctcaagc      360
cttcaaaaag gtgggaaact tagccaatcc aaagcccaaa aatgcgggtt atgctgcgct     420
aacctatgct gacagccttg cggaatttgt gtacgttagg ggcc                      464
```

<210> SEQ ID NO 222
<211> LENGTH: 188
<212> TYPE: DNA
<213> ORGANISM: Corynebacterium glutamiucm R

<400> SEQUENCE: 222

```
cgccgcggcg cccggaaagc cctcagcggc ggggaaaccc gattcgatgg aggcctggaa      60
ttcatcaaaa agcccgggcc cagagggctc gggcttcccc ggcgcaacgt cggttgcggt     120
gttaagttct ggacatgcag aagcctttcg aggatctgtc ccgggagttt gccgcgtcca     180
tcgccgag                                                             188
```

<210> SEQ ID NO 223
<211> LENGTH: 97
<212> TYPE: DNA
<213> ORGANISM: Corynebacterium glutamiucm R

<400> SEQUENCE: 223

```
cggcggcaac aaagccgtag cggttcacgg caccgcccca gagtgttggc tgctggtcga      60
atggcccgcc ggagaagacg aacccaccga ttactgg                              97
```

<210> SEQ ID NO 224
<211> LENGTH: 100
<212> TYPE: DNA
<213> ORGANISM: Corynebacterium glutamiucm R

<400> SEQUENCE: 224

```
agcgtcgcag gaatcggcgc gatcttcctc cttccgatcg gcatcatcat gtgcctgatc      60
gccggattca accgcttcta cgcagcccct aaggtctaaa                           100
```

<210> SEQ ID NO 225
<211> LENGTH: 110
<212> TYPE: DNA
<213> ORGANISM: Corynebacterium glutamiucm R

<400> SEQUENCE: 225

```
tattttgtc ttgagttcgc ggttttgcac tctttccgac atttttcta cccttttccac      60
```

```
acttatgaat cacatcactt ttagtgtggt gtatgacata agctaaagcc          110
```

<210> SEQ ID NO 226
<211> LENGTH: 72
<212> TYPE: DNA
<213> ORGANISM: Corynebacterium glutamiucm R

<400> SEQUENCE: 226

```
agaaaccttt aaggactagc tcgaaaaaca gccaactata gttaagtaat actgaactat   60
tttggaggtg tc                                                       72
```

<210> SEQ ID NO 227
<211> LENGTH: 100
<212> TYPE: DNA
<213> ORGANISM: Corynebacterium glutamiucm R

<400> SEQUENCE: 227

```
acgggaagga ggaacacagt gggtcgatat cccccgtaac cgttactgac tgaccttgtc   60
tctcgacccc taactcacac cacctttgaa aggaacgctc                        100
```

<210> SEQ ID NO 228
<211> LENGTH: 350
<212> TYPE: DNA
<213> ORGANISM: Corynebacterium glutamiucm R

<400> SEQUENCE: 228

```
ttctcgggga aaaggaataa aatggcttgt ggtcagactc acaggggctt ctccaagtca   60
gtggatttat gaggtcccag tgggtacaca ccgggtgtcc tacaacgatc aattgtcaca  120
gattcgactg gcatgctgta ccatctgctt taagcatttt ggtgtttcac tgttgttaac  180
agtgtttcac cgtggagcac tacctaaaga tcatagtcag catcttgggg tgaatgtgac  240
acggtacgct atagtgtcag acaacaacca ggaaactggt cgttgcagag tttttgcaaa  300
attggacatc ctttaacgga ccgcacagag aggcggggaa ggaggtcacg              350
```

<210> SEQ ID NO 229
<211> LENGTH: 60
<212> TYPE: DNA
<213> ORGANISM: Corynebacterium glutamiucm R

<400> SEQUENCE: 229

```
ggcttctgag attagtcggt gtgatccggg aaactaaatg gaaaactaaa atgaaaggca   60
```

<210> SEQ ID NO 230
<211> LENGTH: 138
<212> TYPE: DNA
<213> ORGANISM: Corynebacterium glutamiucm R

<400> SEQUENCE: 230

```
gtgagagaag cctccacaga tagaaatcac aaataaataa cagacccact ctagccgttg   60
cgggttctta ttgaggtcta tagtgggggtg ctacacacta caaaccgtga tttgtttcgt  120
gattggagct gagcccac                                                138
```

<210> SEQ ID NO 231
<211> LENGTH: 117
<212> TYPE: DNA
<213> ORGANISM: Corynebacterium glutamiucm R

<400> SEQUENCE: 231

```
actttaagga gttcaccaag gaggaaaatt atcaccgtct taaaaacggc taaggctttt   60
```

```
ctaaattcgc cgctgcgcac catcacgtgg cgcagcgttg tggcgaataa actccgc        117
```

<210> SEQ ID NO 232
<211> LENGTH: 100
<212> TYPE: DNA
<213> ORGANISM: Corynebacterium glutamiucm R

<400> SEQUENCE: 232

```
gcaagggcaa cgggaatact acagtattta acggcaacgg gattcgagtt attgtcgata     60
atgtgagcgg aaatgtgatt actgttacga aaggctaatt                          100
```

<210> SEQ ID NO 233
<211> LENGTH: 133
<212> TYPE: DNA
<213> ORGANISM: Corynebacterium glutamiucm R

<400> SEQUENCE: 233

```
aaaatagccc caccaaaaag gcggggcatg cctccacaaa gcgcggagaa gaaaaatcaa     60
cggtccaaaa cagtgaaata ccccgctag tgcgaggaat gaacacacta tagcacgaaa    120
agagaagaag tat                                                       133
```

<210> SEQ ID NO 234
<211> LENGTH: 127
<212> TYPE: DNA
<213> ORGANISM: Corynebacterium glutamiucm R

<400> SEQUENCE: 234

```
acccactgct tgaaacactt aaagcaccgg cagccttcat ggttaccggt gctttcctgc     60
tcttttacaa agcctccacc tatgattggc taagatcctc ttccccgcac tgaaagctca   120
acgatcc                                                              127
```

<210> SEQ ID NO 235
<211> LENGTH: 162
<212> TYPE: DNA
<213> ORGANISM: Corynebacterium glutamiucm R

<400> SEQUENCE: 235

```
acccctaacc catattagaa caaggatttg tgcgcttttc ctgttctggt gtgggttttc     60
ctcacatcta acaatcgaat aactgttcga ataaaaggtt gaaggtgtcc cacccccacg   120
gcacaatgga tggcaagaac acatgaatcc aggggatac tc                       162
```

<210> SEQ ID NO 236
<211> LENGTH: 84
<212> TYPE: DNA
<213> ORGANISM: Corynebacterium glutamiucm R

<400> SEQUENCE: 236

```
ggtgtccctt caactgcgtt gctttagtgc cctttagtat atagagacgt cccgctgctt     60
tcttcggcga tctagaatgt gggc                                            84
```

<210> SEQ ID NO 237
<211> LENGTH: 292
<212> TYPE: DNA
<213> ORGANISM: Corynebacterium glutamiucm R

<400> SEQUENCE: 237

```
gttttagata acaagaccag cacagaccac catatctacg accccaaaaa cagactccaa     60
gctccgcggc gacgaagccg cgctcgcgcc accgaccaag cagccggtcc aggtttaaag   120
```

-continued

```
attttgcttt tcgacgctcc cctccacctc attcaatgcg gcggagggga ctttcttacg      180
tgttcagtat ataggaaaaa gcgtttgaat agcaccttg cgttcgaaag tgtaatcgag       240
tatagtggtt ggtattagca cggggaacta aacgggaaag ggggaagaca cc             292
```

<210> SEQ ID NO 238
<211> LENGTH: 100
<212> TYPE: DNA
<213> ORGANISM: Corynebacterium glutamiucm R

<400> SEQUENCE: 238

```
actacctcga cccatcacgc acactcgaga tggagcgtta cgacgccaac cgcgatgaca      60
tcaaccaccg cgtagacgcc aatggaacgg aggaacaacc                           100
```

<210> SEQ ID NO 239
<211> LENGTH: 100
<212> TYPE: DNA
<213> ORGANISM: Corynebacterium glutamiucm R

<400> SEQUENCE: 239

```
accttcccac cagctacgcc gtcccagtag gactgaccac cggagtgatc ggcggcctct      60
acctgctgtg gatcctcacc cgacaaaagg ctgtttaact                           100
```

<210> SEQ ID NO 240
<211> LENGTH: 100
<212> TYPE: DNA
<213> ORGANISM: Corynebacterium glutamiucm R

<400> SEQUENCE: 240

```
tcttgcatgc cgtgcaaagt ctgcctgacc tggatgatct tgatcagctc aacatcgaag      60
tcgacataag caaccaggcc gcgacgaaag cggggctgtt                           100
```

<210> SEQ ID NO 241
<211> LENGTH: 231
<212> TYPE: DNA
<213> ORGANISM: Corynebacterium glutamiucm R

<400> SEQUENCE: 241

```
aggacctgct ttcttgaatg gaagacccat ccagattgga agtatgatgt cagatgtcta      60 attggggca tagacatgcc tcccccactt caccaccag gacgggttgt gtgcgggatt       120
ttcttatcat acaaaactta tgacacattg ttgtgtgaat cacaaagttt tttaaatttc     180
gaaaaaccac aagcttgtgc gggaaacttc tcgcataact agggtgaggg t              231
```

<210> SEQ ID NO 242
<211> LENGTH: 68
<212> TYPE: DNA
<213> ORGANISM: Corynebacterium glutamiucm R

<400> SEQUENCE: 242

```
gttgttgatg catcaactta tttcttggct atacttgagg ccacgtttcc tcagctcagg      60
agaagtcc                                                              68
```

<210> SEQ ID NO 243
<211> LENGTH: 186
<212> TYPE: DNA
<213> ORGANISM: Corynebacterium glutamiucm R

<400> SEQUENCE: 243

```
caacttctgg atgtcttctt ggttgctcat gacccacagt gtaaatgatt aatcgatcac      60
```

```
taaaaatgat catttaaacc cgactctatt gggatgcccg attctctgca cggtctccga      120
tttagaatat aaaggcctta taggctgtat ttttacggag aacgtggggt tgacatccgc      180
tggaaa                                                                 186

<210> SEQ ID NO 244
<211> LENGTH: 142
<212> TYPE: DNA
<213> ORGANISM: Corynebacterium glutamiucm R

<400> SEQUENCE: 244
ttcaaggaca tatgaagctg tcgaacatgt gagtgctcga cagcttttcc atttcgaaaa       60
atagccttgt attcgaaaat gtgatcgggt aaggtggttg gtattagcac ggggaactaa      120
acgggaaagg ggggaagata cc                                               142

<210> SEQ ID NO 245
<211> LENGTH: 647
<212> TYPE: DNA
<213> ORGANISM: Corynebacterium glutamiucm R

<400> SEQUENCE: 245
gtttttggga gttgtgggcc ggtgttggag gggtggttgt ttaataggcg acttcacgta       60
tgcggacttc atgtgcgctg acttcttgcg ctcaacttct catgtgctga cttcactccg      120
gattgctggc atttagtagt gatgtcgtgt gatgagaagt tgagtatgcg aagtcggtac      180
cgagaagtcg acctttagga catttttaga ggagtccacg cagagactct gtctccgtaa      240
gttcgatttc acggttacga tttcgaactg tcaatatccc gggtgcggtt tctcaattac      300
aatttcgcac ttccaatttc tcaagagcga taccactagg aaaagtgcca ttttccgact      360
gaaatcgccg ttgagaaatt gagcgcaagg tatcgagttt gcgaaatcgg taatgcgaaa      420
tcgtaaccgt gaaatcgaac tttaaaccca aatgaccgaa aaagctcaaa ccaacaagca      480
tcaagtaaca cattctcgtg cggacagcgc acggaatcca tagactggtc tgcagaagtt      540
ttacgtgtgg gtttgcttcg gatggggctt taacaagctt cacagatgtt ggttttttcat     600 aggcaagcta tccagaagca ggctttacag aaagtcaggg tgtggca                    647

<210> SEQ ID NO 246
<211> LENGTH: 104
<212> TYPE: DNA
<213> ORGANISM: Corynebacterium glutamiucm R

<400> SEQUENCE: 246
tggaagtttt tcaaagtgtc tgacgttgaa aacggtgagt tcacaactag ggtgaatggt       60
gcacgtgatg ctgcactttt acgtttacta ctttgaggga aaca                       104

<210> SEQ ID NO 247
<211> LENGTH: 204
<212> TYPE: DNA
<213> ORGANISM: Corynebacterium glutamiucm R

<400> SEQUENCE: 247
cgcactcctg acccccacaag cccgcccgca ccagaaagtg ccggcgggcc atctgtgccc      60
cgggctacga gcaccacagt cttttttgcga tccagatctc actttgcggg tacttgatgc     120
ggatcaaggt actttctccg gattgttcat aactaatga gtatcacaga aaacacctaa      180
tcttcatcat gaaaggacac cacc                                             204

<210> SEQ ID NO 248
```

```
<211> LENGTH: 100
<212> TYPE: DNA
<213> ORGANISM: Corynebacterium glutamiucm R

<400> SEQUENCE: 248
tgtcccacac cgccgagaat ttaggaaacc gcgctctgac cggcctcgct gaaatcgaag      60
acaccgacga ccaactcgca cacgcattgg agcgcctgac                          100

<210> SEQ ID NO 249
<211> LENGTH: 100
<212> TYPE: DNA
<213> ORGANISM: Corynebacterium glutamiucm R

<400> SEQUENCE: 249
tccgcgcctg tcgtagcact gcctacctcg gtgggttatg gcgcaggtgc tggaggaatc      60
gcaccacttc tgaccatgct caacgcctgc gcgccgggag                          100

<210> SEQ ID NO 250
<211> LENGTH: 126
<212> TYPE: DNA
<213> ORGANISM: Corynebacterium glutamiucm R

<400> SEQUENCE: 250
ttaagcgtcg tcatccatgc ttagaggaat atgtgaataa aaagggttat cttatgctca      60
tggttatgac ttgcgtgcga cgatatgtgt aatgcaatcg atatctaata atcaggaaa     120 aaggac                                                              126

<210> SEQ ID NO 251
<211> LENGTH: 1000
<212> TYPE: DNA
<213> ORGANISM: Corynebacterium glutamiucm R
<220> FEATURE:
<221> NAME/KEY: misc_feature
<222> LOCATION: (405)..(405)
<223> OTHER INFORMATION: n

<400> SEQUENCE: 251 gagattttc atttatttga tccatcatga ccattaccgt ctggtcattg aaatctgcgt      60
gccttgcaat acgatttaga gtctctcgca tagacacttg ctcgcgctct ttaaactcat    120
tggggccgca attagtttcc tttggagtcc caaccggctt tcttccgaa taatagaaga    180 gatttccctc aagctgtcga agcttagata agagggcacc tagcaatcga agattttggg   240
gacgctcttc atagaccttt gcatatagaa gatcagaacc cttctttttcc caacgccctg   300 gatcgcggtc tgacggaatg tcgctcctaa aaaatctttc ttccttgcag caaagaaaga   360
accaaacacg cggcgtttc ttcggggatt ataaatcctc catanacaaa ggttgggcta    420
tcggagaact tttatgagac gggtgaacaa atgctccggt cgaaccaatc tcatcgatat   480
atgcaagaag caagcaagtc tcccccaaaa cgtttaggaa taagcacgag ggcctgcaaa   540
tgcgaggccc tcggagttgc tgcccggggt attcttgcat gttactgctc aacgcctggc   600
ttacacctcg aagtgtacaa ggagaagaaa cttcacgcaa tcaaccaatt tacccccaag   660
ttttccccac aaatgaagaa tcttgaactg agatgctcac aatttattcg ctaatctgca   720
caaatgctag taacgcgatg ttgagttct ttctcaatct gactccaccg ggggtaacat    780
cttcgaggcg gaccgtttga aactgtattt gtaagggttg gcgcagcctc cttccacttt    840
ggcactcatt gatactgcat cgtcaaaagc gcaaaccgcc cccaccacca taaaggtgat   900
gggggcattt ccaggggtag cactttccaa actgccttat ggacctcggc ccggtgttaa   960
```

```
atttcgagta tttagatcac cttctactca tcgaggcgcc                          1000

<210> SEQ ID NO 252
<211> LENGTH: 142
<212> TYPE: DNA
<213> ORGANISM: Corynebacterium glutamiucm R

<400> SEQUENCE: 252
ataagacacc ctagtggtgg tggagtgatt tttgggtatc gacgacaggt gaattcatgc      60
acgtttgagt gtcccgtgtg tggggtaatg ttgtccaaga gagtgcaagg aaatgctgtg     120
gcggttgaaa ggagtgcctt tc                                              142

<210> SEQ ID NO 253
<211> LENGTH: 100
<212> TYPE: DNA
<213> ORGANISM: Corynebacterium glutamiucm R

<400> SEQUENCE: 253
gccattgcag ggaatttttct ttgtctgcga tgaatccgtt gagcgtgctc gatgtgttgt     60
agatgatcgc catcacacga tgctacctac gatggggatc                           100

<210> SEQ ID NO 254
<211> LENGTH: 100
<212> TYPE: DNA
<213> ORGANISM: Corynebacterium glutamiucm R

<400> SEQUENCE: 254
aacagaagcc acttcccgta cctgcgatta ttccgttttt gtctatcgca gccttggtgg      60
cctctgcggc tgtcttggtt ctgattattg ttcagtagct                           100

<210> SEQ ID NO 255
<211> LENGTH: 100
<212> TYPE: DNA
<213> ORGANISM: Corynebacterium glutamiucm R

<400> SEQUENCE: 255
cggtgtacga catgatcaag gctgtggaca agatggccgt gattgatggc attcgtgtgc      60
tgtcgaaaac tggcggtaaa tctggggatt ggtccgtgca                           100

<210> SEQ ID NO 256
<211> LENGTH: 178
<212> TYPE: DNA
<213> ORGANISM: Corynebacterium glutamiucm R

<400> SEQUENCE: 256
aatgtgacta atcacaccct cagatttcaa cttgctgggg gtgttttttgg cgtgttagca     60 gattttagct tgactctggt ctagggtaga gaccagactt atagctaagt tgcatgctta    120
gaattaacac gcatgttgtt ttgaataaaa catgggtgct gaataatcgg agaaacta      178

<210> SEQ ID NO 257
<211> LENGTH: 100
<212> TYPE: DNA
<213> ORGANISM: Corynebacterium glutamiucm R

<400> SEQUENCE: 257
agcgaatcgg attcagtgat ttgcttgcgg gcgcagaaat gatttttcaa ttagacacac      60
ttagacacac gtaactaaaa cctcagggaa gtgactgata                           100

<210> SEQ ID NO 258
```

```
<211> LENGTH: 100
<212> TYPE: DNA
<213> ORGANISM: Corynebacterium glutamiucm R

<400> SEQUENCE: 258
gcgccaggca gctttgcggt ggcgtttatt gatgcgcttt atgacgtgga tgcccaggct    60
gtggcctcgt tggttgatgt gcgagaggcc tgaaaagtac                         100

<210> SEQ ID NO 259
<211> LENGTH: 100
<212> TYPE: DNA
<213> ORGANISM: Corynebacterium glutamiucm R

<400> SEQUENCE: 259
acgcgttgct ggatatcacc ctggccgtcg atgacaacgc cgaatgcatc gacgccggat    60
gcgccgtacc tgggtgtgtc actggacagg agagtgcgta                         100

<210> SEQ ID NO 260
<211> LENGTH: 156
<212> TYPE: DNA
<213> ORGANISM: Corynebacterium glutamiucm R

<400> SEQUENCE: 260
gaggttttcg ctttcctata caggttatat aagagcttaa acaagactc ccgacatatt     60 agacctgtac gggttgaagc gaaacacttc ccttagagtc aaagtgactg taagatagct   120
caacagttaa agtcagattg accctaaggt ggtttc                             156

<210> SEQ ID NO 261
<211> LENGTH: 106
<212> TYPE: DNA
<213> ORGANISM: Corynebacterium glutamiucm R

<400> SEQUENCE: 261
aataaataga tacagaacac attccattac cgagaattat caaatctcat acattagtct    60 cgtagggca atctcatttt ccatgcagta ttttaagga gtccct                   106

<210> SEQ ID NO 262
<211> LENGTH: 208
<212> TYPE: DNA
<213> ORGANISM: Corynebacterium glutamiucm R

<400> SEQUENCE: 262
acctttctgt aaaagccccc gcttcttcct catggaggag gcggggcttt ttgggccaat    60
atgggagatg ggggagttgg atttggtctg attcgacact tttaaggact gagatttgaa   120
gatggagacc aaggctcaaa gggaatccat gccgtcttgg tttaatgctg caccctgcta   180
atgaaaatca ttactattag gtgtcatg                                     208

<210> SEQ ID NO 263
<211> LENGTH: 61
<212> TYPE: DNA
<213> ORGANISM: Corynebacterium glutamiucm R

<400> SEQUENCE: 263
agtcgaagca gcgctaaacc cctcacagag attgttctgt gaggggtttt agtttttact    60
g                                                                   61

<210> SEQ ID NO 264
<211> LENGTH: 100
<212> TYPE: DNA
```

<213> ORGANISM: Corynebacterium glutamiucm R

<400> SEQUENCE: 264
aggcaaagac tggaccagca accccaattg gttcggatat gcccatgaca ccgctgcaat    60
ttacagcttc cgccccaacc acaggtgaaa aggaataacc    100

<210> SEQ ID NO 265
<211> LENGTH: 187
<212> TYPE: DNA
<213> ORGANISM: Corynebacterium glutamiucm R

<400> SEQUENCE: 265
aatcgcaacc ctagttgagg gggaggattt agtgcatcat ctaaataaaa gtcagctaat    60
aggtgaactt tggtgagacc aaaggtgaac tgccaggtcg accaaattac tcgccaagca    120
gactccgaaa acacgggta attcatatgg cttgtatcta atccatactg aacagaggac    180
ctctcca    187

<210> SEQ ID NO 266
<211> LENGTH: 100
<212> TYPE: DNA
<213> ORGANISM: Corynebacterium glutamiucm R

<400> SEQUENCE: 266
gtgccttccg tcgactacgg ttaaacaaaa agcttttgt ccatttcact ggattcaccg    60
aaagaatgaa tccacactcg atcaccaaag gtagcgatga    100

<210> SEQ ID NO 267
<211> LENGTH: 100
<212> TYPE: DNA
<213> ORGANISM: Corynebacterium glutamiucm R

<400> SEQUENCE: 267
gcaacatccc attcaccacc tgggaaggct ggtacaaact cgacgcagca gagcgcgcac    60
tcggtgaagc cgaaggccgc gagcgtaaga agattgttga    100

<210> SEQ ID NO 268
<211> LENGTH: 100
<212> TYPE: DNA
<213> ORGANISM: Corynebacterium glutamiucm R

<400> SEQUENCE: 268
gaatctgatc tttcccgcac cgttgaactg ctgaaggcta agcctgttgt taaggcaatc    60
aacagtgtga tccgcctcga aagggactaa ttttactgac    100

<210> SEQ ID NO 269
<211> LENGTH: 130
<212> TYPE: DNA
<213> ORGANISM: Corynebacterium glutamiucm R

<400> SEQUENCE: 269
ttcaaactcc tttgaaggtt tgtgatccca gacacttcgt cgaggcgtga taccaatgaa    60
aactcataac gttgaaaatg tcaactatta gttttgaaaa cttacatcgt tcgcttgacg    120
cacagaatgc    130

<210> SEQ ID NO 270
<211> LENGTH: 100
<212> TYPE: DNA
<213> ORGANISM: Corynebacterium glutamiucm R

<400> SEQUENCE: 270
ctcagggctg gctgcactac tgcggttaag agtaaactct tggctaaaaa tcttctcacg    60
ttaactagtg tgccagctgg actcgtctaa ggtggggacc                          100

<210> SEQ ID NO 271
<211> LENGTH: 68
<212> TYPE: DNA
<213> ORGANISM: Corynebacterium glutamiucm R

<400> SEQUENCE: 271
agctctccta aaagaatcgt tgtattggaa tgaccctatt gtaaccgtgc aacgatagta    60
tctaagtt                                                             68

<210> SEQ ID NO 272
<211> LENGTH: 100
<212> TYPE: DNA
<213> ORGANISM: Corynebacterium glutamiucm R

<400> SEQUENCE: 272
taaccatcct cgtctcccta tccggccgtg gcgacaagga cgttgaccac gtgcgccgca    60
ccctcgaaga aaatccagaa ctgatcctga aggacaaccg                          100

<210> SEQ ID NO 273
<211> LENGTH: 100
<212> TYPE: DNA
<213> ORGANISM: Corynebacterium glutamiucm R

<400> SEQUENCE: 273
aagttgcgga aaccttttgac gttttgcaga tgacggcggc gattatgggc gatgtggcgc   60
cacttaacac cattcggggg cttgcgtgag cagcgtaagc                          100

<210> SEQ ID NO 274
<211> LENGTH: 100
<212> TYPE: DNA
<213> ORGANISM: Corynebacterium glutamiucm R

<400> SEQUENCE: 274
gggtggtggt cgcgttgatt gtgtcgctga atctcgcctt gatcggactg ctggtcaccg    60
gtcggggctg accggctgtg gtcttcggta gcgtgagtcc                          100

<210> SEQ ID NO 275
<211> LENGTH: 291
<212> TYPE: DNA
<213> ORGANISM: Corynebacterium glutamiucm R

<400> SEQUENCE: 275
gatttctcct taaatttaga gtgtgagaca cccataggct aggagagaat gggggagagt    60
ggcgctttga ggtgcctgcc gttgtgaata actattttga ggtacgcgtt acctgtggat   120
aactctcttt gacctggaag attggagaga tttaggggag gattgggcgt aactctagtg   180
cgatcagctt ttgaataagc gtttgaatat caccccttgcg ttcgaaaatg tgatcgggta   240
aggtggttgg tattagcacg gggaactaaa cgggaaaggg gggaagatac c             291

<210> SEQ ID NO 276
<211> LENGTH: 100
<212> TYPE: DNA
<213> ORGANISM: Corynebacterium glutamiucm R

<400> SEQUENCE: 276

```
aaccgcgccc aaaatcccgt cgcgatggcc aaatccatgt tccacgccgt tgaagccgga      60
agattagccg cccaagcagg ccgaatcccg caacgccaac                           100

<210> SEQ ID NO 277
<211> LENGTH: 100
<212> TYPE: DNA
<213> ORGANISM: Corynebacterium glutamiucm R

<400> SEQUENCE: 277
cttgctcttg atggccgcta cgcgcagctg tatcaacgat ggagtgctca atagttcgaa      60
tccgccacaa actccggaga tttggggtag aaacgaagac                           100

<210> SEQ ID NO 278
<211> LENGTH: 100
<212> TYPE: DNA
<213> ORGANISM: Corynebacterium glutamiucm R

<400> SEQUENCE: 278
tcggaacttg gcatcgacca cgtcatcttc aacatccagc gccgaccagc aagcgaagta      60
ctgacccaga tttacgaaga agtgctcccc cacctctaaa                           100

<210> SEQ ID NO 279
<211> LENGTH: 70
<212> TYPE: DNA
<213> ORGANISM: Corynebacterium glutamiucm R

<400> SEQUENCE: 279
gctttaaggc cctccggggc ctttttttgct tttcgacgcc tacctccttc ggaggcgtat     60
tctgtcgttc                                                            70

<210> SEQ ID NO 280
<211> LENGTH: 100
<212> TYPE: DNA
<213> ORGANISM: Corynebacterium glutamiucm R

<400> SEQUENCE: 280
gcacgtccac gcgccggact tgcgcgccta tttacaagca cgcttatcga cgtaattaca     60
ctcggtggaa accgtcgcgg aaaaatggag gatcctcgcc                           100

<210> SEQ ID NO 281
<211> LENGTH: 341
<212> TYPE: DNA
<213> ORGANISM: Corynebacterium glutamiucm R

<400> SEQUENCE: 281
gtttcgtggc attttaatca gttggggctt tccagaattt ctggagggcc ccatcttttg     60
tgcatttttc taaggggctt caatagcata tttaccttg aggagcgtga cagttttctc     120
tcgttttcgg tcagtgcgcg gttgcggggg tgaaaactag acttatgggt ctatttgatc    180
ataattcccc tgaactgcta ttatggtgta aaaatagaca gatctgttta atctttatag    240
acagcttcgg ttaatttggt cacactaatg caataaattc ctgtctacag cgttacagtt    300
aatgaattca attcaaccgc taaacgcaag gagtgctacc c                        341

<210> SEQ ID NO 282
<211> LENGTH: 98
<212> TYPE: DNA
<213> ORGANISM: Corynebacterium glutamiucm R

<400> SEQUENCE: 282
```

```
cgctgctcct gttaactctt ggctttctgc tctgtctcag ccatactgga ccttccagta    60
caggggaagg tcaagcgcgg ccacggaggg agacagca                            98

<210> SEQ ID NO 283
<211> LENGTH: 418
<212> TYPE: DNA
<213> ORGANISM: Corynebacterium glutamiucm R

<400> SEQUENCE: 283
tttcgatgga atgtggcgac cctcacgatc gcatgtcatg acaataacac attgtcctga    60
caaagcaata catttccgaa aattttctaa aacgattcac gaaaatgcgc aaaaccccag   120
gacaacgccc cggttttcat tcaaagattt tgcttgtcga cgaaaacccc ctcgctttgg   180
aaggtacggg gttaacaaag ttgcacgtta tgacctgcaa actctgccct tttcactaaa   240
tttcgctact cattccccaa tacaagtgat aatgtcagat caataaaagc cctggatgac   300
acaaaagtcc tgcataaaca cggattcacc aagaccacca cccgcaattc agttacattg   360
ttcaaatgtc ctaacacatt tacatgagct tgttgggcgg gcaacgaaag gagacatc     418

<210> SEQ ID NO 284
<211> LENGTH: 100
<212> TYPE: DNA
<213> ORGANISM: Corynebacterium glutamiucm R

<400> SEQUENCE: 284
cctatccaca cggcatgggc ggagtaggcc tggcacagca gacgctggat aaaggcgacg    60
ccaactaaac attaggacgc caaacattag gattggaggc                        100

<210> SEQ ID NO 285
<211> LENGTH: 278
<212> TYPE: DNA
<213> ORGANISM: Corynebacterium glutamiucm R

<400> SEQUENCE: 285
gggttgtttt cccgcactca acgcagtttt tgagtgcggg ttttttcatt ctttttttact    60 tttcaaacac gtataaacat tgctattcaa acaaatgggc acccctcaaa actcgcacat   120
acccagcaat tatcagaggt tctaataatc cccttagcct ctgctcgaat tcttgaaaac   180
ttcaataaac aggtgtccac catagggaac ataatctaca gctgcagcca aggttttttcc   240 taggctactg ccatattccc tctatttagg agactccc                           278

<210> SEQ ID NO 286
<211> LENGTH: 77
<212> TYPE: DNA
<213> ORGANISM: Corynebacterium glutamiucm R

<400> SEQUENCE: 286
catgcgccaa cagcaaatat tagtaaaatg ttagaaatag ctgtttttga ttcactttgc    60
gcatgtaggc tgtgacc                                                   77

<210> SEQ ID NO 287
<211> LENGTH: 100
<212> TYPE: DNA
<213> ORGANISM: Corynebacterium glutamiucm R

<400> SEQUENCE: 287
atgtgggtga gataaccgac cgtgatgtcg ccctagcaaa agtcatcgac gcccacgcca    60
agaccttgaa catttcggca gaggcttaag gttaaagatt                        100
```

<210> SEQ ID NO 288
<211> LENGTH: 128
<212> TYPE: DNA
<213> ORGANISM: Corynebacterium glutamiucm R

<400> SEQUENCE: 288
agtgtaaaaa gccgtccgaa ccaaaggtcc acacctctgc acgagtagaa gctcacccaa    60
gttttcaaag tgccgttgat tcttgacaac cacccgccgc tccttagagc agatttgaaa   120
agcgcatc                                                            128

<210> SEQ ID NO 289
<211> LENGTH: 100
<212> TYPE: DNA
<213> ORGANISM: Corynebacterium glutamiucm R

<400> SEQUENCE: 289
gccttactcc cgaggaagat cagcagctca ttaggatcaa cgcccttatc agcaaagtta    60
cccgtcagat tcgcattgtc actgagggag cagcaaaaca                         100

<210> SEQ ID NO 290
<211> LENGTH: 100
<212> TYPE: DNA
<213> ORGANISM: Corynebacterium glutamiucm R

<400> SEQUENCE: 290
atggtcgtgc cgaatttccg gtttggatgg gctttgggat gtaatgggag cggatcggcg    60
tgatcgtgcc ggttttctt gcgttggtag tcttggggct                          100

<210> SEQ ID NO 291
<211> LENGTH: 228
<212> TYPE: DNA
<213> ORGANISM: Corynebacterium glutamiucm R

<400> SEQUENCE: 291
attgagtcat cttggcagag catgcacaat tctgcagggc atagattggt tttgctcgat    60
ttacaatgtg attttttcaa caaaaataac acatggtctg accacatttt cggacataat   120
cgggcataat taaaggtgta acaaaggaat ccgggcacaa gctcttgctg attttctgag   180
ctgctttgtg ggttgtccgg ttagggaaat caggaagtgg gatcgaaa                228

<210> SEQ ID NO 292
<211> LENGTH: 183
<212> TYPE: DNA
<213> ORGANISM: Corynebacterium glutamiucm R

<400> SEQUENCE: 292
ttcaagcccc ccgtttcaat tgaaagtttg aactcggctt tgatgcgaa ttttccccca     60 attcgcaaac ttttcaatcg accttccggg aactcttcgt agccctttta cgacagttac   120
ataattgcag gttagagggt tcacaggcag ttccaatctg ccccaaatca cactcgtccc   180
att                                                                 183

<210> SEQ ID NO 293
<211> LENGTH: 100
<212> TYPE: DNA
<213> ORGANISM: Corynebacterium glutamiucm R

<400> SEQUENCE: 293
atcaggtgtt gcagcgttat ttgactgact tggggttgac tcctcagggt cgtaagaact    60

```
tgggtttgga ttctggggat gatgaacaag acgggtggtg              100

<210> SEQ ID NO 294
<211> LENGTH: 100
<212> TYPE: DNA
<213> ORGANISM: Corynebacterium glutamiucm R

<400> SEQUENCE: 294
agatctagcc aacgaacttg atttcatcga gctggaagag acagaggcag agcagcaatt   60
gaagtggctt ggccttatgc agttttttgg aagtagataa                        100

<210> SEQ ID NO 295
<211> LENGTH: 100
<212> TYPE: DNA
<213> ORGANISM: Corynebacterium glutamiucm R

<400> SEQUENCE: 295
cttgcaaaca ggcgtggtgg tggcgttcat tggctcacca attttccttt atttactgct   60
cagcatgcgc aagcgacgcg gattggggct gtaaaaactc                        100

<210> SEQ ID NO 296
<211> LENGTH: 251
<212> TYPE: DNA
<213> ORGANISM: Corynebacterium glutamiucm R

<400> SEQUENCE: 296
aatttagaaa atccgccgtt ccacacaagg aacggcggat ttttgatga ctaagtgagt    60 ttggatgcgg aagatttggg ctatttccat aaatcgaacc aggtgaccga gagttagaag  120
cctggagagg acggttcgct tggaatcttt cccctttgttc gagggtcctg cctttttatct 180 gggtggtgga gttatgaaaa acttgcgtat tagaccaaga gccgcttttt tcggggagtc  240
tttggtctcc a                                                       251

<210> SEQ ID NO 297
<211> LENGTH: 126
<212> TYPE: DNA
<213> ORGANISM: Corynebacterium glutamiucm R

<400> SEQUENCE: 297
atctacctct ttttcttaat ctcttacatc tttacaggaa acccttgac ggcatcaatg    60 ggtggtatct agtatcgact agaacgttat agtagaacgt tctagtaaaa cttggaagga  120
tgaaaa                                                             126

<210> SEQ ID NO 298
<211> LENGTH: 100
<212> TYPE: DNA
<213> ORGANISM: Corynebacterium glutamiucm R

<400> SEQUENCE: 298
agaacctgcg cctgctcgcc agctggacgg tcaccggtac tgataaaaca ggcactgaca   60
gggccttcca cccggcggac gatgtcccta gtctggagga                        100

<210> SEQ ID NO 299
<211> LENGTH: 238
<212> TYPE: DNA
<213> ORGANISM: Corynebacterium glutamiucm R

<400> SEQUENCE: 299
aacctgccat cttagtgctt aacaccactt gaatgggagg agttcgcgat agttcacagc   60
```

-continued

| | |
|---|---|
| atttaattca caaaaccgca gatagtagca ctctcccacc ctcaataggg ctcaacctgt | 120 |
| gcactgtaac ccatcgcccg tcaatcaagc tgtcaaaaaa aatacaagtt aggtcacaaa | 180 |
| atgatttcag tcgtgagaac catcacatat aaaacatctc atgatctaac atttcttc | 238 |

<210> SEQ ID NO 300
<211> LENGTH: 100
<212> TYPE: DNA
<213> ORGANISM: Corynebacterium glutamiucm R

<400> SEQUENCE: 300

| | |
|---|---|
| accaaccgcc acgcggtatc aataatttcc gctaggcggc cagtgggggga tcgggaaaaa | 60 |
| tcactggtct ttagactcca caaaatttgc aagtgcttta | 100 |

<210> SEQ ID NO 301
<211> LENGTH: 483
<212> TYPE: DNA
<213> ORGANISM: Corynebacterium glutamiucm R

<400> SEQUENCE: 301

| | |
|---|---|
| cccataccag ccccaaccag acaggcctga caagattcga gaatttccac agcttttggc | 60 |
| acgtgtgtct ggttttttgct cccgataacc ggacaggtgt gccaaaatca tagactttc | 120 |
| gccaatcttg tcacgcctgt ctggcccgaa tcagcattcg aacgccatga ccaaaccaca | 180 |
| ctgcccacgg ctcaggtttt cccggttcat gggcagcgtg gtctggtttc gacggcttga | 240 |
| aaccagacac aaatgcccag agttgtcgaa tttccagttc gtgggcactg tggtttggtc | 300 |
| gagcttaaaa ttggagccgg aactcaaaaa acttgcccct tcagaatcgc gtctaaggca | 360 |
| cgatcgcaat gtgatctata caaacacccg tttgagaatc tcaacctctt aaaacagcgc | 420 |
| agactattga tttggcaact accctatata tttgagtgtt tattgtcgaa aaggggttt | 480 |
| caa | 483 |

<210> SEQ ID NO 302
<211> LENGTH: 800
<212> TYPE: DNA
<213> ORGANISM: Corynebacterium glutamiucm R

<400> SEQUENCE: 302

| | |
|---|---|
| gatttcctcg ttcccatctc ggctgcatgc gcgcacgatt ttaaagtgtg tatctgggcc | 60 |
| atttagtgat gttggtggtt cccattgagg gcaccatgta catcctaggc gtttgctgga | 120 |
| gcaaatacc tgtgaaaaat ctgatcctga aaatttttaaa aactgcgttc acatcaaccg | 180 |
| gcttgtcata cctaacggtt aatagtttta aactacggat gccctaaaga gcaacttctt | 240 |
| gctttgagac ttaactcacc gcgggcattt atgctggtaa atgctcacgt tcaattatgg | 300 |
| cagcgtcgca cagatatgac cacaaagaat taaaattgtt tgaaaatttc tttaggttta | 360 |
| tcaattttgt accgccaaaa cgcgcggtaa ctgcatgaag tctcttcttt aattaaattc | 420 |
| atccgaccag cgaatgagac cagttgactg actggttata taacctggcc acacttgagc | 480 |
| gccctcaaat ggaattggaa cgacttttat aggcgctaca tcggagaaat ttgacccgtt | 540 |
| tttcacaatc tcctagagct cccgaggcta gctagaacaa cgcacattcg ggcactttcc | 600 |
| gaccttttcg atagccgtat atgccatgga cccactcctc aattgggcga ccgttagact | 660 |
| tgaaacacca aggctagaga tttaactaa agagtctcct catggattcc catttggagc | 720 |
| cttatttaca caggccacct ggcttgtttc ccaccgcgat gtgccacaat aacgccataa | 780 |
| cagaaaggca tactgacaca | 800 |

<210> SEQ ID NO 303
<211> LENGTH: 1000
<212> TYPE: DNA
<213> ORGANISM: Corynebacterium glutamiucm R

<400> SEQUENCE: 303

| | | |
|---|---|---|
| ttagcgttca acccgtcaac aaatgttgcg tcaacagtca acttcacgta acattaagac | 60 |
| atgccacgaa aggagaaaca catgcaagac aagcttttgg gacgccaaca agcggcccac | 120 |
| attctcggga tttccctgtc caaactcgac gaactcaggc attccggcca catcaaatac | 180 |
| ggccacatag gaagccgaat cttcatccca caatccgagg tcaacgcatt catcgaagaa | 240 |
| gtcatgcggg catgaaaata ccccgacaca ggaaacattt ggactgccat ccaaggtgca | 300 |
| tgttaacggc cagggtatgc gcacgaaact aaggagaatc aatgcagttt gattataaca | 360 |
| caccaagcga tgatgaaaca ttgccagaac gcaaagagcg actgcgttcg ccccacacta | 420 |
| tccaaaggct tgtcattgaa gcagcaatgc tgaaaaggct ttacgcgctc cacaatgact | 480 |
| tcaaagccga agttgccgaa gcgctcaacc ctggcgattc cattaaggca aaaaatgcgc | 540 |
| aggcgctaga cattgggaca gtcaccatgt cgtcgccaaa taacaaggct gtccctactg | 600 |
| atgagtccat tttggtggcg gaagcgcagg aacgtggcat ggagctggtg gaccgcctgc | 660 |
| caaacaacga caccccctgaa gctgttgcaa ttatagacta cctgctggag cacgcagcgc | 720 |
| acctactgcc agcccccacg gtctccaaag atgatttaga gactatcgct aaggacgtgc | 780 |
| tggaagcgtg gcaggagaca ggccggaaac ctttgggctg ggaaatcaaa caagcatcca | 840 |
| ccccatccat atcagttcgg cctggcacgt caaaggtcgc taaagcggca attgaccaca | 900 |
| tcgtcggtga agttcaccaa ctcctcccgg agactcccca actcgaaaag aagaaagaag | 960 |
| cctaaccatg actactgttg ataagtacga aaattctgga | 1000 |

<210> SEQ ID NO 304
<211> LENGTH: 100
<212> TYPE: DNA
<213> ORGANISM: Corynebacterium glutamiucm R

<400> SEQUENCE: 304

| | | |
|---|---|---|
| aaacgtattc cttgatctgc gcatcaaggt gctgaagaac tggcagtccg atccaaaggc | 60 |
| tttgaaccgc ctgggctttt agctttaagg gggtgagttc | 100 |

<210> SEQ ID NO 305
<211> LENGTH: 100
<212> TYPE: DNA
<213> ORGANISM: Corynebacterium glutamiucm R

<400> SEQUENCE: 305

| | | |
|---|---|---|
| ttcatcatgg cactgcccgg ctccacgggt gcggcgcgcg atgccacggc tgtcctcgac | 60 |
| ccgctcattg atcacatcac tggaactctg caaggccacc | 100 |

<210> SEQ ID NO 306
<211> LENGTH: 99
<212> TYPE: DNA
<213> ORGANISM: Corynebacterium glutamiucm R

<400> SEQUENCE: 306

| | | |
|---|---|---|
| gtttgctcct taaaacacca atacttctcc tccatctttc cctcaaaagc aattctgcgc | 60 |
| acgagatacg gcaaaattca cggagtaggg tggcttaac | 99 |

<210> SEQ ID NO 307

```
<211> LENGTH: 100
<212> TYPE: DNA
<213> ORGANISM: Corynebacterium glutamiucm R

<400> SEQUENCE: 307
ctggagattt ccgatttcca gcgcgcccgc atcgacgcga atgctcagga attgcaggcc    60
gagcgcgagg cagtgcgcga cttgctctaa tctttaacgc                         100

<210> SEQ ID NO 308
<211> LENGTH: 763
<212> TYPE: DNA
<213> ORGANISM: Corynebacterium glutamiucm R

<400> SEQUENCE: 308
tccaattggg cacacctcct tagcaaccac gctatgcgag agttgcagct cgacgagagc    60
aaagatggca ggattgatca ccaggatcga tctttaaata aggactattt cttacctgga   120
agtaacattt tggccgttga ggataatacc tttggtgcat tttgagccaa aaaattcttg   180
gcctctggat taatagttgc caccacagca ctcgcaacca aaactgagcc tataataaat   240
gcttctttat ttatctgcag tgattgcaga ttaaatcttt tgttgttgac gtcatgctcc   300
ataagcttgt cgtcaaggcg ttctagccga tcgaaagcat ctcggcgact ttcttctgat   360
gaattagggt cgctaataac ttgcgtaagt atgcttttcg tcttatcaaa actgtcataa   420
agcctatctg agctgtattt attgctagat agggcctgtt ggaaagaatc ggccattgct   480
tgagacactt tcaccatagt gttatgagac acgccctaag ccaccgtggc ctccgctgca   540
atcatcaggg gatcatcagg ggatgacggt gagtattcca cctaccaaca accgcagtga   600
gggcctccag tgtccaggac gcgagatgtt ttcctgaccg cgtgtgggaa ggctggtttt   660
atgaagtcgt cggcatttttt cgcttggatg acctgggggt ggcacttctt accggtactg   720
gcaggccctc ctttccgggt gggcgctgat ctagcatgga gac                     763

<210> SEQ ID NO 309
<211> LENGTH: 100
<212> TYPE: DNA
<213> ORGANISM: Corynebacterium glutamiucm R

<400> SEQUENCE: 309
tggatcgtcc tcgccttcac attcgtcggc cttggccttg ctctcctcgc gatgaagcaa    60
tggcgattcc gcgtcagcta ctgggtataa ggagcaccac                         100

<210> SEQ ID NO 310
<211> LENGTH: 100
<212> TYPE: DNA
<213> ORGANISM: Corynebacterium glutamiucm R

<400> SEQUENCE: 310
cgaaaccatg ctcggcggta gacagctggg ctaagcggtt ggctaattga gcaacggaca    60
tggacaccca ccttagttcg gcgggttaag ctgtgtaacc                         100

<210> SEQ ID NO 311
<211> LENGTH: 100
<212> TYPE: DNA
<213> ORGANISM: Corynebacterium glutamiucm R

<400> SEQUENCE: 311
ccacctttga acgtgagggg atcttggagc gtgatgagta tgactcgcta gtgattggtg    60
actttggttc tgctgtgctc aaccacgtta ggagtgggat                         100
```

```
<210> SEQ ID NO 312
<211> LENGTH: 52
<212> TYPE: DNA
<213> ORGANISM: Corynebacterium glutamiucm R

<400> SEQUENCE: 312
gatttaagtg aatatcgcga tgaaacagca ggtggggaaa gattttcaac cc            52

<210> SEQ ID NO 313
<211> LENGTH: 100
<212> TYPE: DNA
<213> ORGANISM: Corynebacterium glutamiucm R

<400> SEQUENCE: 313
ccgccatctt ttcttcttgg atgttgtggg cgttgggctt aagtctcgca atcattctga   60
tcactttgct gtggatcgtc cgacgcaaga aaggccctca                         100

<210> SEQ ID NO 314
<211> LENGTH: 100
<212> TYPE: DNA
<213> ORGANISM: Corynebacterium glutamiucm R

<400> SEQUENCE: 314
ggcgggaaat tacaatcagg catcggcgtt gtcgttgatg tttgcgatta tcggtatcgt   60
ggcgctcgcg ttgacggtgc gcagccagaa ggagttttag                         100

<210> SEQ ID NO 315
<211> LENGTH: 100
<212> TYPE: DNA
<213> ORGANISM: Corynebacterium glutamiucm R

<400> SEQUENCE: 315
ctccaccctg gcgaatagaa caaacaaggt tcttcgcatg aaggactacc acccagaact   60
gaaggtctaa aagcttttcc cgcccggttc aatagcgtta                         100

<210> SEQ ID NO 316
<211> LENGTH: 52
<212> TYPE: DNA
<213> ORGANISM: Corynebacterium glutamiucm R

<400> SEQUENCE: 316
attgtaggta gtctcgtggg cacaactgaa atcttattga aaaggagtgt cc            52

<210> SEQ ID NO 317
<211> LENGTH: 100
<212> TYPE: DNA
<213> ORGANISM: Corynebacterium glutamiucm R

<400> SEQUENCE: 317
gtcacctcac caccgaggac ttccagaacg aaggcgcaga ccacatcatc gattctgtag   60
cgatcatccc agcgttgatc ctcaactagg cataaaactc                         100

<210> SEQ ID NO 318
<211> LENGTH: 100
<212> TYPE: DNA
<213> ORGANISM: Corynebacterium glutamiucm R

<400> SEQUENCE: 318
tgggcggtgc acttcttgct ctgtctgatc cggaggctga gtgggaggaa atccgcgtta   60
aatcacggcc tctgctgaat ttatttgggg ttgaattccc                         100
```

<210> SEQ ID NO 319
<211> LENGTH: 100
<212> TYPE: DNA
<213> ORGANISM: Corynebacterium glutamiucm R

<400> SEQUENCE: 319
gctggctatc ctcaattccg ctcgggtcgc agtgccacgc ggagcgatta gtgattttga    60
tacgcaagaa aaagtttctt agcagggtaa cctaaatgtc                         100

<210> SEQ ID NO 320
<211> LENGTH: 82
<212> TYPE: DNA
<213> ORGANISM: Corynebacterium glutamiucm R

<400> SEQUENCE: 320
ctctcgaata ggccatttct tacttcatcg acaatactgg cttagtagaa aatgctgtcc    60
agaactgttg aaggagttga aa                                            82

<210> SEQ ID NO 321
<211> LENGTH: 100
<212> TYPE: DNA
<213> ORGANISM: Corynebacterium glutamiucm R

<400> SEQUENCE: 321
ctgccggctg ggtaagaaaa ggtcgtggcg gcgtttatga agtccccact gagcggatca    60
tcccgctact aaccatcatt tctgccagtg agaatcacta                         100

<210> SEQ ID NO 322
<211> LENGTH: 766
<212> TYPE: DNA
<213> ORGANISM: Corynebacterium glutamiucm R

<400> SEQUENCE: 322
actcccgggt tttgcttggt tttccggata ccgtcctatt tgaccgacgt ctggggtggg    60
gtggatcttt cggccacctg gtcgaatttt cctcaacccc actacccaga aagtacaaag   120
agcacaggag ccgttttata aggatcaaat ttctcagaga ggtataattg aagcatttca   180
gcctcttata tacgatcctg agaggaccct gattctagag ttccagatag taattgcagg   240
ctgactgtca tatctgacca aaaccgacct cgccaatccg agtcttggcc tccaacgtat   300
atttcggctc cgaatatgtc tgaacatccc aataatatcg acaatacgat atatttttta   360
tgcatgcctc tcgaaaataa ttcgaatctt caaaagattg aaggttacgt ctcaaaaatc   420
accaaaaaaa cggcaacaaa gtcactaacg attccttaag ttctggggcg tgcgacacca   480
aaatggaacg ctggaagagc tagtaaagaa ccgcgtctag ttaaaagccc atcaaaactc   540
aattcatttg cgacttcagt aataggtgac gtcactaaat caattaacct aaaagggcgt   600
caatcacctg tttgaagtag tgattcctag atctataaat aactggaaag aacgcagagc   660
tgaaaaaaga cgcacagaag ctacacacat agctacatcg tcagcaccaa agccggaaca   720
agaactacag caaccgacga cactcaacga gcgcgacctc caagac                 766

<210> SEQ ID NO 323
<211> LENGTH: 100
<212> TYPE: DNA
<213> ORGANISM: Corynebacterium glutamiucm R

<400> SEQUENCE: 323
gcaagtggaa ccacgatggg aacggtaact gctgccgctg cggtattact cgtagtttca    60

| | |
|---|---|
| gaaattaggt gtcgatgcag caatacggaa ctttgccaat | 100 |

<210> SEQ ID NO 324
<211> LENGTH: 53
<212> TYPE: DNA
<213> ORGANISM: Corynebacterium glutamiucm R

<400> SEQUENCE: 324

| | |
|---|---|
| cggattgaac ccaagacggt tttcttcgcc ggggagctcg accccggaaa ccg | 53 |

<210> SEQ ID NO 325
<211> LENGTH: 65
<212> TYPE: DNA
<213> ORGANISM: Corynebacterium glutamiucm R

<400> SEQUENCE: 325

| | |
|---|---|
| aaattcgctt ttcgacgcct ccctcaatgc gacgcttaaa gcatctacgg acctttgagg | 60 |
| tcacc | 65 |

<210> SEQ ID NO 326
<211> LENGTH: 100
<212> TYPE: DNA
<213> ORGANISM: Corynebacterium glutamiucm R

<400> SEQUENCE: 326

| | |
|---|---|
| gcctgtggca cgggagctcc cagcggcaag gtgagtctga cctcgtggaa cgttggcgaa | 60 |
| cgccccgctg cgatgttccc accaaggaag gactaggcgg | 100 |

<210> SEQ ID NO 327
<211> LENGTH: 100
<212> TYPE: DNA
<213> ORGANISM: Corynebacterium glutamiucm R

<400> SEQUENCE: 327

| | |
|---|---|
| gctgaggttg agacccagct gaacaccatc tacacccgcg acatcgaacc acttatttaa | 60 |
| tccgagcact tcagctacac ctatttaagg aggctgtgac | 100 |

<210> SEQ ID NO 328
<211> LENGTH: 438
<212> TYPE: DNA
<213> ORGANISM: Corynebacterium glutamiucm R

<400> SEQUENCE: 328

| | |
|---|---|
| tggcatggcc agctaagaaa ttcgaaccga cttcattgat ccttggctcg actcgctcag | 60 |
| cgacgaagtt tatgacgcag tacttgccgc cattgaatac cttgccgagc aggggccgac | 120 |
| ctgcggacgc ccattcgtta ataccatctc acaatccaga cataagaaca tgaaagagct | 180 |
| gcggccccgc gaaaaatcac gcgctaagaa catcaggatc gttttcggct tcgatcccca | 240 |
| ccgacatgca attttcttgg tcgccggaga caagaccagt caatgggata agtggtacag | 300 |
| caagcacata ccagagcaga tgaaagattt ggctaccacc tcaaacaact caagaaaggc | 360 |
| aactaacagc tacctactca gggagaaccc gttaatcgaa acaggtacca ctcacccaca | 420 |
| atctttaagg agaacccc | 438 |

<210> SEQ ID NO 329
<211> LENGTH: 100
<212> TYPE: DNA
<213> ORGANISM: Corynebacterium glutamiucm R

<400> SEQUENCE: 329

-continued

```
gacggcgcca actctgcatt cttcgcctca gcgtgcgtgg cagtgtttgc attgatcgtg    60
ggcttctttg taaagaggcc agcccactaa gctaggtcgc                          100

<210> SEQ ID NO 330
<211> LENGTH: 65
<212> TYPE: DNA
<213> ORGANISM: Corynebacterium glutamiucm R

<400> SEQUENCE: 330
gttaatagcc cgcacccacc gcccgcgcgt ttaccccagt tctactggga ttagaatggc    60
taacc                                                                65

<210> SEQ ID NO 331
<211> LENGTH: 70
<212> TYPE: DNA
<213> ORGANISM: Corynebacterium glutamiucm R

<400> SEQUENCE: 331
taaaactgcc ctggttgcaa caattggcaa caagtagata tcgctcagtg tgacgggtga    60
tcataaagtt                                                           70

<210> SEQ ID NO 332
<211> LENGTH: 100
<212> TYPE: DNA
<213> ORGANISM: Corynebacterium glutamiucm R

<400> SEQUENCE: 332
cacaaattga atgatgctc agggaacaat tgcgcaaggc gggtcggttg cctaaaaata     60
ttgggaacat tccgaaacca ggccgaccca aggagaatcc                          100

<210> SEQ ID NO 333
<211> LENGTH: 226
<212> TYPE: DNA
<213> ORGANISM: Corynebacterium glutamiucm R

<400> SEQUENCE: 333
atcttctaac tgctttcttt aaagcacccg cacatgtctg ttgaggtttc acctgtggag    60
acaatctctg ccttcacgga ttcgaactga cacagttgaa ggcatgtcgg gtgctttgcg   120
tattctttgc cagtgtgatt taggcgacac cattaattta ttgggtatcc accaattacc   180
gctgtgagca ctgcaaatta cgtattcgaa agccatgtc caccac                   226

<210> SEQ ID NO 334
<211> LENGTH: 343
<212> TYPE: DNA
<213> ORGANISM: Corynebacterium glutamiucm R

<400> SEQUENCE: 334
gtgctgaact atacagctgt tgctgaacta acttcaacat ggggtggcgt cgttgccaga    60
ggtcgtctgc actttcaggc tgaggccttc actgcgcaag aaggaagcag ctgcctagtt   120
ggcggtgttc ccgacgtgat ttaaaggtga gggctatcgc cggcagcttc cggcccaggc   180
cagcggcgac ccacgtaccg atcaaggtgt cccacttcct aggaagtggg acacccttaa   240
tgaaaccaat tgaaaatgca tagtcccaag agaaaactgt tccacaagct attccaacga   300
actgtctcac gaaccctgct acagaataga cttccggtac gct                     343

<210> SEQ ID NO 335
<211> LENGTH: 100
<212> TYPE: DNA
```

<213> ORGANISM: Corynebacterium glutamiucm R

<400> SEQUENCE: 335

```
cacttgctga agacgcccac atcgaagacc ttgcagatgt aaacgcaaac gcctaactgt    60
ttttcgagct aaacccatcc ttgaaaggat cttttccacc                          100
```

<210> SEQ ID NO 336
<211> LENGTH: 517
<212> TYPE: DNA
<213> ORGANISM: Corynebacterium glutamiucm R

<400> SEQUENCE: 336

```
gtcccgaaac tcttgagccg tcggctggcg acgcccctgg gtgatttgtt ctgcattcac    60
tggaaactta tctcgctttc atatccctcg agcgggagtc ggtgatcggc cactctctaa   120
gcaatgccgg ctttaaaata agcaacttat atgtttctc accacatctg gccgacgacc    180
gcgaagtatg ttgtcgatca cagctaaacg tgtgaatgtg aagttaccta actcacattg    240
caatgcgata gcgatttgga aaactcgctc ccccaatac cttaacttga acttaaaagt     300
agtgttttac ctgcatttat aaagttccc gatctacccc ctctttgccc cgaaatacccc    360
cttttgcaaa gattgcaaac acaacagtgc aatagttaac gggcttcaca tatcaccatt   420
ctgtctggtt ttaggctatg ttcgggtcgt ttaggcaaaa atagttttgt gggatgaaac   480
gcataatccc tcagttttgc gcaatcgata gcctgaa                            517
```

<210> SEQ ID NO 337
<211> LENGTH: 180
<212> TYPE: DNA
<213> ORGANISM: Corynebacterium glutamiucm R

<400> SEQUENCE: 337

```
aagcgattct gcacattttt taacatcccc aaggcgtgat ttcgattttc ggaatcacgc    60
ctttcctatt tccgcgttaa ataccaggt caacacacac aggaaccgtt cagaaacctt    120
ccagattact cagttttttaa tttcactttt ttgagaagta ttacttttat attagttctc   180
```

<210> SEQ ID NO 338
<211> LENGTH: 441
<212> TYPE: DNA
<213> ORGANISM: Corynebacterium glutamiucm R

<400> SEQUENCE: 338

```
gatctcgcac cttcctgcat taaaactcta aagtttaat aataagacta gtataaatcc    60
cttacgcttt tacgcagggg tcattcaccc agtcagattt tggtcccacg ggttttcacc   120
atcctagcaa ctagaacccc tcaaaccctg atccccctcag aaactgacag ataacaccta   180
ctgctttaac cccgtcctga cctgcaaaaa caagttatct acaagaattc accggagatt    240
cacctcaaca cataaccgca ggtcagaacg ggcgtactgg caggagttcg cctgcatatg   300
gccatttagt cagctttgct tcactaacaa gtcacaattt gttcatcatt gcggtcgaca   360
ctgttgtctc gggcgaacac cccacatcag agaacgcgat caaagctata aaaagtagct   420
gacaataggg agtatttgaa g                                             441
```

<210> SEQ ID NO 339
<211> LENGTH: 100
<212> TYPE: DNA
<213> ORGANISM: Corynebacterium glutamiucm R

<400> SEQUENCE: 339

```
ttgactatct cgaattaggt gagggctggg agccagaaat tttgtgctct gatgctgttg      60
aaattttaga aaatctcatc aaggaactaa ggggaattcc                           100

<210> SEQ ID NO 340
<211> LENGTH: 100
<212> TYPE: DNA
<213> ORGANISM: Corynebacterium glutamiucm R

<400> SEQUENCE: 340
ctcgcagaga tcgccagcgg ctggctagaa attgaagcca agcgccgggc gcggaaggcg      60
ctggctgagg ccttcggcgc ggaggtccag ccactgccgc                           100

<210> SEQ ID NO 341
<211> LENGTH: 100
<212> TYPE: DNA
<213> ORGANISM: Corynebacterium glutamiucm R

<400> SEQUENCE: 341
tttttctgca gtgaattccg aggttgatca gttgattgag tatatgaccg ttcatgcgga      60
gagctatcgc agttagtccg ctcgcacttc ggaggccttg                           100

<210> SEQ ID NO 342
<211> LENGTH: 100
<212> TYPE: DNA
<213> ORGANISM: Corynebacterium glutamiucm R

<400> SEQUENCE: 342
ccgacaatcc agtggaactt ccctatcgct gtgatgcatt tttactttca cgttccggta      60
ccctggcagg cagatcttcc aatctttagg agccctcgcc                           100

<210> SEQ ID NO 343
<211> LENGTH: 54
<212> TYPE: DNA
<213> ORGANISM: Corynebacterium glutamiucm R

<400> SEQUENCE: 343
tggtaatttc tttcgctaat agtcaaatga tcatttgagt gttagtgttt tctc            54

<210> SEQ ID NO 344
<211> LENGTH: 111
<212> TYPE: DNA
<213> ORGANISM: Corynebacterium glutamiucm R

<400> SEQUENCE: 344
aacgacaatc ctagaagcct tcggtcaata aatttcagca aattcccgat ctccacgacg      60
cgtcatctca attccaccta ggcttggacg caggttagaa aggagccttc g              111

<210> SEQ ID NO 345
<211> LENGTH: 272
<212> TYPE: DNA
<213> ORGANISM: Corynebacterium glutamiucm R

<400> SEQUENCE: 345
aagcgagatt ttgccagact tgtccagggt ttctgaaatt tatatataca agtttgggaa      60
aagttaaccc aatcttcact tttgagctga aagtatcca aaactccacc gaacagacat     120
tgacttattg gttttatgaa gtttttgaac gcaaaaggaa tttaataaga aaaagcccct    180
tcgattcaag aattttcatg tagagtaatg aaacaaatat ctacaagttt taaaattgaa    240
gtccaaaatc tagacaagtg tccaggaatc tc                                   272
```

<210> SEQ ID NO 346
<211> LENGTH: 100
<212> TYPE: DNA
<213> ORGANISM: Corynebacterium glutamiucm R

<400> SEQUENCE: 346
gcgggagtgg acgggccgcc agccatcggg gcgacaatca cgggagtttt caacgtgtca    60
aggatgctca tgtcaccatc ctaggcgcgc ctgccatagg                          100

<210> SEQ ID NO 347
<211> LENGTH: 100
<212> TYPE: DNA
<213> ORGANISM: Corynebacterium glutamiucm R

<400> SEQUENCE: 347
ttgagcgatc acagcaccga gatctgtgct gaagaattca atgattgggt tgatgattgc    60
gttgaagtcc atgtctaaca gggtagtaca aaagccaaaa                          100

<210> SEQ ID NO 348
<211> LENGTH: 100
<212> TYPE: DNA
<213> ORGANISM: Corynebacterium glutamiucm R

<400> SEQUENCE: 348
gcgtttagct ccaagaaagt cagtgctgtg catggctcgg tgctgctcat gcttttcggt    60
gtttacatga tgagcatgtt cgcctgattt aggtagcctg                          100

<210> SEQ ID NO 349
<211> LENGTH: 100
<212> TYPE: DNA
<213> ORGANISM: Corynebacterium glutamiucm R

<400> SEQUENCE: 349
agcatcacga caagccttga tcgacgaagc gctcaaccag caggagcaga agaaccacgg    60
cctgccggtc tactctggcc caacgtcggc ggtggaataa                          100

<210> SEQ ID NO 350
<211> LENGTH: 174
<212> TYPE: DNA
<213> ORGANISM: Corynebacterium glutamiucm R

<400> SEQUENCE: 350
acttcgttcg aaactctagg cccgcattag aacaaggatt tgtgcgcttt tcctgttctg    60
gtgtgggttt tcctcacatc taacaatcga ataactgttc gaataaaagg ttgaaggtgt   120
cccaccccca cggcacaatg gatggcaaga acacatgaat ccaggggat actc          174

<210> SEQ ID NO 351
<211> LENGTH: 256
<212> TYPE: DNA
<213> ORGANISM: Corynebacterium glutamiucm R

<400> SEQUENCE: 351
tcacgggtgt ctgagattcg caagcaacgg ccgagttaga accactacgt aggcgtgtcc    60
caccatcacc gcgtcgaaaa gcgccctctc ttaaccccg caaggggta acttttacgc   120 gcacgcgtgc aacgcgctag ttttgacggc agtccccacg ggcgcccgag cacgggctga   180
gatcgcgctg attgctgcgc gagcaccgtt tgaacctgtc cggttagcac cggcgaagga   240
agagaggaat ggtgca                                                   256

<210> SEQ ID NO 352
<211> LENGTH: 100
<212> TYPE: DNA
<213> ORGANISM: Corynebacterium glutamiucm R

<400> SEQUENCE: 352
ccggcgacca gggcgcggga gatgaatgaa acgtcaaaag gcactatgag ggcgtcaata      60
aaaaacttca tttgaaaatg ataaccgtta tcattaagga                          100

<210> SEQ ID NO 353
<211> LENGTH: 100
<212> TYPE: DNA
<213> ORGANISM: Corynebacterium glutamiucm R

<400> SEQUENCE: 353
tcctcggcac ccgctacccc gtcggagttg tcaccggcgc attcggcgcc ccattcctta      60
tctatttact cattcgttcc aaccgcgcgg gagtaaccct                          100

<210> SEQ ID NO 354
<211> LENGTH: 100
<212> TYPE: DNA
<213> ORGANISM: Corynebacterium glutamiucm R

<400> SEQUENCE: 354
tgcagatttt acgtcgcctg cgatcggggg atccggcgca acgtcaagcc gtggcctttg      60
actctgtctc tggtaaagaa gcagttgcgc gctagaaacc                          100

<210> SEQ ID NO 355
<211> LENGTH: 170
<212> TYPE: DNA
<213> ORGANISM: Corynebacterium glutamiucm R

<400> SEQUENCE: 355
ttactgaaag ttctgagcta acacccgcc gcgcttcaat gtggcgggtg tctagtttta       60
gggaacccca tacgaatcgc atcaatctaa tgaaagtcca cgctcagtat ggtttgctta    120
ttaaatctat ccccatttag aacatttgat gcccaacagg agtccgcgca                170

<210> SEQ ID NO 356
<211> LENGTH: 100
<212> TYPE: DNA
<213> ORGANISM: Corynebacterium glutamiucm R

<400> SEQUENCE: 356
ccatcatcgg cgcgcttgga tggtttggaa tgttcgcagt ttgtctgtgg agcacgctgt      60
aaaaggacgt taaaaaccag ccgttgctga ggagaaactc                          100

<210> SEQ ID NO 357
<211> LENGTH: 100
<212> TYPE: DNA
<213> ORGANISM: Corynebacterium glutamiucm R

<400> SEQUENCE: 357
ccggccgcga tgccaccaga gctctgaaag ttctccttgg tgtctatgaa tcagcaacca      60
cccaccagcc ggtctctttg atctaacgga agcttttaaa                          100

<210> SEQ ID NO 358
<211> LENGTH: 100
<212> TYPE: DNA
<213> ORGANISM: Corynebacterium glutamiucm R

<400> SEQUENCE: 358

```
catcaaagtg accgccggcg gcgtcgaatg gtccgttgca ggaaacgcgg aagcagttag    60
tgagatctcc gaaactttaa gcgcactaga ctaacaacac                         100
```

<210> SEQ ID NO 359
<211> LENGTH: 155
<212> TYPE: DNA
<213> ORGANISM: Corynebacterium glutamiucm R

<400> SEQUENCE: 359

```
acgcccacat ccctctctct tttccaggac aatttcctgg taggagagat ttgtcgttgt    60
ttgatctagg tcaaggaatt aacccggaaa ggaccgtatc tttaaaggtg caagcacagg   120
aacatgacga taaagatga aaggacctgg ttacg                              155
```

<210> SEQ ID NO 360
<211> LENGTH: 319
<212> TYPE: DNA
<213> ORGANISM: Corynebacterium glutamiucm R

<400> SEQUENCE: 360

```
ttcttaggtt taaaatcgct ggacaatggg atattcaatt gtttggctcg agcttatgta    60
ctagagaatc ccgcatcaat cccgtctcaa tcttgctttg attttgcttt gattgggcgg   120
gattgcttat tgaaaagacg tattcgagat tgatcgaatg cgtcttttgt caacccttag   180
tgggctcagc ctgtggacaa ccctggatgg ggactgctta ccacaggtg aggactggag    240
atgtttgaag cccgcgataa aacccacgttg aatctgaaag cacagcttaa tcagactttt   300
aaacaatcgt ggggggacag                                              319
```

<210> SEQ ID NO 361
<211> LENGTH: 100
<212> TYPE: DNA
<213> ORGANISM: Corynebacterium glutamiucm R

<400> SEQUENCE: 361

```
tacaacgagt acaacgcttt cgaccagcaa gtattcacct attccgctga cagctacaag    60
cccaccttct aacccgccta tatataagga gtgaatcacc                         100
```

<210> SEQ ID NO 362
<211> LENGTH: 100
<212> TYPE: DNA
<213> ORGANISM: Corynebacterium glutamiucm R

<400> SEQUENCE: 362

```
tctatcgcgc agggattaa gcagctgcga gcaggcaaaa ccaccattgt ggtgagttct     60
tcgcccgcgt tttacaactt ggcggatcgg gtgatttcac                         100
```

<210> SEQ ID NO 363
<211> LENGTH: 100
<212> TYPE: DNA
<213> ORGANISM: Corynebacterium glutamiucm R

<400> SEQUENCE: 363

```
tccgcagtgg aaaaactcac tcgcccaggc tgcgaaaacg cccgcgacac cgtggaaggg    60
gagacaccag cgacttttgc gacatcataa atggtggctt                         100
```

<210> SEQ ID NO 364
<211> LENGTH: 100
<212> TYPE: DNA

<213> ORGANISM: Corynebacterium glutamiucm R

<400> SEQUENCE: 364

```
aggggagccc tgtggacgct gtggcacaca gatcgtccgg gaaaacttca tgaaccgtgg      60
atctcactac tgcccaaact gccagaagcg gcgctagctg                           100
```

<210> SEQ ID NO 365
<211> LENGTH: 135
<212> TYPE: DNA
<213> ORGANISM: Corynebacterium glutamiucm R

<400> SEQUENCE: 365

```
ttctccttaa tttttgggca ttgaccttgg agtttacgcg gatgtgtgag ggaaatctgc      60
tcgatctcgc caatggtatt accctccgtt gtcaggtagg tagaccgggc tacctacctg    120
tcaaggaggt gcgac                                                     135
```

<210> SEQ ID NO 366
<211> LENGTH: 403
<212> TYPE: DNA
<213> ORGANISM: Corynebacterium glutamiucm R

<400> SEQUENCE: 366

```
gtcaatctcc ttggatcgtg gtaggaccgt gagaagacac cgcctcaagg tcgatgccat      60
acattttcta gcacgggtgc ctgacggccc agaaatcaaa aaccctgctc acagccttat    120
aacaggcgga aaggggtgtg actccggtgg gctgggtcac caccgggaca ccaccccaca    180
gccgtgggcg atgtccttct acccgccccg ggtatgcggt gcaggcagtg aaatccctgg    240
tggcgcctgc tgaactgacc aggggaggcg atgccgccgg cccggggtgg ggcacagggg    300
tgacggcggt cgaagggtga tgtttgaaga tttgatgaag gtttccccgc cgggcactga    360
gcgagggtgg tattctcccc tggccggagc gatactgggg tct                      403
```

<210> SEQ ID NO 367
<211> LENGTH: 100
<212> TYPE: DNA
<213> ORGANISM: Corynebacterium glutamiucm R

<400> SEQUENCE: 367

```
atctatgaga cccctcaaaa caccgagaat ttcctcgatg cattcaccaa ggcagttgaa      60
gatctcaccg ctgccgctaa ccaggtttag aattatttaa                          100
```

<210> SEQ ID NO 368
<211> LENGTH: 51
<212> TYPE: DNA
<213> ORGANISM: Corynebacterium glutamiucm R

<400> SEQUENCE: 368

```
ggtgaggtga gttatttaaa gactgcataa tattttgggg agtgaactgg t               51
```

<210> SEQ ID NO 369
<211> LENGTH: 498
<212> TYPE: DNA
<213> ORGANISM: Corynebacterium glutamiucm R

<400> SEQUENCE: 369

```
gaaacaggta cctcaaaggc cccgcaggtt tgatacttgc ggggcctttg gcgtttctag      60
gtgatctggt tgggtcagac gggcaaaaga gaccaaagcg ctcgaagatc cgagggccct    120
tggcctaaaa atgcactttt ccagagagcg aaactgtcat tcgagaccaa aaaatcgacc    180
```

-continued

```
cgccggggga cgcttggtct cgattgacat tccgctacca agcaccgaaa aattgccgcc    240
aggatcaaaa gaaagtggcc ttccagaatc gtctctgagg gcctcaaacc cacaacgcca    300
tacaaacacc taacccagaa tctcgacccg ttaaaaagcc tttgatcgac tagtagcgtt    360
gaggtggttt cgtcgatgaa tactgttgtt actgcgtgag ctggtgatga gccagaatca    420
ggtgactgga atgcctgtgg ttcacgttta ggggatgatt cacaatgaag aagccaactc    480
tatatttaaa tctcgaat                                                  498
```

<210> SEQ ID NO 370
<211> LENGTH: 227
<212> TYPE: DNA
<213> ORGANISM: Corynebacterium glutamiucm R

<400> SEQUENCE: 370

```
cgatatttca gcaaaccgat gctattcgat aagccagaca gcgctctgat cttccatccg    60
agagatcaga gcgctgtctt attccaaaga aatggcctgc agcggggagt gctccccgct    120
tttgagatac ttccatttt cccgctttac ggtgaagttc atcagctaca aagcacatgc    180
cagatagctg aaaaggaaac cactcccctc ctcggaaagc aggaacc                  227
```

<210> SEQ ID NO 371
<211> LENGTH: 96
<212> TYPE: DNA
<213> ORGANISM: Corynebacterium glutamiucm R

<400> SEQUENCE: 371

```
aatttctcat ggtatcacta gaaatttacc gtgaactaat gttagagttt gtttcacgct    60
aaaaagcgta aattaacatg agaaagaaga tttgtt                              96
```

<210> SEQ ID NO 372
<211> LENGTH: 100
<212> TYPE: DNA
<213> ORGANISM: Corynebacterium glutamiucm R

<400> SEQUENCE: 372

```
aacttaaaaa cccctcacaa aagtggcgag ctccccgatt gggactcgcc tcttttcgta    60
ttctcactaa gatcacccga gcgaccttgc ccaccacccc                          100
```

<210> SEQ ID NO 373
<211> LENGTH: 100
<212> TYPE: DNA
<213> ORGANISM: Corynebacterium glutamiucm R

<400> SEQUENCE: 373

```
tggggaattg gggctgatca gggtgacgtg atcgaggggg aggtggtggg cgttgagtga    60
tcaagagttg cctcctgttc ctgaggatca gatgttgggg                          100
```

<210> SEQ ID NO 374
<211> LENGTH: 100
<212> TYPE: DNA
<213> ORGANISM: Corynebacterium glutamiucm R

<400> SEQUENCE: 374

```
ctgcagagat ggtgggcagc accctggtg ctgtacgagt tgcccaacac cgggcgctca    60
cgacacttcg aagcacactt gagcagcagg agaacaagta                          100
```

<210> SEQ ID NO 375
<211> LENGTH: 100
<212> TYPE: DNA

-continued

<213> ORGANISM: Corynebacterium glutamiucm R

<400> SEQUENCE: 375
cacctctacc aagctcaggt cgatgcgtcg atcgcgcgcc tagctgaaaa actcaatacc    60
accatcatca atgacacctt tctgaaggag aactccgatc                         100

<210> SEQ ID NO 376
<211> LENGTH: 100
<212> TYPE: DNA
<213> ORGANISM: Corynebacterium glutamiucm R

<400> SEQUENCE: 376
ggcagaacgc taagggtcaa aacctcacta ccaccgacgc taccgcagca atccgccacg    60
acctatccgc aatcctcgca gcactacagg agaagaaata                         100

<210> SEQ ID NO 377
<211> LENGTH: 135
<212> TYPE: DNA
<213> ORGANISM: Corynebacterium glutamiucm R

<400> SEQUENCE: 377
gtcgcacctc cttgacaggt aggtagcccg gtctacctac ctgacaacgg agggtaatac    60
cattggcgag atcgagcaga tttccctcac acatccgcgt aaactccaag gtcaatgccc   120
aaaaattaag gagaa                                                   135

<210> SEQ ID NO 378
<211> LENGTH: 100
<212> TYPE: DNA
<213> ORGANISM: Corynebacterium glutamiucm R

<400> SEQUENCE: 378
gacgcgatca ggcgctccta cgcacccagg caattaggcc tgagcttatc gacgcatccc    60
tcctcgattc caccgacctc aaagtattgg gactggacaa                         100

<210> SEQ ID NO 379
<211> LENGTH: 100
<212> TYPE: DNA
<213> ORGANISM: Corynebacterium glutamiucm R

<400> SEQUENCE: 379
gtggcaatca acgccgcggt cgtacccaga tcccagtggt cacgcgccat tgtgacaac     60 gattccgtag aagttctcac cgcaattcag ggaggttaaa                         100

<210> SEQ ID NO 380
<211> LENGTH: 79
<212> TYPE: DNA
<213> ORGANISM: Corynebacterium glutamiucm R

<400> SEQUENCE: 380
tcacgggatc ggccgctccc ggggtgggct gacgaccaag ctgcacctgg tctgcgacgg    60
ccgcggcaga ccactgggc                                                79

<210> SEQ ID NO 381
<211> LENGTH: 262
<212> TYPE: DNA
<213> ORGANISM: Corynebacterium glutamiucm R

<400> SEQUENCE: 381
ctggctctga agctgggtgc tcgtgtgaca tgtcagatgg ggtattcgct ggaaggtctc    60

```
actcgtatgg tcagccctcg atgtctttac ggtctgcgct tcggcaaatg gtaattgatc    120
gatctgctgc taaagagatt ttcggtagag ggtcttttgg aagagctcag ccgtatttcg    180
gtcagtcagc aactaactac gcttatcttc cgtgtacgat agaccgtagt taacataagg    240
aatggaatag gagaattgcg gc                                            262
```

<210> SEQ ID NO 382
<211> LENGTH: 100
<212> TYPE: DNA
<213> ORGANISM: Corynebacterium glutamiucm R

<400> SEQUENCE: 382

```
gccaaatact cagtcgtgcg gtattccatg tgggagagct caggatggct gtgcaaatgc     60
ctgcgccact taatgacctc gtcatggtgg cggtccatcc                          100
```

<210> SEQ ID NO 383
<211> LENGTH: 375
<212> TYPE: DNA
<213> ORGANISM: Corynebacterium glutamiucm R

<400> SEQUENCE: 383

```
ttatcctcct ggcctcctca gcacttcaaa cccacatatt ttcacaatag tgactaaaag     60
gtaccgggag atgtgttctt tagatcctgg tccgattaca aatcggacac gattgacttg    120
tctaccctac cagtatttac ccaagaaccg catggcaacc ccttttttgta aggcgcatca   180 taggtgcgaa aagctcctcc cctacccgc ccaatagtta ccttaagtgt tggataataa    240
aaatactggg tctgtgccac attaaagata tggcgatagt cttaaacaat acgtcgttac    300
actggccgat ttgataccctt tcaaaacttt tactcttcat aggagtgcca ggggaactta    360
gaggagcatt aaata                                                    375
```

<210> SEQ ID NO 384
<211> LENGTH: 396
<212> TYPE: DNA
<213> ORGANISM: Corynebacterium glutamiucm R

<400> SEQUENCE: 384

```
ttcagggctt ttaagatgca gaggcaagga acaatgtag ttttccttgcc tattttagcg     60 ttttcagcgg gtggtttccg tggaccagac cacgatgccc acggaaacca taaactggat   120
tcgtgggcat cgtggtctgg tttcgagcgg gaaaaaccag acccagatgc ccaccgatcg   180
cagatttgag gatcgtgagc acgcctgtct ggtttgcctc gataagggtg atttcatggc   240
tgaggatcca aaaagttcga cctcccagaa tcgcttctaa gggcctaaag ttgctctccc    300
taggccgata cccatgtgga aatctcgacg tcttaaatgg acgatgagag ctaaaaccac    360
gaacagctgg gattttccac gataggattg ggtctc                              396
```

<210> SEQ ID NO 385
<211> LENGTH: 100
<212> TYPE: DNA
<213> ORGANISM: Corynebacterium glutamiucm R

<400> SEQUENCE: 385

```
gaatgacctc aatcgctggc atctctggct tttcctgcat gacagatgat tgtaactgtg     60
atgaaataag gccagatgaa gtaactgtgt cgattaagtt                         100
```

<210> SEQ ID NO 386
<211> LENGTH: 100
<212> TYPE: DNA

<213> ORGANISM: Corynebacterium glutamiucm R

<400> SEQUENCE: 386
gggctgaagg gctgggcgga acaataatta ttgaatctac aatcggatcg ggaactggaa    60
tttccgcccg ttttccctat ccacaaaagg accaagataa                          100

<210> SEQ ID NO 387
<211> LENGTH: 78
<212> TYPE: DNA
<213> ORGANISM: Corynebacterium glutamiucm R

<400> SEQUENCE: 387
ggtgggtcct tttgtgaaat tcgatccaag cgggctttga gtaacatgtt accggttact    60
gtggtgaatt gtgcgata                                                  78

<210> SEQ ID NO 388
<211> LENGTH: 100
<212> TYPE: DNA
<213> ORGANISM: Corynebacterium glutamiucm R

<400> SEQUENCE: 388
ggatcgacga agtgcttctt ctctacgttt gccatgccat acattctttc aaactctggg    60
aacaaaagtc acctcaacaa ggcttaaact taacaacatc                          100

<210> SEQ ID NO 389
<211> LENGTH: 100
<212> TYPE: DNA
<213> ORGANISM: Corynebacterium glutamiucm R

<400> SEQUENCE: 389
tcaccacgtt ttcggccatg atgcttaacg acgtctcctt ctatttcttc accgctgtgg    60
gctgcattct cgcctggtta gctggggatc ggttggcgcg                          100

<210> SEQ ID NO 390
<211> LENGTH: 73
<212> TYPE: DNA
<213> ORGANISM: Corynebacterium glutamiucm R

<400> SEQUENCE: 390
tttcatccta tgaatcttgg tgtggttcat gcgttttat gcaatatcaa tcaaaagttg     60
gtacgatgct cgt                                                       73

<210> SEQ ID NO 391
<211> LENGTH: 67
<212> TYPE: DNA
<213> ORGANISM: Corynebacterium glutamiucm R

<400> SEQUENCE: 391
agtcaactcc ttggttcaag tgtcagtatt tttctagtct atcgccccac aggtaggctc    60
aggacac                                                              67

<210> SEQ ID NO 392
<211> LENGTH: 81
<212> TYPE: DNA
<213> ORGANISM: Corynebacterium glutamiucm R

<400> SEQUENCE: 392
gaaaacactt taaatattct aagaaacagt tcaagttttg ctgtagttta gatatgacaa    60
ggcaatgaca caaggagaca a                                              81

<210> SEQ ID NO 393
<211> LENGTH: 80
<212> TYPE: DNA
<213> ORGANISM: Corynebacterium glutamiucm R

<400> SEQUENCE: 393
ccccaattaa ttcgaaacaa ggaagcttcg gcttcctttt tcggcatttc actagcattt    60
agaatttaag gaattagtta                                                80

<210> SEQ ID NO 394
<211> LENGTH: 211
<212> TYPE: DNA
<213> ORGANISM: Corynebacterium glutamiucm R

<400> SEQUENCE: 394
aacttggatt tctcaagcac gctcgctgct tcttcaattt tgattgaaga ggcagcgagt    60
tttttatcga ttttgctaaa acacgctgac aaacgagtaa gataattaga tacataaaag   120
ctgttttagt agtttacttc tgattgtttg tcgtttacgt agacgttttc tccatgccta   180
atccggttta aaaatgagag agcaggtaat c                                  211

<210> SEQ ID NO 395
<211> LENGTH: 56
<212> TYPE: DNA
<213> ORGANISM: Corynebacterium glutamiucm R

<400> SEQUENCE: 395
ttagcccctt ggtttaactc ttcaattgct tttaactaac tgaaaggcac gcaaat        56

<210> SEQ ID NO 396
<211> LENGTH: 498
<212> TYPE: DNA
<213> ORGANISM: Corynebacterium glutamiucm R

<400> SEQUENCE: 396
aaatttaaaa ttccataaat ttagacaatc gacaacgggg ggaaattcct tagatcgaat    60
gggattggca tagaaagtcg cttgaaaacg cttagtggtt gaaacttgat gtaattgcgt   120
gacttaaaaa cctatcttta cctgcagcta tggatgcgat ttcgtctttt cagatggttg   180
tgtgtaaagt tcttaatcga accaaggagc acagcgcaca ggggttcagc acagagactt   240
agtaagtcac ttactgaatt tgttctgaga tcacagtgtg ttagtattcg atgggtcaaa   300
ttaaatatcg gggcgtggcg cagtttggta gcgcacctgc tttgggagca gggggtcgca   360
ggttcaaatc ctgtcgcccc gacttgagga cgagctcggt ttcggacgac gcgagaaatc   420
gcattaatcg tcgaaaaccg ggcttgtttt tgtaatatct gaaactttcc ctttcccgat   480
catccaggag atttactc                                                 498

<210> SEQ ID NO 397
<211> LENGTH: 275
<212> TYPE: DNA
<213> ORGANISM: Corynebacterium glutamiucm R

<400> SEQUENCE: 397
gggagttcca cttcctcaaa gcgccttttg gctaatgtga ccccaaccag tatactgccg    60 gttttggat taggtttggc catcgtgcta gcatatttag gtctcggcga gggtcaagta   120
cttttagtgc tcaaccgtta tcgacgcgat ctagacttct aaagtgcact tttgtgcgct   180
gcctgcgaag actcgaccaa gacattcgag tcggtcgcgg gcatttttta ttttcgcggc   240

```
cgagtgtcca ccttcatcca tgaggagaaa tcact                              275
```

<210> SEQ ID NO 398
<211> LENGTH: 362
<212> TYPE: DNA
<213> ORGANISM: Corynebacterium glutamiucm R

<400> SEQUENCE: 398

```
gggacaatca atcctcgctt ccttcgctgg tgttaaccag acaggttcga acggtcccgc   60
gcagcaacag cgcgcaatct cagcccaatg cattgggcac ccgtggggta agtcgccacc  120
agtcaatccc gacaaccaag atttgtcaac ggttagtgca cccaagtgag gggagcagac  180
cccagtttga aaaccaaggc acacatgtga agaatatttc agttgactg tgcaaacccc   240
gactcacgtt gggcaaacgt gacagcctcg aaaattgaaa cggaaacgaa ccggccgagc  300
accccaaacc tggggaagtg ccgccagggt cctctttccc tactagtaaa aggattgttt  360
at                                                                 362
```

<210> SEQ ID NO 399
<211> LENGTH: 100
<212> TYPE: DNA
<213> ORGANISM: Corynebacterium glutamiucm R

<400> SEQUENCE: 399

```
gacgccaact ccatctgtgt tcatggggat aatccgcaag ctctcgcatt ggtggagaaa   60
atcgtgacca cccttgcagc tcatgaggtt caggtttccc                        100
```

<210> SEQ ID NO 400
<211> LENGTH: 298
<212> TYPE: DNA
<213> ORGANISM: Corynebacterium glutamiucm R

<400> SEQUENCE: 400

```
accgcgattt ggtatttcgg ccgatcctgc cctaaagtaa tagaccgaag tttgaacgat   60
cggccatgcg ccagatcgag ctcaaggttc accgaagacc gtaggtcatc cgcacagcgg  120
atcgaaggtt tcctacccct aggaacggcc cacgcaggaa acacttgaac gccttagatt  180
ccttatgtgg aatgtatagc gccctgtgct cttgcacggg gcttttctca ttggtttatt  240
gaccgtgtga aagctccgcg gatcagtaga ttacacataa gaggaaggag gcgaagta    298
```

<210> SEQ ID NO 401
<211> LENGTH: 332
<212> TYPE: DNA
<213> ORGANISM: Corynebacterium glutamiucm R

<400> SEQUENCE: 401

```
tccgttttttg ccctaaaca ctctcaggtt tctcagtgaa aattgaggat tggtgtcgca   60
tgacgctcca tttgcgcagg cagtaggtag taaatggtta gatactttta aaaggagcc   120
tgccaccca aatagggta aaggactggc atgtaattta caggcgcctg caaggaatag   180
tcccaagaag tcgaaaacta gtcacattag tcacaaaaat cacttaaata acatcttgct   240
tgatttttca tcacaaaagg cttgcacgac tataaagccc cggttaaggt gatcagagaa  300
attcaacctc tctgaaatga aggatccagg aa                                332
```

<210> SEQ ID NO 402
<211> LENGTH: 81
<212> TYPE: DNA
<213> ORGANISM: Corynebacterium glutamiucm R

<400> SEQUENCE: 402

```
ggggaaactc tgatcgggtt gatggaaaag aatcaacctt tcactttcat ccacaattaa      60
gttcttaata ggagaattac t                                                81
```

<210> SEQ ID NO 403
<211> LENGTH: 113
<212> TYPE: DNA
<213> ORGANISM: Corynebacterium glutamiucm R

<400> SEQUENCE: 403

```
agtaccggtt ggacggtaat gtgcaattcg gatatatcaa tagccccgcg gtttcatgtt      60
gaatccatgt aatcgaaaaa cacatcgggg cccacacgag gaggattatt aaa            113
```

<210> SEQ ID NO 404
<211> LENGTH: 61
<212> TYPE: DNA
<213> ORGANISM: Corynebacterium glutamiucm R

<400> SEQUENCE: 404

```
caccccatct aaaaggggct ctctggcaga tatgctctcc ggcagaagag cctcttaatc      60
c                                                                      61
```

<210> SEQ ID NO 405
<211> LENGTH: 100
<212> TYPE: DNA
<213> ORGANISM: Corynebacterium glutamiucm R

<400> SEQUENCE: 405

```
tacgtgcgcc atccaccact aacttgaggt tgccaatcgt gctcatattc aactctcctt      60
aattggtcgc tttcttctaa gaccccacat tagtaaaagc                           100
```

<210> SEQ ID NO 406
<211> LENGTH: 331
<212> TYPE: DNA
<213> ORGANISM: Corynebacterium glutamiucm R

<400> SEQUENCE: 406

```
tgcttttcta accoctgaac tcatgggggt cgatgttacc ggctcgattg agaactcccg      60
cattggctag aaaaacctga ttacttcacg cctctttaag taaaaaatcc tgtgtctttc     120
taacgaaaag acccaaaaag acacgctaaa tcagcctcct atgcaattag tagagcattc     180
acatacaccg tgccaagacc taatttccac gaccgaaact tcactaaatc cgcaggtaga     240
agctttgatg atctacatca caaatttaca atgtgtggtg agttattcat attacccaag     300
gacttgaacc ttaaaaggag ccctaaaaat c                                    331
```

<210> SEQ ID NO 407
<211> LENGTH: 61
<212> TYPE: DNA
<213> ORGANISM: Corynebacterium glutamiucm R

<400> SEQUENCE: 407

```
gttaaaacct tcgcctaaaa cccctccacc tttcaagaca agattttaag gaagtaccac      60
c                                                                      61
```

<210> SEQ ID NO 408
<211> LENGTH: 422
<212> TYPE: DNA
<213> ORGANISM: Corynebacterium glutamiucm R

```
<400> SEQUENCE: 408
aagcttacgc agccgtaagt tttgagtgca gaaaatttc catgtcaagt taaactcgtt      60
aatgaagatg gaaataagt tgtttctaag attaaattaa ggaaagttac atttccgcag     120
gtcggcgtta cccctaagt ctacccctttt ccattgtgcc caaggaaat acatatagac     180 tttcaggtat tagattgcct ttatgaaact atagggaatc taaatccatt gatcgagact    240
tgcagtcgcc tgactccatt tcgcttgagc cagacctcta atggttccga tctttgaatg    300
cactacttgc tggcagtcat ctgaaaaaac gacgttggtt cgtagtcgct ggaaatttga    360
taattcctcc gtcccccttca actagggggt ggaaacccga ctatttccga aggactttc   420 tc                                                                  422

<210> SEQ ID NO 409
<211> LENGTH: 100
<212> TYPE: DNA
<213> ORGANISM: Corynebacterium glutamiucm R

<400> SEQUENCE: 409
cctccgtcat cgccgacgta tcccgcggcc tcggtgaagc catggtgggc atcaacgtat     60
ccgacgtccc agcaccacac cgactcgccg agcgcggctg                          100

<210> SEQ ID NO 410
<211> LENGTH: 100
<212> TYPE: DNA
<213> ORGANISM: Corynebacterium glutamiucm R

<400> SEQUENCE: 410
catgttcctg ggcatcgcct tcgttgaggc cctggcactg atcggccttg ttgctggctt     60
cctgttctaa tcagctaact taaccgaaag ctggtaaacc                          100

<210> SEQ ID NO 411
<211> LENGTH: 100
<212> TYPE: DNA
<213> ORGANISM: Corynebacterium glutamiucm R

<400> SEQUENCE: 411
ttcttggaga tcagctctcc gataacgtga agcgctctgg cacgattgat cgcttcctcg     60
ctgacctcga taccgtggca ccgaacggaa agtaggcgac                          100

<210> SEQ ID NO 412
<211> LENGTH: 181
<212> TYPE: DNA
<213> ORGANISM: Corynebacterium glutamiucm R

<400> SEQUENCE: 412
gtaagcacaa tatcggacag ctccctcacc ggcactatta cagacaacaa atgtgcgtac     60
ttagccacct ttcaaaaggt tgtgacgtga gacatttcct ccaatacctc tccagtgata   120
ttctgtcggt cagcctaacc taagttaatc cgttgttgtt cgagaaagag agaaactttt   180
c                                                                  181

<210> SEQ ID NO 413
<211> LENGTH: 100
<212> TYPE: DNA
<213> ORGANISM: Corynebacterium glutamiucm R

<400> SEQUENCE: 413
aactgctggg caccactgag attcccatgt gggatgtgga ccggtggcaa ccatcgcttc     60
```

```
tcaagcccgg tgattcagtt cgatttgtac aggtgaagaa                        100

<210> SEQ ID NO 414
<211> LENGTH: 173
<212> TYPE: DNA
<213> ORGANISM: Corynebacterium glutamiucm R

<400> SEQUENCE: 414
aagcagcttt ggtgaaggtt tttggagaag taccaccaag ctgttaagct tccaaggtgg    60
ttttgcgact gcggtccgca gcagttgcga aaagtacaca catcatccgg gtttatcttg   120
gatgaatgag tgaaaatttt tcatgcggac tgaaataact tttaggagac acc          173

<210> SEQ ID NO 415
<211> LENGTH: 100
<212> TYPE: DNA
<213> ORGANISM: Corynebacterium glutamiucm R

<400> SEQUENCE: 415
ctgctgcttc cgcaaagaag ctgcacgttt tctccggctc cgagcaccca tacgctgctc    60
agaagcctga ggcctacgag atcaagaagg tggcccagta                         100

<210> SEQ ID NO 416
<211> LENGTH: 576
<212> TYPE: DNA
<213> ORGANISM: Corynebacterium glutamiucm R

<400> SEQUENCE: 416
ccacaccaac ctacagcgat ttcgtggtga acctagcgaa acacctagcg accctcggga    60
ttgggcagtg ggcagataac ggcaaatatg tgtccactac accgccaccg attttttggg   120
gagtcatccc aggcgacacc aatgtgggct atgcgattgg tttgcaggtg taccacgacg   180
acaccacccg cgacaactac acccgcgata ttcgtgtcca atcctggca cgcggtgacc    240 gtcacccagg gtcccctgcg aaaatcttgg accgcatttt caccgccatg cacgacgaat   300
ccaactggac actaaacaac caacagtccg tcctattgtc acgtcaggac acccggccag   360
cagcatcccg agatgcaaac aaaaaactgg tcgcagccag cgaattgggtg tttacactaa  420 acccgtagga gccaaccaat ggttgcaaaa ccaagcaaga agtcactggt ctcaacactc   480
gcccgcaata acgcactcca gtccgcaat cgtggtgaaa ctgactgggt ttacgtccgt    540
ggcctgaccc agtgtgcacc gcagttcacc ggcgaa                            576

<210> SEQ ID NO 417
<211> LENGTH: 231
<212> TYPE: DNA
<213> ORGANISM: Corynebacterium glutamiucm R

<400> SEQUENCE: 417
tattcctccg tgactaggct agatgacgga tccatcatat aactcgcggg agttttggc    60 ctgggctaga catattccat attcaatttt tagttacagc gcaacaggtg taaggtattg   120
gaggttcatt gccaaatcat ggtgatgcat acttaccgaa cccaactcgg cacgatctg   180 gcatccgctg gaaccgacct gaagtttcaa tcctgaggga atcgagagta a            231

<210> SEQ ID NO 418
<211> LENGTH: 366
<212> TYPE: DNA
<213> ORGANISM: Corynebacterium glutamiucm R

<400> SEQUENCE: 418
```

-continued

```
gaactacccc cgtttaccct caaaataagt cctgtgacac acataacacc ccctaatcgt    60
acccgctcac acgctatttt cgaggtgtgg ttcgccttcg gaaacgaatg cccccgcccc   120
acttggataa aagacgaatt cacctgttag tctataacgc gggttgaacc gagaaacccc   180
tcaaggcagc agacattagc cgcagggqtt ttgcggagca cgtcccctgt gatcgttgcg   240
ctgatgtgcg acggagtccg tagcgattac agcgagtttt tcagacgtcc atcgcaccgt   300
gcacaacaac atttcaggtg cacggcccga acacgggaga gaacgctgag cgttacaaca   360
ctgtcc                                                              366
```

<210> SEQ ID NO 419
<211> LENGTH: 937
<212> TYPE: DNA
<213> ORGANISM: Corynebacterium glutamiucm R

<400> SEQUENCE: 419

```
acgcacgtac ataatccccc ggccaacagc ttacttgcgc caggggattc cctatttta    60 tctctgaact gcaaaatctt gagtcaatgt cttcttagcc aatttaaggg aagaatcttc   120
ctagctgggt atatgttata ggcacaagca ccggaggctc ctcagatcga ttctggaggg   180
gtacttttca tcggctcagt cttggttttc atcgcataaa tagcgagacc aaatcaggtg   240
gacgaaaact tctaagctgg cagtctattg gtcatcttgt acggcatcga acaccacaga   300
ccacccccta tgaccaagaa tctcccagtt agcatcccct cggccatatg gtctgatttt   360
ggatttcgcc atccccaaaa caaccccgaa acgcacgacc tcagtgctca gtctgcgcaa   420
tcttccccaa aacctgcccc accaaaagaa ccctcacaca aaaaaatgac ccccaaggat   480
tcccttggag gtcatttta aagttctggt gaacttatgc cacggttgcg gagccgccag   540
cggcttcgat cttttccttg gcagagccgg agaacttgtt agcggtgacg ttcagcttga   600
cgctgatgtc gccgttgcca agaaccttaa ccagttcgtt cttgcggaca agtcctgctg   660
caacgatgtc agcaatgctg acgtcgccgc cctgtgggaa cttctctgcg agatctgcaa   720
tgttaactac ctggtagtca accttgttag ggttcttgaa gccctcagc ttaggaagac    780 gcatctgcag tggcatctgg ccaccttcga atgctgcaga aacctgcttg cgtgccttgg   840
tacccttggt accgcgacct gcagtcttac ccttggatgc ttcgcctcga ccaacgcggg   900
tcttagcttt gtttgagccc gctgctgggc gcaaatc                            937
```

<210> SEQ ID NO 420
<211> LENGTH: 253
<212> TYPE: DNA
<213> ORGANISM: Corynebacterium glutamiucm R

<400> SEQUENCE: 420

```
cactcctgga cttttctcag acacgtatgt ttcactcatg gttgactagt gtaatcctct    60
cctagaattg cacctacttt ggcataggtt ttatttccaa caagctcttt gcagaacaat   120
gctatagatt gttttctagc caatactgtg gttgtggcac tacactttcc acgagttgag   180
gatagctttc gctatccaat cttctatctt gtttccatag taaatccgca tatttattgc   240
caggagaaaa gtt                                                      253
```

<210> SEQ ID NO 421
<211> LENGTH: 100
<212> TYPE: DNA
<213> ORGANISM: Corynebacterium glutamiucm R

<400> SEQUENCE: 421

```
taccacggcc gcgttgcagc tcttgctgac gccgctcgtg aaggtggtct gaaattctaa    60
tgatgaccat ttctaagaac atcaacggaa ggattgcgta                         100
```

<210> SEQ ID NO 422
<211> LENGTH: 100
<212> TYPE: DNA
<213> ORGANISM: Corynebacterium glutamiucm R

<400> SEQUENCE: 422

```
aaccaccacc atgcgtgcag aacgcactgg taacccttc ttgctggcac tgtagggcta    60
agttccgcac tacttctttg aataggtatc gttaataatc                         100
```

<210> SEQ ID NO 423
<211> LENGTH: 100
<212> TYPE: DNA
<213> ORGANISM: Corynebacterium glutamiucm R

<400> SEQUENCE: 423

```
tgtccgttac aagatcgtcc gtggcgcact ggatacccag ggtgttaagg accgcaagca    60
ggctcgttcc cgctacggcg caaagagggg ataattaaaa                         100
```

<210> SEQ ID NO 424
<211> LENGTH: 354
<212> TYPE: DNA
<213> ORGANISM: Corynebacterium glutamiucm R

<400> SEQUENCE: 424

```
gggctagttg tgaaagctgg cttgatggc tggcgaggtt gctgcacttt taaaaaggca     60
aaaaacagcg aaaacacacc ccaggttttt cccgtaaccc cgctaggcta tacaatttcg   120
gtctaaccca gttttcaaa gaaggtcact agcttttccg ctggtcacct tctttttggt   180
ttttcaatgc agagatagta cactttactc tttgtgtgtg gagtcaaacc tcccctttaa   240
ggggtgcgct tggacagcag gacaaattcg ggtcaccacc ggccgccgaa tttagcttcc   300
ttccgaacat attcctggct ggcagttcta gaccgactaa ttcaaggagt catt         354
```

<210> SEQ ID NO 425
<211> LENGTH: 213
<212> TYPE: DNA
<213> ORGANISM: Corynebacterium glutamiucm R

<400> SEQUENCE: 425

```
aattttattt cttggtcagt taccgctaag attgttcagg ttgtctgcgc tcgaatgggc    60
gtggcaacgt ctaacagact ttcctgcgta ttgccgccaa cgaccccggt cgtccggagg   120
agtcacgcgc aggttaaaca agaagggctg aaccggctca ccagcacacg gtgagtgact   180
gtactgccca gtgacctagt gaggaaaatt cac                                213
```

<210> SEQ ID NO 426
<211> LENGTH: 121
<212> TYPE: DNA
<213> ORGANISM: Corynebacterium glutamiucm R

<400> SEQUENCE: 426

```
gaggagggac ctttctagga ggaagtgtct ggccgattgg ctaacaatct ctagttaaat    60
cccgcctcat gaaaccacga tgaaaccaac atgagagttt tttcatccac gttttctggc   120
t                                                                  121
```

<210> SEQ ID NO 427

```
<211> LENGTH: 225
<212> TYPE: DNA
<213> ORGANISM: Corynebacterium glutamiucm R

<400> SEQUENCE: 427
gacctacagg ttctgacaat ttaaatctcc ctacatctgc acaacggatg tagggagttt      60
ttccttatat atgccctcca caaatcccct atcgtgtgag atgtgtttca taggtgcccc     120
caacgttgcc tgttgactgc aaattttccg aaagagtcca tagactactt ctttaagtca     180
tcagatttaa gtagtcagca ttaagtcgcc aatgaaagga catac                     225

<210> SEQ ID NO 428
<211> LENGTH: 902
<212> TYPE: DNA
<213> ORGANISM: Corynebacterium glutamiucm R

<400> SEQUENCE: 428
ggcattgctc tggctttcgg aactagtatc ctcaacccgc tcttttcaac tgttctcacg      60
attgcctttt ggctttccaa atctctatta gaagcagcct tcggaactac accaggaaaa     120
atgctcacac acctgcacgt caaccacgac atacatggtg agctcctaag catctactac     180
tcctcagcaa gaaacgcgtg gatcttgttg gagatcatcc cacctgtcgg cctagtgcta     240
ttcagctttg tagccatttt cctcgtcgct agttgcattc acgcttgcaa cttcgtgggt     300
ttacatgaca aatttgcaca tgtaaatgtc ttgcggaaaa acgaaaaaca ccctctcaac     360
tgctttaaat gcaactgaga gagtgttatt attttgaggg aatgacggga atcgaacccg     420
cgtcatcagc ttggaaggct gaggtaatag ccattatacg acattccac ttgtgaactt      480 ttgcaagaac tcttgtttgg ttcgaagaaa agcatagcgc atattgttgg tttattaaaa     540
atcggcaggc tggcacccgc ttttcgaaca agatttttgg ccagaccaca ttcttaagaa     600 tcccttcga cacatcgcta cttttatcc ggcatctatc cagcaaatgg tcagttaacc       660
tgcagcaagt gtattattgt acatttcctg caattccccc ttatgaaacc cgctaaacct     720
taaagaaaca taagagaatt ttagcaagtg tgcccgtctg gccccataaa atatacaagc     780
acttgtctat aagtccagcg tacatgggat aattttagca agatacctga atgttctta      840 ggttgtaaaa accttagaat aatttcgaca aaaactacct ccttggcgta acctagctaa     900
ac                                                                    902

<210> SEQ ID NO 429
<211> LENGTH: 100
<212> TYPE: DNA
<213> ORGANISM: Corynebacterium glutamiucm R

<400> SEQUENCE: 429
tccacgtcac agggcctcct gaccgaccgt caggctaccg agaagggcgt aggcggagaa      60
gttctcgcct acgtctggta atagggagga ttgactaaat                           100

<210> SEQ ID NO 430
<211> LENGTH: 559
<212> TYPE: DNA
<213> ORGANISM: Corynebacterium glutamiucm R

<400> SEQUENCE: 430
gcccctgatt cgcgcattat aaatgccctc ccgcacgctt tgcgggaggg cttttgcgtg      60
ccaaaagata tcgcttttcg acgtctcccc accccttcgg aggggcgtaa ggtgacatgc     120
acggcaacct tccgttaacc tgtaagacat ctcaaatctt gttaaaaacg accaattgca     180
```

```
caccattttt tcgaccaccc cacttagtca attgtgtaaa ttaccccac attagggtat      240 gtatgacgat tgcttattca aagtttcgct ttaatcgagc cgttattaag tagtgttaca      300
ccttcatggg gtttagctgg aaagttttct ccttgttcac ttaaatagct aacatttctg      360
cagttcaaga tatatttacg ggaaaaatcg tcaaataatt ctttgctgag tttggttgaa      420
aagcaagctg ggaaattttt cccattcgcc ttgacggggt gccaaaatgt gattgaataa      480
ttgagtgacg tcctgagggc gtcagcaaac tggcaaccat caccagcaaa atttgctggt      540
cctctcaagg agatttctc                                                  559

<210> SEQ ID NO 431
<211> LENGTH: 362
<212> TYPE: DNA
<213> ORGANISM: Corynebacterium glutamiucm R

<400> SEQUENCE: 431
agatcgttta gatccgaagg aaaacgtcga aaagcaattt gcttttcgac gccccacccc       60
gcgcgtttta gcgtgtcagt aggcgcgtag ggtaagtggg gtagcggctt gttagatatc      120
ttgaaatcgg ctttcaacag cattgatttc gatgtattta gctggccgtt accctgcgaa      180
tgtccacagg gtagctggta gtttgaaaat caacgccgtt gcccttagga ttcagtaact      240
ggcacatttt gtaatgcgct agatctgtgt gctcagtctt ccaggctgct gatcacagtg      300
aaagcaaaac caattcgtgg ctgcgaaagt cgtagccacc acgaagtcca ggaggacata      360
ca                                                                    362

<210> SEQ ID NO 432
<211> LENGTH: 872
<212> TYPE: DNA
<213> ORGANISM: Corynebacterium glutamiucm R

<400> SEQUENCE: 432
tttctaggac ttcatctctg aaactccccg ctgtagggac ctgaatcgaa aggtctccgc       60
atcggggagt ttttctctat tcagacgagg ctgaagataa gggagagggc tctttaacac      120
acgaggagtg gcgtagagcc tgtagttgcc ttatatgtag cttgtggcgg cgtgaagcaa      180
cgtgcaggcg cgtggaaagc gtagagtttt cttctcctta tataagga gtgttcttcg       240 tcgtgagcat tacgccctag gtcgcctggg gtcggtgtca acttcgctca aattccgctc      300
aaaatccagc tcggtgtggc ttaagaattg ttgtcataac tccaaatctc aaagcataag      360
ccgtcaatgg tgattaatgt cacatggtga gatcattgct gaaactggtg ccgattttc       420 ggctctgtga aaacgatttg actactggaa gtttcctgaa attgcaggtc atctagcttt      480
ctcagggttc taggggagaa cccttagtgg ttggggtctg agtggaggac ttgcgtctcg      540
gtcaaattaa tccgcgataa cggttcgata cgaccaatt ttttcgcttg ggctagacaa       600
gtgttgttgc ggtttcgtaa ccttattgag acattgcggg acggacaccg aatttccgcc      660
agcattacag aaacaaatag acgcttaatc gcaagcatag tttagagaaa ttctttaaat      720
cgtgcggcga gccggggaac caaacgtgtt cctggggtga gtttcccaca agggttctct      780
cgcagagaga gaaggagtgg ggatagggc cttccgctcc gaacccgaca gctaactcgg       840
tcagcaaaca ggaagaattt ggagtttcat ca                                   872

<210> SEQ ID NO 433
<211> LENGTH: 100
<212> TYPE: DNA
<213> ORGANISM: Corynebacterium glutamiucm R
```

```
<400> SEQUENCE: 433
ggtgaaaccg gtagtgaaac cagcggtgaa tccggtagtg aaaccagcgg tgaacgctaa    60
aattttccga acacacccga ggggtctaga cttgcctatc                         100

<210> SEQ ID NO 434
<211> LENGTH: 177
<212> TYPE: DNA
<213> ORGANISM: Corynebacterium glutamiucm R

<400> SEQUENCE: 434
ctcagaaata agaattcccc aggcagaagt attgggatca cgccacgcaa gatcgcgggc    60
atttgctcta aaccaggaga gcaaggctga ttgaaaagtg gtaaatgaca tgtcgaagat   120
gattgtactg cccagtgcat taggtcatac gtcacaccga gtggaataat aaagctt      177

<210> SEQ ID NO 435
<211> LENGTH: 200
<212> TYPE: DNA
<213> ORGANISM: Corynebacterium glutamiucm R

<400> SEQUENCE: 435
gggcgctcct tctcctgcaa attctcttgc gattcttctt gcgatatcag gactccaacc    60
ttatatcgac cgtcgtctca cgcacgaacc atacgcgcgg ttccaaaatt ttcgaggatt   120
tccttgcccc gggtctcgtt tatttttgaa cacgctagaa ttcaagggca gtaactaatt   180
tcaacccggg agaaatacct                                              200

<210> SEQ ID NO 436
<211> LENGTH: 351
<212> TYPE: DNA
<213> ORGANISM: Corynebacterium glutamiucm R

<400> SEQUENCE: 436
ggggagacct ccgggtggga aaacgtttgt tgactgacga ttaatcttaa atcttttggc    60
ttgatttctt gtgctgtgcg ccgaagttca caggctagct atacagaaag tgtcaaatta   120
gacaggtttt cgctacagaa agcgtaatgc tcatcataaa tttatgcagg ggtgacgggg   180
ttagctaaga cctgcgcgta tgcaacgaaa atatgtgtct taagtcgcaa aggtttggct   240
tggttaacta gctgtgttaa cttttcatctt taggtaacct aacctcacta aaactctggg   300
aatactctgg cagttttggt ggattatttt tatagacttt caaggacga c             351

<210> SEQ ID NO 437
<211> LENGTH: 80
<212> TYPE: DNA
<213> ORGANISM: Corynebacterium glutamiucm R

<400> SEQUENCE: 437
ctagacattc ggacaatagt aagatgtgag ctgaaactca gtttccatcc ttattcaacc    60
tggaaggtag ataccgcacc                                               80

<210> SEQ ID NO 438
<211> LENGTH: 77
<212> TYPE: DNA
<213> ORGANISM: Corynebacterium glutamiucm R

<400> SEQUENCE: 438
gtcgccacca ggcgcaccag ttttaccccca aacttttttcg agcgtgctaa acgctcaaca   60
acaggaagga tgccacc                                                  77
```

```
<210> SEQ ID NO 439
<211> LENGTH: 100
<212> TYPE: DNA
<213> ORGANISM: Corynebacterium glutamiucm R

<400> SEQUENCE: 439
gcggaaccgc aatcttgatt cttgtatctg ttgcactgac cacagtgaag cagattgaga      60
gccagctcct gcaaagcaac tacgaaggac ttctaaaata                          100

<210> SEQ ID NO 440
<211> LENGTH: 164
<212> TYPE: DNA
<213> ORGANISM: Corynebacterium glutamiucm R

<400> SEQUENCE: 440
acggacagac tactacttgg cgtgcgtaaa actcaggttg aataaaataa tgcaggtgag      60
ccggtgattt taagacgctt ttcgacgcca ctttcaacca tttccgaacc gccaagaata     120
ctggaatagc ttggatcaag ttttgcagga taaactgtgc aacc                      164

<210> SEQ ID NO 441
<211> LENGTH: 56
<212> TYPE: DNA
<213> ORGANISM: Corynebacterium glutamiucm R

<400> SEQUENCE: 441
agcttttctt ttctaaaaca ttcacaaaca ctcaaaaacc acgaaaggca gggatc          56

<210> SEQ ID NO 442
<211> LENGTH: 128
<212> TYPE: DNA
<213> ORGANISM: Corynebacterium glutamiucm R

<400> SEQUENCE: 442
aagcctattg taggggggcat ctgtttagct tcatatgacc cgaacaccac acatcacaaa     60
ttgaatcggt atcctttggg gtattagttt ccgttttaac gacacgactt gcgaggagtc    120
ttaaaata                                                             128

<210> SEQ ID NO 443
<211> LENGTH: 135
<212> TYPE: DNA
<213> ORGANISM: Corynebacterium glutamiucm R

<400> SEQUENCE: 443
tccgagcagt tgtttcgcaa gaaagcccac gatttcaaca tcgtgggctt tcttgttccc      60
cctatttagt gtggattggt ctttctgtag accacgtgca cgacaagaca atcctaaaca    120
cgtatccttg aatgc                                                     135

<210> SEQ ID NO 444
<211> LENGTH: 100
<212> TYPE: DNA
<213> ORGANISM: Corynebacterium glutamiucm R

<400> SEQUENCE: 444
ccacaccgtg atccgtcccg atacccccaga ggtacgtggc atgatcctgg cagttcgcca     60
cctgatcgtc gtcgaagaag tggcggggga gtaggtaaca                          100

<210> SEQ ID NO 445
<211> LENGTH: 100
<212> TYPE: DNA
```

<213> ORGANISM: Corynebacterium glutamiucm R

<400> SEQUENCE: 445

```
atccccatcg tcatcttcta cttctccacg cagaggcaca tcatcgaagg tgtggctgcc      60
ggtgccgtga agggttaaaa ggtttcgata ggttaaaacc                            100
```

<210> SEQ ID NO 446
<211> LENGTH: 397
<212> TYPE: DNA
<213> ORGANISM: Corynebacterium glutamiucm R

<400> SEQUENCE: 446

```
ctgattcata tgtataacga taggtcgatt gttggtgtgg tgtgcgcgag tcgactgaaa      60
tgttcacgtg gtgaaacttc cgcgatacta ctcatgtttg cgaatttcac atttactaac    120
tttgcaaatt gggggagggg gtagcgcggg ggaggaattc gcatgagaaa ggggaatatc    180
ccgtgcttgt ttattcagct cgaggtggca ggcgtacact ctatattcac ggacaatgtg    240
tacccacgct ttcttgtaag aaacaagaag ggtaacgccc cacgcgtcag tcaaaaatat    300
ggccaacact tgcattcggg tgctggcgat catttatgag atgacgcctt gtgttggtgt    360
tcggcagaga actcgcggag ataaaaggaa gttgaac                             397
```

<210> SEQ ID NO 447
<211> LENGTH: 100
<212> TYPE: DNA
<213> ORGANISM: Corynebacterium glutamiucm R

<400> SEQUENCE: 447

```
tggtcatcga ctccgacgga aacccaactc gcgttggcta ccgtttcgat gaaaacggca      60
agaaggtccg cgtttctcgt cgcaatggga aggatatcta                           100
```

<210> SEQ ID NO 448
<211> LENGTH: 100
<212> TYPE: DNA
<213> ORGANISM: Corynebacterium glutamiucm R

<400> SEQUENCE: 448

```
gatccgccgc ctgcgtaagg acgatcctta caagggtaag ggcatccgct acgagggtga      60
gcagatccgc cgcaaggtcg gaaagacggg taagtaagca                           100
```

<210> SEQ ID NO 449
<211> LENGTH: 98
<212> TYPE: DNA
<213> ORGANISM: Corynebacterium glutamiucm R

<400> SEQUENCE: 449

```
gaaccatcct tatttcggag ttgttctttta actgctgacg tgacgcccgg gggacgaaca      60
cgaaggctga gcttgtcgat ggcgaaggat ttgaaaaa                              98
```

<210> SEQ ID NO 450
<211> LENGTH: 100
<212> TYPE: DNA
<213> ORGANISM: Corynebacterium glutamiucm R

<400> SEQUENCE: 450

```
ctccgtacgc tacttccact agcccattcg tttccgatcg caccgcaacc cgcgacggcg      60
aaaacactca gagcaacgct taagaaggag tggcgaaaaa                           100
```

<210> SEQ ID NO 451

```
<211> LENGTH: 119
<212> TYPE: DNA
<213> ORGANISM: Corynebacterium glutamiucm R

<400> SEQUENCE: 451
atcaggaatc gacatttccg cgcgtctggt gtaccttgaa taggttgctg acgcaacgac    60
cctcctgcta tgccaacgac ggcatggccg aaaaaacaat tactagacca taggaggtg   119

<210> SEQ ID NO 452
<211> LENGTH: 100
<212> TYPE: DNA
<213> ORGANISM: Corynebacterium glutamiucm R

<400> SEQUENCE: 452
ttcgctgcca agccagccac cttggagtcc gtattcatgg acatcgcctc actccagaac    60
acctcgctgc aaaccgccta gaatctttaa ggagcccaca                         100

<210> SEQ ID NO 453
<211> LENGTH: 54
<212> TYPE: DNA
<213> ORGANISM: Corynebacterium glutamiucm R

<400> SEQUENCE: 453
accctactta gacctgactt agtgtgggaa aatttccagg gtagaatgcg acga          54

<210> SEQ ID NO 454
<211> LENGTH: 421
<212> TYPE: DNA
<213> ORGANISM: Corynebacterium glutamiucm R

<400> SEQUENCE: 454
acgtttgatg cacctccagt gggatttatg ccaagaacgc tcaatgaata cttaatcaag    60
aaagttcggc gggttaactg ctaaaagtag tgtacgtgcg catgacgatt cgggcgcgaa   120
ggcgcgtcga aatgggttta atccggcgat atttcgcctt taatccagca cggataaaaa   180
gttctgacat ttgacgtgac atatgccata ccaacgtgca tacttattca aagtgggcgc   240
gaattccgca agattttctc cgaacggaca gaaaagcatg acccgatcct gtttgtttcc   300
gtaggaagta ctattgttta acgcgtacac gtgctcaaca cgacaacgct taaacggctg   360
cacgcgtaac acggcagacc gcacaagctt aagatccac gatcaggaga ctttgacaaa   420
t                                                                  421

<210> SEQ ID NO 455
<211> LENGTH: 267
<212> TYPE: DNA
<213> ORGANISM: Corynebacterium glutamiucm R

<400> SEQUENCE: 455
tagctaaact gcaccactta ccccgcattt cctaggccac atataagggc tttggtgatg    60
cggggttttg cgtgtaaggt agacaatcgc gtgttttta agcatgctca aaatcattca   120
tccccggtgg cccggttacg taaagatcgg caaagatgat caactaaagc gatcatctga   180
agttgtagcg ggaccgagca tccggacggt tactagtggg gtttcatcgt cccagttgtg   240
gccggtaaca aggaagcagg tttaacg                                      267

<210> SEQ ID NO 456
<211> LENGTH: 88
<212> TYPE: DNA
<213> ORGANISM: Corynebacterium glutamiucm R
```

<400> SEQUENCE: 456

```
gtgtcatatc gtaccgtttg cataagcctg ttcgcgcttg gtgaaccttt tctagcacca    60
aaacaaaact ctccctagta tggggtcc                                       88
```

<210> SEQ ID NO 457
<211> LENGTH: 518
<212> TYPE: DNA
<213> ORGANISM: Corynebacterium glutamiucm R

<400> SEQUENCE: 457

```
gaatgaaaaa tcctcctgaa ataaaaggcg ccttaaatcg caaagaaatt ttgttggaag    60
aaataagacg ctgcatttgt taaatctcgt gtcaacgata cggcgaagtt acatctgagg   120
tgaaaagggc acgccaaaat tgacgaaagc tccctcaaac aacgtgcatc agctgactat   180
tgcagcatcc tcaaaggttc ctgaaaacca gattgatttc ctaatacatg caccttgtag   240
gaacgtaggg ggtaagggtg ggggaatttc aagggcaatc aaaaggttga tggtctgtga   300
cgtggcatac accaattgcc tagactttag gtattccacc tgaggattcg ggcatatcgt   360
tgcagttgaa agacatttga cgcccctaaa acgaaaccc acgaagatat ttccaccaaa   420
cacaagatat ggaatcggct ggcaaatagg ctattctgcg aagatagaaa tgaccgtaag   480
gtctctggtt tttgtgtgga caggaaggca gaacacac                           518
```

<210> SEQ ID NO 458
<211> LENGTH: 66
<212> TYPE: DNA
<213> ORGANISM: Corynebacterium glutamiucm R

<400> SEQUENCE: 458

```
gattcttaaa acttttaaga atcagccaga aacattttga ttgaacagga acaaagagaa    60
caaaac                                                               66
```

<210> SEQ ID NO 459
<211> LENGTH: 84
<212> TYPE: DNA
<213> ORGANISM: Corynebacterium glutamiucm R

<400> SEQUENCE: 459

```
tctaggtgag ctaatcggtc tgcgcgtttt tcaagcactt tgcgcagacc cccatccacg    60
taatccacga gggagatcac atcc                                           84
```

<210> SEQ ID NO 460
<211> LENGTH: 188
<212> TYPE: DNA
<213> ORGANISM: Corynebacterium glutamiucm R

<400> SEQUENCE: 460

```
aaaaaattgc ttttcgacgc ttccctccac ccttgaacaa tccacattta agatttatgc    60 ccctttttgtt tgcccccgtt tacaccctcc gtttaatcaa ccgactgtgt gaatgcgctt   120
aaacggacta gggttgtgag cagcatatcc agatttttct ggataaatcc tggaatttct   180
taaaacca                                                            188
```

<210> SEQ ID NO 461
<211> LENGTH: 327
<212> TYPE: DNA
<213> ORGANISM: Corynebacterium glutamiucm R

<400> SEQUENCE: 461

```
gacatctacc ttctaaaata ggcgactact taaggtggaa aaacaagctg attgttatat       60
cgcgaatcac acctatattg ttccttatta acacgcaaca cggatttgaa ttcgggggta      120
ggggtgtggt tagatataca ggttgtctgt gtaggtcgga ctcgcggtgc ttttccgagt      180
cgcgtttccg agaccctcg acgaggctgt aaaaggccaa gcgttcgttg cccacattcg       240
tggagtatgt agacatctgt agtacaaaga ccacgcgtgt ttgggacgga aatccagcac      300
gcattaatcc aggtcaggag accagta                                         327

<210> SEQ ID NO 462
<211> LENGTH: 96
<212> TYPE: DNA
<213> ORGANISM: Corynebacterium glutamiucm R

<400> SEQUENCE: 462
aagcttgctt ctcgacgcaa aaacccatcc ggcgcatccc ttcaatgtta ggggtgcgct       60 gctattttc tccccagttc tacgaaatga cttatt                                 96

<210> SEQ ID NO 463
<211> LENGTH: 194
<212> TYPE: DNA
<213> ORGANISM: Corynebacterium glutamiucm R

<400> SEQUENCE: 463
gtaggtggtg ggagccccaa agttgcggaa aattgttcca actaagggac tatatgtagg       60
tgtgggtaac ctaagttaat cttttgtggg cgtgaggatt tctctgagga atctagacgc      120
agattaactt ccgcttggca gcgaccggga taacaccgcg gttgcggcca cgcaggctca      180
caaaggacac cact                                                       194

<210> SEQ ID NO 464
<211> LENGTH: 242
<212> TYPE: DNA
<213> ORGANISM: Corynebacterium glutamiucm R

<400> SEQUENCE: 464
cgctttagtc tccttaactg ttggcccttt gaattacttt taggccggga catcataggc       60
ttgcagtgta ctccccttt tacggatctc cggcgagcga tgctggatta cgttcatatg      120
ggaagcggat ggatgttccc cagcctactc accgtccaca gatgagtaaa cccggaaaaa      180
cccgtattta gttattggtt ttacctgcgt gggctgaaag tcttcacttt taatccttac      240
ag                                                                    242

<210> SEQ ID NO 465
<211> LENGTH: 871
<212> TYPE: DNA
<213> ORGANISM: Corynebacterium glutamiucm R

<400> SEQUENCE: 465
ttctgctcct cctgtgccgc accggaagcg cggttgatga aggtgtggag agcctcaacg       60
gagaacacaa cgtcgtcaga cttgagaacg tcgtaggtgt tcagctgatc agcggccagg      120
atgtggacgc caggcaggtt gttagcactc ttctgggcgt tgatatcctc acggctcact      180
acgagcagca cggacttacg ctcggtcaga cgctcgatga aagcctttgc agacttggtc      240
gaaggggtct ggccaggcac caattcggag acgacgtgga tacgtgcatt gcgtgcacga      300
tcagacagtg caccgtaaag tgcagccttg atcatcttct taggggtgcg ctgagagtag      360
tcgcgtggct tagggccgtg ggagatgcca ccaccggtga agtgaggtgc gcggatcgag      420
```

```
ccctgacgag cgcgaccggt tcccttctga cggaatggct tacggccacc gccacgtact    480
tcgccacggg tcttggtgga gtgggtgccc tgtcgagctg ctgcaagctg tgcgttgaca    540
acctggtgca gcagtgcgac ggagacctca cggtcaaaaa tctctgcagg gagttctaca    600
gatccgttga tgtttccatc agcggtctga acatccagct tcagattcgt catgcgtgtg    660
caccgccctt cactgcggtc ttaacggtaa cgatgccacc acggttacca gggattgcgc    720
ccttgataag gatgatgttg gcatcggcgt caatcttctg aaccttgagg ttctgggtgg    780
tgacgcggtc attacccatg cggccagcca tacgcttgcc cttgaagatg cgacctgggg    840
tagcagctgc accaatgcca cctacgcggc g                                   871
```

<210> SEQ ID NO 466
<211> LENGTH: 100
<212> TYPE: DNA
<213> ORGANISM: Corynebacterium glutamiucm R

<400> SEQUENCE: 466

```
cgccgaagac tgttgatgcc cttatgcgca tcgaccttcc ggccagcgtc gacgtgaaca     60
ttcagtgatc gacggaattt ttggcagcgg agaataaata                          100
```

<210> SEQ ID NO 467
<211> LENGTH: 243
<212> TYPE: DNA
<213> ORGANISM: Corynebacterium glutamiucm R

<400> SEQUENCE: 467

```
tcttgcactt gttgggtaaa cgcacctact acacccattt ggggcaatcc aaacggatgg     60
gtttcaggtt atgcctgcat gatgactgcg aaagcgcagt tggaaacctc acaacaccac    120
tggttttttc gcttgaccgc gcaaaatatg agaacatagt gagagttaaa ccaagttctg    180
taggtgcttg ttgcagcggg cgcgaaggcg taccactgca acttgcgaat aaaggagtaa    240
aac                                                                  243
```

<210> SEQ ID NO 468
<211> LENGTH: 141
<212> TYPE: DNA
<213> ORGANISM: Corynebacterium glutamiucm R

<400> SEQUENCE: 468

```
gtcctgtggt gtccttattg gggttgtcct gcaagtttta gaaatcatag cgtgagatga     60
caaggaaagg aatatttcga tccggcaaca accccgcgt caggtgggat tatgccgaaa    120
aaatcgctac gatagccact t                                              141
```

<210> SEQ ID NO 469
<211> LENGTH: 422
<212> TYPE: DNA
<213> ORGANISM: Corynebacterium glutamiucm R

<400> SEQUENCE: 469

```
cagtttcact gccaattttt taagcctaac cctctgcata attttgtttg agccgtgtaa     60
tatacacggc ttttctgctt tcaggccaac tttccctccg caaattcacg aaagtttgcg    120
caatcgtttt cgcccacacc ttccccagca cacattccgt tcacactatt tcggggtag    180 ggcaaataac gattcatctc acaaatttct atcaaactat agaaagatat ttgcaaaatt    240
ggcacaaact cccagctcgc tccgaaaaac ctagcaactt agttaatttt ccctcacaaa    300
aatttaggac acagatctcc attcaagttt ggctgtgact catgtcgcac atagtatttc    360
```

```
aagcacagga tcccactcgg ctgaacagct caggggaata ttcataacaa cggaggtcaa    420
tc                                                                   422

<210> SEQ ID NO 470
<211> LENGTH: 410
<212> TYPE: DNA
<213> ORGANISM: Corynebacterium glutamiucm R

<400> SEQUENCE: 470
agcctccttc cacatggcgt ggcctgacaa atgcggtgag attaatttgt acattgggcc     60
aggttagcag cgctaaccgt gccccgcgtg gagcgcgcgc gggaggctga tggagggcgg    120
cgtcgataag cgtgctagga agtttgtgtt ttagtgttca cttgctgtac tctgtccgtt    180
tggactttgc accagaaaac tctatagagc acaacggtgt tttaaagatc catgtaaacg    240
taaacaccta ctttgttgta ggcccccgc catgaatggc gatccgtgtg ggaaatggca    300
gcgagcaaac cgactattga gttcggtgag cgttgagtgg ccagaaaaca cacggttaac    360
gtccaaggtg ggaagggaac cccaacgaga aaggcatcag gtcgtctcta              410

<210> SEQ ID NO 471
<211> LENGTH: 100
<212> TYPE: DNA
<213> ORGANISM: Corynebacterium glutamiucm R

<400> SEQUENCE: 471
aatccaaacg tgcgcttccg cggcgtgtac tttaacccgg agtcatttga tcagatgtgg     60
cagaccaagc aagtgggacc tttcgtggtg gtgacgcaca                         100

<210> SEQ ID NO 472
<211> LENGTH: 100
<212> TYPE: DNA
<213> ORGANISM: Corynebacterium glutamiucm R

<400> SEQUENCE: 472
gacgagctgg gcattgctca gacccgtcgt cttcgtggac tgggtgaccg tcagcgtcgc     60
gcacttctcg agcgtttcgg cttcgaggat taattcttca                         100

<210> SEQ ID NO 473
<211> LENGTH: 335
<212> TYPE: DNA
<213> ORGANISM: Corynebacterium glutamiucm R

<400> SEQUENCE: 473
tgatcctttc gacatcccag aaccgaaaag tatcccggcg aagatggcag cttctgctgt     60
tcgcttctac caaaagtatc tttcgggtct aagatgggt tccacctgtc gttttgatcc    120
agtttgcagc acctatgcat tgaaagccgt ctcagttcat ggggctttta agggaactat    180
tctctccgct gcaaggttgt ccaaatgtgg gccctggcat ccgggtggat tcgacccggt    240
gccaaaccat ggattttggt ccaccgaaac ggtgacatag aagtcctgcc aacaagtaca    300
tagtccctat taatcccaag gagtttcgac tcaca                               335

<210> SEQ ID NO 474
<211> LENGTH: 61
<212> TYPE: DNA
<213> ORGANISM: Corynebacterium glutamiucm R

<400> SEQUENCE: 474
agacacgacg aattagacaa cattagtaat gctggaagaa acaaccgaga gcaggaagaa     60
```

<210> SEQ ID NO 475
<211> LENGTH: 100
<212> TYPE: DNA
<213> ORGANISM: Corynebacterium glutamiucm R

<400> SEQUENCE: 475
ggaaaaagga atcataaagc cacagcgcaa agccactgaa tcaataaaga agcgttaata    60
aagtttgact tgtgcctctg acctgcgttg acttgagtaa                         100

<210> SEQ ID NO 476
<211> LENGTH: 100
<212> TYPE: DNA
<213> ORGANISM: Corynebacterium glutamiucm R

<400> SEQUENCE: 476
cagggacacc gtcagcccct gaccgttctg aaggtaaccg gaatcaagta agccctcggg    60 cttctatga gtttttcctt tagaaggagg gaattaccac                          100

<210> SEQ ID NO 477
<211> LENGTH: 91
<212> TYPE: DNA
<213> ORGANISM: Corynebacterium glutamiucm R

<400> SEQUENCE: 477
tcccctatcc taatccacat ctcggtttat taaactgtta gtgaattccg atgtataaca    60
ctggtccgtt tcaggtgaac ccgtatggtt a                                  91

<210> SEQ ID NO 478
<211> LENGTH: 117
<212> TYPE: DNA
<213> ORGANISM: Corynebacterium glutamiucm R

<400> SEQUENCE: 478
tttttgctta cccggctgcc ccgggtgcac aggaatcttt cgattttcca aacatccttc    60
atggttttaa aaacctttac cgacgtcaaa tagcggtcgt cactcaagga gagttca      117

<210> SEQ ID NO 479
<211> LENGTH: 100
<212> TYPE: DNA
<213> ORGANISM: Corynebacterium glutamiucm R

<400> SEQUENCE: 479
attcgctaaa cctgcgcagg atgagactgc cctcgcagaa agcacattcg acgaagccac    60
cgcgtaaaca gtacgtggtg gaagcttgag aggaagacaa                         100

<210> SEQ ID NO 480
<211> LENGTH: 269
<212> TYPE: DNA
<213> ORGANISM: Corynebacterium glutamiucm R

<400> SEQUENCE: 480
aacgcgatga tcttaaggat ctgaatccgg taacacgaca gaaattggtg ccctttaggt    60
ttcatcattt gaccttggcg tatactgttt tatcagttcc aactaccaac tccgtttcca    120
tggaagctac ccgctttcg ccaccgcaac gtgagtccaa aatttcaca cggtgcacca     180 cacatttagt ggtgtattga ggtgtttctg ggctgcgtga gaaaccattt tccggtggat    240
gatggaagct agacgacgaa agggagcat                                     269

<210> SEQ ID NO 481
<211> LENGTH: 100
<212> TYPE: DNA
<213> ORGANISM: Corynebacterium glutamiucm R

<400> SEQUENCE: 481

```
cgatcgtgtt ctgaacctga atgatggtgt cctgcgcacc aaggttctgc gactcgacaa    60
gtaaagaact ttaaggctct agagaggtag ttgaaggatt                         100
```

<210> SEQ ID NO 482
<211> LENGTH: 126
<212> TYPE: DNA
<213> ORGANISM: Corynebacterium glutamiucm R

<400> SEQUENCE: 482

```
aagctttcac accggttagt ggctcattca aaatgtatgg ccaccaacca attttcacca    60
aagttttatg tggcagggcc agctccggcc cgttaaacca cagaattcca tgaaagggaa   120
tttcta                                                             126
```

<210> SEQ ID NO 483
<211> LENGTH: 100
<212> TYPE: DNA
<213> ORGANISM: Corynebacterium glutamiucm R

<400> SEQUENCE: 483

```
tgcaggtcgt gcaattgttg cggctcgtcg tcgcaagggt cgcgcaaagc tgaccgcgta    60
attttttagc gtcaccacaa taaataaggt gtaagcaaca                        100
```

<210> SEQ ID NO 484
<211> LENGTH: 754
<212> TYPE: DNA
<213> ORGANISM: Corynebacterium glutamiucm R

<400> SEQUENCE: 484

```
tttttatcct tttcatgtgt tggaaacaga gtcatggtag gtcgccttat ttgtcagtgc    60
aagggtttta ttagcttttg gagatagttt ctggctggtt gaaatagttg acatctgtgc   120
aggttggagg cttttgtttc cgacttgggg ttatgtgaag tggggtgctg tgtggcgttt   180
taagcggtcg actgtctgcg gcgacctgtt gtcctagttt tggcgagttg ggtgcttaga   240
agcggtttta gagggggtcg aatttgtgac gattggggct attttgattt ctgctgggtt   300
gctgtgggct tgctgatcaa cttctcgttc caacggggcc tcacgccctc aaacggggac   360
gagttttcgc ataataccccc gtgattagcg caaattttcg actaaaaatg gccttttccc   420
tctggctggg gacggatttt cgcaacttca ggcagtcacg tgtcgagcgg gacatggatg   480
actcaatggg taaggggatt gtggtgcctg tcggatggcg atggttagga ctcaccattt   540
ttaggatgcc acctcgaaaa aacggtgaat cggcacgctt ttaacccctc gaaagtgtgc   600
caattcaaca tattctgcgc ccaaccttca aaaaatggtg aatcctaaca ggcttagggg   660
gcttgcaagg cgggactcat gccggggta tgccttgggg cagttattaa ggataacctt   720
gccttaatta tttggattgc agtaatttaa atga                              754
```

<210> SEQ ID NO 485
<211> LENGTH: 55
<212> TYPE: DNA
<213> ORGANISM: Corynebacterium glutamiucm R

<400> SEQUENCE: 485

```
gtcgcatggt ccaattcatg ggccgcgcta atcaacgta caaggagtac atcta            55
```

<210> SEQ ID NO 486
<211> LENGTH: 239
<212> TYPE: DNA
<213> ORGANISM: Corynebacterium glutamiucm R

<400> SEQUENCE: 486

```
gctgccctta actgcagttt ctgcagttag ctgaccaatg taaagccccc acgacaatgg      60
aactttgact tttaaaattt catcgccgtg ggggcttttg ggcagccagc ccgccgtgtc     120
ccaacgtaat cgactgaata cctgtacgat cacttttag acgggcgggt agggctactg     180
tgccctaacc taagcttgta aagcattaat tatccataca taaggaggat cgccccgta     239
```

<210> SEQ ID NO 487
<211> LENGTH: 347
<212> TYPE: DNA
<213> ORGANISM: Corynebacterium glutamiucm R

<400> SEQUENCE: 487

```
tactgtcaag acatgaaagc ccaatcacct ttaagatcaa cgcctgccgg cgcccttcac      60
atttgaataa gctggcagcc tgcgtttctc caaggcgact gggcttttag tctcattaat     120
gcagttcacc gctgtaagat agctaaatag aaacactgtt tcggcagtgt gttactaaaa     180
aatccatgtc acttgcctcg agcgtgctgc ttgaatcgca agttagtggc aaaatgtaac     240
aagagaatta ccgtaggtg acaaactttt taatacttgg gtatctgtca tggataccc     300
ggtaataaat aagtgaatta ccgtaaccaa caagttgggg taccact                  347
```

<210> SEQ ID NO 488
<211> LENGTH: 179
<212> TYPE: DNA
<213> ORGANISM: Corynebacterium glutamiucm R

<400> SEQUENCE: 488

```
acagcaatta atctgattgc acctgctgca taaatgtgac tagtcaaaca ccgtctaatt      60
acatgtgtgt ggtagaacaa taatgtagtt gtctgcccaa ccgagtgaca ctcccacgat     120
ttacagtggg ggcagacatc ttttcaccaa aatttttacg aaaggcgaga ttttctccc     179
```

<210> SEQ ID NO 489
<211> LENGTH: 100
<212> TYPE: DNA
<213> ORGANISM: Corynebacterium glutamiucm R

<400> SEQUENCE: 489

```
tggcgatacc agctccgagt agggctgcac ttgaaaaagt gagtgtttta gcgatagttg      60
acaccttatt caccctacct ggggagtact ctgggcaaac                          100
```

<210> SEQ ID NO 490
<211> LENGTH: 183
<212> TYPE: DNA
<213> ORGANISM: Corynebacterium glutamiucm R

<400> SEQUENCE: 490

```
aatgggacga gtgtgatttg gggcagattg gaactgcctg tgaaccctct aacctgcaat      60
tatgtaactg tcgtaaaagg gctacgaaga gttcccggaa ggtcgattga aaagtttgcg     120
aattggggga aaattcgcat caaaagccga gttcaaactt tcaattgaaa cggggggctt     180
gaa                                                                  183
```

<210> SEQ ID NO 491
<211> LENGTH: 108
<212> TYPE: DNA
<213> ORGANISM: Corynebacterium glutamiucm R

<400> SEQUENCE: 491
tacttggccg ttataaagac aaaaacaccc ctggtggatt cccaaaagga aattccacca    60
ggggtgttaa gcattcgctt gaagcgaata gcaagaggtc atcagtag              108

<210> SEQ ID NO 492
<211> LENGTH: 240
<212> TYPE: DNA
<213> ORGANISM: Corynebacterium glutamiucm R

<400> SEQUENCE: 492
gcttccacgt ctctttcttc aaattaaact gttaaaacca aaggtggccg gcaccgcaca    60
atgcatgcgg ttccggccac cttgaggtga gtgcttccac gtcactgctt gctatctacc   120
tatcatcgta gattcagcag cacgagagaa gaaatcttat ttgcccagtg ccttgagggt   180
acgagcgttg atctcttcga cttcgccttc agcctcaatg ttgatgatct tgtcaccgta   240

<210> SEQ ID NO 493
<211> LENGTH: 364
<212> TYPE: DNA
<213> ORGANISM: Corynebacterium glutamiucm R

<400> SEQUENCE: 493
cctctcgcgt gccccaacgg ctcctacgat caaaaatcct ccctgcttcc ctcaactgtt    60
tttatatgta tttgtatgtt ttaggcccga ttgcccccata attggggagg gtttcaatgt   120
ccgaatgaag gaaattgtca caatcgggtg ttttgggtcc gatttctttt gaatatgtgg   180
gttacctcac taaggtggaa ggaaggctaa ccagatcata gtcggactgc aatccgctat   240
gaagtacttg gtggcgctgg gaagaagcct tcgttatggg aggtctccca gacacaatcg   300
aatacgggcc ggatatccat ctcggctcat caccccgctt tttaccaaga aagatgagga   360
cctc                                                              364

<210> SEQ ID NO 494
<211> LENGTH: 100
<212> TYPE: DNA
<213> ORGANISM: Corynebacterium glutamiucm R

<400> SEQUENCE: 494
agtaggggat catccagcga agcggtcgca gaggctgtga ggaagctcta agtcgactta    60
agtgcgcgaa gcagaccacc attaggtaga atcacccaac                       100

<210> SEQ ID NO 495
<211> LENGTH: 610
<212> TYPE: DNA
<213> ORGANISM: Corynebacterium glutamiucm R

<400> SEQUENCE: 495
ggcaacgacc tcccagcccc ctgctcagac aaatcatcat caggaggcgt caaaccatgc    60
gtcgcatacc aaccagggcc atgcctaacc cacgcattca caatcgcacg gttacacgca   120
gcatgaatca aacgcttagg ctcattcgac aagtcagcat tgagatgatc cgcatgcaca   180
gtcctacgat caaaattgtt ttcagctttc cgatacatcg ggcgcccgca atactcacac   240
aaatcaccat cacgaagatt gaaccgaaga cgctcgcgag cccgtttgtg ttgcgctttg   300

```
ttgtactgaa cggccattcc acacctccta agtcggtttc cgcagctcag ggagagagag    360
ctggaaagat cactcagagg ggcggagtgc cgttcgaaag gactcagata aaacgacccg    420
ccaggtttgc cgaagatgcg cggacagatg gcgttagccc atggcacggg ctatccagat    480
tgatcaggac tctctcaaga agtgattccc aatactccca tctttatgca ggtatgctat    540
ccacatgaca ataatcaacg ctgatagttc agttatagaa gaagtaaaaa ggcaatttgc    600
aaacagattt                                                           610

<210> SEQ ID NO 496
<211> LENGTH: 375
<212> TYPE: DNA
<213> ORGANISM: Corynebacterium glutamiucm R

<400> SEQUENCE: 496
tatttaatgc tcctctaagt tcccctggca ctcctatgaa gagtaaaagt tttgaaaggt     60
atcaaatcgg ccagtgtaac gacgtattgt ttaagactat cgccatatct ttaatgtggc    120
acagacccag tatttttatt atccaacact taaggtaact attgggcggg gtaggggagg    180
agcttttcgc acctatgatg cgccttacaa aaaggggttg ccatgcggtt cttgggtaaa    240
tactggtagg gtagacaagt caatcgtgtc cgatttgtaa tcggaccagg atctaaagaa    300
cacatctccc ggtacctttt agtcactatt gtgaaaatat gtgggtttga agtgctgagg    360
aggccaggag gataa                                                    375

<210> SEQ ID NO 497
<211> LENGTH: 100
<212> TYPE: DNA
<213> ORGANISM: Corynebacterium glutamiucm R

<400> SEQUENCE: 497
tggagatcgg ttcaatctcc gacgtgaccc cacagccaca caacggctgc cgtccaccaa     60
agcgtcgtcg cgtttaatag ggaaggaaag gtaatacaaa                          100

<210> SEQ ID NO 498
<211> LENGTH: 479
<212> TYPE: DNA
<213> ORGANISM: Corynebacterium glutamiucm R

<400> SEQUENCE: 498 tttctttttaa gtttcgatgc cccggtttcc tgattttgtg cagggaggcc ggggcattgg     60
tgtttgcggg ttagttcggg ccatccgaaa ggaagaaacc aagggcggcc agacagacgt    120
gccaagaatc tggatttccg ccaggttttg gcacgcccgt ctggtttagg cagtgagata    180
ccggacacac gtgccaaaac ttcggctttt tcgccaatct tgtcacgtct gtctggtttg    240
ccttgaaaag ggtgatttca tggccgagac tcctaaaagt ttgacctcac aggattgctt    300
ctaagggcct aaagccggta ttcctaggcc atagcccttc ggggaattcg ggcgcttaaa    360
tcgagaaatt aggccatcaa cttttaataa caatccaatg aataattgga ataggtcgac    420
acctttggag cggagccggt taaaattggc agcattcacc gaaagaaaag gagaaccac    479

<210> SEQ ID NO 499
<211> LENGTH: 1000
<212> TYPE: DNA
<213> ORGANISM: Corynebacterium glutamiucm R

<400> SEQUENCE: 499
ccctacgtat taccgcggct gctggcacgt agttagccgg tgcttcttct ccaggtaccg     60
```

-continued

| | |
|---|---|
| tcaccatagg cttcgtccct agcgaaagga gtttacaacc cgaaggccgt catccccac | 120 |
| gcggcgtcgc tgcatcaggc ttgcgcccat tgtgcaatat tccccactgc tgcctcccgt | 180 |
| aggagtctgg gccgtgtctc agtcccaatg tggccgtaca ccctctcagg ccggctaccc | 240 |
| gtcgacgcct tggtaggcca ttaccccacc aacaagctga taggccgcag gctcatccca | 300 |
| caccgcataa agcttccac accacccta cgatgatgtg aatattcggt attagaccca | 360 |
| gtttcccagg cttatcccaa agtgtagggc agatcaccca cgtgttactc acccgttcgc | 420 |
| cactcatcca ccaaatgcaa gcatctggtt tcagcgttcg acttgcatgt gttaagcacg | 480 |
| ccgccagcgt tcgtcctgag ccaggatcaa actctccaca aaaaacaat aaaaagatt | 540 |
| gtttaggccg tgaaaagccc aacacctgac aaaaacaaca cacccccac caaccattag | 600 |
| aaaatgatca gataatgggg tgttactggc attatcaaaa aataatgat ttaaaaaaaa | 660 |
| caccacaacc cacataagga tcatcgtgtc tttaatgtgg gcctgatccc ttgacgggga | 720 |
| acaagcagac ccacaaaaat catgccaaca ataagtttat tgtttacagt gatggataat | 780 |
| attggcgatc caccacccgg catgacccac caccaaaacc ctcaagggggt taaaagtggt | 840 |
| agtgacaaaa ataataaatg gcacactatt gagttctcaa acaacatacg cacactagga | 900 |
| aattgaggta atatttgcac cttaatctct ttagcagctg aagattcatc gtagttcatt | 960 |
| caaaatttga agtcaacttc gaattaatct ccgtgtcacc | 1000 |

<210> SEQ ID NO 500
<211> LENGTH: 205
<212> TYPE: DNA
<213> ORGANISM: Corynebacterium glutamiucm R

<400> SEQUENCE: 500

| | |
|---|---|
| tcgcggaaac ggcccttaat tgcaagcctg tgacctgcag gtttagcttt tagggggtcct | 60 |
| gccacctttg tgtttgcgaa agtagtgcta gactattcga aaatcgcagg ctgacatcct | 120 |
| tggtattaac caggtgtact ctcgatttct ggatactttg gtattcattt tgtcactaaa | 180 |
| aaccacacga taacggagga acccc | 205 |

<210> SEQ ID NO 501
<211> LENGTH: 1000
<212> TYPE: DNA
<213> ORGANISM: Corynebacterium glutamiucm R

<400> SEQUENCE: 501

| | |
|---|---|
| caccatagtc accgctgtaa tattcctcca caatctggtg cagataggag tcgcggaagt | 60 |
| agttatggtc taagcacgtc gcaatcgcat caataaagct cactcgctgc ccattaggca | 120 |
| tccgtgtact tcgcacctgt cggacatatg catcggtgat attcgacttg gaagaggtag | 180 |
| gcaccctaat aagaattggt agcgtcaggt gctgattcaa atgggactgt atcgctgaat | 240 |
| agccatccaa ggctatattt tttcgacgcg acttgagggc ccaccacact gaatctcctg | 300 |
| ttacttcacc cgagatatat acaccacgaa aaattcgagt cagttgttgc tcgtgaacca | 360 |
| acgattcaat ctgtcgctta gttttccctg agtcaataag ttgttggtag gtccaaattc | 420 |
| ttcttgccat actcaggtta gactgctgga aaggcctaaa ggttcccaat tttcctgccg | 480 |
| atgtgaattc gacaccaaga tttcctgatt ttgaccccca ttttgccaat atcttggtgc | 540 |
| cgaaagtacg cacggaagag agtccaaacg gacaaaaacc cccttccga agaagggtgg | 600 |
| ttttaaatgg tgcccggggg gggacttgaa cccccacgtc cttgcgaaca ctggcacctg | 660 |
| aagccagcgc gtctgccaat tccgccaccc gggcagggtg tctttttgcga cttgttaaag | 720 |

```
atagcacgca cttggcgttg aatgccaaat cggcagctaa atagcggttt cctgaatggc      780
aacaaagttg taaatttatg cattccggtg gtttggccta taactctggc gcggttcacc      840
tctataatga cgctatcgtg cgctttggtt tagaccgtgt gaaggttttt ctaaatgaaa      900
tttcagtcac agggagggac aaagccatgc ccttaggcgt tttctaggag aagacactta      960
tggaacaccc aacttattga aaaaggaggt cgcaaagtt                            1000

<210> SEQ ID NO 502
<211> LENGTH: 100
<212> TYPE: DNA
<213> ORGANISM: Corynebacterium glutamiucm R

<400> SEQUENCE: 502
gtgtggccaa ccaggcacgt caggcacaga tcacccagga aatcacagag attgttggtg       60
gcgcaggcgc gctcgccgac agcggagaaa gtgactaatt                            100

<210> SEQ ID NO 503
<211> LENGTH: 647
<212> TYPE: DNA
<213> ORGANISM: Corynebacterium glutamiucm R

<400> SEQUENCE: 503
acgcaatagt tgcatttta gttaacatcg agctgcaaca acagcaataa acactcaatt       60
acatgacaga aatgatctgg tctcactccc gtccagtgtg agttcgagtc tcaccagggg      120
caccactacc agcggaaact ccgacttgga gaagtgattt cggccaagat gttctagaaa      180
tcaaatccca ctgcggttaa agcagtggga tttcttcatt tttggggtaa ctcgacaaaa      240
atcgcccaga aacttggggg tagtttcaag atcgactagt gcaatctccc caaaccggac      300
acacgtgaca aaactttgga tttcggcctt ctcttgtcac ccctggctgg tttcgaccac      360
ttataaccag tctggtctgc ccgagttgat gcttcgatgc cgaaaaatca tgaggccaca      420
gaatccaatc taacggcctg taaaacctct ccccgactat tgcccgtgc gaagcattag       480 agccttcaaa ttggccacaa atgcgtctga gttgagagac ccaactttct gcaccctacg      540
cccagttttc agcacagatc ccctttgcc agctaccgac ttagtttcgt aacacgtata      600
gtgggaggcg ttttgccaga cgccaaagaa agataattgg attaccct                  647

<210> SEQ ID NO 504
<211> LENGTH: 100
<212> TYPE: DNA
<213> ORGANISM: Corynebacterium glutamiucm R

<400> SEQUENCE: 504
gaagaggtcg aagaagacga cgcagaggat cctgaagaga atcctgatga ggaagaatcc       60
gacgaagaaa ttgagccaga aactgaggct gaagaaacca                            100

<210> SEQ ID NO 505
<211> LENGTH: 225
<212> TYPE: DNA
<213> ORGANISM: Corynebacterium glutamiucm R

<400> SEQUENCE: 505
ggtataaggg cggtttgtgt tgaagccgcc tttaggggta accttggaca gtcgctgttt       60
taggcaatgt cagtaatgcc catttgccca tttcacggcg aatgtgtgaa tgacgtgagg      120 tcatttggc tccgcatgtc taaaacgcaa ttgtaaaacg taagtccaat cagggactca      180
tcatccgagt acctgagccg agaatcagat aaggggtagc cctct                     225
```

<210> SEQ ID NO 506
<211> LENGTH: 100
<212> TYPE: DNA
<213> ORGANISM: Corynebacterium glutamiucm R

<400> SEQUENCE: 506

```
atgcacccgc agagcgtcgc ggccgcggcg accgcaacgc acgtccgcgt cgtggtggcc      60
agcgtcgtca gcgtgctgag cagaagcagg agggctaaac                           100
```

<210> SEQ ID NO 507
<211> LENGTH: 401
<212> TYPE: DNA
<213> ORGANISM: Corynebacterium glutamiucm R

<400> SEQUENCE: 507

```
tcgcacggaa atcttcatcc taatccgatt tagctaagtt atataggtat gagactatgg      60
ctgacttggt gctttattaa tttccccaac gactagggct gaaccccacg tttaaagtca     120
ttcacacttc ttcagcacat tttcagccct gcccagccaa agccttctgg accttttaatt    180 atcagagcat tttccaaatc ccctgtggca aaaatagat caataccgta aaatacgtga     240
gaaaaaatta tataattcac agtgaatcta tggagtggaa caagcctctg acttttgttt     300
tatttgcaag cacatgatgg acattacagc tactgctggt gcatccattg gggtggggcc     360
cacgcagtcg ctagaaaaca ttgcaagtta aggaatacac t                        401
```

<210> SEQ ID NO 508
<211> LENGTH: 643
<212> TYPE: DNA
<213> ORGANISM: Corynebacterium glutamiucm R

<400> SEQUENCE: 508

```
tgtgttcaac cttcttaaaa agttttgggt gggtccacga ccggcaacac caaactccgc      60
gacgggatgc cggtcgtgtt aagacctctg ggacccgccg cggcgaagaa gaagtagatt     120
cgcacgcgaa gtcatgtggt gaagcataca acaactttgt ggtgtgggta gtaactcggg     180
ggggagtttt cttttaaaaa gcttttcgac gcgcagttcc ggtgctgtca tgtttcgggg     240
gaaacattac gagaatggaa tagctcgatg gggaaaattt gcagaatgtg tctgaaatca     300 caataggggtt cgattgcgga atcctgagaa ttgtgaaaac ttttgcggaa tctcaaccgc     360 tttttatgtgt gtgaaaatgt ctaatcctgc ctggttgtgt gatgttttgt gggcaaatta     420
agagaattta acccttttaa cgtggttatt tctgagaggt agataagttt ccatgttgat     480
tagttggcaa attcttatga atcgattgtg agaactattt atgtggtcgt taccctccca     540
tctggcaaag gtgttgatgc gaaaactcgc gaaatcactt gacttttttga gtttgcagtg     600 ggagagcgtc aaaccccaat cttctacgaa aggaattttc acg                        643
```

<210> SEQ ID NO 509
<211> LENGTH: 464
<212> TYPE: DNA
<213> ORGANISM: Corynebacterium glutamiucm R

<400> SEQUENCE: 509

```
ggccccctaac gtacacaaat tccgcaaggc tgtcagcata ggttagcgca gcataacccg      60
catttttggg ctttggattg gctaagtttc ccaccttttt gaaggcttga aatggccca     120 gtttgagacc tgtttcacat taaaggtttt ctctaaatga cgtgctagtg gcgataattt     180
agggcaataa atggttgaat ttgagggctg atggaggtgg tcttgtggcg ttagtccgac     240
```

```
actgaaccct gtggggcgta atggaaaata agtgactaag atcacgtttt ggggtggggg      300
attgcgctct aaagctaggt ctaaagctag gcgacttgac caaaattgat aggctggggc      360
gggtcttctg aagggcttcg gttggggtaa gctggcgatc tgaaatcgcg ctgcattgtg      420
gcgtcgaaaa gcaaaaaaat ttgtagaagg gaagagcgca ccta                      464

<210> SEQ ID NO 510
<211> LENGTH: 98
<212> TYPE: DNA
<213> ORGANISM: Corynebacterium glutamiucm R

<400> SEQUENCE: 510
tttttcaaat ccttcgccat cgacaagctc agccttcgtg ttcgtccccc gggcgtcacg      60
tcagcagtta agaacaact ccgaaataag gatggttc                              98

<210> SEQ ID NO 511
<211> LENGTH: 100
<212> TYPE: DNA
<213> ORGANISM: Corynebacterium glutamiucm R

<400> SEQUENCE: 511
cacccgtaag aacaagcgca acaacccgga ccgtatttcc ctcatgaagt acgatccagt      60
agtccgtaag cacgtcgaat tccgcgagga gcgataatca                           100

<210> SEQ ID NO 512
<211> LENGTH: 100
<212> TYPE: DNA
<213> ORGANISM: Corynebacterium glutamiucm R

<400> SEQUENCE: 512
ttgggttggc atcggatcct gcctgtggcc taagatcagg cagtgttgtt aaaggacgat      60
cggtaatccg aatggatcgt cccgtagtca ggaggaacct                           100

<210> SEQ ID NO 513
<211> LENGTH: 100
<212> TYPE: DNA
<213> ORGANISM: Corynebacterium glutamiucm R

<400> SEQUENCE: 513
cggcgaaagt gactttcgaa tcagttcga cgccgtcgat cgcggcgatt tcctgggcta      60
gcgatgaatc caacacctca ctaacggtag tcttatcctc                           100

<210> SEQ ID NO 514
<211> LENGTH: 272
<212> TYPE: DNA
<213> ORGANISM: Corynebacterium glutamiucm R

<400> SEQUENCE: 514
tctagtcttt ggaggtttgt taggggagag gatccctctt taatgatcga ttaaggaaac      60
cgcggtgtct agggcctcta aaagattgaa ttggtgcacc cgctatccac ccattttgtc     120
catgtcctgc gggatatcca gggggaattg cgcatatgac tggtagaaca agtagtttaa     180
atcatgagac atttcacata tggttcttca tccgagacat gtgttgacgc tgtctgcccc     240 ttttttgaaaa taacacttta aggagatgtg cc                                  272

<210> SEQ ID NO 515
<211> LENGTH: 216
<212> TYPE: DNA
<213> ORGANISM: Corynebacterium glutamiucm R
```

```
<400> SEQUENCE: 515
agcacatcag ggaatccacc tactttgttt tccccctagaa atcccccatt tcatcactcc      60
cgaatggggg taatgcttga tcgatcaatt gagttgcttt atcgatcagg tctgatttct     120
gctgggaatc cccacatttt ggaacgtagc gtcgagaagc gtgcggcgaa gcttttttcgg    180 tcgcggccgt tatcttttta agaggagaaa ttttag                              216

<210> SEQ ID NO 516
<211> LENGTH: 171
<212> TYPE: DNA
<213> ORGANISM: Corynebacterium glutamiucm R

<400> SEQUENCE: 516
aaacgagtca gatcgccttt gtgtggaact actccccttc gaaatggaag tggttgcgcc      60
aagtttttcg ttgcttgggc gttaacgatt ctatatgtac ttccctagaa atcaagtgag     120
cattcatctc attgcagaac gttgaagcat cattgactag gatatgtaga c             171

<210> SEQ ID NO 517
<211> LENGTH: 512
<212> TYPE: DNA
<213> ORGANISM: Corynebacterium glutamiucm R

<400> SEQUENCE: 517
gggggctaga accacagggg aggcaaggtc aaggggccg atttttaaag tcacctaact       60
attgtccccc gtgaatcagg ttgggcaaaa tatttgaagc aaattgtgag cagggcgcaa     120
ctaggaaagt ggtgtgcttt cactttttgg gggctggggt tgggttaagc ttcgcgggct     180
ctacggttgg tctgagcttt attcctgggc tttgggaggc ttgcaaacag gaggcatgca     240
aatttggggg tagtgcaggg ccttgaaatc ccacctcaca gatagtattc aggcatttcc     300
tgtcacgatg gtttatcctt gggacacaac atcaaagtgg ggtacatcat atgcttccgg     360
ttgaagtgac ctatctgaaa agactggtcg aaccttgaag caatggtgtg aactgcgtta     420
acgaattttg tcggacgtta aaatggtcgc attctgcttg ctgaagtggc acacctatgt     480
gttctgcttg ggtatagcag tgcgggaaaa at                                  512

<210> SEQ ID NO 518
<211> LENGTH: 100
<212> TYPE: DNA
<213> ORGANISM: Corynebacterium glutamiucm R

<400> SEQUENCE: 518
gctgtcacca aagaacgtgc gcgtgcagct ttccgaggca aagacgacta gtctttaatc      60
caagtaagta ccggttcaga cagttaaacc agaaagacga                           100

<210> SEQ ID NO 519
<211> LENGTH: 311
<212> TYPE: DNA
<213> ORGANISM: Corynebacterium glutamiucm R

<400> SEQUENCE: 519
gcgctctagc gtatcaacta gctgcagttg ttatgtgcac agcaggggat tgacagtctt      60
ctggctcagt tcggttgtt ggtcacaaat gaatcacgtg tacccttttgg tgggaaagtc    120 attgaaaacg tcgcacacct aagtcgcatg cagaaggcgc acgcctaaat tgtgcagata    180
acctaaactg ggtgcattta gtgtggggat gaggcacgag atcatccatc gtcggttcca    240
tagaatgggg agctgtcgaa tgctgataga tatttggtga ccagagatta gagcaaagga    300
```

-continued

| tcattttcat c | 311 |

<210> SEQ ID NO 520
<211> LENGTH: 133
<212> TYPE: DNA
<213> ORGANISM: Corynebacterium glutamiucm R

<400> SEQUENCE: 520

| gcgttatagt ctagagcgag caggcgagat gtgaagtacc tacacgcctt aagtgcaaat | 60 |
| gaattcacaa ttgccagaag atgcacagga tgtaatctag atttcccaag ttcagtgggg | 120 |
| caaaatgact tat | 133 |

<210> SEQ ID NO 521
<211> LENGTH: 133
<212> TYPE: DNA
<213> ORGANISM: Corynebacterium glutamiucm R

<400> SEQUENCE: 521

| atgaaaaagg tcgctattaa aagcttcttg cacaagtcgc ccagatagcg agcggaccac | 60 |
| tcggtcaact gaataacccc actaaacact tcacagcccg aacacacggg caccagaaag | 120 |
| ggaacgacac ctc | 133 |

<210> SEQ ID NO 522
<211> LENGTH: 823
<212> TYPE: DNA
<213> ORGANISM: Corynebacterium glutamiucm R

<400> SEQUENCE: 522

| cacgacggcg acgaacgatc atgtcatcgc tgtaacgctt aggcttgcgg gtgcggcctt | 60 |
| ccttctgtcc ccatggggag actgggtggc gaccaccaga agtcttacct tcaccaccac | 120 |
| cgtgtgggtg gtcgaccggg ttcataacga caccacggac ggttgggcgc cagcccttcc | 180 |
| aacgcatacg accagcttta ccccaacgaa tgttgatctg ctcggcgttg ccgacctcac | 240 |
| caacagtcgc gcggcagcgg atgtctacgc gtcggatctc ggaggatggc atacgcagaa | 300 |
| ctgcgtagga gccttcctta ccaagaagct ggatggaagc gccagcggaa cgtgccagct | 360 |
| ttgcacctgc gcctggcttc aactccacat tgtggatggt ggtaccagtt gggatgttac | 420 |
| gcagtggcag gttgttacca accttgatgt cggctgcagc gccggactcg ataacggtgc | 480 |
| cctgggtcag gcccttcggt gcgaggatgt aacgcttctc gccatcgaag tagtgaagca | 540 |
| gtgcaatgtt agcggtacgg tttgggtcgt actcgatgtg agcgaccttc gccaatacgc | 600 |
| catccttgtc attacgacgg aagtcgatga cgcggtagcg gcgcttgtgt ccaccaccgc | 660 |
| ggtgacgggt ggtgatgtgg ccgtgagagt tacgtccgcc ggtcttgctc agtgggcgga | 720 |
| gaagtgactt ctcaggggtc gaacgggtga tctccgtgaa catggaaacg gagcttgcgc | 780 |
| ggcgacccgg ggttgtcggc ttgtacttac gaatagccat aat | 823 |

<210> SEQ ID NO 523
<211> LENGTH: 132
<212> TYPE: DNA
<213> ORGANISM: Corynebacterium glutamiucm R

<400> SEQUENCE: 523

| tttggtggta aaaccgtcg aattggggcc tatttcgccg tttctcgcgt tgtgcgtggt | 60 |
| actacgtggg gacctaagcg tgtaagatag aaacgtctgt atcggataag tagcgaggag | 120 |
| tgttcgttaa aa | 132 |

<210> SEQ ID NO 524
<211> LENGTH: 100
<212> TYPE: DNA
<213> ORGANISM: Corynebacterium glutamiucm R

<400> SEQUENCE: 524
cctacgacgt tctcaagtct gacgacgttg tgttctccgt tgaggctctc cacaccttca    60
tcaaccgcgc ttccggtgcg gcacaggagg agcagaacta                         100

<210> SEQ ID NO 525
<211> LENGTH: 146
<212> TYPE: DNA
<213> ORGANISM: Corynebacterium glutamiucm R

<400> SEQUENCE: 525
ggtgttcatt ttagccgatc tggtcataac caggggtgtg gttttggtga ctgaagcggg    60
acaggagcgc ctagtaaaaa gcaaggctgg aaaacagata agccctaagt gcccacatgt   120
ctaccgatca cggtagattg ttcttt                                        146

<210> SEQ ID NO 526
<211> LENGTH: 130
<212> TYPE: DNA
<213> ORGANISM: Corynebacterium glutamiucm R

<400> SEQUENCE: 526
gtcagcttgc tcacttaaag cttcgaaata agcccttaag ttctcattct tttgttagac    60
ttgttcacta attacagaca tccaggggct tagattttta accctgtca taagtttttg   120 ggaaggtcac                                                          130

<210> SEQ ID NO 527
<211> LENGTH: 775
<212> TYPE: DNA
<213> ORGANISM: Corynebacterium glutamiucm R

<400> SEQUENCE: 527
tttcggggag cttcgggctc gcttcttggc aatgtaagcg gtgagttagc tttcgaccaa    60
accacactgc ccacgaatcc tagaaatggg atccgtgggc attcctgtct ggtttaacgg   120
ccttgaaacc ggacaggatt gcccaaagta gtcgaatttc agttcttgg gcatgtgtgt   180 ttggtcaggt ttagtcgggt cgaaaaatga actcggaacc ggtaaaaagt gacctcacag   240
aatcgcttct aagggccgtt caaagtgttg cctatacaaa cacatgttct gactgcccga   300
cctcttaaaa tggcgttaaa tggcgcgaaa tggaaaacgc ctcgtggcct ggatggagcg   360
ttagtaccag accagtacga gaccagacat acgtgacaaa aaatcctgaa aagtggaatc   420
attgtcacgc ctgtctggtt tagctctggt tcgggacggg catggaatgg aggcagcgta   480
ccgaagcctt gacccgcggc ccgacaagcc aaaagtcctc aaaacaaacc caccccgccg   540
gagacgtgaa taaaattcgc agctcattcc atcagcgtaa acgcagcttt ttgcatggtg   600
agacaccttt gggggtaaat ctcacagcat gaatctctgg gttagatgac tttctgggtg   660
ggggagggtt tagaatgttt ctagtcgcac gccaaaaccc ggcgtggaca cgtctgcagc   720
cgacgcggtc gtgcctgttg taggcggaca ttcctagttt ttccaggagt aactt         775

<210> SEQ ID NO 528
<211> LENGTH: 456
<212> TYPE: DNA
<213> ORGANISM: Corynebacterium glutamiucm R -continued

```
<400> SEQUENCE: 528
tttgttttcc cctccttttc tgttttccac acaaccgaag cttcaagggg aaaacaaggg      60
ctttaaaagt tatccacaga tccgaagtga tccgcgtcct ggggtgaaaa gttatccaca     120
ggaagcggag gggcggattg aaaaattcag cgaaatgcga aaaggtggag gggaaatgct    180
gcgagtcttg cggattcccg gcgtggcatt gaaaaaagtc taaagttgaa cttaagattg    240
aggtcattct gaagttgtga cctgcatcag aagagttaca tacccacata tgtaaccttc    300
tggactaaga tcacgacaga ctgaaaagaa ctgaagactc tcaaggcata gcccacgtgt    360
gtttgtcggg ccggaagcgg ggaactttcg ggacggatct aactcattgc gggcctgtgc    420
gcagtatcca aaaatcaaaa tgagaaggaa aacttc                              456

<210> SEQ ID NO 529
<211> LENGTH: 378
<212> TYPE: DNA
<213> ORGANISM: Corynebacterium glutamiucm R

<400> SEQUENCE: 529
ttgagtttta cttacctttc aacgagacaa tgcggaggga acaactttag tcacattagt     60
aacttcagtt aacttctttt cctcctgtca cattaatcgc agaatattta ctgtcaataa    120
ggatcaaagt gaatttctgg gtttccctaa agattcacca agatccgag acatattaga    180 acaacgtttt cttgttttgt ttgtcgtaca tcgatgcagt tccgttacaa aattctgaaa    240
aaaccagcaa atctttaga gatttgcctc acaatgtgcg gaacgggcga taatgcgagt    300
acagtgatac cgttctaaaa caatggactc gttttacaag tcctccatat ttctttatcc    360
ggcaggagaa tgcccca                                                   378

<210> SEQ ID NO 530
<211> LENGTH: 149
<212> TYPE: DNA
<213> ORGANISM: Corynebacterium glutamiucm R

<400> SEQUENCE: 530
acacttattc acaaatcatt ggactgtgat aactacccaa gagtgtcaca acttggtaac     60
gtgtgggcgg aaaaacaaga taggcatcga gaggtatcag cggtccatac cgccgatggg    120
tacatatcaa ttttttgccgg aggagaatt                                     149

<210> SEQ ID NO 531
<211> LENGTH: 75
<212> TYPE: DNA
<213> ORGANISM: Corynebacterium glutamiucm R

<400> SEQUENCE: 531
ctaaacaagc tttgattaac aagtccctgt attgtgtaaa tcgcttattg cacacaattg     60
aaaaaggaca ttgtt                                                      75

<210> SEQ ID NO 532
<211> LENGTH: 263
<212> TYPE: DNA
<213> ORGANISM: Corynebacterium glutamiucm R

<400> SEQUENCE: 532
agaattaagc cctttacctt cattgcgtat tgagaggtca ggggcttaat tggagccggt     60
gacgggaatc gaacccgcgc cgcctgcttg ggaagcaggg gttctaccat tgaactacac    120
cggcagtgta aaaggtggct cttaattaag ggccgagaat aaggctagca cgataaaaat    180
```

```
cagcgccagc accacgcgcc ccaggaacct catcgcagca acccgtggcc caaccctgaa    240
cgctgaacgc tacactggtt gac                                            263
```

<210> SEQ ID NO 533
<211> LENGTH: 313
<212> TYPE: DNA
<213> ORGANISM: Corynebacterium glutamiucm R

<400> SEQUENCE: 533

```
gcctcggcca ctgcctccgc ctttacgagc atttccgcct gagcgggata tatctccacg     60
aaacgtcatg aaagaaatca tggcacatta catagggaaa ccgacaggtt tgggtgtaac   120
aaaatggacg caatcgaaaa ctgactgcac ctaataaacc actcaaggtt caaggcaaac   180
cagatggcgg gtacaatgcg tgtgttgcct gtttctgggc tgcatgcccg ccctttttgg   240
gtggttgagc ttattgttta aggctccaga aaccatcgac tgatcaaaac caagcggaag   300
gacttccacc aac                                                       313
```

<210> SEQ ID NO 534
<211> LENGTH: 210
<212> TYPE: DNA
<213> ORGANISM: Corynebacterium glutamiucm R

<400> SEQUENCE: 534

```
gtgactgatc ttaaaggact ggggacacac ctaggcactt gcggggtgc tctgaccgca      60 tgcaatgact attaatccct atgggggatt gtgctacagg acacattggg tctaaactca   120
ctctcaactc accaagattg ttcaacaatc tgcgattggt gtgcaagcta ccccaatcat   180
tttgaaagcc cccacgaaag gagcgcgaca                                     210
```

<210> SEQ ID NO 535
<211> LENGTH: 100
<212> TYPE: DNA
<213> ORGANISM: Corynebacterium glutamiucm R

<400> SEQUENCE: 535

```
aagccgttaa aagttgagac tcgcgctgag aatctcgcag aaaactccga agctcccgct      60
aaggtagcta ccggaatcaa atcttaggga aggaaaacat                          100
```

<210> SEQ ID NO 536
<211> LENGTH: 565
<212> TYPE: DNA
<213> ORGANISM: Corynebacterium glutamiucm R

<400> SEQUENCE: 536

```
taattatcca atccgagattt aacccacaaa gaagctttac cttctcttaa gagcttttag     60
agcaaaataa aatgacccgg aagctcatct cacgcaacca gcaggccttt aatcagtcaa   120
ttaaagccac gttagcaaca tatctcctgt caagaaaata acagattgaa ttcactgtcc   180
agttatgggt ttttcggatt caccccccca tgcagcggaa atgctaactt tcttcagtgg   240
attccaacct ttttttgccat aaaccgtgca ccggagcaaa acctctcact ttaagtaact   300
tcattttgca acctggtatt agtgtgaacg cattttttatg agttatcgat tccgaaatcc   360
ggatttgcct gttaacgttg ttgcttgagt tctcgatgta aatgaaaggt gcgccacaat   420
ctgttcctag atgcggtgtg caacgggctg ttagcccagc tttggtttat attgtcgatt   480
agtgggttta cgccctgcag tcccgtattt accccatata ggtaatgcca gggctaccaa   540
ccacaagttc acgagggaaa gacgt                                         565
```

<210> SEQ ID NO 537
<211> LENGTH: 496
<212> TYPE: DNA
<213> ORGANISM: Corynebacterium glutamiucm R

<400> SEQUENCE: 537

| | | |
|---|---|---|
| ggcatgacta tagcgtgatc accatcacct taaccactct tggcattgag gtgttgcaaa | 60 |
| gttgttgatt ttcgcttttc gacgcagccc gccgccatca ggctcccggc gtggtcgggc | 120 |
| cacatgcgcc ccgggaactt tttgggcacc tacggtgcaa cagttgcgaa aattgtgtca | 180 |
| cctgcgcaaa gccttgcttc gattcgggga attcgggtgt ctaaacttttt tgattgatac | 240 |
| caaacggggt tagaaactgt tcggatcggt atcctgtgag gaagctcacc ttggttttag | 300 |
| aatgttgaaa aagcctcagg tttccgcagg tagagcacac tcaattaaat gagcgtcaaa | 360 |
| cgacaataaa gtaaggctac cctaataagt ggggtttat gcctctaaat agccagttgg | 420 |
| gggcggtagg ggagcgtccc atgactggtt aatgcctcga tctgggacgt acagtaacaa | 480 |
| cgacactgga ggtgcc | 496 |

<210> SEQ ID NO 538
<211> LENGTH: 200
<212> TYPE: DNA
<213> ORGANISM: Corynebacterium glutamiucm R

<400> SEQUENCE: 538

| | | |
|---|---|---|
| catttatttg gtaattgggc aacatcactg atactcttga acgctgttgt ccatctttga | 60 |
| tgtgagcatt ccagtgacat gcggacagga ccttgggttc gttgcacttt atgccaagca | 120 |
| gtttatttaa aactgcggga gaaacactcc tcgatgggtt tgtacacaac tttaactaga | 180 |
| aagttcaaga ggtatttgcg | 200 |

<210> SEQ ID NO 539
<211> LENGTH: 191
<212> TYPE: DNA
<213> ORGANISM: Corynebacterium glutamiucm R

<400> SEQUENCE: 539

| | | |
|---|---|---|
| tgaaacgacc ttctagaagc atcgtttaga attgctttta agtgaataag gaacagcaca | 60 |
| gaattaaggc ctcggattta tccctcacgc tacttctcaa gtggcgccaa ggtaagttgt | 120 |
| acttttctg tccaaaatat tgttttttcc gtagataggt tatcgaacgg aaattacttg | 180 |
| gcaataccgc t | 191 |

<210> SEQ ID NO 540
<211> LENGTH: 100
<212> TYPE: DNA
<213> ORGANISM: Corynebacterium glutamiucm R

<400> SEQUENCE: 540

| | | |
|---|---|---|
| tgggtggata gcgagcgact gctgggaagc gggtctcctg gggtgagaat tccctcgcc | 60 |
| acgagacggc ggatctgttc tgtgagctgc gtggggatgg | 100 |

<210> SEQ ID NO 541
<211> LENGTH: 100
<212> TYPE: DNA
<213> ORGANISM: Corynebacterium glutamiucm R

<400> SEQUENCE: 541

| | | |
|---|---|---|
| agggcgccag gggcatccag ccattaaagc ttttcgacga gccctcgccc atgtggccaa | 60 |

```
agaatcttat ttggaggctc gtctagtaga gtgagttctt                          100
```

<210> SEQ ID NO 542
<211> LENGTH: 111
<212> TYPE: DNA
<213> ORGANISM: Corynebacterium glutamiucm R

<400> SEQUENCE: 542

```
aaagttttac ctttaaaaac tacccgcacg cagcacgaac ctgttcagtg atgcaaatca     60
ccgctaaaat attgtggacg ttaccccgc ctaccgctac gatttcaaaa c              111
```

<210> SEQ ID NO 543
<211> LENGTH: 488
<212> TYPE: DNA
<213> ORGANISM: Corynebacterium glutamiucm R

<400> SEQUENCE: 543

```
aagaccctaa aaacgcctct ggagaaaaat cccggatgcc gttaggcatg cgggattttc     60
gggcttttac cccttcgct cacacccgca accgggcgtc gaaaagcgtg ctctttgaaa    120
ttgtgacaag gataacaacg gtaacgaatt gatataggtg agcgtggttt aagttgcatc    180
attggggtg caaagttttg taaacacgca attcaaatca caaatctgta accctgacgg     240
gtagggttgg ccacgttcac ttcactgtca ttggcatgaa gcttttgggg tccttgtggc    300
cttgaaagtg tgcaggattt ttgaattctc tttggagttt tcggcgcgta tgtcagataa    360
aaaataactg ctggctacaa tggcacgtga agaacagtat gataaatgga aattccagtc    420
atgagagatt cttgtggctg agtcccggcc ctgcctgggg ccaccgttaa atcgaaggga    480
atccgcaa                                                             488
```

<210> SEQ ID NO 544
<211> LENGTH: 100
<212> TYPE: DNA
<213> ORGANISM: Corynebacterium glutamiucm R

<400> SEQUENCE: 544

```
ctgcacgtgc actgcacgag cagttccagc tgggcggcga agacgaagcc gtcgtttatg     60
caggcaccgg acgctaaagt tttaaaggag tagttttaca                          100
```

<210> SEQ ID NO 545
<211> LENGTH: 100
<212> TYPE: DNA
<213> ORGANISM: Corynebacterium glutamiucm R

<400> SEQUENCE: 545

```
ttgacgccga tgccaacatc atccttatca agggcgcaat ccctggtaac cgtggtggca     60
tcgttaccgt taagaccgca gtgaagggcg gtgcacacgc                          100
```

<210> SEQ ID NO 546
<211> LENGTH: 1000
<212> TYPE: DNA
<213> ORGANISM: Corynebacterium glutamiucm R

<400> SEQUENCE: 546

```
aatttctaaa gtggctctgt gccgagacga aacactacaa aaaatacttg tagggctata     60
cacttgatcg catcaataaa tcgattttga ttgatggcct tctgtatcct tatttggcta    120
cccttagtga ggctttgacc gttgtcggca aggtctcata agggtactga taatttcgga    180
ttacactttt atttttcaat tagccattgc gcgatggcgt ctagaatgaa tcaaaagctg    240
```

```
cgccttgtct tgatgcgatc aaagattaag atgagcaata tttggatcgt caaagattga    300
gagcaaattt atgcacccgg atgaatcgag agacccgcat cagattgagc agctgcggat    360
tgcggaggtc cctgtggccc ctaaagatgc atctttaacg ctcgaggaat taactgatga    420
aacacggaat gatggaaata aggcacaaga ctggcaggga gaactgtcta acttaaatcg    480
acgtatttct aaagccgatc aagcactttg cgaggaaaag aaaatttccc agaatttgca    540
agaaaagctc aaagtagaaa agcaacaaaa tgctgatttg agaaaacagc tggacaaggt    600
gcaaagccag cttaaatcgc tccgagcatc gacaacgatg aaggctggcc gacttgttgc    660
cactccttat cattttctta ttaatagtgc ggcaaagatt aaaagattct tcacggatca    720
agatctggtg cgaaagattc cggccaaacc aaaaaagatc gttacaccag tgtcgaaacc    780
atctgtggaa cgcctattaa atgacgcgtg gtataaccgc ggttcaattc aagactccta    840
tcaaattctg agtagtctag aagatgcgac ttctgagcta tccgaaaaag gactgattct    900
taaacagcgc gttgaggcgg cttatcgtct ttttaaacag ggggttgaga ttccggttcg    960
cacgcaaggg tgtgcttata aacctgaatc tgggcgtgtc                          1000

<210> SEQ ID NO 547
<211> LENGTH: 100
<212> TYPE: DNA
<213> ORGANISM: Corynebacterium glutamiucm R

<400> SEQUENCE: 547
acggcacttt tgtcggtggt acgcgcattg atcagcctga gcagattgcg gtgggcacgg     60
atatccgtat tggtcgtaca acagtgaggc ttgttccctg                          100

<210> SEQ ID NO 548
<211> LENGTH: 246
<212> TYPE: DNA
<213> ORGANISM: Corynebacterium glutamiucm R

<400> SEQUENCE: 548
gcctacgata aagtcaattt gatattttct ccaaggtatt aaattcccac ctagagacga     60
ttaaattcgt agctcattca actacaaaac ttgcccaccg aaagtatcac cccaaaattg    120 attattttg actaacataa aagcgcctca gataatttaa tggtgaacat tttacaaaaa    180
cgcctatttt caggcgtact cttaagcgcc cttgcttttc cagtagttgc aacaccagct    240
aatgct                                                               246

<210> SEQ ID NO 549
<211> LENGTH: 65
<212> TYPE: DNA
<213> ORGANISM: Corynebacterium glutamiucm R

<400> SEQUENCE: 549 agttttagc gtacctaccc tgcgggaaat gaccttaaat gacccgtggg ataggattgc      60
ctatt                                                                 65

<210> SEQ ID NO 550
<211> LENGTH: 1000
<212> TYPE: DNA
<213> ORGANISM: Corynebacterium glutamiucm R

<400> SEQUENCE: 550
atccacacct tgacgccgat gcgtccgaaa gtggtgtgag cctcgtaggt gccgtaatcg     60
atttctgcgc gaagggtgtg cagtggaacg cgaccttcgt ggtagcgctc ggtgcgggac    120
```

```
atctcggcac cgccgagacg accggagcac acgaccttga tgcccttaac ctgtggctga      180
cgcattgcag actggatagc cttgcgcatt gcgcggcgga atgccacgcg gttggtcagc      240
tgctcagcga tggactgtgc caccagctta gcgtttgcat cgacgttctt gacctcgagg      300
atgttgaggg caacctgctt accggtgagc ttctcgagct cacggcggat gcggtcagcc      360
tcagcgccac gacgaccaat gacgatgcct gggcgagcgg tgtggatgtc tacgcgaacg      420
cggtcgcggg tgcgctcgat gacgacgtcg gcgatgccgg cacggtcgag gcccttggac      480
aggaattcgc gaatcttgat gtcttctgcg acgtagtcag cgtaagactt gtcggcgtac      540
caatgggact tccagtcgga agtgatgccc aaacggaggc cgtgtggatg gatcttctgg      600
cccactagtt ggctccttcc ttctggctct caacgaccac ggtgatgtgg ctgctgcgct      660
tacggatctg gaatgcgcgt ccctgagcac gtggctggaa gcgcttcatg gttgaccttt      720
cgttggcgta agcctcggag ataaccaggg tgcgtggatc caggccgaag ttgttctcag      780
cgttagctgc tgcagatgca acaaccttttg ctacaggctc agatgctgcc tgtggcgcat      840
acttcaggat tgacagtgct tcgacgacgg tcttgccgcg aacaagatca atgacgcgac      900
gtgccttcat tgggctgacg cggacgaagc gagcagtcgc gcttgcggag tgatgttgt      960 cactcatcgc ttatcgacgt cccttcttgt cgtccttgac                          1000

<210> SEQ ID NO 551
<211> LENGTH: 100
<212> TYPE: DNA
<213> ORGANISM: Corynebacterium glutamiucm R

<400> SEQUENCE: 551
ttccacgccc agggaccgtc cacacttcgg tgcctgtgaa agggtgaatc tgtttgatcg       60
tgccgtcagc catggtgcga atgggggtga cagaaaaaga                            100

<210> SEQ ID NO 552
<211> LENGTH: 100
<212> TYPE: DNA
<213> ORGANISM: Corynebacterium glutamiucm R

<400> SEQUENCE: 552
gtgttatttt cttggcggac ggtcgtatcg tgaaccagtt gtttgatccc accatcgagg       60
aaatcttggc cacgatgaac ggaattgagg atattgccta                            100

<210> SEQ ID NO 553
<211> LENGTH: 266
<212> TYPE: DNA
<213> ORGANISM: Corynebacterium glutamiucm R

<400> SEQUENCE: 553
cccaaaaagc gttagatgaa acttcccacc cgaatccaca agaactcggg tgccctcaat       60
ttcacatacc cctaagcgaa acactatgcg agctttccgc cagaaggcca agcacccttt      120
cgattaaccc cgacaaactt ttaaggcaag cctaaattag gtaaaccctta aacagtcgcc      180 attgaagaaa ttgaagaatt ttaaaaacaa acaaccttca acgcgctaac aagcatcttc      240
ccagtctcgt taccggagtt tctcac                                           266

<210> SEQ ID NO 554
<211> LENGTH: 56
<212> TYPE: DNA
<213> ORGANISM: Corynebacterium glutamiucm R

<400> SEQUENCE: 554
```

```
ggcagcgagc ctacactaaa tgactgtcca agcaactgaa gggaggcgtg tgaacc         56
```

<210> SEQ ID NO 555
<211> LENGTH: 100
<212> TYPE: DNA
<213> ORGANISM: Corynebacterium glutamiucm R

<400> SEQUENCE: 555

```
attgatttct gttctggcga tccaggcttg gatatttcac aaatggttca tgaaacccaa    60
cgtgcacgac tatttatgag ttaagaagga gaaaagaaaa                         100
```

<210> SEQ ID NO 556
<211> LENGTH: 100
<212> TYPE: DNA
<213> ORGANISM: Corynebacterium glutamiucm R

<400> SEQUENCE: 556

```
tttggtgcag atcacgcacc ttcgggcgaa caccctcaaa gatatttggg aatagggtc     60
atcgtgcagg cccccacacc caacgcgtaa cataacggtc                         100
```

<210> SEQ ID NO 557
<211> LENGTH: 100
<212> TYPE: DNA
<213> ORGANISM: Corynebacterium glutamiucm R

<400> SEQUENCE: 557

```
gcaccactgt tggtggcgga cgacccgtgt acacaggacc agccattgtg gatgccacca    60
acgttgatgt cattgctgaa gccgttgggg agggtctgcg                         100
```

<210> SEQ ID NO 558
<211> LENGTH: 100
<212> TYPE: DNA
<213> ORGANISM: Corynebacterium glutamiucm R

<400> SEQUENCE: 558

```
cccactggcc gcttcggcga atgaatcccc gctgtctatt ccttggggca tcaacgagta    60
cttcgctaaa atcgctgagc ctctgaagta aaactgcttg                         100
```

<210> SEQ ID NO 559
<211> LENGTH: 100
<212> TYPE: DNA
<213> ORGANISM: Corynebacterium glutamiucm R

<400> SEQUENCE: 559

```
ccggaacatg ccgtcgaaaa gctaaccggc ccatctattg atggcctgga gctgttcctg    60
tccgccgttg gcaccatcgc ggcttaagag gagtcaaaat                         100
```

<210> SEQ ID NO 560
<211> LENGTH: 187
<212> TYPE: DNA
<213> ORGANISM: Corynebacterium glutamiucm R

<400> SEQUENCE: 560

```
ggcttccggg gcgatctaaa cccgcattga ataggcgatt aggtgttttg gggcaacgta    60
tgtaaacttg tcccttgctg ttgtcgtaaa tattcgttat cgccccgtca gctggcatgc   120
tcgcgccccg gtcacccggt gcggcgcgtc ttctaactga atgtgggcgg ctaggagaaa   180
gtaagtt                                                            187
```

<210> SEQ ID NO 561

```
<211> LENGTH: 100
<212> TYPE: DNA
<213> ORGANISM: Corynebacterium glutamiucm R

<400> SEQUENCE: 561
ggctaccaag cgcgcttatg tgactcttcg cgaaggcagc gactccatcg acatcttcaa    60
cggctccgtc gcttaagacg tcgatagaaa aggacacatt                         100

<210> SEQ ID NO 562
<211> LENGTH: 100
<212> TYPE: DNA
<213> ORGANISM: Corynebacterium glutamiucm R

<400> SEQUENCE: 562
cactgccaca gctgccaatc accgttgatg aagagggcta cctcatcgcc gctggtaact    60
tcattgagcc agtcggccct gcattctggg agcgtaagtc                         100

<210> SEQ ID NO 563
<211> LENGTH: 177
<212> TYPE: DNA
<213> ORGANISM: Corynebacterium glutamiucm R

<400> SEQUENCE: 563
atagcaattt gttttatacg gaccagccgc gaatccgaga atctccatgg ataaacagtg    60
tagtgcgcaa ggggcgctcc cccatcattc cctcaaggtg tgaagatacg gttaggatag   120
aaaagaattt tttgacgttg gacattctca aaatcaagta gcaagggatc aaactct      177

<210> SEQ ID NO 564
<211> LENGTH: 148
<212> TYPE: DNA
<213> ORGANISM: Corynebacterium glutamiucm R

<400> SEQUENCE: 564
tacggctcca aggacgtttg ttttctgggt tagttacccc aaaaagcgta tacagagacc    60
aatgattttt cattaaaaag gcagggattt gttataagta tgggtcgtat tctgtgcgac   120
gggtgtacct cggctagaat ttctcccc                                      148

<210> SEQ ID NO 565
<211> LENGTH: 138
<212> TYPE: DNA
<213> ORGANISM: Corynebacterium glutamiucm R

<400> SEQUENCE: 565
gtcctctacc ctagtatcgc cgcctccatc tgatgtctgg ggtgtctgta attttcacgt    60
ctcctggcgt ttttaagacg aattacaaca attcgttcac gattgagcca aattgggcgt   120
cttgcttagg tttcgggg                                                 138

<210> SEQ ID NO 566
<211> LENGTH: 100
<212> TYPE: DNA
<213> ORGANISM: Corynebacterium glutamiucm R

<400> SEQUENCE: 566
agccgaacca tcatcgcgcc tttcgaaatt ccagtatcag taatcctggg catcatcggc    60
gcagtggtct tcgtgatcat gattgtgagg caacgtggcc                         100

<210> SEQ ID NO 567
<211> LENGTH: 124
<212> TYPE: DNA
```

<213> ORGANISM: Corynebacterium glutamiucm R

<400> SEQUENCE: 567

| | |
|---|---|
| atttagcgga tgattctcgt tcaacttcgg ccgaagccac ttcgtctgtc ataatgacag | 60 |
| ggatggtttc ggccgttttt gcatgaaacc aaaaaatacg attttcaagg agcatgtaca | 120 |
| gcac | 124 |

<210> SEQ ID NO 568
<211> LENGTH: 725
<212> TYPE: DNA
<213> ORGANISM: Corynebacterium glutamiucm R

<400> SEQUENCE: 568

| | |
|---|---|
| gtcttcgggc aactttctgc gcttggaagt aaaagggcca gggatcgtta acgatctgac | 60 |
| ccaacaacta taaccctgaa gctgtcagtt cctagcaccc tagattcttc acgcagtctc | 120 |
| ccaaacgatg aaaacgcccc aaaactggcg acaccgaact attgaaaacg cggagattag | 180 |
| ttgaccagtc accaatttgg gggtggttca agttttgca agttttcaa tttctaggtt | 240 |
| gttaatatcc cctgaggttg cgttataggg tggcgaattg catggggaaa gctactcggc | 300 |
| acccatcctt gtcgtgtgca tcacaaactt tgctaaactg tgtaccagtc cacttattgt | 360 |
| gggattttta atgccttaaa ggccagcatt ttcaccctct agcggggttg aatgctggcc | 420 |
| ttgagggtgc agaactaaat agcagcacat cggcacaatt gatctgagtt ctattggcgt | 480 |
| gaccgtggct actgattacg gtggctgtgg gtggtcggga atgatgtaac caacgtgatt | 540 |
| gtggggaat tggctctcac ttcggatatg gctaaaccgc atttatcggt atagcgtgtt | 600 |
| aaccggacca gattgggaaa gaaatgtgtc gagtaacaaa aactgacatg cgcttggcgc | 660 |
| atcccagttg gtaagaataa acgggactac ttccgtaatc cggaagagtt tttttccgaa | 720 |
| caaat | 725 |

<210> SEQ ID NO 569
<211> LENGTH: 100
<212> TYPE: DNA
<213> ORGANISM: Corynebacterium glutamiucm R

<400> SEQUENCE: 569

| | |
|---|---|
| acaagaccct cgatgctgcg gctgcgttgg accaagcgcc cgctgtcgag gatggacgtt | 60 |
| ttatggttcc gcagattctg ggtgagggcg actaataatt | 100 |

<210> SEQ ID NO 570
<211> LENGTH: 100
<212> TYPE: DNA
<213> ORGANISM: Corynebacterium glutamiucm R

<400> SEQUENCE: 570

| | |
|---|---|
| cctctgacca gaccgcaatc accgcgggtg gacagaccat tgatttccag aacggcacca | 60 |
| tccgtcaggt caatggccga attgaggagt ctcgctaata | 100 |

<210> SEQ ID NO 571
<211> LENGTH: 572
<212> TYPE: DNA
<213> ORGANISM: Corynebacterium glutamiucm R

<400> SEQUENCE: 571

| | |
|---|---|
| cgcttttcga cgagcccccc accttcgccg ccaccagagt gccggcggtc aatgtgggtg | 60 |
| ggctatttca ctgcggggca ctgaaagtaa aaacgcaact ttcttacaga acagggttgt | 120 |

```
ctttcagacg actatgtggt taactacttg ggttgcttta acacggcgtg aattaaccat    180
gccagttggt aaggcaaaca tgacaccttc aattggagtc gaggcgcatg aatatgcact    240
tcaacttcag ggggtatcca ctgaagccgg gtgactggtg aaggcggaac cggagaaggg    300
gcatggcaaa taaacagcgg cagttacgtt agggcctaga tcacgcattt tggtcccttc    360
cgatttccct gacttcattg ttgggttcat cgtggcgcgt tttatttgta cagcgcccgt    420
gatccaatgt cagaagcatt tgacaggtca ggttaaacac tggcgttgcg cccgagcccc    480
aagcccggac aacgttatag agaaagaatg aagcgaattc ccaccgcttt tccaaaatgg    540
aagatgtggg acgagcgagg aagaggataa gc                                  572
```

```
<210> SEQ ID NO 572
<211> LENGTH: 100
<212> TYPE: DNA
<213> ORGANISM: Corynebacterium glutamiucm R

<400> SEQUENCE: 572
cctgtggata attggttgtt ggctgatggt gatgtcatta cggtgggtca ttccaatatc     60
gaagttcgta ttgttagtcc ctagagggag aggttgatca                          100
```

```
<210> SEQ ID NO 573
<211> LENGTH: 213
<212> TYPE: DNA
<213> ORGANISM: Corynebacterium glutamiucm R

<400> SEQUENCE: 573
aaggcttcgc tcctaaaact ctttaagagt caggccaact agcccgcccg gttttctcgt     60
gaaaatcagg cggtctttgg cttttctaaa gtgtttctaa agccaccttc gacctcaatt    120
aagcagcaat ccgagccggg ggagcgctgt cagaaatgga ccgtgccacc ccatgacaac    180
atgcttgcac aatgatgact agaataatga ccc                                 213
```

```
<210> SEQ ID NO 574
<211> LENGTH: 100
<212> TYPE: DNA
<213> ORGANISM: Corynebacterium glutamiucm R

<400> SEQUENCE: 574
ccatcgtgtt tattactcac aaccctgagc ttgctgatga atctgatcgg gtggtcacca     60
tggttgacgg gcgcatcatt gggtctgagg tgaaacactc                          100
```

```
<210> SEQ ID NO 575
<211> LENGTH: 100
<212> TYPE: DNA
<213> ORGANISM: Corynebacterium glutamiucm R

<400> SEQUENCE: 575
atgattccgt caccgaagct gacctaaaga aaattgctga aaccctcctc gcaaacaccg     60
tcatcgaaga cttcgatgtg gtgggagttg aggtcgcgaa                          100
```

```
<210> SEQ ID NO 576
<211> LENGTH: 128
<212> TYPE: DNA
<213> ORGANISM: Corynebacterium glutamiucm R

<400> SEQUENCE: 576
tttgttttga cgacgcagta acgcaatcgg ggattgtggt cgattcttta agcaagggta     60
atgtcgaaat atctaggcaa cccgactttt atgtccctgc ttgagttgaa aactgctgtc    120
```

-continued

| gatcaaag | 128 |

<210> SEQ ID NO 577
<211> LENGTH: 370
<212> TYPE: DNA
<213> ORGANISM: Corynebacterium glutamiucm R

<400> SEQUENCE: 577

| gcgctccgtc catcaaacaa tctgacccct gtggaaagtg gggcaattgg ggcagttgta | 60 |
| aaaggcatat cctgaaacta tccacagcac ctgcgggagg gtttgggatt gcaggtcaaa | 120 |
| gtatgtaaac ttgtcggcag cagtgtgtcc gaattgtgtt tcatcatgcc tgaaagcatg | 180 |
| gcgaagggta attttaacta ctgactacgc gcggtggcgt tgaatgcaca ttcaactccg | 240 |
| gagcaacgag gtcccaaaga actcatttga gttttagggt gttgacctgg gaaaccaccg | 300 |
| ctagggtgca ggataaaaac ctgcacaaat ttttaaaacc gaaaccctaa gacttagaaa | 360 |
| ggggcttaac | 370 |

<210> SEQ ID NO 578
<211> LENGTH: 100
<212> TYPE: DNA
<213> ORGANISM: Corynebacterium glutamiucm R

<400> SEQUENCE: 578

| tgagctaccc ggacgaagct actgctctcg aggctctgcg ccgcgctggc cagaagcttc | 60 |
| catgcaaggt ccgtatcgtc aagagggagg atcagctcta | 100 |

<210> SEQ ID NO 579
<211> LENGTH: 508
<212> TYPE: DNA
<213> ORGANISM: Corynebacterium glutamiucm R

<400> SEQUENCE: 579

| gtaaagttct aaagctttac ttatagcact ttcggtaggt gtcgagaaaa ttcccaaatt | 60 |
| gcggaaaatt cacatacttt gtgccacaaa gtgataaaca tcacaaaatt ttataactca | 120 |
| gccattcatg caggccagaa catgcaaaac cttgcacgct ctggccttt gttatgtaac | 180 |
| tgttgtgaaa gatgtatcaa aagttaccaa ggtgacttaa tgttcagata tcgactcatg | 240 |
| ggttgttttc caaaacttga atcaatttga gtaacagtag ttatcaagcg ttaaaccttg | 300 |
| aaacttccac tcttttact gatgagcatt tgggcaaacg gggaagcttg ctggagatgc | 360 |
| aataaatcgg tgaatggttg atgcaataaa gaggagagtg gcccatagtt tccgctacgg | 420 |
| aacgcggagt ctttacgttt caattcttgg caagtgtcta gcgtcaaggc ttgatatgtg | 480 |
| aagggattcg gattgaacag gagaacat | 508 |

<210> SEQ ID NO 580
<211> LENGTH: 100
<212> TYPE: DNA
<213> ORGANISM: Corynebacterium glutamiucm R

<400> SEQUENCE: 580

| gcgatgctcg aacgcgcaga acgctcctgg gtagacaaag ccactgcata cgatttgcgc | 60 |
| tggtcagatc actcaccact gaacgtgatc tactcctaaa | 100 |

<210> SEQ ID NO 581
<211> LENGTH: 54
<212> TYPE: DNA
<213> ORGANISM: Corynebacterium glutamiucm R

```
<400> SEQUENCE: 581
actttgtcac cctagaccgt ctaaccttta ggtgtgagat taggtgtatt agat          54

<210> SEQ ID NO 582
<211> LENGTH: 159
<212> TYPE: DNA
<213> ORGANISM: Corynebacterium glutamiucm R

<400> SEQUENCE: 582
tcgttatgtc attgtgatgc tcccgtgaac ataaacggga cttactggct ttacttaagt    60
aacagctatg taaaagacca ggtcaggttc gggtcggttt aggtacgaaa cccatttttc   120
ggtttgcttt ccaggtttcc ccaagtaaag gtgagtttt                          159

<210> SEQ ID NO 583
<211> LENGTH: 100
<212> TYPE: DNA
<213> ORGANISM: Corynebacterium glutamiucm R

<400> SEQUENCE: 583
cgtggacgat gccatggttg gccacaagct gggcgaattc gccccctacca agaccttcaa   60 gggtcacgtc aaggacgaca agaagggacg tcgataagcg                         100

<210> SEQ ID NO 584
<211> LENGTH: 100
<212> TYPE: DNA
<213> ORGANISM: Corynebacterium glutamiucm R

<400> SEQUENCE: 584
gctgtgggct actcaattcc acccagaaaa atcaggtgac gcaggcgcaa agctactgcg    60
aaactggatc aactacatct aacagatagg atcaatattc                         100

<210> SEQ ID NO 585
<211> LENGTH: 439
<212> TYPE: DNA
<213> ORGANISM: Corynebacterium glutamiucm R

<400> SEQUENCE: 585
cagccactat ccttaatttg cagtcaggta gattccagtt gatagtcgaa atctaattaa    60
acctatagct gtcttaacgt tcgaatctct agaaatgtta acaggtggca tgaaagttac   120
ccaccgaagc aagatttagc cttgagagtt tcagactttc gcatctagac ctgtgctgca   180
ctctctaaac gcgcaccgaa acacctcata gtctgatggt tacgtgctag aaccaacatg   240
tccaatcatg taagttccag ctcttcagga ataattttta gcaaaatctc agcttttttcc  300 tcagttgcta gtgcgcaaaa ttgagggtaa gaatacgaca ttcatatcca agtagtaaag   360
tccgtagaac acggtagaga tcactactta ttcatgaaag tatcgctgcc cagatctcac   420
aaacattgag gattccaaa                                                439

<210> SEQ ID NO 586
<211> LENGTH: 100
<212> TYPE: DNA
<213> ORGANISM: Corynebacterium glutamiucm R

<400> SEQUENCE: 586
cgcgaatggc ttcctcttta gccccgattg cgtggggtgc gtgggcctca aactcgagga    60
gggttaaatc atctgcggaa agcatgctta gaatgttgcc                         100

<210> SEQ ID NO 587
```

```
<211> LENGTH: 985
<212> TYPE: DNA
<213> ORGANISM: Corynebacterium glutamiucm R

<400> SEQUENCE: 587
ttggttagag cagcagcgat ttttagtaag gccaataaca tgttttggct taaacctgtg      60
tcgtgtcaga tggtggcgaa gtagagttcg caaagctagc gaacatgaat tcgtgttcag     120
gaactaaaca gggatcaaac agagaacaga gaacagatcc cgctgcccaa aaatcgcact     180
tttaaggttt gtgggcgtct gtgtgtggtt tgccgctgta agtatcacc acgttatgcg      240
ccctggtgtg atcaagcgtt cgttctgggt cgaaacccca aaagtcacaa ttccccagaa     300
gcgggtcaaa cccatttagc ttattgctta catatcgagg gtttagaaaa gtgatttgtc     360
ggatcagtcg gtttctgcca agtaaataga actttataaa ttttgtggct ctcaaatctt     420
aggccacggc ttccgatttg aaccggaggt tcaaaaggct tatatagaca agattctgca     480
tcgtctcacg agcccctcat tgcctgacac ggtcaatcgt gtgggaggta ccaatccgtg     540
agatttctgc caacgagcga ttcattggcc ccgctgcaga gctggcagaa cacggacata     600
acccaaataa tctgaggtct gccgtttgca gcagcattag cgtttgatgt ggaaggtgat     660
gcagaggctg ttgatctgca agcgcgtctt tcccaagcac gggggaaccc tgaagcatcg     720
gatgctctag ttgctgagct gactggtgtt actgctaatc atccgttggt cagtgcttgt     780
ctgaagtttc cgctcaatcc taagcttctc aagatttcgt aaaaaagctg ccaactaccg     840
taaaaccgca ctactagagg agtgcgtttt tcgttcctga acacattgcg tgctgcaact     900
taattatggt cctcccagct cagtgtgctg tgtggattgt ttattctcgt ccattaagtg     960
atcgagaaaa agttgttgta aagtc                                           985

<210> SEQ ID NO 588
<211> LENGTH: 100
<212> TYPE: DNA
<213> ORGANISM: Corynebacterium glutamiucm R

<400> SEQUENCE: 588
accacggttg tctccattgt cactgtgctg gtcatcgtct acatcatcgc caaccttctc      60
gtggacttga tctacgccgt tctcgatccg aggatccgct                           100

<210> SEQ ID NO 589
<211> LENGTH: 200
<212> TYPE: DNA
<213> ORGANISM: Corynebacterium glutamiucm R

<400> SEQUENCE: 589
cgcaaagctc acacccacga gctaaaaatt catatagtta agacaacatt tttggctgta      60
aaagacagcc gtaaaaacct cttgctcatg tcaattgttc ttatcggaat gtggctaggg     120
cgattgttat gcaaaagttg ttaggttttt tgcggggttg tttaaccccc aaatgaggga     180
agaaggtaac cttgaactct                                                 200

<210> SEQ ID NO 590
<211> LENGTH: 192
<212> TYPE: DNA
<213> ORGANISM: Corynebacterium glutamiucm R

<400> SEQUENCE: 590
ctgcagggcc tcctggggca cttgatctga cctggttacg tggggtgcac gtatcgaggc      60
gcattataaa tgtatcggcg cttgggctgt atcaacccgc acgtcatcta ttgttgcact     120
```

```
tttgtgcccg aattttgga ttctggacac ccaaaagggg gtttcgtacc aaactcgtga    180
catactaggc gg                                                      192

<210> SEQ ID NO 591
<211> LENGTH: 172
<212> TYPE: DNA
<213> ORGANISM: Corynebacterium glutamiucm R

<400> SEQUENCE: 591
tgcgctactc ctgattggtg tatctgtgat caactaaaaa atttaacgcg tcatgaaaac    60
ccgttactgg gagtccatat tactgaacac ttgcgcgcga ggtgcaccag tccccgaatt   120
caccccatat gcaaggtatc tacatcaaag agcaccggct attgtggagt gc           172

<210> SEQ ID NO 592
<211> LENGTH: 100
<212> TYPE: DNA
<213> ORGANISM: Corynebacterium glutamiucm R

<400> SEQUENCE: 592
cccgttacgg tggcaccgag atcaagttcg gtggcgtgga gtacttgctc ctctccgctc    60
gtgacatcct cgcaatcgtc gagaagtagg ggataagttc                         100

<210> SEQ ID NO 593
<211> LENGTH: 100
<212> TYPE: DNA
<213> ORGANISM: Corynebacterium glutamiucm R

<400> SEQUENCE: 593
tcgaaggctg ggtgcaaaag aagcgccctg gaaccgctgc agcacaagcc gcagaagccg    60
cccaaaacgt ccacaaccag gaaggctaag caggatcctc                         100

<210> SEQ ID NO 594
<211> LENGTH: 100
<212> TYPE: DNA
<213> ORGANISM: Corynebacterium glutamiucm R

<400> SEQUENCE: 594
ggtggatgcc taagtggctg atcgaattc tgccaagttt ggacattgaa ggcaccgccc    60
tggagaagga atgggaggag aagcaggctg cacgttagac                         100

<210> SEQ ID NO 595
<211> LENGTH: 290
<212> TYPE: DNA
<213> ORGANISM: Corynebacterium glutamiucm R

<400> SEQUENCE: 595
ggttgttcct tatttctaat caggtgctgt ctgagcaatg ctcggcagcg cgtgatggaa    60
ttttgtgtgc ggcttggaag tgacgggtca aaggacagc tcgtgtagac cctgcctgga   120
gccttgacaa actccaccaa acaactgcga cgtgtgtcag attactgcag gcttgtggtc   180
aaacctagtt ctttggggcg gagcatcata ccttttaatg tcaggatcgt gcagtgaaga   240
attcaggatg aattactcgc tggaatattg gtggggatag agttgttgtt                290
```

DNA FRAGMENT HAVING PROMOTER FUNCTION

This application is a U.S. national stage of International Application No. PCT/JP2005/016269 filed Sep. 5, 2005.

TECHNICAL FIELD

The present invention relates to a method of inductively-expressing the promoter function which functions in an aerobic *Coryneform* bacterium, and a DNA sequence having the promoter function. More particularly, the present invention relates to a method of inductively-enhancing and/or suppressing expression of the function of various gene promoters which function in a *Coryneform* bacterium, for the purpose of producing a useful substance such as various organic acids and ethanol at a high efficiency, and a DNA sequence having the promoter function.

BACKGROUND ART

A *Coryneform* bacterium is an industrially important aerobic Gram-positive bacterium which has previously been used for producing useful organic compounds such as various amino acids, lactic acid, succinic acid and the like. Particularly, since a *Coryneform* bacterium has a peculiar metabolism function that a metabolism pathway for producing a substance is not deteriorated even under a condition that cell division is suppressed by a method of restricting oxygen supply or the like, a nutrient source such as saccharides and the like which is given to a *Coryneform* bacterium is not consumed for proliferation, and is effectively directed to an objective product. Thus, a raw material nutrient source is effectively utilized, and the technique of producing an objective substance can be easily controlled because of suppression of cell division, and this is why a *Coryneform* bacterium is industrially paid attention.

In order to highly exert such characteristic function of a *Coryneform* bacterium, it becomes necessary to effectively and highly express various protein genes necessary for producing an objective product, and suppress expression of unnecessary protein genes. For doing this, a technique which can enhance and/or suppress the promoter function associated with these protein genes becomes important.

As to a DNA fragment having the promoter function in a *Coryneform* bacterium, some DNA fragments are known.

For example, a DNA fragment having a stronger promoter function than the tac promoter derived from *Escherichia coli* is found out on a chromosome of a *Coryneform* bacterium, and a DNA sequence thereof is known. And, as a method of controlling expression of the promoter function, a method of changing a carbon source composition of saccharides, ethanol and the like which are added to media has been proposed (see Patent Literature 1).

In addition, a promoter DNA sequence associated with a specified enzyme protein (aspartase) gene expressed in a *Coryneform* bacterium has been found out (see Patent Literature 2). However, as a method of expressing the promoter function, there is only stated that "when incorporated into a plasmid vector together with a gene encoding a protein, and is introduced into a host *Coryneform* bacterium, an action of potentiating an expression intensity of the gene is possessed", and nothing is referred to a method of enhancing, and a method of controlling expression of the promoter function.

In addition, a promoter or promoters of exogenous and endogenous genes involved in production of L-glutamic acid and L-lysine which functions in a *Coryneform* bacterium is found out (see Patent Literature 3), but nothing is referred to a method of enhancing expression of those functions.

A technique of using a *Coryneform* bacterium in which the function of a promoter of a dapA gene (dihydrodipicolinic acid synthase gene) has been enhanced by a mutagenesis method, in production of L-lysine has been proposed (see Patent Literature 4). However, nothing is referred to the function enhancement under an anaerobic condition.

Regarding a method of inductively-expressing the promoter function, a recombinant DNA sequence containing a pfl (pyruvate formate lyase gene) promoter which is induced by pyruvic acid and suppressed by oxygen (Patent Literature 5), and a promoter responsive to a stress such as an oxidative stress (addition of peroxidated lipid), an osmotic stress and a glucose starvation stress of a 2-deoxyglucose-6-phosphate dephosphorylase gene of yeast *Saccharomyces cerevisiae* (Patent Literature 6) are also known. Patent Literature 6 refers to chemical inducing methods such as a phosphoric acid-deficient inducing method, a copper addition inducing method and the like, a heat shock inducing method, and the like as methods of inducing various gene promoters in addition to the aforementioned ones.

As described above, DNA sequences of various promoters, and methods of inductively-expressing the promoter function with various drugs or stresses are known, but a method of controlling the promoter function which functions in a *Coryneform* bacterium, which is inductively-enhanced and/or inductively-suppressed in a reaction medium under an anaerobic condition, and a DNA fragment having the promoter function of the present invention are not known.

Patent Literature 1: Japanese Patent Application Laid-Open (JP-A) No. 7-95891
Patent Literature 2: JP-A No. 7-31478
Patent Literature 3: International Publication WO No. 95/23224
Patent Literature 4: JP-A No. 2001-61485
Patent Literature 5: JP-A No. 3-80088
Patent Literature 6: JP-A No. 2000-78977

DISCLOSURE OF THE INVENTION

Problems to be Solved by the Invention

An aerobic *Coryneform* bacterium (including a recombinant) has previously been used in producing a useful organic compound under the aerobic condition (various amino acids) or the anaerobic condition (lactic acid, succinic acid, ethanol or the like).

The present invention relates to a method of inductively-expressing the function of various gene promoter functions in a *Coryneform* bacterium, involved in exertion of the function, in order to highly and effectively exert the function of a *Coryneform* bacterium under an anaerobic condition for producing a useful organic compound under the anaerobic condition, more particularly, provides a method of enhancing and/or suppressing the promoter function associated with these genes for the purpose of effectively and highly expressing various protein genes necessary for producing an objective substance, and suppressing expression of unnecessary protein genes. Also, the present invention is to provide a DNA fragment having the promoter function which enhances and/or suppresses those functions.

By using the technique of the present invention, it becomes possible to effectively perform production of a useful substance under an anaerobic condition.

Means for Solving the Problems

The present inventors thought that, in order to highly exert a substance production function of a *Coryneform* bacterium under an anaerobic condition, a technique of expressing and inducing various gene promoter functions in a *Coryneform* bacterium associated therewith is important, and intensively studied, which resulted in the present invention.

Gene promoters are roughly classified into a constitutive promoter and an inducible promoter and, when a useful substance is produced under an anaerobic condition, since finding a technique of controlling expression of the promoter function which is induced under the anaerobic condition rather than enhancement of the function of a constitutive promoter can effectively express a target gene, a technique of producing a substance highly effectively is obtained.

That is, by inductively-enhancing expression of the function of various protein gene promoters necessary for producing an objective substance, and/or inductively-suppressing expression of the function of unnecessary protein gene promoters, a metabolism pathway which is specialized (concentrated) in an objective production substance is generated in a *Coryneform* bacterium, and a flow of a substance into an unnecessary metabolism pathway can be suppressed. Specifically, productivity of an objective substance is improved, and production of an unnecessary substance such as a byproduct can be suppressed.

The present inventors found out that an extent of expression of various gene promoters can be quantitatively known, for example, by measuring an amount of a produced mRNA using a DNA chip, and a DNA fragment having the promoter function of the present invention can be obtained by comparing a production amount under an aerobic condition and a production amount under an anaerobic condition. The present inventors further studied, resulting in completion of the present invention.

That is, the present invention relates to:
(1) a DNA fragment having the promoter function, which inductively-enhances and/or inductively-suppresses expression of a protein involved in production of a useful substance in an aerobic *Coryneform* bacterium under an anaerobic condition,
(2) the DNA fragment according to (1), wherein the DNA fragment having the promoter function which inductively-enhances expression of a protein involved in production of a useful substance is any one of following DNAS;
(a) a DNA including at least one nucleotide sequence selected from SEQ ID NOS:(1) to (394) of Sequence Listing;
(b) a DNA having the promoter site, which enhances inductively expression of a protein involved in production of a useful substance, wherein the DNA comprises at least one nucleotide sequence selected from SEQ ID NOS: (1) to (394) of Sequence Listing in which sequence one or several nucleotides are deleted substituted or added;
(c) a DNA having the promoter function, which hybridizes with a DNA including a nucleotide sequence complementary with a DNA including at least one nucleotide sequence selected from SEQ ID NOS: (1) to (394) of Sequence Listing under the stringent condition, and inductively-enhances expression of a protein involved in production of a useful substance; or
(d) a DNA having the promoter function, which has at least 80% or more homology with a DNA including at least one nucleotide sequence selected from SEQ ID NOS: (1) to (394) of Sequence Listing, and inductively-enhances expression of a protein involved in production of a useful substance,
(3) the DNA fragment according to (1), wherein the DNA fragment having the promoter function which inductively-suppresses expression of a protein involved in production of a useful substance is any one of following DNAs:
(a) a DNA including at least one nucleotide sequence selected from SEQ ID NOS: (395) to (595) of Sequence Listing;
(b) a DNA having the promoter function, which has a nucleotide sequence in which one or several nucleotides are deleted, substituted or added in a DNA including at least one nucleotide sequence selected from SEQ ID NOS: (395) to (595) of Sequence Listing, and inductively-suppresses expression of a protein involved in production of a useful substance;
(c) a DNA having the promoter function, which hybridizes with a DNA including a nucleotide sequence complementary with a DNA including at least one nucleotide sequence selected from SEQ ID NOS: (395) to (595) of Sequence Listing under the stringent condition, and inductively-suppresses expression of a protein involved in production of a useful substance; or
(d) a DNA having the promoter function, which has at least 80% or more homology with a DNA including at least one nucleotide sequence selected from SEQ ID NOS: (395) to (595) of Sequence Listing, and inductively-suppresses expression of a protein involved in production of a useful substance,
(4) the DNA fragment according to any one of (1) to (3), wherein an extent of enhancement and/or suppression of expression of the promoter function expressed by an expression amount of an mRNA is increased and/or decreased by at least 50% or more than an expression amount in a reaction medium under an aerobic condition,
(5) the DNA fragment according to any one of (1) to (4), wherein the protein involved in production of a useful substance is an enzyme involved in metabolism in a *Coryneform* bacterium,
(6) the DNA fragment according to (5), wherein the enzyme is at least one enzyme or coenzyme involved in a glycolysis pathway, a reductive tricarboxylic acid pathway, an anaplerotic pathway, an amino acid synthesis pathway, a purine synthesis pathway, a pyrimidine synthesis pathway, a cholesterol synthesis pathway, a fatty acid synthesis pathway, and a pathway derived from these pathways,
(7) the DNA fragment according to (6), wherein the useful substance is an organic acid, an amino acid, an alcohol, a steroid, a nucleic acid, a fatty acid or a physiologically active substance,
(8) the DNA fragment according to (7), wherein the organic acid is at least one organic acid selected from pyruvic acid, citric acid, isocitric acid, aconitic acid, 2-oxoglutaric acid, succinic acid, fumaric acid, malic acid, oxaloacetic acid, itaconic acid, lactic acid, acetic acid, gluconic acid, 2-ketogluconic acid, 5-ketogluconic acid, D-araboascorbic acid, kojic acid, tetradecane-1,14-dicarboxylic acid, cuminic acid and inosinic acid,
(9) the DNA fragment according to (7), wherein the amino acid is at least one amino acid selected from aspartic acid, threonine, glutamic acid, proline, glycine, alanine, cysteine, valine, isoleucine, leucine, tyrosine, phenylalanine, histidine, lysine, arginine, serine, asparagine, glutamine, hydroxylysine, cystine, methionine, tryptophan, β-alanine, γ-aminobutyric acid (GABA), homocysteine, ornithine, 5-hydroxytryptophan, 3,4-dihydroxyphenylalanine (dopa), triiodotyronine, 4-hydroxyproline and thyroxine,
(10) the DNA fragment according to (7), wherein the alcohol is at least one alcohol selected from methanol, ethanol and butanol, and
(11) a method of inducing the promoter function of the DNA fragment having the promoter function as defined in (1), including culturing an aerobic *Coryneform* bacterium at an oxidation-reduction potential of a reaction medium of −200 millivolts to −500 millivolts under an anaerobic condition.

Effect of the Invention

Since the DNA fragment having the promoter function of the present invention can highly express a target gene necessary for producing a useful substance at a high efficiency under an anaerobic condition, and can suppress expression of an unnecessary gene, an objective useful substance can be produced at a high efficiency. That is, by enhancing expression of the function of various protein gene promoters necessary for producing an objective useful substance, or by suppressing expression of the function of unnecessary protein gene promoters, a metabolism pathway which is specialized (concentrated) in an objective product is generated in a Coryneform bacterium, and flow of a substance into an unnecessary metabolism pathway can be suppressed. Specifically, productivity of an objective substance is improved, and production of an unnecessary substance such as a byproduct can be suppressed.

The DNA fragment having the promoter function of the present invention, when introduced into a plasmid or on a chromosome where it can autonomously-replicate in a Coryneform bacterium so that the fragment is situated upstream of a gene encoding a protein (for example, enzyme or the like), which produces an objective useful substance whose expression should be enhanced or suppressed, so as to function, can generate a transformant of a Coryneform bacterium which can produce an objective useful substance highly and effectively under an anaerobic condition.

A Coryneform bacterium transformed using the DNA fragment having the promoter function of the present invention produces highly and at a high efficiency useful substances such as an organic acid such as lactic acid and succinic acid, an alcohol and an amino acid. A purified useful substance can be used in a broad range of application fields as a raw material for polymer synthesis or a raw material for medicaments, or in cosmetic utility and food additive utility.

BRIEF DESCRIPTION OF THE DRAWINGS

FIG. 1 shows correlation of fluorescent signal intensities of Cy3 and Cy5.

BEST MODE FOR CARRYING OUT THE INVENTION

In the present invention, the "promoter" refers to a region on a DNA to which an RNA polymerase specifically binds for initiating transcription of a gene. The "DNA fragment having the promoter function" is a DNA fragment obtained from a chromosomal DNA of an aerobic Coryneform bacterium or an artificially synthesized DNA fragment, and the DNA fragment has a function of initiating transcription of a gene, that is, an ability to transcribe a gene, and means a DNA fragment which is presumed to contain the promoter.

Regarding expression of the promoter function, a term "induce" is generally used in many cases when the expression is enhanced, but in the present invention, a term "induce" is used in order to mean that increase or decrease in the expression is induced by intracellular and extracellular factors. And, an extent thereof can be indicated by an expression amount of an mRNA.

Therefore, the "inductively-enhance" in the present invention means that, since a reaction medium is under the specified condition (anaerobic condition), expression of a DNA sequence having the induced promoter function is increased, that is, enhanced, and refers to that an extent of expression of the promoter function indicated by an expression amount of an mRNA is enhanced by at least about 50% or more, preferably about 100% or more relative to an expression amount in a reaction medium under an aerobic condition.

The "inductively-suppress" means that, since a reaction medium is under the specified condition (anaerobic condition), expression of a DNA sequence including an induced promoter site is decreased, that is, suppressed, and refers to that an extent of expression of the promoter function indicated by an expression amount of an mRNA is decreased by at least about 50% or more, preferably around about 90% relative to an expression amount in a reaction medium under an aerobic condition.

The Coryneform bacterium used in the present invention refers to a group of microorganisms defined in Bargeys Manual of Determinative Bacteriology, vol. 8, p. 599, 1974.

Specifically, examples include Corynebacterium bacteria, Brevibacterium bacteria, Arthrobacter bacteria, Mycobacterium bacteria and Micrococcus bacteria.

More specifically, examples of Corynebacterium bacteria include Corynebacterium glutamicum FERM P-18976, ATCC3032, ATCC13058, ATCC13059, ATCC13060, ATCC13232, ATCC13286, ATCC13287, ATCC13655, ATCC13745, ATCC13746, ATCC13761, ATCC14020 and ATCC31831.

Examples of Brevibacterium bacteria include Brevibacterium lactofermentum ATCC13869, Brevibacterium flavum MJ-233 (FERM P-1497) and MJ-233AB-41 (FERM BP-1498), and Brevibacterium ammoniagenes ATCC6872.

Examples of Arthrobacter bacteria include Arthrobacter globiformis ATCC8010, ATCC4336, ATCC21056, ATCC31250, ATCC31738 and ATCC35698.

Examples of Micrococcus bacteria include Micrococcus freudenreichii No. 239 (FERMP-13221), Micrococcus luteus No. 240 (FERMP-13222), Micrococcus ureae IAM1010 and Micrococcus roseus IFO3764.

As the aerobic Coryneform bacterium used in the present invention, Corynebacterium glutamicum R (FERM P-18976), Corynebacterium glutamicum ATCC13032 and the like are particularly preferable.

In addition, the aerobic Coryneform bacterium used in the present invention may be a naturally occurring wild-type variant (for example, FERM P-18977, FERM P-18978 strain and the like), or an artificial strain utilizing biotechnology such as gene recombination (for example, FERM P-17887, FERM P-17888, FERM P-18979 and the like).

In the present invention, a Coryneform bacterium cell under an aerobic condition, which is used in the following procedure, is obtained by proliferating and culturing the aforementioned Coryneform bacterium under an aerobic condition.

Culturing of the Coryneform bacterium can be performed using a normal nutrient medium containing a carbon source, a nitrogen source and an inorganic salt. In culturing, for example, glucose, molasses and the like, as a carbon source, and, for example, ammonia, ammonium sulfate, ammonium chloride, ammonium nitrate and urea as a nitrogen source can be used alone, or by mixing them. In addition, as the inorganic salt, for example, potassium monohydrogen phosphate, potassium dihydrogen phosphate and magnesium sulfate can be used. Besides, if necessary, nutrients such as peptone, meat extract, yeast extract, corn steep liquor, casamino acid, and various vitamins such as biotin and thiamine may be appropriately added to a medium.

A culture can be obtained by culturing a bacterium using a jar fermenter while the air is bubbled, and recovering cells under an aerobic condition with a DO (dissolved oxygen concentration) of not less than 6 ppm. A culturing temperature is about 20° C. to 40° C., preferably about 25° C. to 35° C. A pH at culturing is in a range of about 5 to 10, preferably about 7 to 8, and a pH during culturing can be adjusted by adding an acid or an alkali. A carbon source concentration at initiation of culturing is about 1 to 20% (W/V), preferably about 2 to 5% (W/V).

Examples of a method of obtaining the *Coryneform* bacterium cell under an anaerobic condition include a method of washing and recovering bacterium cells which have been aerobically cultured using the jar fermenter or the like. A method of recovering and separating cultured bacterium cells from the thus obtained culture is not particularly limited and, for example, the known methods such as centrifugation and membrane separation can be used. Then, cultured bacterium cells of the *Coryneform* bacterium which have been recovered and separated from the thus obtained culture are subjected to the condition of production reaction of an organic compound under the reduced state (oxidation-reduction potential of the reaction solution is about −200 millivolts to −500 millivolts), like the method disclosed, for example, in JP-A No. 2004-194570, and are separated and recovered. The thus obtained bacterium cells can be used in the present invention as the *Coryneform* bacterium cell under an anaerobic condition.

As a method of obtaining a DNA fragment having the promoter function, which is inductively-enhanced or inductively-suppressed under an anaerobic condition of the present invention, a method of (a) extracting an mRNA from the *Coryneform* bacterium cell under an aerobic condition and from the *Coryneform* bacterium cell under an anaerobic condition, respectively and (b) totally analyzing a change in individual mRNA amounts in a cell using a DNA chip which can handle all genes is most effective.

Examples of the DNA fragment having the promoter function which is inductively-enhanced under an anaerobic condition of the present invention include DNA fragments represented by SEQ ID NOS.:(1) to (394) of Sequence Listing, and examples of the DNA fragment having the promoter function which is inductively-suppressed include DNA fragments represented by the aforementioned SEQ ID NOS.: (395) to (595).

A DNA having the promoter function, which has a nucleotide sequence in which one or several nucleotides are deleted, substituted or added in each DNA sequence represented by the aforementioned SEQ ID NOS., and inductively-enhances or inductively-suppresses expression of a protein involved in production of a useful substance, is included. When refers to the "one or several nucleotides are deleted, substituted or added" for a nucleotide sequence, this means that, by the well-known technical method such as a site-specific mutagenesis method, or to a naturally occurring extent, 1 to several nucleotides are deleted, substituted or added.

In addition, the DNA fragment having the promoter function under an anaerobic condition of the present invention includes a DNA having the promoter function, which hybridizes with a DNA including a nucleotide sequence complementary with respective DNA fragments represented by the aforementioned SEQ ID NOSs, respectively, under a stringent condition, and inductively-enhances or inductively-suppresses expression of a protein involved in production of a useful substance. The DNA which can hybridize under the stringent condition means a DNA obtained by using the aforementioned DNA as a probe and employing a colony hybridization method, a plague hybridization method, a Southern blot hybridization method or the like. The stringent condition refers to, for example, a hybridizing condition of a SSC solution having a salt concentration of about 0.1 to 2-fold concentration (a composition of a SSC solution having a 1-fold concentration consists of 150 mM sodium chloride, and 15 mM sodium citrate) at a temperature of about 65° C.

Furthermore, the DNA fragment having the promoter function under an anaerobic condition of the present invention includes a DNA having the promoter function, which has at least about 80% or more homology with respective DNA sequences represented by the aforementioned SEQ ID NOS., respectively, and inductively-enhances or inductively-suppresses expression of a protein involved in production of a useful substance. The DNA having homology refers to a DNA having preferably about 80% or more homology, more preferably, a DNA having about 90% or more homology, further preferably a DNA having about 95% or more homology under a highly stringent condition. The highly stringent condition refers to, for example, a condition of a sodium concentration of about 19 to 40 mM, preferably about 19 to 20 mM, and a temperature of about 50 to 70° C., preferably about 60 to 65° C. Particularly, the case of a sodium concentration of about 19 mM and a temperature of about 65° C. is the most preferable condition.

An extent of enhancement or suppression of the promoter function in the DNA fragment having the promoter function under an anaerobic condition of the present invention can be expressed by an expression amount of an mRNA as an index. For example, the "enhancement of expression" refers to that an expression amount of an mRNA in a reaction medium under an anaerobic condition, of the *Coryneform* bacterium is increased by at least about 50% or more, that is, increased to about 1.5-fold or more relative to an expression amount of an mRNA in a reaction medium under an aerobic condition. In addition, the "suppression of expression" refers to that an expression amount of an mRNA in a reaction medium under an anaerobic condition, of the *Coryneform* bacterium is decreased by at least about 50% or more, that is, decreased to about ½ or less relative to an expression amount of mRNA in a reaction medium under an aerobic condition.

As a method of obtaining a DNA fragment having the promoter function, which is inductively-enhanced or inductively-suppressed under a non-aerobic condition, of the present invention, a method of (a) extracting an mRNA from the *Coryneform* bacterium cell under an aerobic condition and from the *Coryneform* bacterium cell under a non-aerobic condition, respectively and (b) totally analyzing a change in individual mRNA amounts in a cell using a DNA chip which can handle all genes, is most effective.

The DNA chip can be manufactured by amplifying an ORF (open reading frame) of each gene by PCR based on gene information obtained from, for example, entire genome analysis of a *Coryneform* bacterium (see *C. glutamicum* R strain) (Hiroshi Nonaka, Kaori Nakata, Naoko Okai, Mariko Wada, Yumiko Sato, Kos Peter, Masayuki Inui, Hideaki Yukawa "*Corynebacterium glutamicum* R Genome Analysis", Japan Agricultural Chemical Society, April 2003, Yokohama, Japan Agricultural Chemical Society 2003 Annual Meeting Lecture Abstract, p. 20), spotting the amplified DNA fragment on an array slide, and performing a fixation treatment, for example, by the Takara Array Slide Standard method.

A method of extracting a total RNA from the *Coryneform* bacterium cell can be performed, for example, by QIAGEN RNeasy Mini Kit (manufactured by Qiagen), in which, for example, a cell suspension is treated with lysozyme, and glass beads are added, followed by vibration grinding (details are described in Examples). In Addition to the aforementioned kit, commercially available RNA extraction kits, for example, MORA-EXTRACT (manufactured by Cosmo Bio), Total RNA Isolation Mini Kit (manufactured by Agilent), RNA Isolation Kit (manufactured by Stratagene), Isogen (manufactured by Nippon Gene), Trizol (manufactured by Invitrogen), QuickPick mRNA-mini kit (manufactured by BIO NOBILE) and the like can be preferably used, being not limited.

A label of a probe used in the DNA chip can be made by performing synthesis of a cDNA with a random primer using a total RNA as a template, and marker (for example, fluorescent label or radioactive isotope) labeling, which is a conventional method. In the present invention, as the total RNA, a total RNA (Cy5) extracted from the *Coryneform* bacterium cell under an aerobic condition, or RNA (Cy3) extracted from the *Coryneform* bacterium cell under an anaerobic condition is used.

Hybridization, washing and drying of the DNA chip are preferably automation-treated with, for example, Amersham Biosciences Lucidea SlidePro or the like, in order to suppress a variation in data as much as possible.

It is suitable to digitalize and normalize detected image data, for example, with Axon Instruments GenePix Pro 5.0 or the like. In an experiment, a value obtained by averaging experimental data from at least three times of experiments is preferably adopted.

A gene corresponding to a sample having the resulting data (Ratio of Meands (Cy3/Cy5); signal intensity under a non-aerobic condition/signal intensity under an aerobic condition) which is about 1.5-fold (about 50% increase) or more, or about 0.5-fold (about 50% decrease) or less is extracted from genome information, and a sequence from 1 bp upstream of an initiation codon of each gene to a terminus of an upstream gene of the gene (in the case of the same direction transcription; to 1 bp downstream of a termination codon of an upstream gene, in the case of reverse direction transcription gene; to 1 bp upstream of an initiation codon of an upstream gene) can be selected as an inducible promoter.

As a protein involved in production of a useful substance, an enzyme related to metabolism in the *Coryneform* bacterium is preferable. Examples of such enzyme include enzymes involved in a glycolysis pathway, a reductive tricarboxylic acid pathway, an anaplerotic pathway, an amino acid synthesis pathway, a purine synthesis pathway, a pyrimidine synthesis pathway, a cholesterol synthesis pathway or a fatty acid synthesis pathway, or a pathway derived from these pathways, and enzymes involved in a glycolysis pathway, a reductive tricarboxylic acid pathway, an anaplerotic pathway or an amino acid synthesis pathway are more preferable.

Examples of the enzyme involved in a glycolysis pathway are not limited to, but include hexokinase, glucokinase, phosphoglucoseisomerase, phosphofructosekinase, aldolase, triosephosphate isomerase, glycerin aldehyde-3-phosphate dehydrogenase, phosphoglycerate kinase, phosphoglyceromutase, enolase and pyruvate kinase.

Examples of the enzyme involved in a reductive tricarboxylic acid pathway are not limited to, but include pyruvate synthase, citrate synthase, aconitate hydratase, isocitrate dehydrogenase, 2-oxoglutamate dehydrogenase, succinyl CoA synthase, succinate dehydrogenase, fumarate hydratase, malate dehydrogenase, isocitrate lyase and malate synthase.

Examples of the enzyme involved in an anaplerotic pathway are not limited to, but include pyruvate carboxylase, phosphoenolpyruvate carboxylase and phosphoenolpyruvate carboxykinase.

Examples of the enzyme involved in an amino acid synthesis pathway include all enzymes which generate an amino acid, including amino acid synthase, and amino acid synthetase. Specifically, examples are not limited to, but include aspartate aminotransferase, asparaginase, glutamate-alanineaminotransferase, phosphoglycerate dehydrokinase, phosphoserineaminotransferase, phosphoserine phosphatase, serine dehydratase, glycinehydroxymethyl transferase, glycine synthase, threonine aldolase, threonine dehydratase, threonine synthase, homoserine kinase, homoserine dehydrogenase, aspartate semialdehyde dehydrogenase, cystine reductase, histidinol dehydrogenase, phenylalanine hydroxylase, glutamine synthetase, ligase, asparagine synthase and tryptophan synthase.

Examples of the enzyme involved in a purine synthesis pathway include enzymes involved in a pentose phosphate cycle (for example, glucose-6-phosphate dehydrogenase, lactonase, 6-phosphogluconate dehydrogenase, ribulonate 3-epimerase, ribosephosphate isomerase and the like), ribosephosphate pyrophosphokinase, amidophosphoribosyl transferase, glycineamidoribotide synthase, glycineamidoribotideformyl transferase, formylglycineamidoribotide synthase, AIR(5-aminoimidazoleribotide)synthetase, 5-aminoimidazole-4-(N-succinocarboxamide)ribotide synthetase, adenylosuccinate lyase, 5-aminoimidazole-4-carboxamideribotideformyl transferase, inosinemonophosphate(IMP) cyclohydrolase, adenylosuccinate synthase, adenylosuccinate lyase, adenylate kinase, IMP dehydrogenase, GMP (guanicine 5'-phosphate)synthetase, and guanylate kinase.

Examples of the enzyme involved in a pyrimidine synthesis pathway include carbamoylphosphate synthase II, aspartate carbamoyl transferase, dihydroorotase, orotate reductase, dihydroorotate dehydrogenase, orotate phosphoribosyl transferase, OMP(orotidinemonophosphate)decarboxylase, cytidine deaminase, uridine phospholitase, deoxyuridine phosphorylase, dihydrouracil dehydrogenase, dihydropyrimidinase and thymidine phosphorylase.

Examples of the enzyme involved in a cholesterol synthesis pathway include 3-hydroxy-3-methylglutaryl CoA reductase, and lanosterol synthase.

Examples of the enzyme involved in a fatty acid synthesis pathway include fatty acid synthase, long chain fatty acid acylation coenzyme A, acetyl CoA carboxylase, and acyltransferase.

Examples of the enzyme involved in a pathway derived from the aforementioned respective pathways are not limited to, but include lactate dehydrogenase which produces lactic acid from pyruvic acid, pyruvate decarboxylase or alcohol dehydrogenase which produces an alcohol from pyruvic acid, and pyruvate oxidase which produces acetic acid from pyruvic acid, and also include malate synthase and isocitrate lyase in a glyoxylate cycle.

It is suitable that the DNA fragment having the promoter function of the present invention is introduced into a plasmid or on a chromosome where it can autonomously-replicate in the *Coryneform* bacterium, so as to be situated upstream of a gene encoding a protein involved in production of the useful substance. Like this, by arranging the DNA fragment having the promoter function upstream of a gene encoding a protein involved in production of a useful substance, an objective useful substance can be produced highly and effectively under an anaerobic condition.

In addition, in the present invention, in place of a gene encoding a protein involved in production of the useful substance, an expression gene which is not possessed by the *Coryneform* bacterium, for example, a gene encoding a useful protein produced in a plant may be arranged.

Examples of the useful substance include organic acid, amino acid, alcohol, steroid, nucleic acid, fatty acid and a physiologically active substance.

Examples of the organic acid include pyruvic acid, citric acid, isocitric acid, aconitic acid, 2-oxoglutalic acid, succinic acid, fumaric acid, malic acid, oxaloacetic acid, itaconic acid, lactic acid, acetic acid, gluconic acid, 2-ketogluconic acid, 5-ketogluconic acid, D-araboascorbic acid, kojic acid, tetradecane-1,14-dicarboxylic acid and cuminic acid. In addition, the organic acid also includes purine nucleotide such as inosinic acid, being not limiting.

Examples of the amino acid include aspartic acid, threonine, glutamic acid, proline, glycine, alanine, cysteine, valine, isoleucine, leucine, tyrosine, phenylalanine, histidine, lysine, arginine, serine, asparagine, glutamine, hydroxylysine, cystine, methionine and tryptophan. In addition, in the present invention, examples of the amino acid are not limited to, but include special amino acids such as β-alanine, γ-alanine (GABA), homocysteine, ornithine, 5-hydroxytryptophan, 3,4-dihydroxyphenylalanine (DOPA), triiodotyronine, 4-hydroxyproline, and thyroxine.

As the alcohol, any alcohol is preferable as far as it is an alcohol which is produced by alcohol fermentation, and examples are not limited to, but include methanol, ethanol, butanol and the like.

Examples of the steroid include entities having a perhydrocyclopentanophenanthrene skeleton as a fundamental structure, such as cholesterol, cholic acids (for example, taurocholic acid, glycocholic acid, and the like), sex hormones (for example, progestogen, androgen, follicle steroid and the like) and adrenal cortical hormones (for example, cortisol, corticosterone, aldosterone and the like). Also, plant saponins, digitoxin and the like are included, being not limited.

Examples of the nucleic acid include an RNA and a DNA.

Examples of the fatty acid include palmitic acid, myristic acid and stearic acid. Examples of the fatty acid also include sphingoid, prostaglandin, arachidonic acid, and eicosatetraenoic acid, being not limited.

Examples of the physiologically active substance are not limited to, but include hormones (for example, insulin, growth hormone, ACTH, oxytocin, vasopressin, thyroxine, TRH, LHRH and the like), vitamins (for example, vitamin $B_1$, vitamin $B_2$, vitamin $B_6$, pantothenic acid, folic acid, biotin, vitamin K, and the like), histamine, serotonin and interleukin.

The useful substance of the present invention is not limited to the aforementioned substances, but any substance can be preferably utilized as far as it is a substance which is produced by the *Coryneform* bacterium of the present invention.

The present invention will be explained in more detail below by way of Examples, but the present invention is not limited to them.

Example 1

Obtaining of *Coryneform* Bacterium Cell Under Aerobic Condition and Under Anaerobic Condition (1) Culturing of *Coryneform* bacterium, *Corynebacterium glutamicum* R (FERM P-18976) under aerobic condition:
(Preparation of culture medium); 500 mL of a medium consisting of 2 g of urea, 7 g of ammonium sulfate, 0.5 g of $KH_2PO_4$, 0.5 g of $K_2HPO_4$, 0.5 g of $MgSO_4.7H_2O$, 6 mg of $FeSO_4.7H_2O$, 4.2 mg of $MnSO_4.7H_2O$, 200 µg of biotin, 200 µg of thiamine hydrochloride, 2 g of yeast extract, 7 g of casamino acid, and 1000 mL of distilled water was dispensed into a flask of a volume of 1 L, this was heat-sterilized at 120° C. for 10 minutes, the flask was cooled to room temperature, and the flask was used as a seed culture medium. Similarly, 1000 mL of a medium having the same composition was placed into a glass jar fermenter of a volume of 2 L, this was heat-sterilized at 120° C. for 10 minutes, and this was used as a regular culture medium.

(Culturing): One seed culture medium was inoculated with a *Coryneform* bacterium, *Corynebacterium glutamicum* R (FERM P-18976) under the sterile condition, this was aerobically shaking-cultured at 33° C. for 12 hours to obtain a seed culturing solution. 50 mL of this seed culturing solution was inoculated on the jar fermenter, and culturing was initiated at a temperature of 33° C. at a ventilation amount of 1 vvm (Volume/Volume/Minute). A dissolved oxygen concentration (DO) started at around 7, and DO gradually began to decrease with proliferation, therefore, when a DO value reached 6, the *Coryneform* bacterium was recovered to obtain a *Coryneform* bacterium cell under an aerobic condition. On the other hand, aerobic culturing was continued as it was, and the cell was cultured overnight. 200 mL of a culturing solution was subjected to a centrifuge (5000 rotations, 15 min) to remove the supernatant. The thus obtained wet bacterium cell was used in the following reaction.

(2) Preparation of Reaction Solution for Anaerobic Reaction

A reaction stock consisting of 7 g of ammonium sulfate, 0.5 g of $KH_2PO_4$, 0.5 g of $K_2HPO_4$, 0.5 g of $MgSO_4.7H_2O$, 6 mg of $FeSO_4.7H_2O$, 4.2 mg of $MnSO_4.7H_2O$, 200 µg of biotin, 200 µg of thiamine hydrochloride, and 1000 mL of distilled water was prepared, and autoclaved at 120° C. for 20 minutes. 500 mL of this reaction stock was introduced into a glass reaction vessel having a volume of 1 L. This reaction vessel was provided with a pH adjusting device, a temperature maintaining device, an in-vessel reaction solution stirring device and a reduction potential measuring device.

(3) Implementation of Reaction

After the culturing, the prepared *Coryneform* bacterium cell was suspended in 500 mL of the reaction stock in the reaction vessel. 200 mM glucose was added, a reaction temperature was maintained at 33° C., and an organic compound production reaction was initiated. An oxidation-reduction potential at a reaction was −200 mV at an early stage, but was reduced immediately after initiation of the reaction, and the reaction was continued while maintaining the potential at −400 mV. Four hours after the reaction, the bacterium cell was recovered to obtain a *Coryneform* bacterium cell under an anaerobic condition. The reaction medium solution thereupon was analyzed using liquid chromatography, and it was found that 186 mM (16.7 g/L) (value after 3 hours) lactic acid was produced.

Example 2

Selection of Promoter which is Inductively-Promoted or Inductively-Suppressed Under Anaerobic Condition (1) Extraction of Total RNA from *Coryneform* Bacterium Cells Under Aerobic Condition and Under Anaerobic Condition Extraction of an RNA was performed with QIAGEN RNeasy Mini Kit (Qiagen). *Coryneform* bacterium cells under the aerobic condition and under the anaerobic condition recovered in Example 1 were recovered, QIAGEN RNA protect Bacteria Reagent was immediately added at an amount which is 2-fold an amount of the culturing solution, and this was stirred well and incubated at room temperature for 5 minutes to stabilize an RNA. After centrifugation, the supernatant was removed, and the cell was suspended in a RLT Buffer (QIAGEN RNeasy Mini Kit) containing β-mercaptoethanol to a final concentration of 15 to 20 dry cell weight/L. 0.5 mg of 0.1 mm zirconia/silica beads (BioSpec Products, Inc.) and 1 mL of a cell suspension were placed into a 2 mL FastPrep Tube (Qbiogene, Inc., Ca, USA), this was ground at a speed of 6.0 for 45 seconds with FastPrep•FP120 (Qbiogene), and cooled for 1 minute in ice. This procedure was repeated three times to mechanically grind bacterium cells. After centrifugation at 15,000 rpm for 2 minutes, the supernatant was transferred to another vessel, and 99% EtOH at an amount which is 0.56-fold an amount of the supernatant was added, followed by slow mixing. A sample was applied to the RNeasy Mini column, this was centrifuged at 10,000 rpm for 15 seconds, and the waste solution was discarded. 350 µL Buffer RW1 was applied to the column, this was allowed to stand at room temperature for 5 minutes, and centrifuged at 10,000 rpm for 15 seconds for washing, and the waste solution was discarded. Using the RNase-Free DNase Set, the mixed genome DNA was degraded on the column. A DNaseI solution obtained by adding 10 µL of a DNase I stock solution to 70 µL of Buffer RDD was applied to the column, and this was incubated at room temperature for 15 minutes to degrade a DNA. 350 µL Buffer RW1 was applied to the column, this was allowed to stand at room temperature for 5 minutes, and centrifuged at 10,000 rpm for 15 seconds, and the waste solution was discarded. 500 µL Buffer RPE was applied to the column, this was centrifuged at 10,000 rpm for 15 seconds, and the waste solution was discarded. Again, 500 µL Buffer RPE was added to the column, this was centrifuged at 10,000 rpm for 2 minutes, and the waste solution was discarded. In order to completely remove Buffer RPE, this was centrifuged at 15,000 rpm for 1 minute. For elution, the column was transferred to a new 1.5 mL tube, and 60 µL RNase free water was added, followed by centrifugation at 15,000 rpm for 1 minute. In order to obtain an RNA having a higher concentration, the eluate was added to the column once more, followed by centrifugation at 15,000 rpm for 1 minute.

A concentration of an RNA was calculated by measuring an absorbance at O.D.$_{260}$ with a spectrophotometer (O.D.$_{260}$× 40 µg/mL). In addition, each sample was thermally degenerated at 95° C. for 5 minutes, and subjected to agarose gel electrophoresis to investigate the presence or the absence of mixing of a DNA, and degradation of an RNA. It was confirmed that all samples had a value of O.D.$_{260}$/O.D.$_{280}$ in a range of 1.8 to 2.1.

(2) Manufacturing of DNA Chip which can Handle all Genes

As a DNA chip, a Stanford manner was adopted. The presence of 3080 genes is presumed from total genome analysis of *C. glutamicum* R strain (see Hiroshi Nonaka, Kaori Nakata, Naoko Okai, Mariko Wada, Yumiko Sato, Kos Peter, Masayuki Inui, Hideaki Yukawa "*Corynebacterium glutamicum* R genome Analysis", Nippon Agricultural Chemical Society, April 2003, Yokohama, Nippon Agricultural Chemical Society 2003 Annual Meeting Lecture Abstract, p. 20). Based on the gene (ORF) information, a PCR primer of a pair of a sequence of 20 nucleotides from a third nucleotide of an initiation codon (ATG) to downstream of each gene, and a sequence of 20 nucleotides from a first nucleotide of a termination codon (TAA) to upstream was designed for all genes, and a DNA fragment including an ORF sequence of each gene was amplified by PCR. By electrophoresis on a 1% agarose gel, it was confirmed that the amplification product is a single band, and indicates an objective size. When a plurality of bands were confirmed, an experiment was repeated so that a single band was obtained, by optimizing the PCR condition such as an annealing temperature and the like. The finally obtained DNA sample was spotted on 1×3 inch Takara Slide with a spotter, and fixation-treated by the Takara array slide standard method. In order to obtain quantitativity, spotting of 2 points was performed as to each gene.

(3) DNA Chip Analysis

Regarding a DNA chip, using a total RNA of *Corynebacterium glutamicum* R strain as a template, synthesis of a cDNA with a random primer (9mer), and fluorescent labeling (in Cy5, a total RNA extracted from the *Coryneform* bacterium cell under the aerobic condition was used and, in Cy3, an RNA extracted from the *Coryneform* bacterium cell under the anaerobic condition was used) were performed to make a labeled probe. In cDNA synthesis and a labeling reaction, Amersham Biosciences CyScribe cDNA Post Labeling Kit (Amersham Biosciences Corp. USA) was used, and this was according to the protocol. 3 µL random nonamer primers were added to 8 µL total RNA (30 µg), and this was heated at 70° C. for 5 minutes, and allowed to stand at room temperature for 10 minutes to anneal a primer to an RNA. To this RNA was added a reaction reagent (5× CyScript buffer 4 µL, 0.1 M DTT, 2 µL, CyScribe Post-Labeling nucleotide mix, 1 µL, CyScribe Post-Labeling Amino Allyl-dUTP, 1 µL, 100 U/µL CyCcript reverse transcriptase, 1 µL), and this was incubated at 42° C. for 3 hours. After the reaction solution was cooled on ice, in order to alkali-degrade an RNA, 2 µL of 2.5 M NaOH was added, and this was incubated at 37° C. for 15 minutes. Then, 10 µL of 2 M HEPES Buffer was added to perform neutralization. Using CyScribe GFX Purification Kit (Amersham Biosciences), an AA-modified cDNA probe was purified. Centrifugation upon a purification procedure was performed at room temperature in all cases. The reaction solution was mixed with 500 µL Capture Buffer, and the mixture was applied to the GFX column, followed by centrifugation at 13,800×g for 30 seconds. The waste solution was discarded, 600 µL 80% EtOH was applied to the column, and this was centrifuged at 13,800×g for 30 seconds, and this procedure was repeated three times. After the column was centrifuged at 13,800×g for 10 seconds, the column was transferred to a new 1.5 mL tube, 60 µL of 0.1 M NaHCO$_3$ (pH 9.0) was added, and this was allowed to stand at room temperature for 5 minutes. After centrifugation at 13,800×g for 1 minute, in order to recover a solution of a high concentration, the eluate was added to the column again, followed by centrifugation at 13,800×g for 1 minute. The reaction solution after purification was added to a tube containing a Cy3 or Cy5 reactive dye, and the materials were completely dissolved, followed by incubation at room temperature for 3 hours while light was shielded.

15 µL of 4M Hydroxylamine HCl was added, and this was stirred and mixed, followed by incubation at room temperature for 15 minutes while the light was shielded. Using CyScribe GFX Purification Kit (Amersham), a CyDye-labeled cDNA was purified. The reaction solution was mixed with 500 µL of Capture Buffer, and the mixture was applied to the GFX column, followed by centrifugation at 13,800×g for 30 seconds. The waste solution was discarded, 600 µL of Wash Buffer was applied to the column, this was centrifuged at 13,800×g for 30 seconds, and this procedure was repeated three times. After the column was centrifuged at 13,800×g for 10 seconds, the column was transferred to a new 1.5 mL tube, 60 μL of Elution Buffer was added, and this was allowed to stand at room temperature for 5 minutes. After centrifugation at 13,800×g for 1 minute, in order to recover the solution of a high concentration, the eluate was added to the column once more, and this was centrifuged at 13,800×g for 1 minute to recover a purified CyDye-labeled cDNA probe. Cy3 and Cy5-labeled cDNAs were placed into one tube, 100 μL of 2× Hybridization buffer (12×SSC, 0.4% SDS, 10×Denhardt's solution, 0.2 mg/mL denatured salmon sperm DNA) was added, and this was heated at 95° C. for 2 minutes, and cooled to room temperature. Steps of hybridization, washing and drying of a microarray were performed using Lucidea Slide Pro (Amersham Biosciences Corp. USA). Hybridization was performed at 60° C. for 14 hours. Washing was performed with Wash 1 (2×SSC, 0.2% SDS) for 6 minutes, with Wash 2 (0.2×SSC, 0.2% SDS) for 6 minutes, with Wash 3 (0.2×SSC) two times and with isopropanol once.

(4) Microarray Data Analysis

A fluorescent signal of the microarray was detected and imaged with FUJIFILM Fluorescent Image Analyzer FLA-8000 (Fuji, Tokyo, Japan). The detection condition was at 635 nm in Cy5, and at 532 nm in Cy3. The detected image data were digitalized and normalized using Axon Instruments GenePix Pro 5.0 (Axon Instruments, Inc., CA, USA). A color tone (Cy5; green, Cy3; red) was adjusted for every channel, an image was synthesized, and a spot was surrounded with a grid, followed by digitalization. As normalization, global normalization was adopted. Assuming that a sum of expression intensities of all genes is the same between cells to be compared, a fluorescent intensity ratio of all allays was corrected (normalized) so that medians of fluorescent intensity ratios of all signals of Cy5 and Cy3 became equal. For spots which seemed to be defective in reproductivity and quantitativeness (a spot having a half or less size, a spot having a stain or a flaw, a spot of a region where the background was high), values were excluded at an analysis stage. From a value calculated by GenePix Pro, Ratio of Meands (Cy3/Cy5) was used as an expression ratio.

(5) Selection of Inductively-Enhancing Promoter and Inductively-Suppressing Promoter Under Anaerobic Condition The expression ratio obtained in the (4) was expressed with a scatter plot (see FIG. 1). A central oblique line indicates that a value of Cy3/Cy5 is 1, that is, there is neither increase nor decrease in gene expression due to a difference in the culturing condition. On the other hand, two oblique lines situated while holding this have a value of Cy3/Cy5 of 2 or 0.5, indicating 2-fold increase or decrease. This experiment was performed plural times, and it was confirmed that data is obtained with better reproducibility.

A gene corresponding to a sample having this Ratio of Meands (Cy3/Cy5) of 1.5-fold (50% increase) or more or 0.5-fold (50% decrease) or less expression ratio was extracted from genome information, and a sequence from 1 bp upstream of an initiation codon of each gene to a terminus of a gene upstream of the gene (in the case of the same direction transcription; to 1 bp downstream of a termination codon of an upstream gene, in the case of a reverse direction transcription gene; to 1 bp upstream of an initiation codon of an upstream gene) was selected as an inducible promoter. As a result, there were 394 kinds (Table 1) having Ratio of Meands (Cy3/Cy5) of a 1.5-fold (50% increase) expression ratio, and 201 kinds (Table 2) having a 0.5-fold (50% degrease) expression ratio.

TABLE 1

Inductively-enhancing promotor under anaerobic condition and expression ratil

| No. | Cy3/Cy5 |
|---|---|
| 1 | 26.64 |
| 2 | 19.47 |
| 3 | 15.27 |
| 4 | 10.48 |
| 5 | 10.39 |
| 6 | 8.04 |
| 7 | 6.16 |
| 8 | 6.12 |
| 9 | 6.00 |
| 10 | 5.49 |
| 11 | 5.30 |
| 12 | 4.87 |
| 13 | 4.86 |
| 14 | 4.86 |
| 15 | 4.84 |
| 16 | 4.71 |
| 17 | 4.68 |
| 18 | 4.60 |
| 19 | 4.54 |
| 20 | 4.50 |
| 21 | 4.42 |
| 22 | 4.36 |
| 23 | 4.17 |
| 24 | 4.09 |
| 25 | 3.92 |
| 26 | 3.89 |
| 27 | 3.76 |
| 28 | 3.69 |
| 29 | 3.59 |
| 30 | 3.52 |
| 31 | 3.49 |
| 32 | 3.49 |
| 33 | 3.37 |
| 34 | 3.30 |
| 35 | 3.29 |
| 36 | 3.21 |
| 37 | 3.10 |
| 38 | 3.10 |
| 39 | 3.08 |
| 40 | 3.00 |
| 41 | 3.00 |
| 42 | 3.00 |
| 43 | 2.98 |
| 44 | 2.96 |
| 45 | 2.95 |
| 46 | 2.95 |
| 47 | 2.93 |
| 48 | 2.91 |
| 49 | 2.88 |
| 50 | 2.77 |
| 51 | 2.74 |
| 52 | 2.66 |
| 53 | 2.63 |
| 54 | 2.62 |
| 55 | 2.57 |
| 56 | 2.56 |
| 57 | 2.56 |
| 58 | 2.55 |
| 59 | 2.54 |
| 60 | 2.53 |
| 61 | 2.51 |
| 62 | 2.51 |
| 63 | 2.46 |
| 64 | 2.45 |
| 65 | 2.44 |
| 66 | 2.43 |
| 67 | 2.41 |
| 68 | 2.37 |
| 69 | 2.37 |
| 70 | 2.28 |
| 71 | 2.26 |
| 72 | 2.25 |
| 73 | 2.24 |
| 74 | 2.23 |
| 75 | 2.22 |

TABLE 1-continued

Inductively-enhancing promotor under anaerobic condition and expression ratil

| No. | Cy3/Cy5 |
|---|---|
| 76 | 2.20 |
| 77 | 2.20 |
| 78 | 2.20 |
| 79 | 2.19 |
| 80 | 2.18 |
| 81 | 2.17 |
| 82 | 2.17 |
| 83 | 2.17 |
| 84 | 2.15 |
| 85 | 2.15 |
| 86 | 2.15 |
| 87 | 2.14 |
| 88 | 2.14 |
| 89 | 2.14 |
| 90 | 2.13 |
| 91 | 2.12 |
| 92 | 2.10 |
| 93 | 2.10 |
| 94 | 2.10 |
| 95 | 2.07 |
| 96 | 2.06 |
| 97 | 2.05 |
| 98 | 2.05 |
| 99 | 2.04 |
| 100 | 2.03 |
| 101 | 2.02 |
| 102 | 2.02 |
| 103 | 2.01 |
| 104 | 1.99 |
| 105 | 1.99 |
| 106 | 1.99 |
| 107 | 1.97 |
| 108 | 1.97 |
| 109 | 1.95 |
| 110 | 1.94 |
| 111 | 1.94 |
| 112 | 1.93 |
| 113 | 1.93 |
| 114 | 1.92 |
| 115 | 1.92 |
| 116 | 1.92 |
| 117 | 1.92 |
| 118 | 1.91 |
| 119 | 1.91 |
| 120 | 1.89 |
| 121 | 1.89 |
| 122 | 1.89 |
| 123 | 1.88 |
| 124 | 1.88 |
| 125 | 1.88 |
| 126 | 1.88 |
| 127 | 1.87 |
| 128 | 1.87 |
| 129 | 1.87 |
| 130 | 1.87 |
| 131 | 1.86 |
| 132 | 1.85 |
| 133 | 1.85 |
| 134 | 1.85 |
| 135 | 1.84 |
| 136 | 1.84 |
| 137 | 1.84 |
| 138 | 1.84 |
| 139 | 1.83 |
| 140 | 1.83 |
| 141 | 1.83 |
| 142 | 1.83 |
| 143 | 1.82 |
| 144 | 1.82 |
| 145 | 1.82 |
| 146 | 1.82 |
| 147 | 1.82 |
| 148 | 1.82 |
| 149 | 1.82 |
| 150 | 1.82 |
| 151 | 1.82 |
| 152 | 1.81 |
| 153 | 1.81 |
| 154 | 1.81 |
| 155 | 1.80 |
| 156 | 1.80 |
| 157 | 1.80 |
| 158 | 1.80 |
| 159 | 1.79 |
| 160 | 1.79 |
| 161 | 1.78 |
| 162 | 1.78 |
| 163 | 1.78 |
| 164 | 1.77 |
| 165 | 1.77 |
| 166 | 1.77 |
| 167 | 1.77 |
| 168 | 1.77 |
| 169 | 1.77 |
| 170 | 1.77 |
| 171 | 1.77 |
| 172 | 1.76 |
| 173 | 1.76 |
| 174 | 1.76 |
| 175 | 1.76 |
| 176 | 1.76 |
| 177 | 1.76 |
| 178 | 1.76 |
| 179 | 1.75 |
| 180 | 1.75 |
| 181 | 1.75 |
| 182 | 1.74 |
| 183 | 1.74 |
| 184 | 1.74 |
| 185 | 1.73 |
| 186 | 1.73 |
| 187 | 1.73 |
| 188 | 1.73 |
| 189 | 1.73 |
| 190 | 1.73 |
| 191 | 1.72 |
| 192 | 1.72 |
| 193 | 1.72 |
| 194 | 1.72 |
| 195 | 1.72 |
| 196 | 1.72 |
| 197 | 1.71 |
| 198 | 1.71 |
| 199 | 1.71 |
| 200 | 1.71 |
| 201 | 1.71 |
| 202 | 1.71 |
| 203 | 1.71 |
| 204 | 1.70 |
| 205 | 1.70 |
| 206 | 1.69 |
| 207 | 1.69 |
| 208 | 1.69 |
| 209 | 1.69 |
| 210 | 1.69 |
| 211 | 1.69 |
| 212 | 1.69 |
| 213 | 1.69 |
| 214 | 1.69 |
| 215 | 1.69 |
| 216 | 1.68 |
| 217 | 1.68 |
| 218 | 1.68 |
| 219 | 1.68 |
| 220 | 1.68 |
| 221 | 1.68 |
| 222 | 1.68 |
| 223 | 1.68 |
| 224 | 1.68 |
| 225 | 1.67 |

TABLE 1-continued

Inductively-enhancing promotor under anaerobic condition and expression ratil

| No. | Cy3/Cy5 |
|---|---|
| 226 | 1.67 |
| 227 | 1.67 |
| 228 | 1.67 |
| 229 | 1.67 |
| 230 | 1.67 |
| 231 | 1.66 |
| 232 | 1.66 |
| 233 | 1.66 |
| 234 | 1.66 |
| 235 | 1.66 |
| 236 | 1.66 |
| 237 | 1.65 |
| 238 | 1.65 |
| 239 | 1.65 |
| 240 | 1.65 |
| 241 | 1.65 |
| 242 | 1.65 |
| 243 | 1.65 |
| 244 | 1.65 |
| 245 | 1.65 |
| 246 | 1.65 |
| 247 | 1.65 |
| 248 | 1.65 |
| 249 | 1.65 |
| 250 | 1.65 |
| 251 | 1.65 |
| 252 | 1.65 |
| 253 | 1.64 |
| 254 | 1.64 |
| 255 | 1.64 |
| 256 | 1.64 |
| 257 | 1.64 |
| 258 | 1.64 |
| 259 | 1.64 |
| 260 | 1.63 |
| 261 | 1.63 |
| 262 | 1.63 |
| 263 | 1.63 |
| 264 | 1.62 |
| 265 | 1.62 |
| 266 | 1.62 |
| 267 | 1.62 |
| 268 | 1.62 |
| 269 | 1.61 |
| 270 | 1.61 |
| 271 | 1.61 |
| 272 | 1.61 |
| 273 | 1.61 |
| 274 | 1.61 |
| 275 | 1.61 |
| 276 | 1.60 |
| 277 | 1.60 |
| 278 | 1.60 |
| 279 | 1.60 |
| 280 | 1.60 |
| 281 | 1.60 |
| 282 | 1.60 |
| 283 | 1.60 |
| 284 | 1.59 |
| 285 | 1.59 |
| 286 | 1.59 |
| 287 | 1.59 |
| 288 | 1.59 |
| 289 | 1.59 |
| 290 | 1.58 |
| 291 | 1.58 |
| 292 | 1.58 |
| 293 | 1.58 |
| 294 | 1.58 |
| 295 | 1.58 |
| 296 | 1.58 |
| 297 | 1.58 |
| 298 | 1.58 |
| 299 | 1.58 |
| 300 | 1.57 |
| 301 | 1.57 |
| 302 | 1.57 |
| 303 | 1.57 |
| 304 | 1.57 |
| 305 | 1.57 |
| 306 | 1.57 |
| 307 | 1.57 |
| 308 | 1.57 |
| 309 | 1.57 |
| 310 | 1.56 |
| 311 | 1.56 |
| 312 | 1.56 |
| 313 | 1.56 |
| 314 | 1.56 |
| 315 | 1.56 |
| 316 | 1.56 |
| 317 | 1.56 |
| 318 | 1.56 |
| 319 | 1.55 |
| 320 | 1.55 |
| 321 | 1.55 |
| 322 | 1.55 |
| 323 | 1.55 |
| 324 | 1.55 |
| 325 | 1.55 |
| 326 | 1.55 |
| 327 | 1.55 |
| 328 | 1.55 |
| 329 | 1.55 |
| 330 | 1.55 |
| 331 | 1.55 |
| 332 | 1.54 |
| 333 | 1.54 |
| 334 | 1.54 |
| 335 | 1.54 |
| 336 | 1.54 |
| 337 | 1.54 |
| 338 | 1.54 |
| 339 | 1.54 |
| 340 | 1.54 |
| 341 | 1.54 |
| 342 | 1.54 |
| 343 | 1.53 |
| 344 | 1.53 |
| 345 | 1.53 |
| 346 | 1.53 |
| 347 | 1.53 |
| 348 | 1.53 |
| 349 | 1.53 |
| 350 | 1.53 |
| 351 | 1.53 |
| 352 | 1.53 |
| 353 | 1.53 |
| 354 | 1.53 |
| 355 | 1.53 |
| 356 | 1.53 |
| 357 | 1.53 |
| 358 | 1.52 |
| 359 | 1.52 |
| 360 | 1.52 |
| 361 | 1.52 |
| 362 | 1.52 |
| 363 | 1.52 |
| 364 | 1.52 |
| 365 | 1.52 |
| 366 | 1.52 |
| 367 | 1.52 |
| 368 | 1.52 |
| 369 | 1.52 |
| 370 | 1.51 |
| 371 | 1.51 |
| 372 | 1.51 |
| 373 | 1.51 |
| 374 | 1.51 |
| 375 | 1.51 |

TABLE 1-continued

Inductively-enhancing promotor under anaerobic condition and expression ratil

| No. | Cy3/Cy5 |
|---|---|
| 376 | 1.51 |
| 377 | 1.51 |
| 378 | 1.51 |
| 379 | 1.51 |
| 380 | 1.51 |
| 381 | 1.50 |
| 382 | 1.50 |
| 383 | 1.50 |
| 384 | 1.50 |
| 385 | 1.50 |
| 386 | 1.50 |
| 387 | 1.50 |
| 388 | 1.50 |
| 389 | 1.50 |
| 390 | 1.50 |
| 391 | 1.50 |
| 392 | 1.50 |
| 393 | 1.50 |
| 394 | 1.50 |

TABLE 2

Expression-suppressing promotor under anaerobic condition and expression ratio

| No | Cy3/Cy5 |
|---|---|
| 395 | 0.10 |
| 396 | 0.11 |
| 397 | 0.12 |
| 398 | 0.13 |
| 399 | 0.14 |
| 400 | 0.14 |
| 401 | 0.14 |
| 402 | 0.14 |
| 403 | 0.14 |
| 404 | 0.16 |
| 405 | 0.16 |
| 406 | 0.16 |
| 407 | 0.17 |
| 408 | 0.17 |
| 409 | 0.17 |
| 410 | 0.17 |
| 411 | 0.18 |
| 412 | 0.19 |
| 413 | 0.19 |
| 414 | 0.20 |
| 415 | 0.20 |
| 416 | 0.21 |
| 417 | 0.21 |
| 418 | 0.21 |
| 419 | 0.21 |
| 420 | 0.22 |
| 421 | 0.22 |
| 422 | 0.22 |
| 423 | 0.22 |
| 424 | 0.22 |
| 425 | 0.22 |
| 426 | 0.23 |
| 427 | 0.23 |
| 428 | 0.24 |
| 429 | 0.24 |
| 430 | 0.24 |
| 431 | 0.24 |
| 432 | 0.24 |
| 433 | 0.24 |
| 434 | 0.25 |
| 435 | 0.26 |
| 436 | 0.26 |
| 437 | 0.26 |
| 438 | 0.27 |
| 439 | 0.27 |

TABLE 2-continued

Expression-suppressing promotor under anaerobic condition and expression ratio

| No | Cy3/Cy5 |
|---|---|
| 440 | 0.27 |
| 441 | 0.27 |
| 442 | 0.27 |
| 443 | 0.28 |
| 444 | 0.28 |
| 445 | 0.28 |
| 446 | 0.28 |
| 447 | 0.28 |
| 448 | 0.28 |
| 449 | 0.28 |
| 450 | 0.29 |
| 451 | 0.30 |
| 452 | 0.30 |
| 453 | 0.30 |
| 454 | 0.30 |
| 455 | 0.31 |
| 456 | 0.31 |
| 457 | 0.31 |
| 458 | 0.31 |
| 459 | 0.31 |
| 460 | 0.31 |
| 461 | 0.31 |
| 462 | 0.31 |
| 463 | 0.32 |
| 464 | 0.32 |
| 465 | 0.32 |
| 466 | 0.33 |
| 467 | 0.33 |
| 468 | 0.33 |
| 469 | 0.33 |
| 470 | 0.33 |
| 471 | 0.33 |
| 472 | 0.33 |
| 473 | 0.33 |
| 474 | 0.33 |
| 475 | 0.33 |
| 476 | 0.33 |
| 477 | 0.33 |
| 478 | 0.34 |
| 479 | 0.34 |
| 480 | 0.34 |
| 481 | 0.34 |
| 482 | 0.34 |
| 483 | 0.34 |
| 484 | 0.34 |
| 485 | 0.34 |
| 486 | 0.35 |
| 487 | 0.35 |
| 488 | 0.35 |
| 489 | 0.35 |
| 490 | 0.35 |
| 491 | 0.35 |
| 492 | 0.36 |
| 493 | 0.36 |
| 494 | 0.36 |
| 495 | 0.37 |
| 496 | 0.37 |
| 497 | 0.37 |
| 498 | 0.37 |
| 499 | 0.37 |
| 500 | 0.37 |
| 501 | 0.37 |
| 502 | 0.37 |
| 503 | 0.38 |
| 504 | 0.38 |
| 505 | 0.38 |
| 506 | 0.38 |
| 507 | 0.38 |
| 508 | 0.39 |
| 509 | 0.39 |
| 510 | 0.39 |
| 511 | 0.40 |
| 512 | 0.40 |
| 513 | 0.40 |
| 514 | 0.40 |

TABLE 2-continued

Expression-suppressing promotor under anaerobic condition and expression ratio

| No | Cy3/Cy5 |
|---|---|
| 515 | 0.40 |
| 516 | 0.40 |
| 517 | 0.40 |
| 518 | 0.41 |
| 519 | 0.41 |
| 520 | 0.41 |
| 521 | 0.41 |
| 522 | 0.41 |
| 523 | 0.41 |
| 524 | 0.42 |
| 525 | 0.42 |
| 526 | 0.42 |
| 527 | 0.42 |
| 528 | 0.42 |
| 529 | 0.42 |
| 530 | 0.42 |
| 531 | 0.42 |
| 532 | 0.43 |
| 533 | 0.43 |
| 534 | 0.43 |
| 535 | 0.43 |
| 536 | 0.43 |
| 537 | 0.43 |
| 538 | 0.43 |
| 539 | 0.43 |
| 540 | 0.43 |
| 541 | 0.43 |
| 542 | 0.44 |
| 543 | 0.44 |
| 544 | 0.44 |
| 545 | 0.44 |
| 546 | 0.44 |
| 547 | 0.44 |
| 548 | 0.44 |
| 549 | 0.44 |
| 550 | 0.44 |
| 551 | 0.44 |
| 552 | 0.44 |
| 553 | 0.45 |
| 554 | 0.45 |
| 555 | 0.45 |
| 556 | 0.45 |
| 557 | 0.46 |
| 558 | 0.46 |
| 559 | 0.46 |
| 560 | 0.46 |
| 561 | 0.46 |
| 562 | 0.46 |
| 563 | 0.46 |
| 564 | 0.46 |
| 565 | 0.46 |
| 566 | 0.47 |
| 567 | 0.47 |
| 568 | 0.47 |
| 569 | 0.47 |
| 570 | 0.47 |
| 571 | 0.47 |
| 572 | 0.47 |
| 573 | 0.47 |
| 574 | 0.48 |
| 575 | 0.48 |
| 576 | 0.48 |
| 577 | 0.48 |
| 578 | 0.48 |
| 579 | 0.48 |
| 580 | 0.48 |
| 581 | 0.48 |
| 582 | 0.48 |
| 583 | 0.49 |
| 584 | 0.49 |
| 585 | 0.49 |
| 586 | 0.49 |
| 587 | 0.49 |
| 588 | 0.49 |
| 589 | 0.49 |
| 590 | 0.50 |
| 591 | 0.50 |
| 592 | 0.50 |
| 593 | 0.50 |
| 594 | 0.50 |
| 595 | 0.50 |

No; SEQ ID NO.
Cy3/Cy5: Expression ratio

Example 3

Conformation of Inductive Enhancement and Inductive Suppression by Real Time Quantitative RT-PCR Analysis In order to study enhancement or suppression data of an inducible promoter obtained by DNA chip analysis, an expression ratio thereof was analyzed by real time quantitative RT-PCR. As a sample to be analyzed, among 394 kinds of inductively-enhancing promoters which showed a 1.5-fold or more expression ratio, three kinds of SEQ ID NOS. 3, 22 and 47 (NOS of Table 1) were randomly selected and, on the other hand, among 201 kinds of inductively-suppressing promoters which showed a 0.5-fold or less expression ratio, three kinds of SEQ ID NOS. 410, 474 and 502 (NOS of Table 2) were randomly selected.

Real time quantitative RT-PCR analysis was performed with QIAGEN QuantiTect SYBR Green RT-PCR Kit (Qiagen) using a total RNA as a template. A gene-specific primer was designed using Applied Biosystems Primer Express Software v2.0 (Applied Biosystems, USA). A real time PCR experiment was performed with ABI PRISM 7000 Sequence Detection System (Applied Biosystems, USA), and a PCR reaction was performed using 96-Well Optical Reaction Plate (Applied Biosystems) and Optical Adhesive Covers (Applied Biosystems). A composition of a PCR reaction solution was adjusted with (50 μL/1 sample); Total RNA, 60 ng, 2× QuantiTect SYBR Green RT-PCR Master Mix, 25 μL, Primer Forward, 0.5 μM, Primer Reverse, 0.5 μM, QuantiTect RT Mix, 0.5 μL. The PCR reaction was performed at 50° C. 30 min, 95° C. 15 min, (95° C. 15 sec, 57° C. 20 sec, 60° C. 1 min)×40 cycles. After completion of the PCR reaction, for calculating an expression amount, a comparative $C_T$ method of quantitating an expression amount ratio for every specimen, and comparing specimens by the expression ratio was used. At a center of a place where all samples were exponentially proliferating (a place where samples were proliferating at a straight proliferation curve), a Threshold line was set, and the number of cycles intersecting with this line was adopted as a $C_T$ value, and a ratio of an expression amount was calculated.

As a result, expression ratios of inductively-enhancing promoters SEQ ID NOS. 3, 22 and 47 (NOS in Table 1) (results are in Table 3) which showed a 1.5-fold or more expression ratio, and inductively-suppressing promoters SEQ ID NOS. 410, 474 and 502 (NOS in Table 2) (results are in Table 4) which showed a 0.5-fold or less expression ratio were well in agreement with DNA chip analysis results, respectively.

TABLE 3

Expression ratio of inductively-enhancing promoter by real time quantitative RT-PCR analysis

| SEQ ID NO same as in Table 1 | Cy3/Cy5 DNA chip | real time quantitative RT-PCR |
|---|---|---|
| 3 | 15.27 | 17.19 |
| 22 | 4.36 | 4.51 |
| 47 | 2.93 | 2.57 |

TABLE 4

Expression ratio of inductively-suppressing promoter by real time quantitative RT-PCR analysis

| SEQ ID NO same as in Table 2 | Cy3/Cy5 DNA chip | real time quantitative RT-PCR |
|---|---|---|
| 410 | 0.17 | 0.59 |
| 474 | 0.33 | 0.44 |
| 502 | 0.37 | 0.41 |

INDUSTRIAL APPLICABILITY

The DNA fragment of the present invention is useful as a primer which is introduced into a transformed *Coryneform* bacterium producing a useful substance such as lactic acid and succinic acid highly and at a high efficiency. A *Coryneform* bacterium in which the DNA fragment of the present invention has been introduced can be utilized in producing an organic acid, an alcohol, an amino acid or the like. In addition, the produced organic acid can be used as a polymer synthesis raw material or a medicament raw material, or in a wide field such as cosmetic utility and food additive utility. For example, succinic acid and a derivative thereof are useful in a biodegradable plastic raw material or in utility of a green washing solvent which does not bring out environmental pollution.

The invention claimed is:

1. A vector comprising a DNA fragment comprising SEQ ID NO:32 and a heterologous gene.

2. A transformant of a *Coryneform* bacterium transformed with the vector of claim 1, wherein the vector is inserted in a plasmid or a chromosome upstream of a gene encoding an enzyme involved in metabolism in the *Coryneform* bacterium, and wherein the plasmid or chromosome can autonomously-replicate in the *Coryneform* bacterium.

3. The transformant according to claim 2, wherein the enzyme is at least one enzyme or coenzyme involved in a glycolysis pathway, a reductive tricarboxylic acid pathway, an anaplerotic pathway, an amino acid synthesis pathway, a purine synthesis pathway, a pyrimidine synthesis pathway, a cholesterol synthesis pathway, a fatty acid synthesis pathway, or a pathway derived from one or more of these pathways.

* * * * *